US006919371B2

(12) United States Patent  
O'Connor et al.

(10) Patent No.: US 6,919,371 B2  
(45) Date of Patent: Jul. 19, 2005

(54) 2,6-SUBSTITUTED CHROMAN DERIVATIVES USEFUL AS BETA-3 ADRENORECEPTOR AGONISTS

(75) Inventors: Stephen J. O'Connor, Guilford, CT (US); Gaetan H. Ladouceur, Branford, CT (US); William H. Bullock, Easton, CT (US); Ann-Marie Campbell, Monroe, CT (US); Miao Dai, Briarwood, NY (US); Robert Dally, Indianapolis, IN (US); Jacques Dumas, Bethany, CT (US); Holia N. Hatoum-Mokdad, Hamden, CT (US); Uday Khire, Hamden, CT (US); Wendy Lee, Hamden, CT (US); Qingjie Liu, Milford, CT (US); Derek B. Lowe, Hamden, CT (US); Steven R. Magnuson, Hamden, CT (US); Ning Qi, Hamden, CT (US); Tatiana E. Shelekhin, Ridgefield, CT (US); Quanrong Shen, Fishers, IN (US); Roger A. Smith, Madison, CT (US); Ming Wang, Milford, CT (US)

(73) Assignee: Bayer Pharmaceuticals Corporation, West Haven, CT (US)

( * ) Notice: Subject to any disclaimer, the term of this patent is extended or adjusted under 35 U.S.C. 154(b) by 0 days.

(21) Appl. No.: 10/666,903

(22) Filed: Sep. 17, 2003

(65) Prior Publication Data

US 2004/0072828 A1 Apr. 15, 2004

Related U.S. Application Data

(63) Continuation of application No. 10/131,448, filed on Apr. 22, 2002, now Pat. No. 6,660,752.
(60) Provisional application No. 60/324,518, filed on Sep. 26, 2001, and provisional application No. 60/285,719, filed on Apr. 23, 2001.

(51) Int. Cl.[7] .................... A61K 31/352; C07D 311/58
(52) U.S. Cl. ................ 514/456; 546/282.1; 546/282.7; 549/398; 549/404; 514/337; 514/456
(58) Field of Search ................ 549/398, 404; 549/426; 546/282.1, 282.7; 514/456, 337

(56) References Cited

U.S. PATENT DOCUMENTS

| 3,706,764 A | 12/1972 | Nakanishi et al. ........... 260/327 |
| 3,803,176 A | 4/1974 | Christensen et al. ...... 260/345.2 |
| 4,647,579 A | 3/1987 | Kabbe et al. ................ 514/456 |
| 4,650,812 A | 3/1987 | Cohen et al. ................ 514/456 |
| 4,654,362 A | 3/1987 | Van Lommen et al. ...... 514/452 |
| 5,393,775 A | 2/1995 | Le Baut et al. .............. 514/456 |
| 5,451,677 A | 9/1995 | Fisher et al. ................ 546/138 |
| 5,516,917 A | 5/1996 | Djuric et al. ................ 548/525 |
| 5,541,197 A | 7/1996 | Fisher et al. ................ 514/311 |
| 5,561,142 A | 10/1996 | Fisher et al. ................ 514/312 |
| 5,663,194 A | 9/1997 | Newshaw .................... 514/456 |
| 5,977,154 A | 11/1999 | Bell et al. .................... 514/394 |
| 6,051,586 A | 4/2000 | Ladouceur et al. .......... 514/337 |
| 6,469,031 B1 * | 10/2002 | Connell et al. .............. 514/337 |

FOREIGN PATENT DOCUMENTS

| DE | 2511647 | 9/1975 | ......... C07D/311/22 |
| EP | 0079637 | 5/1983 | ......... C07D/311/24 |
| EP | 0091749 | 10/1983 | ......... C07C/143/78 |
| EP | 0328251 | 8/1989 | ......... C07C/103/178 |
| EP | 0611003 | 8/1994 | ......... C07C/311/21 |
| EP | 0801060 | 10/1997 | ......... C07D/209/42 |
| FR | 2746395 | 9/1997 | ......... C07D/409/12 |
| JP | 8198866 | 8/1996 | |
| JP | 08198866 | * 8/1996 | |
| WO | 9429290 | 12/1994 | ......... C07D/307/85 |
| WO | 9525104 | 9/1995 | ......... C07D/405/12 |
| WO | 9529159 | 11/1995 | ......... C07D/213/30 |
| WO | 9735835 | 10/1997 | ......... C07C/217/74 |
| WO | 9746556 | 12/1997 | ......... C07D/413/10 |
| WO | 9832753 | 7/1998 | ......... C07D/417/12 |
| WO | 9965877 | 12/1999 | ......... C07D/213/80 |

OTHER PUBLICATIONS

CAPLUS AN: 2004:615587, Iatropoulos et al, abstract of "The function and pathology of brown adipose tissue in animals and humans," Journal of Toxicologic Pathology (2004), vol. 17 (2), pp. 147–153.*

CAPLUS AN: 2001:699585, Cederberg et al, "FOXC2 is a winged helix gene that counteracts obesity, hypertriglyceridemia, and diet–induced insulin resistance," Cell (2001), vol. 106 (5), pp. 563–573.*

CAPLUS AN: 200122029, Manraj et al, "Genetic & environmental nature of the insulin resistance syndrome in Indo–Mauritian subjects with premature coronary heart disease: contribution of beta–3 adrenoreceptor gene . . . ", Diabetologia (2001), vol. 44 (1) pp. 115.*

CAPLUS AN: 2000:165957, Proenza et al,m "Association of sets of alleles of genes encoding beta–3 adrenorecepto . . . ", International Journal of Obesity (2000), vol. 24 (1), pp. 93–100.*

Hu, B., Ellingboe, J., Gunawan, I., Han, S., Largis, E., Li, Z., Malamas, M., Mulvey, R., Oliphant, A., Sum, F.–W., Tillett, J., Wong, V., "2,4–Thiazolidinediones as Potent and Selective Human ꓱ3 Agonists", Bioorganic & Medicinal Chemistry Letters, 11: 757–760 (2001).

Murata, M., Watanabe, S., and Masuda, Y., "Novel Palladium(0)–Catalyzed Coupling Reaction of Dialkozyborane with Aryl Halides: Convenient Synthetic Route to Arylboronates", J. Org., Chem., 62: 6458–6459 (1997).

* cited by examiner

Primary Examiner—Joseph K. McKane  
Assistant Examiner—Janet L. Coppins  
(74) Attorney, Agent, or Firm—Susan M. Pellegrino

(57) ABSTRACT

This invention relates to novel 2,6-substituted chroman derivatives which are useful in the treatment of beta-3 adrenoreceptor-mediated conditions.

24 Claims, No Drawings

2,6-SUBSTITUTED CHROMAN DERIVATIVES USEFUL AS BETA-3 ADRENORECEPTOR AGONISTS

This application is a continuation of Ser. No. 10/131,448 filed Apr. 22, 2002 now U.S. Pat. No. 6,660,752.

This application claims benefit of U.S. Provisional Application Ser. No. 60/285,719, filed Apr. 23, 2001, and U.S. Provisional Application Ser. No. 60/324,518, filed on Sep. 26, 2001, the contents of which are incorporated herein by reference in their entirety.

FIELD OF THE INVENTION

This invention relates to novel chroman compounds, pharmaceutical compositions containing such compounds, and methods of treating beta-3 adrenoreceptor-mediated conditions with such compositions.

BACKGROUND OF THE INVENTION

Adrenoreceptors, or adrenergic receptors, are sites on effector organs that are innervated by postganglionic adrenergic fibers of the sympathetic nervous system, and are classified as either alpha-adrenergic or beta-adrenergic receptors. Alpha-adrenergic receptors respond to norepinephrine and to such blocking agents as phenoxybenzamine and phentolamine, whereas beta-adrenergic receptors respond to epinephrine and to such blocking agents as propranolol.

Beta-adrenergic receptors are sub-classified as beta-1, beta-2, and beta-3 adrenoreceptors. Generally, beta-1 stimulation causes cardiostimulation, whereas beta-2 stimulation causes bronchodilation and vasodilation.

Beta-3 receptors are found on the cell surface of both white and brown adipocytes where their stimulation promotes both lipolysis and energy expenditure. Agonists of beta-3 adrenoreceptors are known to be useful in the treatment of hyperglycemia (diabetes) and obesity in mammals, as well as in the treatment of gastrointestinal disorders and neurogenetic inflammation (U.S. Pat. No. 5,561,142). Additionally, they are known to lower triglyceride and cholesterol levels and to raise high-density lipoprotein levels in mammals (U.S. Pat. No. 5,451,677). Accordingly, they are useful in the treatment of conditions such as hypertriglyceridemia, hypercholesterolemia, and in lowering high-density lipoprotein levels. They also may be useful in treating patients with Syndrome X, impaired fasting glucose, and/or impaired glucose tolerance, as well as in the treatment of atherosclerotic and cardiovascular diseases and related conditions.

Additionally, it is also believed that the compounds of this invention are effective in the treatment of ocular hypertension and glaucoma, and in the treatment of urinary disorders including pollakiuria and incontinence, as well as in the treatment of prostate disease and as topical anti-inflammatory agents.

It has now been found that certain novel chroman derivatives are effective as beta-3 agonists and are useful in the treatment of beta-3 adrenoreceptor-mediated conditions.

DESCRIPTION OF THE INVENTION

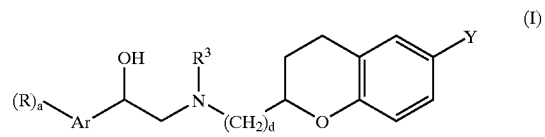

(I)

wherein,
R is independently
  hydroxy,
  oxo,
  halo,
  cyano,
  nitro,
  $C_1$–$C_{10}$ alkyl,
  $C_1$–$C_{10}$ haloalkyl,
  $CF_3$,
  $NR^1R^1$,
  $SR^1$,
  $OR^1$,
  $SO_2R^2$,
  $OCOR^2$,
  $NR^1COR^2$,
  $COR^2$,
  $NR^1SO_2R^2$,
  phenyl, or
  a 5- or 6-membered heterocycle with from 1 to 4 heteroatoms selected from O, S, and N;
  each cyclic moiety being optionally substituted with
    hydroxy,
    $R^1$,
    halo,
    cyano,
    $NR^1R^1$,
    $SR^1$,
    $CF_3$,
    $OR^1$,
    $C_3$–$C_8$ cycloalkyl,
    $NR^1COR^2$,
    $COR^2$,
    $SO_2R^2$,
    $OCOR^2$,
    $NR^1SO_2R^2$,
    $C_1$–$C_{10}$ alkyl, or
    $C_1$–$C_{10}$ alkoxy;
$R^1$ is
  hydrogen,
  $(CH_2)_d$—O—$(CH_2)_d R^5$ where each d is selected independently, or
  $C_1$–$C_{10}$ alkyl optionally substituted with 1 to 4 substituents each independently selected from
    hydroxy,
    halo,
    $CO_2 C_1$–$C_4$-alkyl,
    $CO_2H$,
    $C_1$–$C_{10}$alkoxy,
    $S(O)_b C_1$–$C_{10}$ alkyl,
    $S(O)_b$-phenyl optionally substituted with halo, $C_1$–$C_4$ alkyl, $C_1$–$C_4$ alkoxy, $SO_2$—$C_1$–$C_4$alkyl, or $CO_2 C_1$–$C_4$alkyl; or phenyl optionally substituted with $CO_2C_1$–$C_4$-alkyl, $CO_2H$, halo, or $C_1$–$C_{10}$alkyl; or $C_3$–$C_8$ cycloalkyl, phenyl, or naphthyl, each optionally substituted with 1 to 4 substituents each independently selected from halo, nitro, oxo, $C_1$–$C_{10}$ alkyl, $C_1$–$C_{10}$ alkoxy, $C_1$–$C_{10}$ alkylthio, $CO_2C_1$–$C_4$-alkyl, and $CO_2H$, and when two $R^1$ groups are attached to N as $NR^1R^1$, these $R^1$ groups may form together with the nitrogen to which they are attached, a heterocyclic ring containing 4 to 7 C atoms, 1 to 2 N atoms, and 0 to 1 O or S atoms;

$R^2$ is $R^1$, $OR^1$, $NR^1R^1$, $NHS(O)_b$phenyl optionally substituted with $C_1$–$C_4$alkyl, $C_1$–$C_4$ alkoxy, halo or nitro;

$NHS(O)_b$naphthyl, $NHS(O)_bC_1$–$C_{10}$ alkyl optionally substituted with fluoro up to the perfluoro level, or a 5- or 6-membered heterocycle with one or more heteroatoms selected from O, S, and N, said heterocyclic moiety being optionally substituted with $R^1$;

$R^3$ is hydrogen, $C_1$–$C_{10}$ alkyl, or $COR^2$;

$R^4$ is hydrogen, $C_1$–$C_{10}$ alkyl, $C_1$–$C_{10}$ alkyl-phenyl, or $C_1$–$C_{10}$ alkyl-pyridyl;

$R^5$ is hydrogen or COOH;

$R^6$ is hydrogen, $C_1$–$C_{10}$ alkyl optionally substituted with 1 to 4 substituents each independently selected from halo, phenyl, or phenyl-$COR^2$, or $C_1$–$C_{10}$ alkyl-$S(O)_bC_1$–$C_{10}$ alkyl optionally substituted with $COR^2$ or $C_3$–$C_8$ cycloalkyl;

Ar is phenyl optionally fused to a 5- or 6-membered heterocycle containing one or more heteroatoms each independently selected from O, S, and N, said bicyclic moiety being optionally fused to a phenyl, or a 5- or 6-membered heterocycle containing one or more heteroatoms each independently selected from N, S, and O, optionally fused to phenyl;

Y is halo, $NO_2$, $R^6$, $SR^1$, $S(O)_b$-phenyl-$CO_2R^1$,

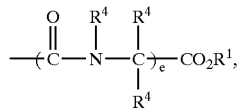

where, when the two $R^4$ groups attached to the same C are both alkyl, they optionally may be joined so that, when taken together with the C to which they are attached, they form a spiro ring of 3, 5, or 6 C atoms, or where the $R^4$ attached to N and one $R^4$ attached to the adjacent C are both alkyl, they optionally may be joined so that, taken together with the atoms to which they are attached, they form a 5- or 6-membered heterocyclic ring;

with the proviso that when e is 1, at least one $R^4$ group must be $C_1$–$C_{10}$ alkyl-phenyl or $C_1$–$C_{10}$ alkyl-pyridyl, or two $R^4$ groups must form one of said spiro or heterocyclic ring moieties, phenyl optionally fused to one or two phenyl rings, or to a 5- or 6-membered heterocycle containing one or more heteroatoms each independently selected from N, S, and O, or a 5- or 6-membered heterocycle containing one or more heteroatoms each independently selected from N, S and O, optionally fused to a phenyl ring, each cyclic moiety being optionally substituted with one or more substituents independently selected from $COR^2$, $CONR^1S(O)_2R^9$, $COCH_2SO_2$-thiazolyl optionally substituted with alkyl or amino, halo, $NO_2$, $OR^1$, $R^1$, $SR^1$, O—$C_1$–$C_6$-alkyl substituted by $C_3$–$C_6$-cycloalkyl, O-phenyl optionally substituted by $SO_2CH_3$, $SO_2NH_2$, $SO_2NR^1R^7$, $NR^1R^1$, $NR^1COC_1$–$C_6$alkyl,

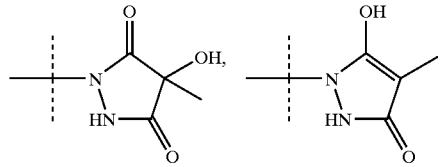

$C_1$–$C_{10}COR^2$, phenyl optionally substituted with halo, $C_1$–$C_4$ alkyl, or $C_1$–$C_4$ alkoxy, tetrazolo;

$R^7$ is phenyl or heteroaryl containing 3–6 C and 1–3 O, N, or S atoms, each optionally substituted by $C_1$–$C_4$alkyl, CN, $NO_2$, CO—$C_1$–$C_4$alkyl, $C_1$–$C_4$alkoxy, or $C_1$–$C_4$ haloalkyl,

CO—$R^8$,

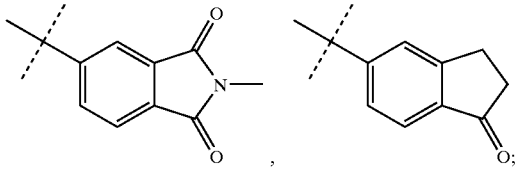

$R^8$ is $C_1$–$C_6$ alkyl optionally substituted with $C_1$–$C_4$ alkoxy, $N(CH_3)_2$, or one or two $CF_3$, $C_3$–$C_6$-cycloalkyl, phenyl optionally substituted with $C_1$–$C_4$ alkoxy, halo, or $C_1$–$C_4$ alkyl, NH-phenyl optionally substituted with $C_1$–$C_4$ alkyl, halo, $C_1$–$C_4$alkoxy, or $C_1$–$C_4$ haloalkoxy, NH-cyclohexyl;

$R^9$ is $C_3$–$C_6$ cycloalkyl, thienyl optionally substituted with $C_1$–$C_4$ alkyl or isoxazolyl, pyridyl optionally substituted with —$SO_2$—$C_1$–$C_4$alkyl, pyrazolyl optionally substituted with halo or $C_1$–$C_4$ alkyl, isoxazolyl optionally substituted with $C_1$–$C_4$ alkyl, or

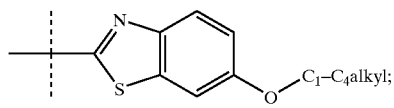

a is 0, 1, 2, 3, 4, or 5;
b is 0, 1, or 2;
d is 1, 2, or 3;
e is 1 or 2;
and pharmaceutically acceptable salts and esters thereof.

The terms identified above have the following meaning throughout:

$C_1$–$C_{10}$alkyl means straight or branched chain alkyl groups having from one to about ten carbon atoms, which may be saturated, unsaturated, or partially saturated. Such groups include methyl, ethyl, n-propyl, isopropyl, n-butyl, isobutyl, sec-butyl, tert-butyl, as well as vinyl, allyl, propynyl, butenyl, butadienyl, isopropenyl, methyleneyl, ethylenyl, propenyl, ethynyl, and the like.

$C_1$–$C_{10}$ haloalkyl means straight or branched chain alkyl groups having from about one to about ten carbon atoms where any C—C bond may be saturated or unsaturated, the alkyl groups being substituted at any available carbon atom with one or more halogen atoms, and includes such groups as trifluoromethyl, trichloromethyl, pentafluoroethyl, fluoromethyl, 6-chlorohexyl, and the like.

The term $C_1$–$C_{10}$ alkoxy means straight or branched chain alkoxy groups having from one to about ten carbon atoms where any C—C bond may be saturated or unsaturated, and includes such groups as methoxy, ethoxy, n-propoxy, isopropoxy, n-butoxy, isobutoxy, sec-butoxy, tert-butoxy, and the like.

The term $C_1$–$C_{10}$ alkylthio means straight or branched chain alkylthio groups having from one to about ten carbon atoms where any C—C bond may be saturated or unsaturated, and includes such groups as methylthio, ethylthio, n-propylthio, isopropylthio, n-butylthio, isobutylthio, sec-butylthio, tert-butylthio, and the like.

$C_3$–$C_8$ cycloalkyl means saturated mono cyclic alkyl groups of from 3 to about 8 carbon atoms, and includes such groups as cyclopropyl, cyclopentyl, cyclohexyl, and the like.

Halo includes fluoro, chloro, bromo, and iodo, unless specifically stated otherwise.

R, $R^2$, Ar, and Y each include any 5- or 6-membered saturated or unsaturated heterocyclic group having any combination of one or more N, S, or O atoms with the point of attachment being at any available position on the heterocyclic ring. Where there is more than one heteroatom in a single cyclic group, each heteroatom shall be chosen independently of any other heteroatom, in each occurrence, with the proviso that any single heterocyclic ring may not contain more than two oxygen or sulfur atoms. These moieties include such 5-membered heterocyclic groups as furyl, thienyl, pyrrolyl, oxazolyl, thiazolyl, imidazolyl, pyrazolyl, isoxazolyl, isothiazolyl, tetrahydrofuryl, dihydrofuryl, pyrrolidinyl, pyrrolinyl, dihydrothienyl, tetrahydrothienyl, dioxolyl, dithiolanyl, oxazolinyl, oxazolidinyl, isoxazolinyl, isoxazolidinyl, thiazolinyl, thiazolidinyl, isothiazolinyl, isothiazolidinyl, imidazolinyl, imidazolidinyl, pyrazolinyl, pyrazolidinyl, triazolyl, triazolinyl, triazolidinyl, oxadiazolyl, thiadiazolyl, furazanyl, tetrazolyl, and the like. It also includes such 6-membered heterocyclic rings such as pyridyl, pyrimidinyl, pyrazinyl, pyridazinyl, pyranyl, dihydropyranyl, thiopyranyl, triazinyl, dioxanyl, piperidinyl, piperazinyl, pyrazinyl, morpholinyl, and the like Ar and Y also each include phenyl fused to any 5- or 6-membered heterocyclic ring described above to form a bicyclic moiety, which may be saturated or unsaturated and may have any combination of one or more N, S, or O atoms with the point of attachment being any at available position on the phenyl ring. These include such phenyl fused 5-membered heterocyclic groups as benzofuryl, dihydrobenzofuryl, benzothienyl, dihydrobenzothienyl, indolyl, indazolyl, indolinyl, indazolinyl, benzoxazolyl, benzoxazolinyl, benzothiazolyl, benzothiazolinyl, benzimidazolyl, benzimidazolinyl, benzisoxazolyl, benzisoxazolinyl, benzothiadiazolinyl, benzisothiazolyl, benzisothiazolinyl, benzotriazolyl, benzoxadiazolyl, benzoxadiazolinyl, benzothiadiazolyl, benzopyrazolinyl, and the like. It also includes such phenyl fused 6-membered heterocyclic groups as quinolyl, isoquinolyl, quinazolinyl, quinoxalinyl, cinnolinyl, chromenyl, phthalazinyl, dihydrobenzopyranyl, benzothiopyranyl, dihydrobenzothiopyranyl, benzoxazinyl, benzodioxanyl, benzodioxenyl, and the like.

Ar also includes phenyl fused to any 5- or 6-membered heterocyclic ring to form a bicyclic moiety as described above, which is further fused on the heterocyclic ring to a second phenyl ring, forming a tricyclic system, with the point of attachment to the core structure of the compound of Formula I being at any available position of the first phenyl ring. These include such groups as carbazolyl, carbazolinyl, acridinyl, xanthenyl, phenoxathiinyl, phenoxazinyl, phenanthridinyl, dibenzofuryl, dibenzopyranyl, dibenzodioxanoyl, phenazinyl, thianthrenyl, and the like.

Ar also includes any 5- or 6-membered saturated or unsaturated heterocyclic ring having any combination of one or more N, S, or O atoms as described above, which is further fused to a phenyl ring, with the point of attachment to the core molecule of Formula I being at any available position on the heterocyclic ring. These include such phenyl-fused with 5-membered hetero-bicyclic moieties as benzofuryl, dihydrobenzofuryl, benzothienyl, dihydrobenzothienyl, indolyl, indazolyl, indolizinyl, indolinyl, indazolinyl, benzoxazolyl, benzoxazolinyl, benzothiazolyl, benzothiazolinyl, benzimidazolyl, benzimidazolinyl, benzisoxazolyl, benzisoxazolinyl, benzisothiazolyl, benzoisothiazolinyl, benzopyrazolinyl and the like. It also includes such phenyl-fused with 6-membered hetero-bicyclic groups as quinolyl, isoquinolyl, quinazolinyl, quinoxalinyl, cinnolinyl, chromenyl, phthalazinyl, dihydrobenzopyranyl, benzothiopyranyl, dihydrobenzothiopyranyl, benzoxazinyl, benzodioxanyl, benzodioxenyl, and the like.

$C_1$–$C_{10}$-alkyl-phenyl means saturated straight or branched chain alkyl groups having from one to about ten carbon atoms where the phenyl moiety is attached at any available position on the alkyl group. Examples of these moieties include benzyl, 2-phenylethyl, 3-phenylpropyl, 2-phenylpropyl, 1-methyl-2-phenylethyl, 5-phenylpentyl, 4-phenylhexyl, and the like.

$C_1$–$C_{10}$-alkyl-pyridyl means straight or branched chain saturated alkyl groups having from one to about ten carbon atoms where the pyridyl moiety is attached at any available position on the alkyl group. The pyridyl group may be attached to the alkyl group from any available position on the pyridine ring. Examples of these include pyridyl, 2-(2-pyridyl)ethyl, 3-(4-pyridyl)-propyl, 2-(3-pyridyl)-propyl, 1-methyl-2-(3-pyridyl)-ethyl, 5-(3-pyridyl)-pentyl, 4-(4-pyridyl)-hexyl, and the like.

$S(O)_b$-phenyl-$CO_2R^1$ means a phenylthio, a phenylsulfinyl, or a phenylsulfonyl group, where the $CO_2R^1$ moiety is attached at any available position on the phenyl ring.

When any moiety is described as being substituted, it can have one or more of the indicated substituents that can be located at any available position on the moiety. When there are two or more substituents on any moiety, each term shall be defined independently of any other in each occurrence. For example, $NR^1R^1$ may represent $NH_2$, $NHCH_3$, $N(CH_3)CH_2CH_2CH_3$, and the like.

Examples of the compound of Formula I, which are illustrative of the present invention but not limiting in any way, are listed in Table 1.

TABLE 1

Illustrative Examples of the Invention

| Entry No. | R | a | Ar | R³ | d | Y |
|---|---|---|---|---|---|---|
| 1 | 6-(2,5-dimethylpyrrol-1-yl) | 1 | 3-pyridyl | H | 1 | 4-(CO₂H)phenyl |
| 2 | 6-(2,5-dimethylpyrrol-1-yl) | 1 | 3-pyridyl | H | 2 | 4-(CO₂H)phenyl |
| 3 | 6-(2,5-dimethylpyrrol-1-yl) | 1 | 3-pyridyl | H | 3 | 4-(CO₂H)phenyl |
| 4 | 6-NH₂ | 1 | 3-pyridyl | H | 1 | I |
| 5 | 6-NH₂ | 1 | 3-pyridyl | H | 1 | Br |
| 6 | 6-NH₂ | 1 | 3-pyridyl | H | 1 | —NO₂ |

TABLE 1-continued

Illustrative Examples of the Invention $$(R)_a-Ar-\overset{OH}{CH}-CH_2-\underset{(CH_2)_d}{\overset{R^3}{N}}-chroman-6-Y$$

(I)

| Entry No. | R | a | Ar | R³ | d | Y |
|---|---|---|---|---|---|---|
| 7 | 6-NH₂ | 1 | 3-pyridyl | H | 1 | —≡—t-Bu |
| 8 | 6-NH₂ | 1 | 3-pyridyl | H | 1 | —≡—Ph |
| 9 | 6-NH₂ | 1 | 3-pyridyl | H | 1 | —S—CH₂—CO₃Et |
| 10 | 6-NH₂ | 1 | 3-pyridyl | H | 2 | —S—CH₂—CO₃H |
| 11 | 6-NH₂ | 1 | 3-pyridyl | H | 1 | —CH(SCH₃)—CO₂Et |
| 12 | 6-NH₂ | 1 | 3-pyridyl | H | 2 | —CH(SCH₃)—CO₂H |
| 13 | 6-NH₂ | 1 | 3-pyridyl | H | 1 | —CH₂—C₆H₄—CO₂H |
| 14 | 6-NH₂ | 1 | 3-pyridyl | H | 2 | —CH₂—C₆H₄—CO₂H |

TABLE 1-continued
Illustrative Examples of the Invention
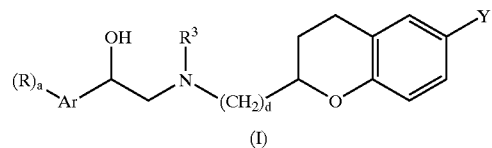
(I)
| Entry No. | R | a | Ar | R³ | d | Y |
|---|---|---|---|---|---|---|
| 15 | 6-NH₂ | 1 | 3-pyridyl | H | 3 | —CH₂—C₆H₄—CO₂H (4-) |
| 16 | — | 0 | Ph | H | 1 | 3-(methylthio)benzoic acid, —S— linked |
| 17 | — | 0 | Ph | H | 1 | 3-(methylsulfonyl)benzoic acid |
| 18 | — | 0 | 3-pyridyl | H | 1 | N-acetyl-L-phenylalanine |
| 19 | — | 0 | 3-pyridyl | H | 2 | N-acetyl-L-phenylalanine (homo) |
| 20 | 6-NH₂ | 1 | 3-pyridyl | H | 1 | N-acetyl-N-(pyridin-2-ylmethyl)glycine |
| 21 | — | 0 | 3-pyridyl | H | 1 | N-acetyl-L-proline |

TABLE 1-continued
Illustrative Examples of the Invention
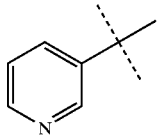
(I)
| Entry No. | R | a | Ar | R³ | d | Y |
|---|---|---|---|---|---|---|
| 22 | — | 0 | 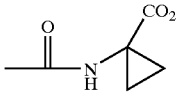 | H | 1 | 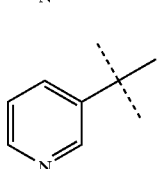 |
| 23 | — | 0 | 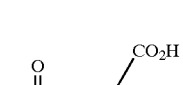 | H | 2 | 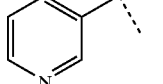 |
| 24 | — | 0 | 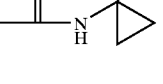 | H | 1 | 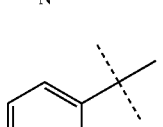 |
| 25 | — | 0 | 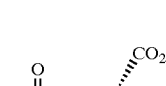 | H | 1 | 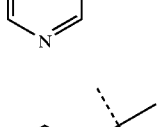 |
| 26 | — | 0 | Ph | H | 1 | 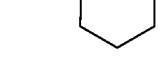 |
| 27 | — | 0 | 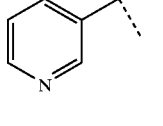 | H | 3 | 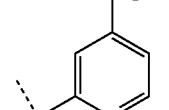 |
| 28 | — | 0 | 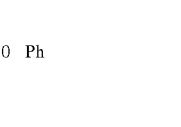 | H | 1 | 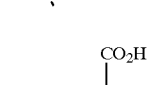 |

TABLE 1-continued
Illustrative Examples of the Invention
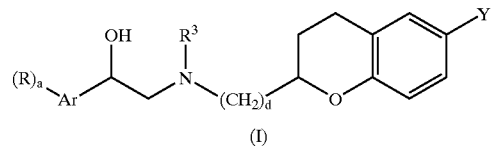
(I)
| Entry No. | R | a | Ar | R³ | d | Y |
|---|---|---|---|---|---|---|
| 29 | — | 0 | 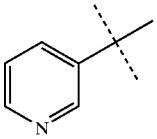 | H | 1 | 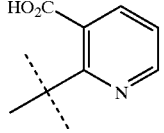 |
| 30 | — | 0 | 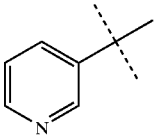 | H | 1 | 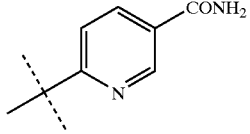 |
| 31 | — | 0 | 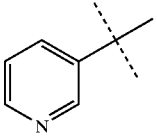 | H | 1 | 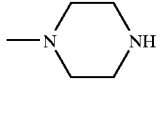 |
| 32 | — | 0 | 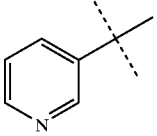 | H | 1 | 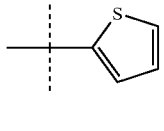 |
| 33 | — | 0 | 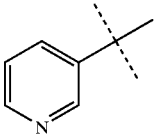 | H | 1 | 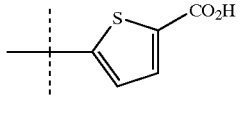 |
| 34 | — | 0 | 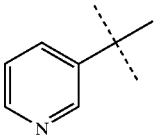 | H | 1 | 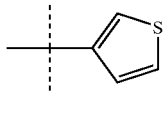 |
| 35 | — | 0 | 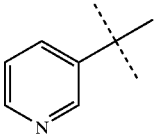 | H | 1 | 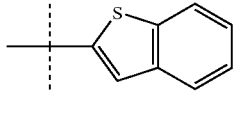 |
| 36 | — | 0 | 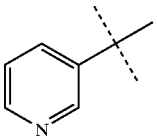 | H | 1 | 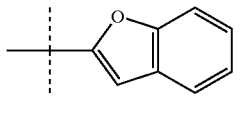 |

TABLE 1-continued

Illustrative Examples of the Invention

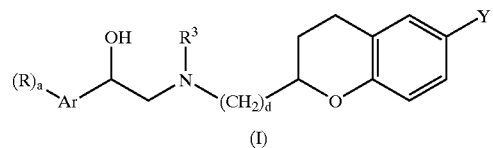

(I)

| Entry No. | R | a | Ar | R³ | d | Y |
|---|---|---|---|---|---|---|
| 37 | — | 0 | 3-pyridyl | H | 1 | 5-(ethoxycarbonyl)furan-2-carboxylic acid (ethyl 5-substituted furan-2-carboxylate with CO₂H) |
| 38 | — | 0 | 3-pyridyl | H | 1 | 2-naphthyl |
| 39 | — | 0 | 3-pyridyl | H | 1 | 1-naphthyl |
| 40 | — | 0 | 3-pyridyl | H | 1 | benzo[1,3]dioxol-5-yl |
| 41 | — | 0 | 3-pyridyl | H | 1 | 1-methyl-2-(carboxy)-1H-indol-3-yl |
| 42 | — | 0 | 3-pyridyl | H | 1 | 2-substituted-5-phenyloxazole-4-carboxylic acid |
| 43 | — | 0 | 3-pyridyl | H | 1 | ethyl 2-substituted-5-phenyloxazole-4-carboxylate |

TABLE 1-continued
Illustrative Examples of the Invention
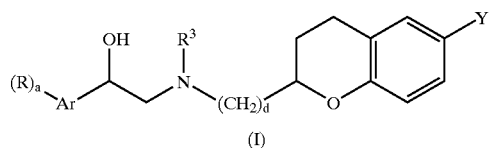
(I)
| Entry No. | R | a | Ar | R³ | d | Y |
|---|---|---|---|---|---|---|
| 44 | — | 0 | 3-pyridyl | H | 1 | 2-methyl-1-methyl-5-phenyl-imidazole-4-CO₂Et |
| 45 | — | 0 | 3-pyridyl | H | 1 | 2-methyl-1-methyl-5-phenyl-imidazole-4-CO₂H |
| 46 | — | 0 | 3-pyridyl | H | 1 | 2-methyl-4-phenyl-thiazole-5-CO₂Et |
| 47 | — | 0 | 3-pyridyl | H | 1 | 2-methyl-4-phenyl-thiazole-5-CO₂H |
| 48 | — | 0 | Ph | H | 1 | 4-CO₂H-phenyl |
| 49 | — | 0 | Ph | H | 2 | 4-CO₂H-phenyl |
| 50 | — | 0 | Ph | H | 3 | 4-CO₂H-phenyl |
| 51 | 6-NH₂ | 1 | 3-pyridyl | H | 1 | 4-CO₂H-phenyl |
| 52 | 6-NH₂ | 1 | 3-pyridyl | H | 2 | 4-CO₂H-phenyl |

TABLE 1-continued

Illustrative Examples of the Invention $$(R)_a\text{-Ar}\overset{OH}{-}\overset{|}{CH}-CH_2-\overset{R^3}{\underset{|}{N}}-(CH_2)_d-\text{chroman-Y}$$

(I)

| Entry No. | R | a | Ar | R³ | d | Y |
|---|---|---|---|---|---|---|
| 53 | 6-NH₂ | 1 | pyridin-3-yl | H | 3 | 4-CO₂H-phenyl |
| 54 | — | 0 | pyridin-3-yl | H | 1 | 4-Cl-phenyl |
| 55 | — | 0 | pyridin-3-yl | H | 1 | 4-F-phenyl |
| 56 | — | 0 | pyridin-3-yl | H | 1 | 4-I-phenyl |
| 57 | — | 0 | pyridin-3-yl | H | 1 | 4-Br-phenyl |
| 58 | — | 0 | pyridin-3-yl | H | 1 | 2-CF₃-phenyl |
| 59 | — | 0 | pyridin-3-yl | H | 1 | 3-NO₂-phenyl |
| 60 | — | 0 | pyridin-3-yl | H | 1 | 3-NH₂-phenyl |

TABLE 1-continued
Illustrative Examples of the Invention
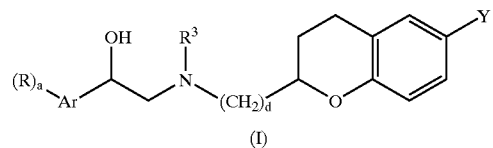
(I)
| Entry No. | R | a | Ar | R³ | d | Y |
|---|---|---|---|---|---|---|
| 61 | — | 0 | 3-pyridyl | H | 1 | 3-Cl-phenyl |
| 62 | — | 0 | 3-pyridyl | H | 1 | 3-OMe-phenyl |
| 63 | — | 0 | 3-pyridyl | H | 1 | 3-Br-phenyl |
| 64 | — | 0 | 3-pyridyl | H | 1 | 3-OEt-phenyl |
| 65 | — | 0 | 3-pyridyl | H | 1 | 2-Me-phenyl |
| 66 | — | 0 | 3-pyridyl | H | 1 | 2-Cl-phenyl |
| 67 | — | 0 | 3-pyridyl | H | 1 | 4-CF₃-phenyl |
| 68 | — | 0 | 3-pyridyl | H | 1 | 4-Me-phenyl |

TABLE 1-continued
Illustrative Examples of the Invention
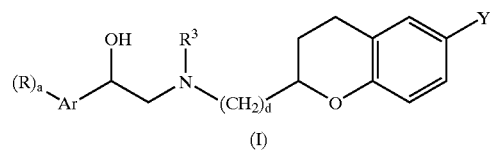
(I)
| Entry No. | R | a | Ar | R³ | d | Y |
|---|---|---|---|---|---|---|
| 69 | — | 0 | 3-pyridyl | H | 1 | phenyl |
| 70 | — | 0 | 3-pyridyl | H | 1 | 4-SMe-phenyl |
| 71 | — | 0 | 3-pyridyl | H | 1 | 2,4-diCl-phenyl |
| 72 | — | 0 | 3-pyridyl | H | 1 | 3-Cl-4-F-phenyl |
| 73 | — | 0 | 3-pyridyl | H | 1 | 3,4,5-triOMe-phenyl |
| 74 | — | 0 | 3-pyridyl | H | 1 | 3,5-di(CF₃)-phenyl |
| 75 | — | 0 | 3-pyridyl | H | 1 | 3,5-diCl-phenyl |
| 76 | — | 0 | 3-pyridyl | H | 1 | 2-HO-5-Br-phenyl |

TABLE 1-continued

Illustrative Examples of the Invention $$\text{(R)}_a\text{Ar}-\overset{OH}{\underset{}{CH}}-CH_2-\underset{R^3}{\underset{|}{N}}-(CH_2)_d-\text{chroman-O-Ar-Y}$$

(I)

| Entry No. | R | a | Ar | R³ | d | Y |
|---|---|---|---|---|---|---|
| 77 | — | 0 | 3-pyridyl | H | 1 | 4-Me, 2-NO₂, phenyl (attached at 5-position) |
| 78 | — | 0 | 3-pyridyl | H | 1 | phenanthren-9-yl |
| 79 | — | 0 | 3-pyridyl | H | 1 | 4-(1H-tetrazol-5-yl)phenyl |
| 80 | — | 0 | 3-pyridyl | H | 2 | 4-(1H-tetrazol-5-yl)phenyl |
| 81 | — | 0 | 3-pyridyl | H | 3 | 4-(1H-tetrazol-5-yl)phenyl |
| 82 | — | 0 | 3-pyridyl | —CO₂-t-Bu | 1 | 4-(1H-tetrazol-5-yl)phenyl |
| 83 | — | 0 | 3-pyridyl | H | 1 | 4-CO₂Me-phenyl |
| 84 | 6-NH₂ | 1 | 3-pyridyl | H | 1 | 4-CO₂Me-phenyl |

TABLE 1-continued
Illustrative Examples of the Invention
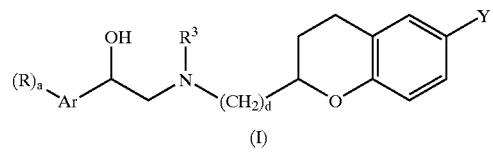
(I)
| Entry No. | R | a | Ar | R³ | d | Y |
|---|---|---|---|---|---|---|
| 85 | — | 0 | Ph | h | 1 | —⟨C₆H₄⟩—CO₂Me |
| 86 | — | 0 | 3-pyridyl | —CO₂-t-Bu | 1 | —⟨C₆H₄⟩—CO₂Me |
| 87 | — | 0 | 3-pyridyl | H | 1 | —⟨C₆H₄⟩—CH... CO₂H |
| 88 | — | 0 | 3-pyridyl | H | 1 | —⟨C₆H₄⟩—C(=O)NH₂ |
| 89 | — | 0 | 3-pyridyl | H | 1 | —⟨C₆H₄⟩—C(=O)N(Et)₂ |
| 90 | — | 0 | 3-pyridyl | H | 1 | —⟨C₆H₄⟩—C(=O)NH-i-Bu |
| 91 | — | 0 | 3-pyridyl | H | 1 | —⟨C₆H₄⟩—C(=O)NHPh |
| 92 | — | 0 | 3-pyridyl | H | 1 | —⟨C₆H₄⟩—C(=O)NHMe |
| 93 | — | 0 | 3-pyridyl | H | 1 | —⟨C₆H₄⟩—C(=O)NHEt |

TABLE 1-continued
Illustrative Examples of the Invention
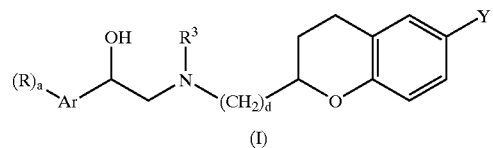
(I)
| Entry No. | R | a | Ar | R³ | d | Y |
|---|---|---|---|---|---|---|
| 94 | — | 0 | 3-pyridyl | H | 1 | 4-(C(O)NH-t-Bu)phenyl |
| 95 | — | 0 | 3-pyridyl | H | 1 | 4-(C(O)NHCH₂Ph)phenyl |
| 96 | — | 0 | 3-pyridyl | H | 1 | 4-(pyrrolidinylcarbonyl)phenyl |
| 97 | — | 0 | 3-pyridyl | H | 1 | 4-(piperidinylcarbonyl)phenyl |
| 98 | — | 0 | 3-pyridyl | H | 1 | 4-(morpholinylcarbonyl)phenyl |
| 99 | — | 0 | 3-pyridyl | H | 1 | 4-(piperazinylcarbonyl)phenyl |
| 100 | — | 0 | 3-pyridyl | H | 1 | 4-(4-methylpiperazinylcarbonyl)phenyl |
| 101 | — | 0 | 3-pyridyl | H | 1 | biphenyl |

TABLE 1-continued
Illustrative Examples of the Invention
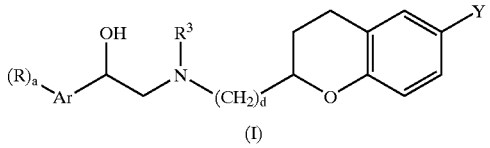
| Entry No. | R | a | Ar | R³ | d | Y |
|---|---|---|---|---|---|---|
| 102 | — | 0 | 3-pyridyl | H | 1 | 4-cyclopropylphenyl |
| 103 | — | 0 | 3-pyridyl | H | 1 | 4-cyclohexylphenyl |
| 104 | — | 0 | 3-pyridyl | H | 1 | 3-cyclopentylphenyl |
| 105 | — | 0 | 3-pyridyl | H | 1 | 4-(methoxymethyl)phenyl |
| 106 | — | 0 | 3-pyridyl | H | 1 | 4-(propoxymethyl)phenyl |
| 107 | 4-OH | 1 | Ph | H | 1 | 4-CO₂H-phenyl |
| 108 | 6-OH | 1 | 3-pyridyl | H | 1 | 4-CO₂H-phenyl |
| 109 | 4-CN | 1 | Ph | H | 1 | 4-CO₂H-phenyl |
| 110 | 2-Me | 1 | Ph | H | 1 | 4-CO₂H-phenyl |

TABLE 1-continued
Illustrative Examples of the Invention
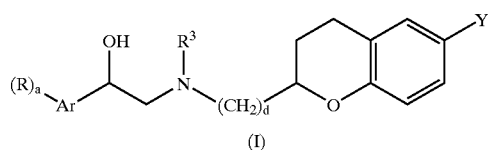
(I)
| Entry No. | R | a | Ar | R³ | d | Y |
|---|---|---|---|---|---|---|
| 111 | 3-Et | 1 | Ph | H | 1 | 4-CO₂H-C₆H₄- |
| 112 | 3-CF₃ | 1 | Ph | H | 1 | 4-CO₂H-C₆H₄- |
| 113 | 3-NH₂ | 1 | Ph | H | 1 | 4-CO₂H-C₆H₄- |
| 114 | 3-NH-Me | 1 | Ph | H | 1 | 4-CO₂H-C₆H₄- |
| 115 | 3-N(Et)₂ | 1 | Ph | H | 1 | 4-CO₂H-C₆H₄- |
| 116 | 4-OMe | 1 | Ph | H | 1 | 4-CO₂H-C₆H₄- |
| 117 | 2,3,5,6-tetra-Cl | 4 | Ph | H | 1 | 4-CO₂H-C₆H₄- |
| 118 | 4-Oet | 1 | Ph | H | 1 | 4-CO₂H-C₆H₄- |
| 119 | 4-O-cyc-Pr | 1 | Ph | H | 1 | 4-CO₂H-C₆H₄- |
| 120 | 2,3,4,5,6-penta-F | 5 | Ph | H | 1 | 4-CO₂H-C₆H₄- |
| 121 | 2,4-di-Cl | 2 | Ph | H | 1 | 4-CO₂H-C₆H₄- |
| 122 | 2,4-di-Me | 2 | Ph | H | 1 | 4-CO₂H-C₆H₄- |

TABLE 1-continued
Illustrative Examples of the Invention
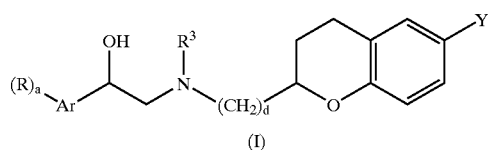
(I)
| Entry No. | R | a | Ar | R³ | d | Y |
|---|---|---|---|---|---|---|
| 123 | 2,4-di-Cl | 2 | Ph | —CO₂-t-Bu | 1 | 4-C₆H₄-CO₂H |
| 124 | 2,4,5-tri-Cl | 3 | Ph | H | 1 | 4-C₆H₄-CO₂H |
| 125 | 3-CONH-i-Bu | 1 | Ph | H | 1 | 4-C₆H₄-CO₂H |
| 126 | 2,4-di-Me-6-Cl | 3 | Ph | H | 1 | 4-C₆H₄-CO₂H |
| 127 | 4-(1H-tetrazol-5-yl) | 1 | Ph | H | 1 | 4-C₆H₄-CO₂H |
| 128 | 3-NO₂ | 1 | Ph | H | 1 | 4-C₆H₄-CO₂H |
| 129 | 2-Cl | 1 | Ph | H | 1 | 4-C₆H₄-CO₂H |
| 130 | 4-SMe | 1 | Ph | H | 1 | 4-C₆H₄-CO₂H |
| 131 | 3-SO₂Me | 1 | Ph | H | 1 | 4-C₆H₄-CO₂H |
| 132 | 4-O-C(=O)Me | 1 | Ph | H | 1 | 4-C₆H₄-CO₂H |
| 133 | 4-C(=O)Me | 1 | Ph | H | 1 | 4-C₆H₄-CO₂H |
| 134 | 3-CO₂H | 1 | Ph | H | 1 | 4-C₆H₄-CO₂H |

TABLE 1-continued
Illustrative Examples of the Invention
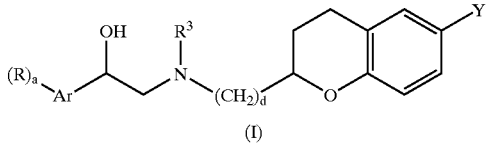
(I)
| Entry No. | R | a | Ar | R³ | d | Y |
|---|---|---|---|---|---|---|
| 135 | 3-NH—SO₂Me | 1 | Ph | H | 1 | 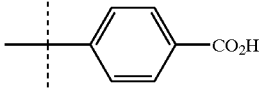 |
| 136 | 4-NH—C(=O)Me | 1 | Ph | H | 1 | 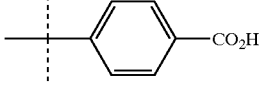 |
| 137 | — | 0 | 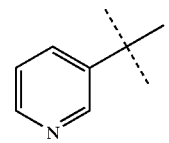 | H | 1 | 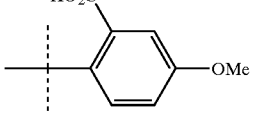 |
| 138 | — | 0 | 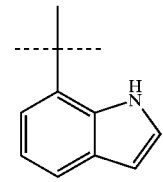 | H | 1 | 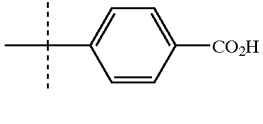 |
| 139 | — | 0 | 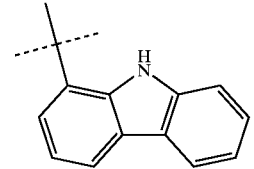 | H | 1 | 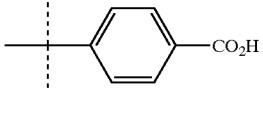 |
| 140 | 2-Me | 1 | 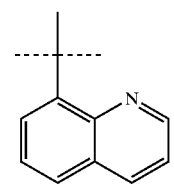 | H | 1 | 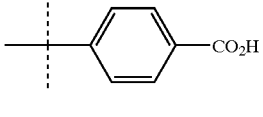 |
| 141 | — | 0 | 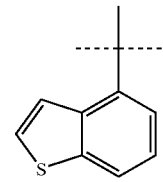 | H | 1 | 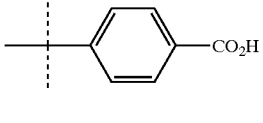 |
| 142 | — | 0 | 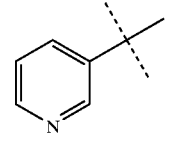 | H | 1 | 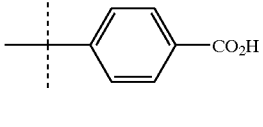 |

TABLE 1-continued
Illustrative Examples of the Invention
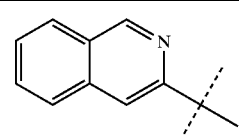
(I)
| Entry No. | R | a | Ar | R³ | d | Y |
|---|---|---|---|---|---|---|
| 143 | — | 0 | 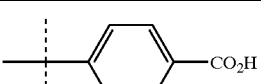 | H | 1 | 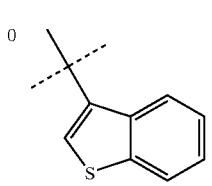 -CO₂H |
| 144 | — | 0 | 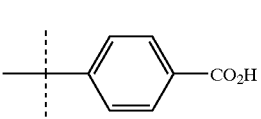 | H | 1 | -CO₂H |
| 145 | — | 0 | 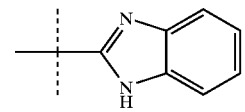 | H | 1 | -CO₂H |
| 146 | — | 0 | Ph | CO₂-t-Bu | 1 | -CO₂H |
| 147 | 6-NH₂ | 1 |  | CO₂Me | 1 | -CO₂H |
| 148 | — | 0 | Ph | CONH₂ | 1 | -CO₂H |
| 149 | — | 0 | Ph | Me | 1 | -CO₂H |
| 150 | 6-NH₂ | 1 | 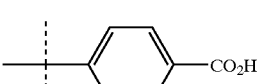 | Et | 1 | -CO₂H |
| 151 | — | 0 | 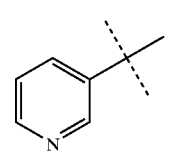 | COMe | 1 | -CO₂H |

TABLE 1-continued
Illustrative Examples of the Invention
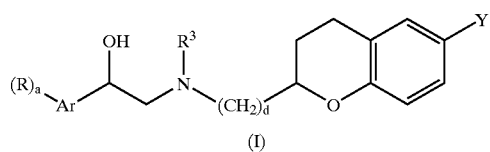
(I)
| Entry No. | R | a | Ar | R³ | d | Y |
|---|---|---|---|---|---|---|
| 152 | 6-NH₂ | 1 | 3-pyridyl | H | 1 | 3-(COOH)phenyl |
| 153 | — | 0 | 3-pyridyl | H | 1 | 6-COOH-naphth-2-yl |
| 154 | — | 0 | 3-pyridyl | H | 1 | 7-COOH-2,3-dihydrobenzofuran-5-yl |
| 155 | — | 0 | 3-pyridyl | H | 1 | 6-COOH-naphth-2-yl |
| 156 | — | 0 | 3-pyridyl | H | 1 | 2-COOH-quinolin-8-yl |
| 157 | — | 0 | 3-pyridyl | H | 1 | 2-NO₂-4-Me-phenyl |
| 158 | — | 0 | 3-pyridyl | H | 1 | 1,5-diMe-3-COOH-pyrazol-4-yl |
| 159 | — | 0 | 3-pyridyl | H | 1 | 4-COOMe-thien-2-yl |

TABLE 1-continued
Illustrative Examples of the Invention
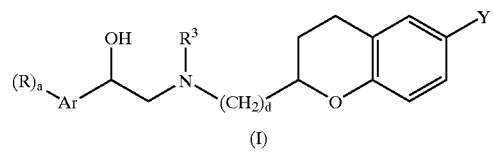
(I)
| Entry No. | R | a | Ar | R³ | d | Y |
|---|---|---|---|---|---|---|
| 160 | — | 0 | 3-pyridyl | H | 1 | 4-(thiophene-2-carboxylic acid)yl |
| 161 | — | 0 | 3-pyridyl | H | 1 | 5-(furan-2-carboxylic acid)yl |
| 162 | — | 0 | 3-pyridyl | H | 2 | 2-(5-phenyl-4-ethoxycarbonyl-oxazol)yl |
| 163 | — | 0 | 3-pyridyl | H | 2 | 2-(4-phenyl-5-carboxy-thiazol)yl |
| 164 | — | 0 | 3-pyridyl | H | 1 | 6-(pyridine-3-carboxylic acid)yl |
| 165 | — | 0 | 3-pyridyl | H | 1 | 2-(benzothiophene-5-carboxylic acid)yl |
| 166 | — | 0 | 3-pyridyl | H | 2 | 3-(1-methyl-2-carboxy-indol)yl |

TABLE 1-continued

Illustrative Examples of the Invention

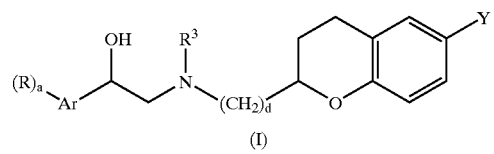

(I)

| Entry No. | R | a | Ar | R³ | d | Y |
|---|---|---|---|---|---|---|
| 167 | — | 0 | 3-pyridyl | H | 1 | 2-substituted benzofuran-5-COOH |
| 168 | — | 0 | 3-pyridyl | H | 1 | -C(O)NH-CH(Me)-C(O)NH-CH2-COOH |
| 169 | — | 0 | 3-pyridyl | H | 1 | -C(O)NH-CH(CH2Ph)-C(O)NH-CH(iPr)-COOH |
| 170 | — | 0 | 3-pyridyl | H | 1 | -C(O)N(Me)-CH2-C(O)NH-C(cyclopropyl)-COOH |
| 171 | — | 0 | 3-pyridyl | H | 1 | 2-Me-4-substituted-benzoic acid |
| 172 | — | 0 | 3-pyridyl | H | 1 | 2-F-4-substituted-benzoic acid |
| 173 | — | 0 | 3-pyridyl | H | 1 | 3-substituted-benzamide (CONH2) |
| 174 | — | 0 | 3-pyridyl | H | 1 | 2-(1H-tetrazol-5-yl)phenyl |

TABLE 1-continued
Illustrative Examples of the Invention
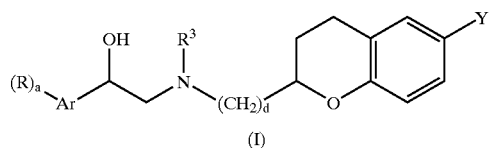
(I)
| Entry No. | R | a | Ar | R³ | d | Y |
|---|---|---|---|---|---|---|
| 175 | — | 0 | 3-pyridyl | H | 2 | 4-(1H-tetrazol-5-yl)phenyl |
| 176 | 2-oxo-3-CH₃— | 2 | 3-pyridyl | H | 1 | 4-CO₂H-phenyl |
| 177 | — | 0 | 2-pyrazinyl | H | 1 | 4-CO₂H-phenyl |
| 178 | 3,5-Cl₂— | 2 | 2-pyrimidinyl | H | 1 | 4-CO₂H-phenyl |
| 179 | 4-Ph | 1 | Ph | H | 1 | 4-CO₂H-phenyl |
| 180 | 4-Cl (3-Cl phenyl) | 1 | Ph | H | 1 | 4-CO₂H-phenyl |
| 181 | 4-H₃C-phenyl | 1 | Ph | H | 1 | 4-CO₂H-2-pyridyl |
| 182 | 4-F₃C-phenyl | 1 | Ph | H | 1 | 4-CO₂H-phenyl |
| 183 | 4-Br | 1 | Ph | H | 1 | 4-CO₂H-phenyl |
| 184 | 3-I | 1 | Ph | H | 1 | 4-CO₂H-phenyl |

TABLE 1-continued

Illustrative Examples of the Invention

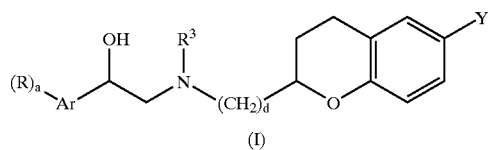

(I)

| Entry No. | R | a | Ar | R³ | d | Y |
|---|---|---|---|---|---|---|
| 185 | 3-CF₃CF₂— | 1 | Ph | H | 1 | -C₆H₄-(1H-tetrazol-5-yl) |
| 186 | 4-CH₂=CHCH₂— | 1 | Ph | H | 1 | -C₆H₄-CO₂H |
| 187 | 4-t-Bu- | 1 | Ph | H | 1 | -C₆H₄-CO₂H |
| 188 | 4-n-hexyl- | 1 | Ph | H | 1 | -C₆H₄-CO₂H |
| 189 | 4-n-docecyl- | 1 | Ph | H | 1 | -C₆H₄-(1H-tetrazol-5-yl) |
| 190 | 2-CF₃(CH₂)₃— | 1 | Ph | H | 1 | -C₆H₄-CO₂H |
| 191 | 4-(6-methylpyridin-3-yl) | 1 | Ph | H | 1 | -C₆H₄-CO₂H |
| 192 | 4-(thiophen-2-yl) | 1 | Ph | H | 1 | -C₆H₄-CO₂H |
| 193 | 3-(tetrahydrofuran-2-yl) | 1 | Ph | H | 1 | 2-pyridinyl-4-CO₂H |
| 194 | 4-(1-methylimidazol-2-yl) | 1 | Ph | H | 1 | -C₆H₄-CO₂H |
| 195 | 4-(4,5-dimethylthiazol-2-yl) | 1 | Ph | H | 1 | -C₆H₄-CO₂H |

TABLE 1-continued

Illustrative Examples of the Invention

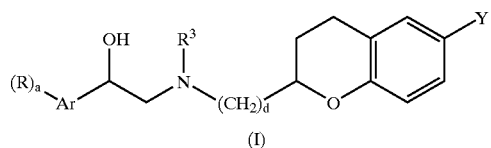

(I)

| Entry No. | R | a | Ar | R³ | d | Y |
|---|---|---|---|---|---|---|
| 196 | 3-oxazol-2-yl | 1 | Ph | H | 1 | 4-C₆H₄-CO₂H |
| 197 | 4-CH₃OCH₂CH₂N(Me)- | 1 | Ph | H | 1 | 4-C₆H₄-CO₂H |
| 198 | 3-Ph-NH— | 1 | Ph | H | 1 | 4-C₆H₄-CO₂H |
| 199 | 2-cyclopropyl-NH— | 1 | Ph | H | 1 | 4-C₆H₄-CO₂Me |
| 200 | 4-(3-Cl-C₆H₄)-NH— | 1 | Ph | H | 1 | 4-C₆H₄-CO₂H |
| 201 | — | 0 | tetrahydrofuran-2-yl | H | 1 | 4-C₆H₄-CO₂Me |
| 202 | — | 0 | tetrahydrothiophen-2-yl | H | 1 | 4-C₆H₄-CO₂H |
| 203 | — | 0 | furan-2-yl | H | 1 | —CH₂-C₆H₄-CO₂H |
| 204 | — | 0 | thiophen-2-yl | H | 1 | 2-pyridyl-4-CO₂H |
| 205 | — | 0 | thiophen-2-yl | H | 1 | 4-C₆H₄-CO₂H |
| 206 | — | 0 | thiophen-2-yl | H | 1 | 4-C₆H₄-CO₂H |

TABLE 1-continued
Illustrative Examples of the Invention
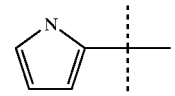
(I)
| Entry No. | R | a | Ar | R³ | d | Y |
|---|---|---|---|---|---|---|
| 207 | 2-Me | 1 | 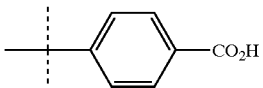 | H | 1 | 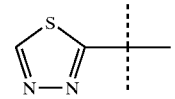 |
| 208 | — | 0 | 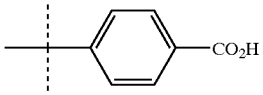 | H | 1 | 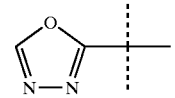 |
| 209 | — | 0 | 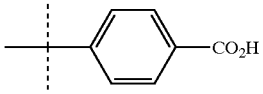 | H | 1 | 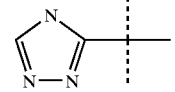 |
| 210 | 2-Me | 1 | 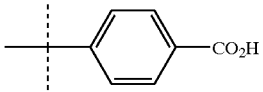 | H | 1 | 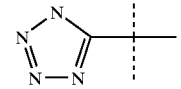 |
| 211 | 2-Me- | 1 | 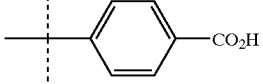 | H | 1 | 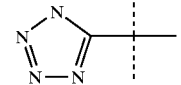 |
| 212 | 2-Me- | 1 | 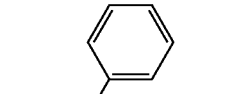 | H | 1 | 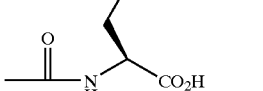 |
| 213 | 2-Me | 1 | 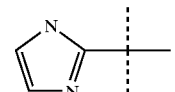 | H | 1 | 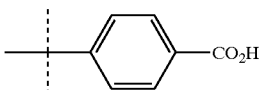 |
| 214 | — | 0 | 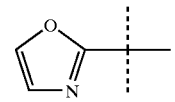 | H | 1 | 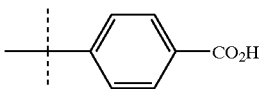 |
| 215 | — | 0 | 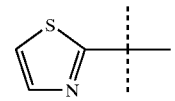 | H | 1 | 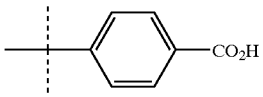 |
| 216 | — | 0 | 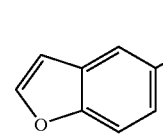 | H | 1 | 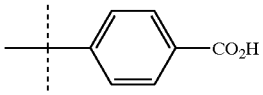 |

TABLE 1-continued
Illustrative Examples of the Invention
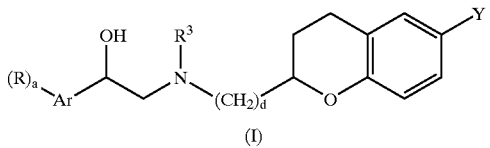
(I)
| Entry No. | R | a | Ar | R³ | d | Y |
|---|---|---|---|---|---|---|
| 217 | — | 0 | 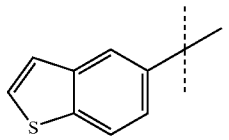 | H | 1 | 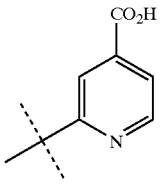 |
| 218 | — | 0 | 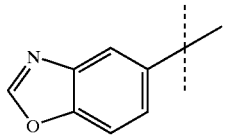 | H | 1 | 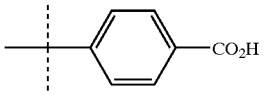 |
| 219 | 5-Me | 1 | 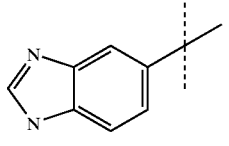 | H | 1 | 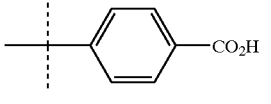 |
| 220 | — | 0 | 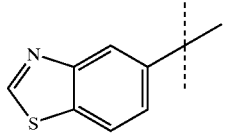 | H | 1 | 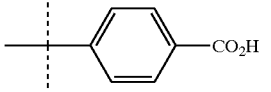 |
| 221 | — | 0 | 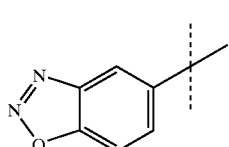 | H | 1 | 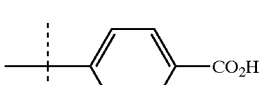 |
| 222 | — | 0 | 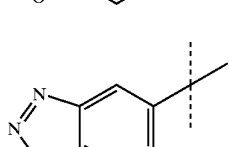 | H | 1 | 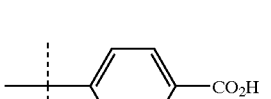 |
| 223 | 5-Me- | 1 | 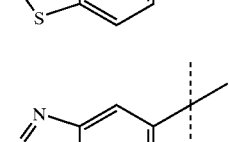 | H | 1 |  |
| 224 | 5-Me- | 1 | 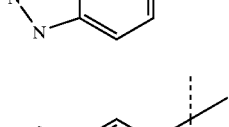 | H | 1 |  |

TABLE 1-continued
Illustrative Examples of the Invention
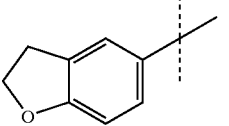
| Entry No. | R | a | Ar | R³ | d | Y |
|---|---|---|---|---|---|---|
| 225 | — | 0 |  | H | 1 | 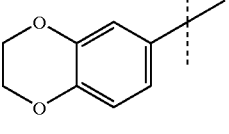 |
| 226 | — | 0 |  | H | 1 | 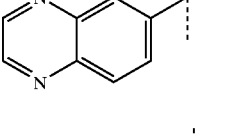 |
| 227 | — | 0 |  | H | 1 | 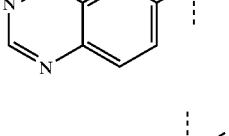 |
| 228 | — | 0 |  | H | 1 | 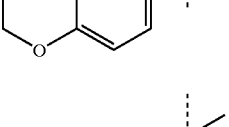 |
| 229 | — | 0 |  | H | 1 | 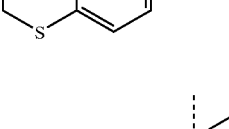 |
| 230 | — | 0 |  | H | 1 | 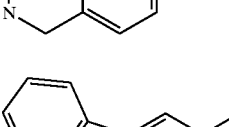 |
| 231 | 5-Me | 1 |  | H | 1 |  |
| 232 | — | 0 |  | H | 1 |  |

TABLE 1-continued

Illustrative Examples of the Invention

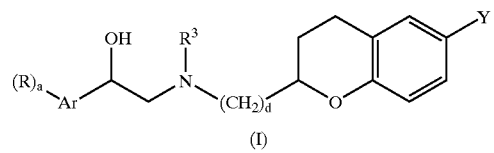

(I)

| Entry No. | R | a | Ar | R³ | d | Y |
|---|---|---|---|---|---|---|
| 233 | — | 0 | dibenzofuran-2-yl | H | 1 | 1-(acetamido)cyclopropane-CO₂H |
| 234 | — | 0 | xanthene-2-yl | H | 1 | (2S)-1-acetylpiperidine-2-CO₂H |
| 235 | — | 0 | acridin-2-yl | H | 1 | 2-yl-1-methyl-5-phenyl-imidazole-4-CO₂Et |
| 236 | — | 0 | phenazin-2-yl | H | 1 | 4-C₆H₄-CO₂H |
| 237 | — | 0 | phenanthridin-2-yl | H | 1 | 2-yl-5-phenyl-oxazole-4-CO₂H |
| 238 | — | 0 | benzofuran-2-yl | H | 1 | 4-C₆H₄-CO₂H |
| 239 | — | 0 | benzoxazol-2-yl | H | 1 | 4-C₆H₄-CO₂H |
| 240 | H | 0 | benzothiazol-2-yl | H | 1 | 4-C₆H₄-CO₂H |
| 241 | 3-Me | 1 | indazol-3-yl | H | 1 | 4-C₆H₄-CO₂H |

TABLE 1-continued
Illustrative Examples of the Invention
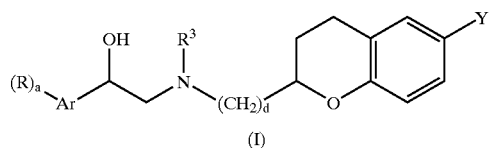
(I)
| Entry No. | R | a | Ar | R³ | d | Y |
|---|---|---|---|---|---|---|
| 242 | — | 0 | 2,3-dihydrobenzofuran-3-yl | H | 1 | 4-CO₂H-phenyl |
| 243 | — | 0 | tetrahydrofuran-3-yl | H | 1 | 4-CO₂H-phenyl |
| 244 | — | 0 | tetrahydrothiophen-3-yl | H | 1 | 4-CO₂H-phenyl |
| 245 | 3-Me | 1 | pyrrolidin-3-yl | H | 1 | 4-CO₂H-phenyl |
| 246 | — | 0 | 1,4-dioxan-2-yl | H | 1 | 4-CO₂H-phenyl |
| 247 | 3-Me | 1 | morpholin-2-yl | H | 1 | 4-CO₂H-phenyl |
| 248 | 3-Me | 1 | 1,4-oxathian-2-yl | H | 1 | 4-CO₂H-phenyl |
| 249 | 6-NH₂ | 1 | pyridin-3-yl | H | 1 | 2-pyridyl-4-CO₂H |

TABLE 1-continued
Illustrative Examples of the Invention
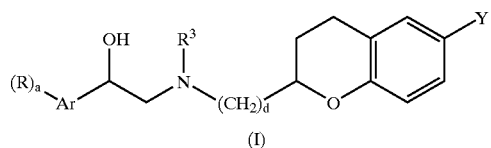
(I)
| Entry No. | R | a | Ar | R³ | d | Y |
|---|---|---|---|---|---|---|
| 250 | 6-NH₂ | 1 | 3-pyridyl | H | 1 | 2-CO₂H-phenyl |
| 251 | 6-NH₂ | 1 | 3-pyridyl | H | 2 | 2-(4-CO₂H)pyridyl |
| 252 | 2-NH₂ | 1 | 4-pyridyl | H | 1 | 2-CO₂H-phenyl |
| 253 | 2-NH₂ | 1 | 4-pyridyl | H | 1 | 4-CO₂H-phenyl |
| 254 | 2-NH₂ | 1 | 4-pyridyl | H | 1 | 2-(4-CO₂H)pyridyl |
| 255 | 2-NH₂ | 1 | 4-pyridyl | H | 1 | 2-CO₂H-phenyl |
| 256 | 2-NH₂ | 1 | 4-pyridyl | H | 2 | 4-CO₂H-phenyl |
| 257 | 2-NH₂ | 1 | 4-pyridyl | H | 2 | 2-(4-CO₂H)pyridyl |

TABLE 1-continued
Illustrative Examples of the Invention
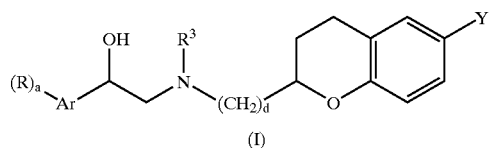
(I)
| Entry No. | R | a | Ar | R³ | d | Y |
|---|---|---|---|---|---|---|
| 258 | 4-NH₂ | 1 | 2-pyridyl | H | 1 | 4-CO₂H-phenyl |
| 259 | 4-NH₂ | 1 | 2-pyridyl | H | 1 | 2-(4-CO₂H)-pyridyl |
| 260 | 4-NH₂ | 1 | 2-pyridyl | H | 1 | 2-CO₂H-phenyl |
| 261 | 4-NH₂ | 1 | 2-pyridyl | H | 2 | 4-CO₂H-phenyl |
| 262 | 4-NH₂ | 1 | 2-pyridyl | H | 2 | 2-(4-CO₂H)-pyridyl |
| 263 | 4-NH₂ | 1 | 2-pyridyl | H | 2 | 2-CO₂H-phenyl |
| 264 | — | 0 | 2-pyridyl | H | 1 | 4-CO₂H-phenyl |
| 265 | — | 0 | 2-pyridyl | H | 1 | 2-CO₂H-phenyl |

TABLE 1-continued
Illustrative Examples of the Invention
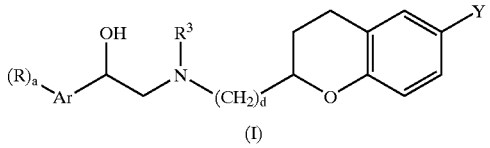
(I)
| Entry No. | R | a | Ar | R³ | d | Y |
|---|---|---|---|---|---|---|
| 266 | — | 0 | 2-pyridyl | H | 1 | 4-(NHSO₂—Ph)-phenyl |
| 267 | — | 0 | 2-pyridyl | H | 1 | 4-(NHSO₂—Me)-phenyl |
| 268 | — | 0 | 2-pyridyl | H | 1 | 4-(SO₂NH—CO—NHPh)-phenyl |
| 269 | — | 0 | 2-pyridyl | H | 1 | 3-(SO₂NH₂)-phenyl |
| 270 | — | 0 | 2-pyridyl | H | 1 | 3-(5-hydroxy-4-methyl-3-oxo-2,3-dihydro-1H-pyrazol-1-yl)phenyl |
| 271 | — | 0 | 2-pyridyl | H | 1 | 4-(NHCO—Ph)-phenyl |
| 272 | — | 0 | 2-pyridyl | H | 1 | 3-(NHCO—Me)-phenyl |
| 273 | — | 0 | 2-pyridyl | H | 1 | 4-(SO₂NH-2-pyrimidyl)-phenyl |

TABLE 1-continued

Illustrative Examples of the Invention

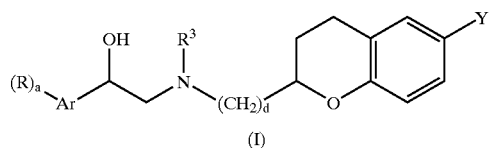

(I)

| Entry No. | R | a | Ar | R³ | d | Y |
|---|---|---|---|---|---|---|
| 274 | — | 0 | 2-pyridyl | H | 2 | -C6H4-NHSO2-Ph |
| 275 | — | 0 | 2-pyridyl | H | 2 | 3-(NHCO-Me)-C6H4- |
| 276 | — | 0 | 2-pyridyl | H | 2 | 4-(SO2NH-2-pyrimidinyl)-C6H4- |
| 277 | — | 0 | 2-pyridyl | H | 1 | 2-OMe-4-(SO2NH-2-thiazolyl)-C6H3- |
| 278 | — | 0 | 2-pyridyl | H | 2 | 2-OMe-4-(SO2NH-2-thiazolyl)-C6H3- |
| 279 | — | 0 | 2-pyridyl | H | 1 | 4-(C(O)CH2SO2-Ph)-C6H4- |
| 280 | — | 0 | 2-pyridyl | H | 2 | 4-(C(O)CH2SO2-Ph)-C6H4- |

The present invention includes compounds of Formula I wherein Y is halo; $R^6$; $SR^1$; $S(O)_b$-phenyl-$CO_2R^1$; or phenyl optionally fused to one or two phenyl rings or to a 5- or 6-membered heterocycle containing one or more heteroatom each independently selected from N, S, and O; or a 5- or 6-membered heterocycle containing one or more heteroatom each independently selected from N, S, and O, optionally fused to a phenyl ring; each cyclic moiety being optionally substituted with one or more substituents independently selected from $COR^2$, halo, $NO_2$, $OR^1$, $R^1$, $SR^1$, $SO_2NR^1R^7$, $NR^1R^1$, $C_1-C_{10}COR^2$, phenyl, or tetrazolo.

Another set of compounds of Formula I includes those compounds wherein Y is phenyl optionally fused to one or two phenyl rings or to a 5- or 6-membered heterocycle containing one or more heteroatom independently selected from N, S, and O; or a 5- or 6-membered heterocycle containing one or more heteroatom each independently selected from N, S, and O, optionally fused to a phenyl ring; each cyclic moiety being optionally substituted with one or more substituents independently selected from $COR^2$, halo, $NO_2$, $OR^1$, $R^1$, $SR^1$, $SO_2NR^1R^7$, $NR^1R^1$, $C_1-C_{10}COR^2$, phenyl, or tetrazolo; and d is 1 or 2.

Another set of compounds of Formula I includes those compounds wherein Y is phenyl optionally fused to one or two phenyl rings or to a 5- or 6-membered heterocycle containing one or more heteroatom each independently selected from N, S, and O; or a 5- or 6-membered heterocycle containing one or more heteroatom each independently selected from N, S, and O, optionally fused to a phenyl ring; each cyclic moiety being optionally substituted with one or more substituents independently selected from $COR^2$, halo, $NO_2$, $OR^1$, $R^1$, $SR^1$, $SO_2NR^1R^7$, $NR^1R^1$, $C_1$–$C_{10}COR^2$, phenyl, or tetrazolo; d is 1 or 2; and Ar is phenyl optionally fused to a 5- or 6-membered heterocycle containing one or more heteroatoms each independently selected from O, S, and N; or a 5- or 6-membered heterocycle containing one or more heteroatoms each independently selected from N, S, and O, optionally fused to phenyl.

Another set of compounds of Formula I includes those compounds wherein Y is phenyl optionally fused to one or two phenyl rings or to a 5- or 6-membered heterocycle containing one or more heteroatom each independently selected from N, S, and O; or a 5- or 6-membered heterocycle containing one or more heteroatom each independently selected from N, S, and O, optionally fused to a phenyl ring; each cyclic moiety being optionally substituted with one or more substituents independently selected from $COR^2$ halo, $OR^1$, $R^1$ or $NR^1R^1$; d is 1; Ar is phenyl or a 5- or 6-membered heterocycle containing one or more N atoms; and a is 0, 1, 2, or 3.

In addition, the present invention specifically includes the following compounds:

2-[4-(ethoxycarbonyl)phenoxy]-4-[(2R)-2-({[(2R)-2-hydroxy-2-(3-pyridinyl)ethyl]amino}methyl)-3,4-dihydro-2H-chromen-6-yl]benzoic acid (Example 197);

4-[(2R)-2-({[(2R)-2-hydroxy-2-(3-pyridinyl)ethyl]amino}methyl)-3,4-dihydro-2H-chromen-6-yl]-2-isobutylbenzoic acid (Example 211);

N-{3-[(2R)-2-({[(2R)-2-hydroxy-2-(3-pyridinyl)ethyl]amino}methyl)-3,4-dihydro-2H-chromen-6-yl]benzoyl}-2-methylbenzenesulfonamide (Example 91);

4-[(2R)-2-({[(2R)-2-hydroxy-2-(3-pyridinyl)ethyl]amino}methyl)-3,4-dihydro-2H-chromen-6-yl]-2-isobutoxybenzoic acid (Example 183);

N-{3-[(2R)-2-({[(2R)-2-hydroxy-2-(3-pyridinyl)ethyl]amino}methyl)-3,4-dihydro-2H-chromen-6-yl]benzoyl}4-methoxybenzenesulfonamide (Example 92);

N-{3-[(2R)-2-({[(2R)-2-hydroxy-2-(3-pyridinyl)ethyl]amino}methyl)-3,4-dihydro-2H-chromen-6-yl]benzoyl}-1-propanesulfonamide (Example 97);

4-[(2R)-2-({[(2R)-2-hydroxy-2-(3-pyridinyl)ethyl]amino}methyl)-3,4-dihydro-2H-chromen-6-yl]-N-(4-methoxybenzoyl)benzenesulfonamide (Example 300);

N-(2-cyano-4-nitrophenyl)-3-[(2R)-2-({[(2R)-2-hydroxy-2-(3-pyridinyl)ethyl]amino}methyl)-3,4-dihydro-2H-chromen-6-yl]benzenesulfonamide (Example 259);

2-(4-chlorophenoxy)-4-[(2R)-2-({[(2R)-2-hydroxy-2-(3-pyridinyl)ethyl]amino}methyl)-3,4-dihydro-2H-chromen-6-yl]benzoic acid (Example 194);

N-(4,6-dimethoxy-2-pyrimidinyl)-4-[(2R)-2-({[(2R)-2-hydroxy-2-(3-pyridinyl)ethyl]amino}methyl)-3,4-dihydro-2H-chromen-6-yl]-2-(trifluoromethoxy)benzenesulfonamide (Example 274);

2-(4-fluorophenoxy)-4-[(2R)-2-({[(2R)-2-hydroxy-2-(3-pyridinyl)ethyl]amino}methyl)-3,4-dihydro-2H-chromen-6-yl]benzoic acid (Example 193);

4-[(2R)-2-({[(2R)-2-hydroxy-2-(3-pyridinyl)ethyl]amino}methyl)-3,4-dihydro-2H-chromen-6-yl]-N-(3-methoxybenzoyl)benzenesulfonamide (Example 293);

4-fluoro-N-{3-[(2R)-2-({[(2R)-2-hydroxy-2-(3-pyridinyl)ethyl]amino}methyl)-3,4-dihydro-2H-chromen-6-yl]benzoyl}benzenesulfonamide (Example 295);

4-[(2R)-2-({[(2R)-2-hydroxy-2-(3-pyridinyl)ethyl]amino}methyl)-3,4-dihydro-2H-chromen-6-yl]-2-(4-methylphenoxy)benzoic acid (Example 195);

4-[(2R)-2-({[(2R)-2-hydroxy-2-(3-pyridinyl)ethyl]amino}methyl)-3,4-dihydro-2H-chromen-6-yl]-2-(2-phenylethyl)benzoic acid (Example 213);

3-chloro-4-[(2R)-2-({[(2R)-2-hydroxy-2-(3-pyridinyl)ethyl]amino}methyl)-3,4-dihydro-2H-chromen-6-yl]benzoic acid (Example 124);

N-(4-fluorobenzoyl)-4-[(2R)-2-({[(2R)-2-hydroxy-2-(3-pyridinyl)ethyl]amino}methyl)-3,4-dihydro-2H-chromen-6-yl]benzenesulfonamide (Example 295);

4-[(2R)-2-({[(2R)-2-hydroxy-2-(3-pyridinyl)ethyl]amino}methyl)-3,4-dihydro-2H-chromen-6-yl]-3-methoxybenzoic acid (Example 125);

4-[(2R)-2-({[(2R)-2-hydroxy-2-(3-pyridinyl)ethyl]amino}methyl)-3,4-dihydro-2H-chromen-6-yl]-2-phenoxybenzoic acid (Example 192);

N-(4-cyanophenyl)-4-[(2R)-2-({[(2R)-2-hydroxy-2-(3-pyridinyl)ethyl]amino}methyl)-3,4-dihydro-2H-chromen-6-yl]-2-(trifluoromethoxy)benzenesulfonamide (Example 262);

4-[(2R)-2-({[(2R)-2-hydroxy-2-(3-pyridinyl)ethyl]amino}methyl)-3,4-dihydro-2H-chromen-6-yl]-N-(4-methoxy-6-methyl-2-pyrimidinyl)-2-(trifluoromethoxy)benzenesulfonamide (Example 275);

4-[(2R)-2-({[(2R)-2-hydroxy-2-(3-pyridinyl)ethyl]amino}methyl)-3,4-dihydro-2H-chromen-6-yl]-N-(3,3,3-trifluoropropanoyl)benzenesulfonamide (Example 284);

2-hydroxy-4-[(2R)-2-({[(2R)-2-hydroxy-2-(3-pyridinyl)ethyl]amino}methyl)-3,4-dihydro-2H-chromen-6-yl]benzoic acid (Example 180);

3-((1R)-2-{[((2R)-6-{4-[({[(4-fluorophenyl)amino]carbonyl}amino)sulfonyl]phenyl}-3,4-dihydro-2H-chromen-2-yl)methyl]amino}-1-hydroxyethyl)pyridine (Example 327);

4-[(2R)-2-({[(2R)-2-hydroxy-2-(3-pyridinyl)ethyl]amino}methyl)-3,4-dihydro-2H-chromen-6-yl]-N-(2-pyrimidinyl)benzenesulfonamide (Example 249);

N-benzoyl-4-[(2R)-2-({[(2R)-2-hydroxy-2-(3-pyridinyl)ethyl]amino}methyl)-3,4-dihydro-2H-chromen-6-yl]benzenesulfonamide (Example 294);

4-[(2R)-2-({[(2R)-2-hydroxy-2-(3-pyridinyl)ethyl]amino}methyl)-3,4-dihydro-2H-chromen-6-yl]-2-propoxybenzoic acid (Example 186);

N-({4-[(2R)-2-({[(2R)-2-hydroxy-2-(3-pyridinyl)ethyl]amino}methyl)-3,4-dihydro-2H-chromen-6-yl]-2-pyridinyl}carbonyl)-4-methoxybenzenesulfonamide (Example 80);

3-((1R)-1-hydroxy-2-{[((2R)-6-{4-[({[(4-methylphenyl)amino]carbonyl}amino)sulfonyl]phenyl}-3,4-dihydro-2H-chromen-2-yl)methyl]amino}ethyl)pyridine (Example 326);

3-((1R)-2-{[((2R)-6-{4-[({[(4-chloro-2-methylphenyl)amino]carbonyl}amino)sulfonyl]phenyl}-3,4-dihydro-2H-chromen-2-yl)methyl]amino}-1-hydroxyethyl)pyridine (Example 330);

N-(ethoxyacetyl)$_4$-[(2R)-2-({[(2R)-2-hydroxy-2-(3-pyridinyl)ethyl)amino}methyl)-3,4-dihydro-2H-chromen-6-yl]benzenesulfonamide (Example 286);

N-(3,3-dimethylbutanoyl)-4-[(2R)-2-({[(2R)-2-hydroxy-2-(3-pyridinyl)ethyl]amino}methyl)-3,4-dihydro-2H-chromen-6-yl]benzenesulfonamide (Example 287);

4-[(2R)-2-({[(2R)-2-hydroxy-2-(3-pyridinyl)ethyl]amino}methyl)-3,4-dihydro-2H-chromen-6-yl]-N-(4-methyl-2-pyrimidinyl)benzenesulfonamide (Example 268);

4-[(2R)-2-({[(2R)-2-hydroxy-2-(3-pyridinyl)ethyl]amino}methyl)-3,4-dihydro-2H-chromen-6-yl]-2-[4-(methylsulfonyl)phenoxy]benzoic acid (Example 198);

4-[(2R)-2-({[(2R)-2-hydroxy-2-(3-pyridinyl)ethyl]amino}methyl)-3,4-dihydro-2H-7-chromen-6-yl]-3-methylbenzoic acid (Example 88);

4-{2-[(2R)-2-({[(2R)-2-hydroxy-2-(3-pyridinyl)ethyl]amino}methyl)-3,4-dihydro-2H-chromen-6-yl]ethyl}benzoic acid (Example 215);

N-(2,2-dimethylpropanoyl)-4-[(2R)-2-({[(2R)-2-hydroxy-2-(3-pyridinyl)ethyl]amino}methyl)-3,4-dihydro-2H-chromen-6-yl]benzenesulfonamide (Example 292);

3-[(1R)-2-({[(2R)-6-(4-{[(anilinocarbonyl)amino]sulfonyl}phenyl)-3,4-dihydro-2H-chromen-2-yl]methyl}amino)-1-hydroxyethyl]pyridine (Example 328);

2-ethoxy-4-[(2R)-2-({[(2R)-2-hydroxy-2-(3-pyridinyl)ethyl]amino}methyl)-3,4-dihydro-2H-chromen-6-yl]benzoic acid (Example 185);

4-[(2R)-2-({[(2R)-2-hydroxy-2-(3-pyridinyl)ethyl]amino}methyl)-3,4-dihydro-2H-chromen-6-yl]-N-(4-methoxy-6-methyl-2-pyrimidinyl)benzenesulfonamide (Example 273);

3-{(1R)-2-[({(2R)-6-[4-({[(cyclohexylamino)carbonyl]amino}sulfonyl)phenyl]-3,4-dihydro-2H-chromen-2-yl}methyl)amino]-1-hydroxyethyl}pyridine (Example 329);

N-(cyclopropylcarbonyl)-4-[(2R)-2-({[(2R)-2-hydroxy-2-(3-pyridinyl)ethyl]amino}methyl)-3,4-dihydro-2H-chromen-6-yl]benzenesulfonamide (Example 285);

2-chloro-5-fluoro-4-[(2R)-2-({[(2R)-2-hydroxy-2-(3-pyridinyl)ethyl]amino}methyl)-3,4-dihydro-2H-chromen-6-yl]benzoic acid (Example 122);

4-[(4-[R)-2-({[(2R)-2-hydroxy-2-(3-pyridinyl)ethyl]amino}methyl)-3,4-dihydro-2H-chromen-6-yl]benzoic acid (Example 148);

4-[(2R)-2-({[(2R)-2-hydroxy-2-(3-pyridinyl)ethyl]amino}methyl)-3,4-dihydro-2H-chromen-6-yl]-2-methylbenzoic acid (Example 149);

2-fluoro-4-[(2R)-2-({[(2R)-2-hydroxy-2-(3-pyridinyl)ethyl]amino}methyl)-3,4-dihydro-2H-chromen-6-yl]benzoic acid (Example 150);

4-[(2R)-2-({[(2R)-2-hydroxy-2-(3-pyridinyl)ethyl]amino}methyl)-3,4-dihydro-2H-chromen-6-yl]-3-propoxybenzoic acid (Example 130);

4-[(2R)-2-({[(2R)-2-hydroxy-2-(3-pyridinyl)ethyl]amino}methyl)-3,4-dihydro-2H-chromen-6-yl]-2-isopropoxybenzoic acid (Example 188);

4-[(2R)-2-({[(2R)-2-hydroxy-2-(3-pyridinyl)ethyl]amino}methyl)-3,4-dihydro-2H-chromen-6-yl]-N-(1,3-thiazol-2-yl)benzenesulfonamide (Example 265);

4-[(2R)-2-({[(2R)-2-hydroxy-2-(3-pyridinyl)ethyl]amino}methyl)-3,4-dihydro-2H-chromen-6-yl]-2-(4-methoxyphenoxy)benzoic acid (Example 196);

3-(cyclopropylmethoxy)-4-[(2R)-2-({[(2R)-2-hydroxy-2-(3-pyridinyl)ethyl]amino}methyl)-3,4-dihydro-2H-chromen-6-yl]benzoic acid (Example 132);

4-[(2R)-2-({[(2R)-2-hydroxy-2-(3-pyridinyl)ethyl]amino}methyl)-3,4-dihydro-2H-chromen-6-yl]benzenesulfonamide (Example 325);

5-[(2R)-2-({[(2R)-2-hydroxy-2-(3-pyridinyl)ethyl]amino}methyl)-3,4-dihydro-2H-chromen-6-yl]-4'-methyl-1,1'-biphenyl-2-carboxylic acid (Example 205);

N-{6-[(2R)-2-({[(2R)-2-hydroxy-2-(3-pyridinyl)ethyl]amino}methyl)-3,4-dihydro-2H-chromen-6-yl]-3-pyridinyl}benzenesulfonamide (Example 319);

4-[(2R)-2-({[(2R)-2-hydroxy-2-(3-pyridinyl)ethyl]amino}methyl)-3,4-dihydro-2H-chromen-6-yl]-N-(3-pyridinyl)benzenesulfonamide (Example 253);

4-[(2R)-2-({[(2R)-2-hydroxy-2-(3-pyridinyl)ethyl]amino}methyl)-3,4-dihydro-2H-chromen-6-yl]-2-methoxybenzoic acid (Example 184);

4-chloro-N-{6-[(2R)-2-({[(2R)-2-hydroxy-2-(3-pyridinyl)ethyl]amino}methyl)-3,4-dihydro-2H-chromen-6-yl]-3-pyridinyl}benzenesulfonamide (Example 320);

4-[(2R)-2-({[(2R)-2-hydroxy-2-(3-pyridinyl)ethyl]amino}methyl)-3,4-dihydro-2H-chromen-6-yl]-3-isobutoxybenzoic acid (Example 133);

N-{6-[(2R)-2-({[(2R)-2-hydroxy-2-(3-pyridinyl)ethyl]amino}methyl)-3,4-dihydro-2H-chromen-6-yl]-3-pyridinyl}methanesulfonamide (Example 321);

3-{2-[(2R)-2-({[(2R)-2-hydroxy-2-(3-pyridinyl)ethyl]amino}methyl)-3,4-dihydro-2H-chromen-6-yl]ethyl}benzoic acid (Example 216);

3-[(1E)-1-hexenyl]-4-[(2R)-2-({[(2R)-2-hydroxy-2-(3-pyridinyl)ethyl]amino}methyl)-3,4-dihydro-2H-chromen-6-yl]benzoic acid (Example 128);

3-[(2R)-2-({[(2R)-2-hydroxy-2-(3-pyridinyl)ethyl]amino}methyl)-3,4-dihydro-2H-chromen-6-yl]-N-(2-pyrimidinyl)benzenesulfonamide (Example 261);

4-[(2R)-2-({[(2R)-2-hydroxy-2-(3-pyridinyl)ethyl]amino}methyl)-3,4-dihydro-2H-chromen-6-yl]-2-(2-methoxyethoxy)benzoic acid (Example 187);

4-[(2R)-2-({[(2R)-2-hydroxy-2-(3-pyridinyl)ethyl]amino}methyl)-3,4-dihydro-2H-chromen-6-yl]-2,6-dimethylbenzoic acid (Example 121);

4-[(2R)-2-({[(2R)-2-(6-amino-3-pyridinyl)-2-hydroxyethyl]amino}methyl)-3,4-dihydro-2H-chromen-6-yl]benzoic acid (Example 385);

3-[(2R)-2-({[(2R)-2-(6-amino-3-pyridinyl)-2-hydroxyethyl]amino}methyl)-3,4-dihydro-2H-chromen-6-yl]benzoic acid (Example 386);

(1R)-1-(6-amino-3-pyridinyl)-2-[({(2R)-6-[4-(1H-tetraazol-5-yl)phenyl]-3,4-dihydro-2H-chromen-2-yl}methyl)amino]ethanol (Example 384);

5-{4-[(2R)-2-({[(2R)-2-hydroxy-2-(3-pyridinyl)ethyl]amino}methyl)-3,4-dihydro-2H-chromen-6-yl]phenyl}-3-phenyl-1,215, 315,4-thiatriazole-2-carboxylic acid (Example 166);

5-{4-[(2R)-2-({[(2R)-2-hydroxy-2-(3-pyridinyl)ethyl]amino}methyl)-3,4-dihydro-2H-chromen-6-yl]phenyl}-2-furoic acid (Example 159);

5-{4-[(2R)-2-({[(2R)-2-hydroxy-2-(3-pyridinyl)ethyl]amino)methyl)-3,4-dihydro-2H-chromen-6-yl]phenyl}-2-thiophenecarboxylic acid (Example 154);

5-{4-[(2R)-2-({[(2R)-2-hydroxy-2-(3-pyridinyl)ethyl]amino}methyl)-3,4-dihydro-2H-chromen-6-yl]phenyl}-3-thiophenecarboxylic acid (Example 156);

4-{4-[(2R)-2-({[(2R)-2-hydroxy-2-(3-pyridinyl)ethyl]amino}methyl)-3,4-dihydro-2H-chromen-6-yl]phenyl}-2-thiophenecarboxylic acid (Example 157);

6-[(2R)-2-({[(2R)-2-(6-amino-3-pyridinyl)-2-hydroxyethyl]amino}methyl)-3,4-dihydro-2H-chromen-6-yl]nicotinic acid (Example 151);

5-[(2R)-2-({[(2R)-2-(6-amino-3-pyridinyl)-2-hydroxyethyl]amino}methyl)-3,4-dihydro-2H-chromen-6-yl]nicotinic acid (Example 142);

2-[(2R)-2-({[(2R)-2-(6-amino-3-pyridinyl)-2-hydroxyethyl]amino}methyl)-3,4-dihydro-2H-chromen-6-yl]-4-pyridinecarboxylic acid (Example 158);

1-({[(2R)-2-({[(2R)-2-(6-amino-3-pyridinyl)-2-hydroxyethyl]amino}methyl)-3,4-dihydro-2H-chromen-6-yl]carbonyl}amino)cyclopropanecarboxylic acid (Example 366); and 4-[(2R)-2-({[(2R)-2-(3-chlorophenyl)-2-hydroxyethyl]amino}methyl)-3,4-dihydro-2H-chromen-6-yl]benzoic acid (Example 344).

Representative salts of the compounds of Formula I include the conventional non-toxic salts and the quaternary ammonium salts which are formed, for example, from inorganic or organic acids or bases by means well known in the art. For example, such acid addition salts include acetate, adipate, alginate, ascorbate, aspartate, benzoate, benzenesulfonate, bisulfate, butyrate, citrate, camphorate, camphorsulfonate, cinnamate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, methanesulfonate, 2-naphthalenesulfonate, nicotinate, nitrate, oxalate, pamoate, pectinate, persulfate, 3-phenylpropionate, picrate, pivalate, propionate, succinate, sulfonate, tartrate, thiocyanate, tosylate, and undecanoate.

Base salts include alkali metal salts such as potassium and sodium salts, alkaline earth metal salts such as calcium and magnesium salts, and ammonium salts with organic bases such as dicyclohexylamine salts and N-methyl-D-glucamine. Additionally, basic nitrogen containing groups may be quaternized with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

The esters in the present invention are non-toxic, pharmaceutically acceptable esters such as alkyl esters such as methyl, ethyl, propyl, isopropyl, butyl, isobutyl or pentyl esters. Additional esters such as phenyl-$C_1$–$C_5$ alkyl may be used, although methyl ester is preferred. The compound of Formula I may be esterified by a variety of conventional procedures including reacting the appropriate anhydride, carboxylic acid, or acid chloride with the alcohol group of the Formula I compound. The appropriate anhydride is reacted with the alcohol in the presence of an acylation catalyst such as 1,8-bis[dimethylamino]naphthalene or N,N-dimethylaminopyridine. An appropriate carboxylic acid may be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and optionally, an acylation catalyst. Esterification may also be reached using the appropriate carboxylic acid in the presence of trifluoroacetic anhydride and optionally, pyridine, or in the presence of N,N-carbonyldiimidazole with pyridine. Reaction of an acid chloride with the alcohol may be carried out with an acylation catalyst such as 4-DMAP or pyridine.

Sensitive or reactive groups on the compound of Formula I may need to be protected during any of the above methods for forming esters, and protecting groups may be added and removed by conventional methods well known in the art.

One skilled in the art would readily know how to successfully carry out these as well as other methods of esterification of alcohols.

The compounds of this invention may, either by nature of asymmetric centers or by restricted rotation, be present in the form of isomers. Any isomer may be present in the (R)-, (S)-, or (R,S) configuration, preferably in the (R)- or (S)- configuration, whichever is most active, The configurational isomers of Formula I, in which both the hydroxyl group attached to the side chain containing the Ar—X- moiety and the (CH$_2$)$_d$ group attached to the dihydrochromenyl ring are above the plane, as depicted below, are preferred.

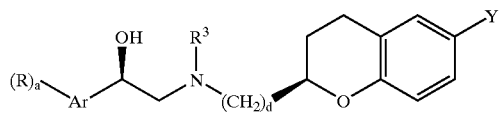

All isomers, whether separated, pure, partially pure, or in racemic mixture, of the compounds of this invention are encompassed within the scope of this invention. The purification of said isomers and the separation of said isomeric mixtures may be accomplished by standard techniques known in the art.

Geometric isomers by nature of substituents about a double bond or a ring may be present in cis (=Z-) or trans (=E-) form, and both isomeric forms are encompassed within the scope of this invention.

The particular process to be utilized in the preparation of the compounds of this invention depends upon the specific compound desired. Such factors as the selection of the specific Ar and Y moieties and the specific substituents on the various moieties, all play a role in the path to be followed in the preparation of the specific compounds of this invention. These factors are readily recognized by one of ordinary skill in the art.

For synthesis of any particular compound, one skilled in the art will recognize that the use of protecting groups may be required for the synthesis of compounds containing certain substituents. A description of suitable protecting groups and appropriate methods of adding and removing such groups may be found in: Protective Groups in Organic Synthesis, Second Edition, T. W. Greene, John Wiley and Sons, New York, 1991. For example, after preparation of a compound according to Reaction Scheme 1, in order to enable purification of the end product by, for example, flash chromatography, compounds of Formula I wherein $R^3$ is H, may be selectively protected, for example, as a carbamate derivative obtained by, for example, treatment with a reagent such as di-tert-butyl dicarbonate or other means known in the art. After purification, the carbamate group can easily be removed by treatment with an acid such as HCl or trifluoroacetic acid by means known in the art.

In the Reaction Schemes below, one skilled in the art will recognize that reagents and solvents actually used may be selected from several reagents and solvents well known in the art to be effective equivalents. When specific reagents or solvents are shown in a Reaction Scheme, therefore, they are meant to be illustrative examples of conditions desirable for the execution of that particular Reaction Scheme. Abbreviations not identified in accompanying text are listed later in this disclosure under "Abbreviations and Acronyms."

General Methods of Preparation of Formula I Compounds

In general, Formula I compounds may be prepared by standard techniques known in the art and by known processes analogous thereto. In particular, three such standard methods may be used, the selection of which may be based, among other considerations, upon the availability of the required individual starting materials. These three methods are illustrated in Reaction Schemes 1, 2, and 3 below.

The compounds of Formula I where each variable may be any moiety within that variable's definition may be synthesized according to Reaction Scheme 1 wherein an appropriate epoxide 1a or chlorohydrin 1b (preparation of 1a is described in WO 99/32475) is coupled with the appropriate amine 2 (preparation of 2 is described below in Reaction Schemes 12, 13, and 14). This reaction of Reaction Scheme 1 is typically carried out in an aprotic solvent such as dimethyl sulfoxide, dimethyl formamide, acetonitrile, or in an alcohol such as ethanol, isopropanol, or propanol at temperature from about −10° C. to reflux. Compounds in which $R^3$ is other than hydrogen may be prepared by reaction of compound I in which $R^3$ is H, by selective N-alkylation of N-acylation reactions with known compounds of formula $R^3$-halo (where $R^3$ is acyl or alkyl) or $[R^3]_2O$ (where $R^3$ is acyl). Protection of the hydroxyl group, for example as a TBDMS ether, may be required prior to N-alkylation reactions; O-deprotection is carried out under standard conditions well known in the art.

REACTION SCHEME 1

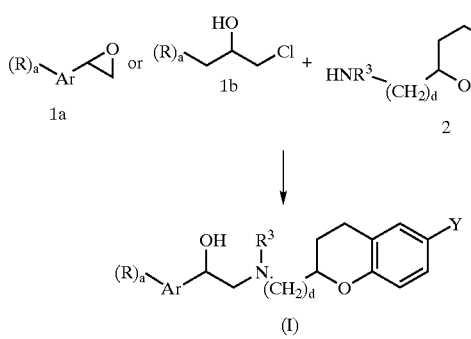

Alternatively, Formula I compounds, where each variable may be any moiety within that variables definition, except that d=1, may be prepared by a reductive amination as shown in Reaction Scheme 2. Reaction of an aldehyde of Formula 4 (preparation described below in Reaction Scheme 9) with an amino alcohol of Formula 3 (preparation described in WO 98/32475) followed by reduction gives the desired transformation to Formula Ia compounds. Compounds in which $R^3$ is other than hydrogen may be prepared by reaction of compound 1a in which $R^3$ is H by selective N-alkylation or N-acylation reactions with known compounds of formula $R^3$-halo (where $R^3$ is alkyl or acyl) or $[R^3]_2O$ (where $R^3$ is acyl). Protection of the hydroxyl group, for example, as a TBDMS ether, may be required prior to N-alkylation reactions. O-deprotection is carried out under standard conditions well known in the art.

REACTION SCHEME 2

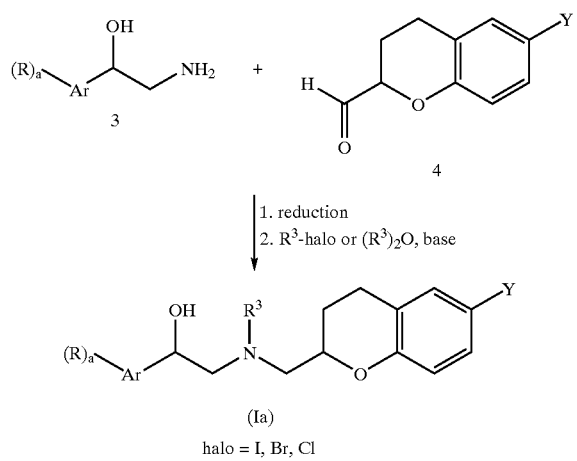

A third general route to Formula I compounds, where each variable may be any moiety within that variable's definition except that d=1, is shown in Reaction Scheme 3. An amino alcohol 3 and a carboxylic acid 5 (preparation described in Reaction Schemes 10 and 11) are coupled to provide an amide of Formula 6. Reduction of the Formula 6 amides with an appropriate reagent such as borane-dimethylsulfide complex provides the Formula I compounds where $R^3$ is H. Formula I compounds in which $R^3$ is other than H may be similarly prepared as described above for Reaction Schemes 1 and 2.

REACTION SCHEME 3

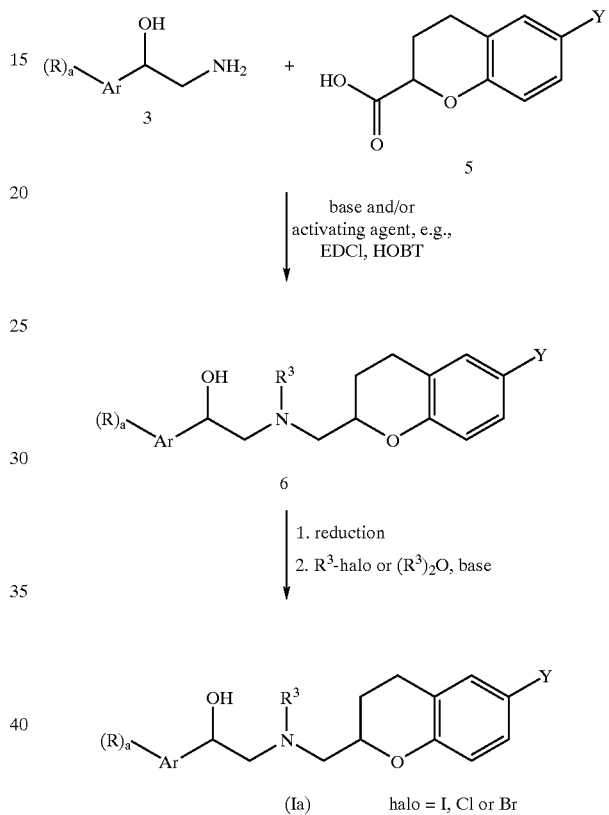

Reaction Scheme 4 shows that compounds of Formula I or Formula Ia where Y is any alkenyl, cycloalkenyl, phenyl, or a 5-or 6-membered heterocyclic ring may be prepared from compounds of Formula I or Formula Ia where Y is a halogen, using the following additional methods described below. For example, a compound of Formula I, wherein Y is iodo, may be prepared by Reaction Scheme 1 using corresponding starting materials 2 or 4, where Y is iodo, each of which may be prepared by Reaction Schemes 12 or 9, respectively. The resulting Formula I compound is then protected by standard methods to give a compound of Formula 7a. The compound of Formula 7a is then converted to the boronic ester 8, which is then subjected to Suzuki coupling reactions with a halo-Y compound, in which Y is any alkenyl, cycloalkenyl, phenyl, naphthyl, or a 5-or 6-membered heterocycle to provide Formula 7 compounds as shown in Reaction Scheme 4. Deprotection of Formula 7 compounds by acid or fluoride-catalyzed hydrolysis provides the corresponding Formula I compounds.

REACTION SCHEME 4

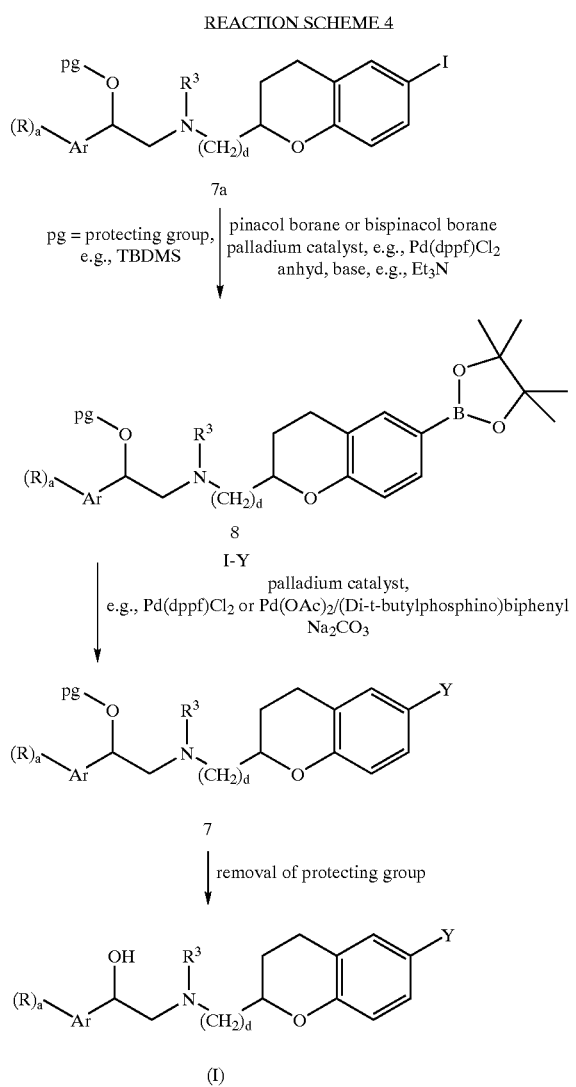

The coupling may also be performed in the reverse manner, that is, a boronic ester derivative 10 prepared from a halophenyl compound 9 may be added to the iodo compound of Formula 7b, as shown in Reaction Scheme 5 to give Formula Ib compounds.

REACTION SCHEME 5

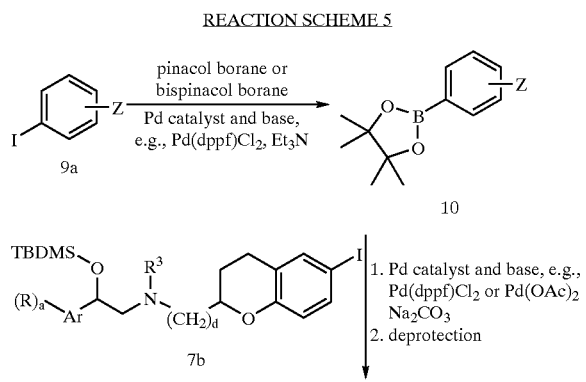

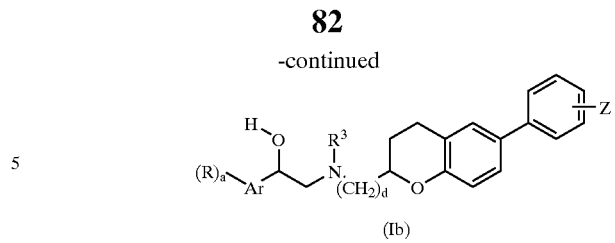

Z = $CO_2R^1$, F, $R^1$, $OR^1$, phenyl or tetrazolo
halo = I, Cl, or Br

Formula I compounds in which Y is an aryl group further substituted by a $S(O)_bR^2$ or $NHS(O)_bR^2$ group may be prepared by elaboration of the corresponding Formula 7 compounds in which Y is an aryl group substituted by $CO_2H$ as shown in Reaction Scheme 6.

Reaction Scheme 6

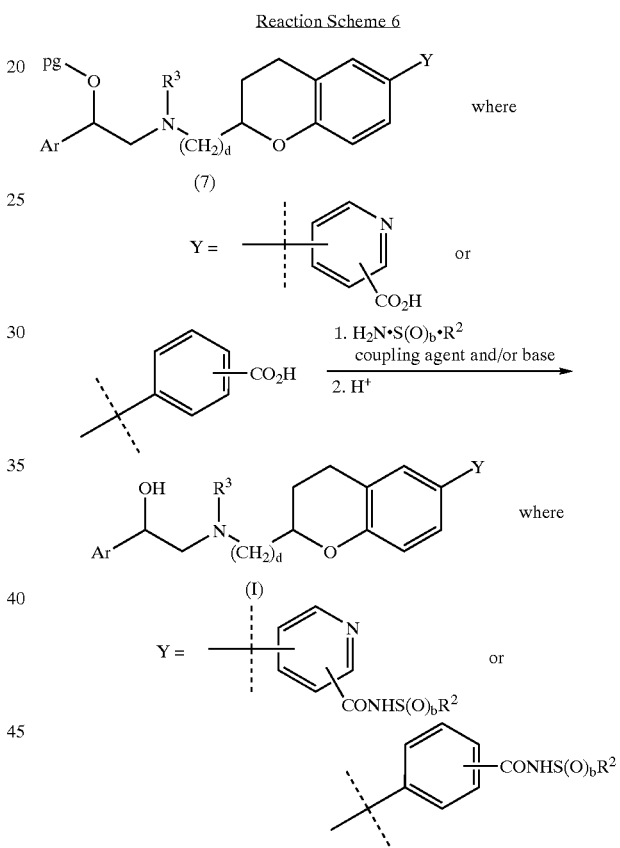

Formula I compounds wherein Y is

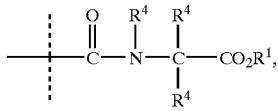

and $R^1$ and $R^4$ are as described above, may be prepared by a sequence shown in Reaction Scheme 7. The iodo compound of Formula 7a may be converted to the carboxylic acid of Formula 7c by palladium-catalyzed carboxylation. This may then be coupled with an amino acid using standard peptide synthesis techniques, deprotected and hydrolyzed to give compounds of Formula Ic. This method may be repeated to give Formula I compounds where Y is

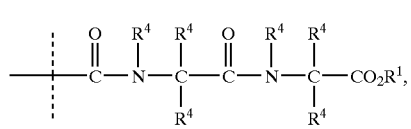

by an analogous sequence of reactions performed on the Formula Ic compounds.

REACTION SCHEME 7

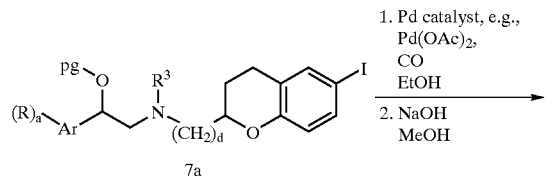

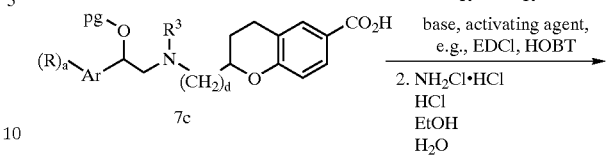

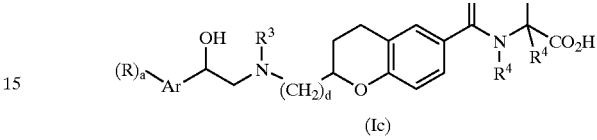

pg = TBDMS
R' = lower alkyl

Formula Id compounds of Reaction Scheme 8 may be prepared according to Reaction Scheme 1 or 3, starting from the known Formula 5 compound (U.S. Pat. No. 6,051,586) in which Y=NO$_2$. Other Formula I compounds wherein Y is NR$^1$R$^1$ may be prepared from the nitro compound of Formula Id by reduction to Ie followed by dialkylation with the appropriate alkylating agents, such as R$^1$-halo, R$^1$—OTs, or R$^1$—OMs to If (Reaction Scheme 7).

REACTION SCHEME 8

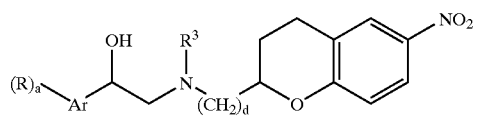

(Id)

reduction

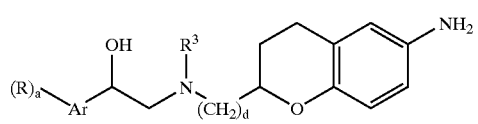

(Ie)

alkylation, e.g., 2 eq R$^1$-halo, base alkylation, e.g., halo-alkyl-halo or halo-alkyl-O-alkyl-halo, etc., base

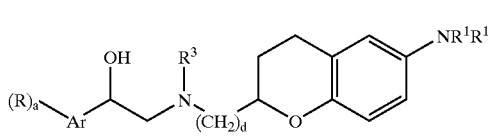

(If)

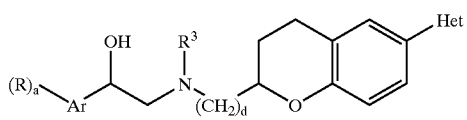

(Ig)

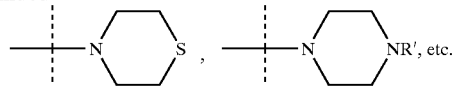

R' = lower alkyl

Reaction Scheme 9 shows how other Formula I compounds in which Y is S(O)$_b$Ph—CO$_2$R$^1$ and b is 0 may be prepared by diazotization of Ie and nucleophilic displacement with a arylthiol to give arylthioethers of Formula Ih. Oxidation of the Formula Ih compound with mCPBA or Oxone® gives the Formula Ii compound in which Y is —S(O)$_b$Ph—CO$_2$R$^1$ and b=1 or the Formula Ij compound in which Y is —S(O)$_b$Ph—CO$_2$R$^1$ and b=2, depending on the number of equivalents of oxidant used in the reaction.

Formula I compounds in which Y is SR$^1$ may be similarly prepared by methods analogous to Reaction Scheme 9, by substituting HSR$^1$ in place of the arylthiol in the first step.

REACTION SCHEME 9

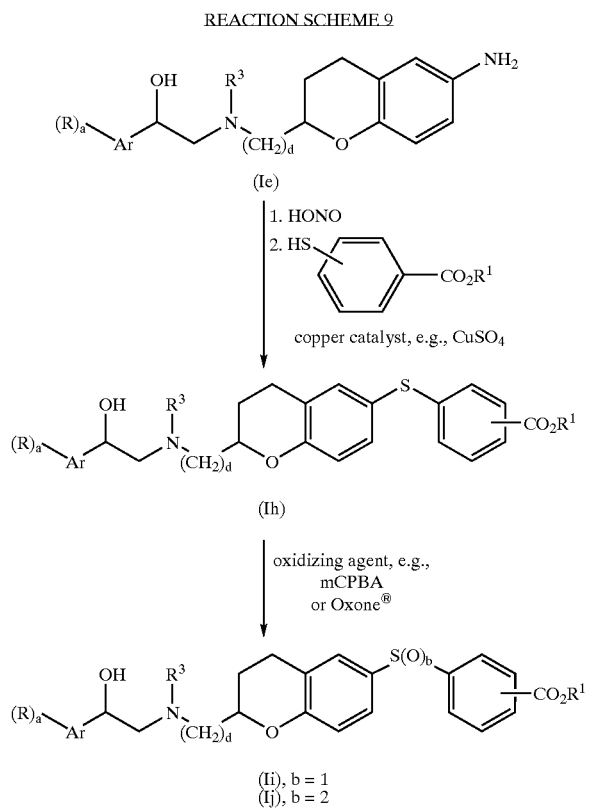

The salts and esters of the Formula I compounds of the invention may be readily prepared by conventional chemical processes.

General Method of Preparation of Intermediates

The starting materials required to carry out the above described reactions (e.g., epoxides 1a, chlorohydrins 1b, amines 2, amino alcohols 3, aldehydes 4, and carboxylic acids 5) are in many cases commercially available or may be readily prepared by methods known to those skilled in the art. The following routes are exemplary of such methods, but are not intended to be limiting in any way.

The epoxides 1a of Reaction Scheme 1 are commercially available or may be prepared according to one of the many procedures described in the literature known to those skilled in the art. For example, as described in WO 99/32475, the epoxides of a formula 1a may be prepared by the reaction of an aryl methyl ketone with a selective halogenating agent such as NBS, followed by ketone reduction with, for example, sodium borohydride to a give a chlorohydrin 1b (a halo alcohol). Base-catalyzed cyclization of this alcohol with, for example, potassium carbonate, gives the epoxides of formula 1a. This method is general for the conversion of substituted methyl aryl ketones of general formula (R)$_a$—Ar—C(=O)CH$_3$ to the corresponding epoxides of formula 1a.

The amino alcohols 3 may be prepared by ring opening of the epoxides 1a with a nitrogen nucleophile, such as phthalimide, in the presence of a base to form an intermediate which may be cleaved or hydrolyzed as described in WO 98/32475. This sequence is general for conversion of epoxides of formula 1a to the amino alcohols of formula 3.

Synthesis of aldehyde starting materials of Formula 4 may be accomplished from the carboxylic acid of Formula 5 by reduction with borane followed by oxidation, for example, under Swern conditions as shown in Reaction Scheme 10. This method is compatible with a wide variety of Y groups, although in some cases, a protecting group may also be employed and removed in a subsequent step.

REACTION SCHEME 10

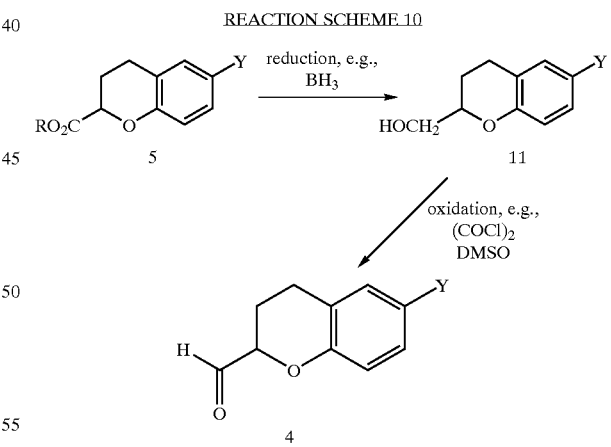

The carboxylic acids of Formula 5 are generally available from the known unsubstituted chroman carboxylic acid 5a (WO 99/32476) by various aromatic substitution reactions at the 6-position of the chroman ring and further elaboration of these products. For example, halogenation (e.g., iodination) of 5a gives the 6-iodo compound 5b and nitration gives predominantly the 6-nitro analog 5c (U.S. Pat. No. 6,051,586) as shown in Reaction Scheme 11.

REACTION SCHEME 11

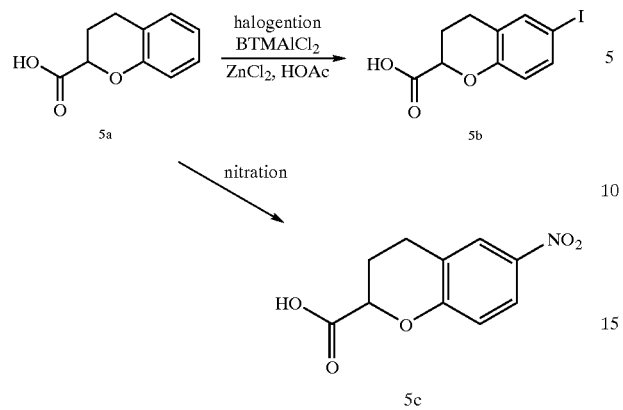

Compounds of Formula 5 where Y is any alkenyl, cycloalkenyl, phenyl, naphthyl, or a 5- or 6-membered heterocycle may be prepared by Suzuki coupling of a halo-Y group to an iodo chroman boronic ester 12 prepared from the iodo chroman acid 5b.

REACTION SCHEME 12

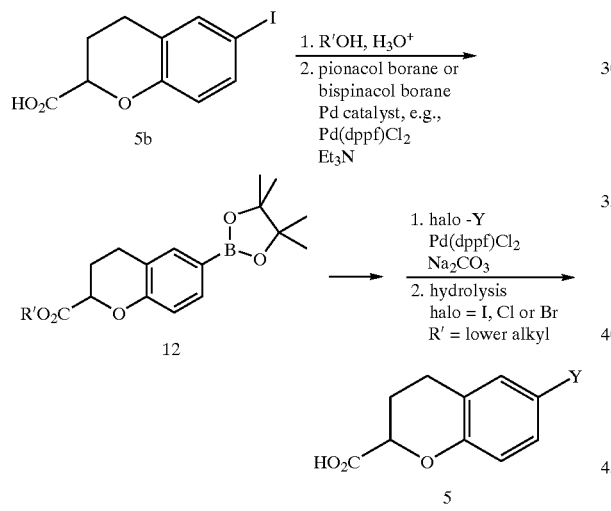

The amine starting materials of Formula 2, in which d=1, are generally available by standard methods involving conversion of a carboxylic acid 5 to an amide of Formula 13. Reduction with borane or further conversion of the Formula 13 amide to the nitrile of Formula 14 and then reduction by hydrogenation gives the desired Formula 2a compounds. This sequence is shown in Reaction Scheme 13 for Formula 2 amines wherein d=1 and $R^3$ is H. Formula 2 amines in which $R^3$ is other than H may be prepared by standard alkylation or acylation methods known in the art.

REACTION SCHEME 13

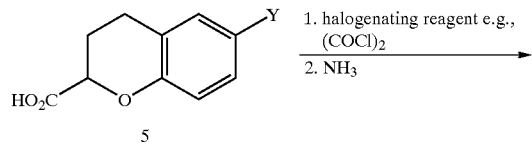

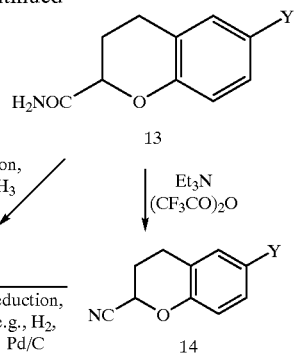

Formula 2 amines in which d is 2 or 3 may be prepared by standard homologation sequences of a variety of known intermediates where d=1. For example, aldehydes of Formula 4 can undergo an alkyl chain extension according to well known procedures such as that described by Wittig et al., (Chem. Ber., 2514, 1962) and the process may be repeated in order to prepare the acetic and propionic acid homologues of Formula 5 by a method analogous to Reaction Scheme 13, to provide a variety of Formula 2 amines in which d=2 or 3.

Formula 2 amines in which Y is other than hydrogen or halo may be prepared by palladium-catalyzed coupling reactions on the N-protected amine of Formula 15a followed by deprotection, as shown in Reaction Scheme 14. Formula 2 amines prepared in this way in which the Y group is substituted by an acid, ester, alcohol, ketone, sulfide, or nitro group may provide additional Formula 2 amines by manipulation of those functional groups by directed hydrolysis, esterification, reduction, oxidation, or reduction reactions of the Y group.

REACTION SCHEME 14

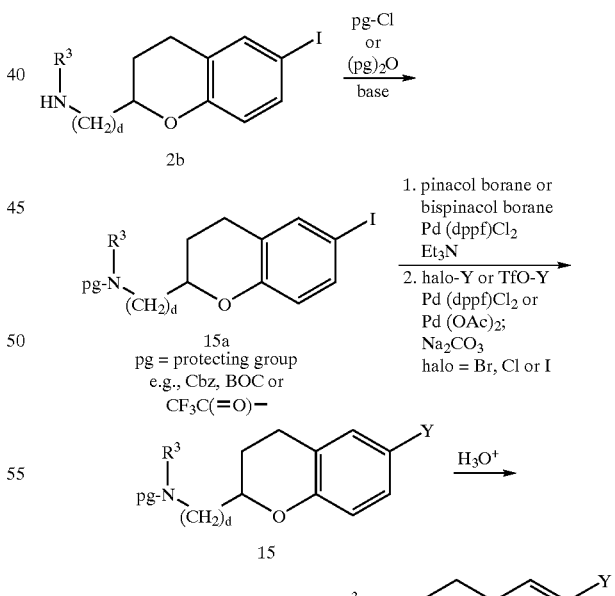

Similarly, the amine 2c, after protection, may be directly substituted at the 6-position of the chroman under Friedel- Crafts alkylation conditions to provide the compounds of Formula 15 in which Y is any alkyl or cycloalkyl group. An example of this where Y is an optionally substituted alkanoic acid group (15c) is shown in Reaction Scheme 15.

REACTION SCHEME 15

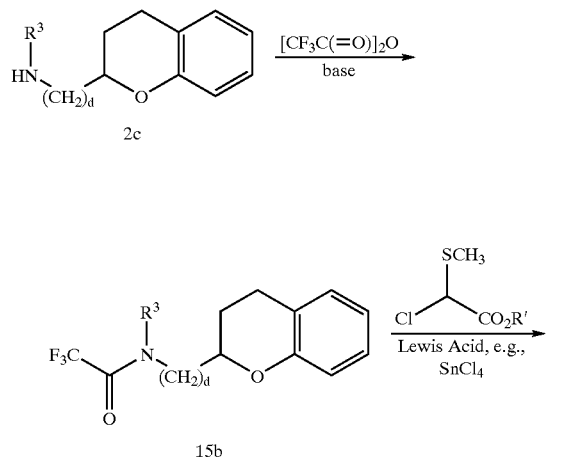

R' = lower alkyl

Alcohol intermediates of Formula 11 in which Y is other than hydrogen or halo may also be prepared from the iodo alcohol 11a by the previously described Suzuki coupling methodology as shown in Reaction Scheme 16. This may be accomplished either directly or via a 4-step sequence involving protection of the alcohol to 16a, for example, as a t-butyldimethylsilyl ether, conversion of the iodide to the boronic ester, Suzuki coupling to 16, and finally deprotection to 11.

REACTION SCHEME 16

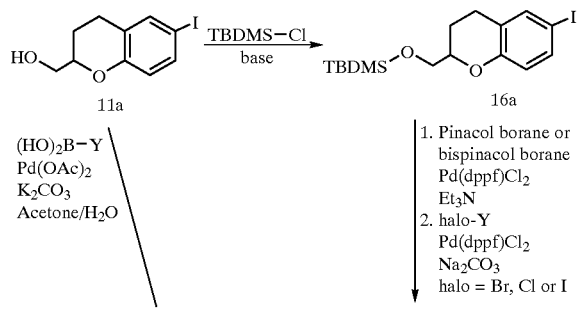

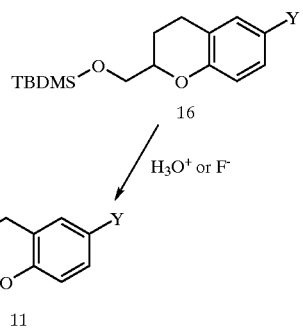

The halo-Y compounds used in Reaction Schemes 12, 14, and 16 where halo is iodo, chloro, or bromo and Y is any alkenyl, cycloalkenyl, phenyl, naphthyl, or a 5- or 6-membered heterocycle, are either commercially available or synthesized by standard methods known to those skilled in the art. One such standard method is direct halogenation of compounds of formula H—Y which are either commercially available or known in the art. Other methods include the functional group conversion of HO—Y or $H_2N$—Y compounds to halo-Y or TfO—Y compounds by standard substitution methods.

Particular illustrations of this are the preparation of halo-Y compounds of Formula 9b or 9c where Y represents an oxazole or a thiazole, prepared by direct halogenation of the unsubstituted compound or by diazotization of a corresponding amino group as shown in Reaction Scheme 17.

REACTION SCHEME 17

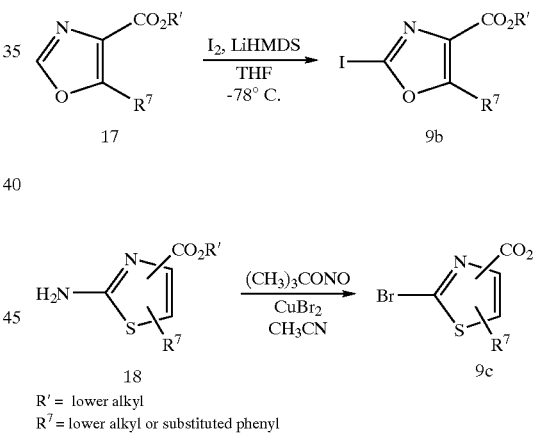

R' = lower alkyl
$R^7$ = lower alkyl or substituted phenyl

The heterocyclic intermediates 17 and 18 used to prepare 9b and 9c are accessible by standard methods from acyclic materials. Three examples of such heterocycles are shown in Reaction Schemes 18, 19, and 20.

REACTION SCHEME 18

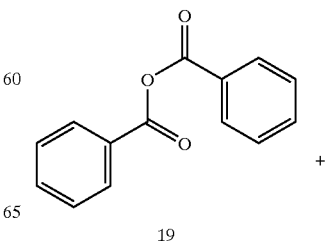

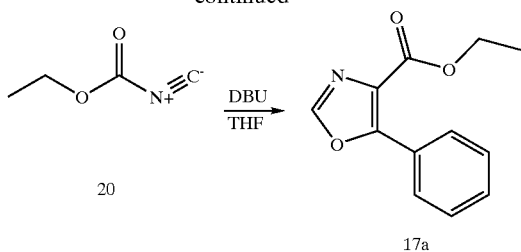

REACTION SCHEME 19

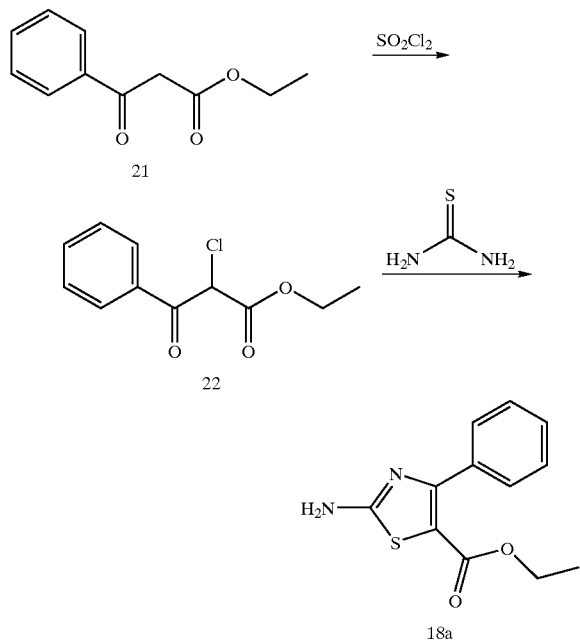

REACTION SCHEME 20

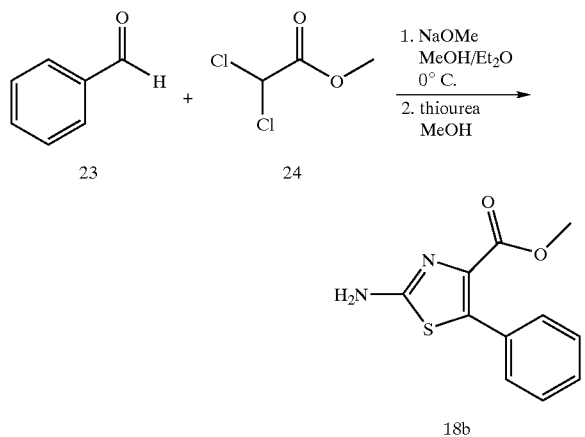

Using a combination of the above Reaction Schemes and the knowledge of one skilled in the art, all of compounds of Formula I may be prepared.

The following specific examples are presented to further illustrate the invention described herein, but they are not intended nor should they be construed to limit the scope of the invention in any way.

Abbreviations and Acronyms

When the following abbreviations are used herein, they have the following meaning:

$Ac_2O$ acetic anhydride
anhy anhydrous
$BH_3$ borane
BOC tert-butyloxycarbonyl
$BTMAlCl_2$ benzyltrimethylammonium dichloriodate
n-BuLi n-butyllithium
t-BuLi t-butyllithium
Cbz benzyloxycarbonyl
CDI carbonyldiimidazole
Celite® diatomaceous earth filter agent,® Celite Corp.
CI-MS chemical ionization mass spectroscopy
conc. concentrated
mCPBA 3-chloroperoxybenzoic acid
dec. decomposition
DBU 1,8-diazabicyclo[5.4.0]undec-7-ene
DMAP 4-dimethylaminopyridine
DME dimethoxyethane
DMF N,N-dimethylformamide
DMSO dimethylsulfoxide
EDCl 1-(3-dimethylaminopropyl)-3-ethylcarbodiimide
EtOAc ethyl acetate
EtOH ethanol (100%)
$Et_2O$ diethyl ether
$Et_3N$ triethylamine
HPLC ES-MS high performance liquid chromatography-electrospray mass spectroscopy
HOBT 1-hydroxybenzotriazole hydrate
KOtBu potassium tert-butoxide
$LiAlH_4$ lithium aluminum hydride
$LiBH_4$ lithium borohydride
LiHMDS lithium bis(trimethylsilyl)amide
MeOH methanol
MSTFA N-methyl-N-(trimethylsilyl)trifluoroacetamide
$NaBH_4$ sodium borohydride
$Na(OAc)_3BH$ sodium triacetoxyborohydride
NMM 4-methylmorpholine
Oxone® potassium peroxymonosulfate,® E. I. du Pont de Nemours & Co., Inc. Corp.
$Ph_3P$ triphenylphosphine
$Pd(dppf)Cl_2$ [1,1 '-bis(diphenylphosphino)ferrocene] dichloropalladium(II)
$Pd(PPh_3)_4$ tetrakis(triphenylphosphine)palladium(0)
$Pd(OAc)_2$ palladium acetate
rt room temperature
TBAF tetrabutylammonium fluoride
TBDMS tert-butyldimethylsilyl
TBDMSCl tert-butyldimethylsilyl chloride
TBDMSOTf tert-butyldimethylsilyl trifluoromethanesulfonate
THF tetrahydrofuran
TFA trifluoroacetic acid
TLC thin layer chromatography
Tf trifluoroacetyl General Experimental Procedures HPLC-electrospray mass spectra (HPLC ES-MS) were obtained using a Hewlett-Packard 1100 HPLC equipped with a quaternary pump, a variable wavelength detector, a YMC Pro C18 2.0 mm×23 mm column, and a Finnigan LCQ ion trap mass spectrometer with electrospray ionization. Gradient elution from 90% A to 95% B over 4 minutes was used on the HPLC. Buffer A was 98% water, 2% Acetonitrile, and 0.02% TFA. Buffer B was 98% Acetonitrile, 2% water, and 0.018% TFA. Spectra were scanned from 140–1200 amu using a variable ion time according to the number of ions in the source.

Combinatorial/parallel reactions were carried out in 8-mL glass vials with Teflon-lined screw caps, or in a polypropylene reaction block consisting of a 8×12 matrix of ninety-six 2.0-mL reaction wells, with each reaction well incorporating a 15–45 micron polyethylene frit. Reaction blocks of this type are commercially available as FlexChem™ reactor blocks from Robbins Scientific Corporation, Sunnyvale, Calif. The reactor blocks are sealed with rubber gaskets and a clamping device, and can be heated with mixing by rotation in an oven (Robbins Scientific).

EXAMPLE 1
Method A. Preparation of racemic 2-chloro-1-(3-pyridinyl) ethanol

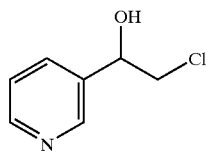

Sodium borohydride (198 mg, 5.2 mmol) was added to a 0° C. suspension of 2-chloro-1-(3-pyridinyl)ethanone hydrochloride (500 mg, 2.6 mmol) in ethanol (13 mL). After stirring at 0° C. for 1 hour, the reaction was adjusted to pH 5 with 1 N aqueous HCl. The solution was concentrated in vacuo to remove ethanol, and the residue was partitioned between dichloromethane and water. The organic layer was separated, dried ($Na_2SO_4$), and concentrated to provide the title compound as a crude material that was used directly in following steps: $^1$H NMR ($CDCl_3$) δ 8.54 (s, 1 H), 8.48 (d, J=6.2 Hz, 1 H), 7.76 (d, J=7.9 Hz, 1 H), 7.32–7.28 (m, 1 H), 4.95–4.91 (m, 1 H), 3.75–3.62 (m, 2 H).

Method B: Preparation of (1R)-2-chloro-1-(3-pyridinyl) ethanol

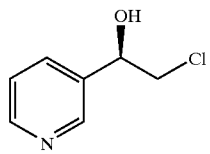

To a cold (ice bath) solution of 3-(2-chloroacetyl)pyridine hydrochloride (120 g, 624 mmol) in 500 mL of $H_2O$, was added $NaHCO_3$ (52.8 g, 624 mmol) slowly. After addition, 500 mL of $CH_2Cl_2$ was added, and this mixture was stirred for 10 minutes. The organic layer was separated, and the aqueous layer was washed with $CH_2Cl_2$ (2×150 mL). The combined organic layers were dried over anhydrous $Na_2SO_4$, the solids removed by filtration, and solvent removed in vacuo at room temperature. Anhydrous THF (600 mL) was added to the residue, and the resulting solution of this crude chloroketone was kept cold (dry ice) under Ar, until used as described below.

In an oven-dried 5 L round bottom flask, a solution of (R)-(+)-2-(α,α)-diphenylprolinol (7.8 g, 31.2 mmol) in 600 mL anhydrous THF was stirred at room temperature under Ar and to it, was added $B(OCH_3)_3$ (4.8 mL, 42 mmol), and the solution was stirred at room temperature for one hour. $BH_3S(CH_3)_2$ 2M/THF (624 mL, 1.25 mol) was then added. After the solution was stirred at room temperature for 20 minutes, the cold chloroketone THF solution was then slowly added at a rate of 30 mL/hour at room temperature. After the addition, HPLC analysis showed the reaction was complete providing 97% for the desired enantiomer of chlorohydrin. MeOH (200 mL) was added slowly and solution was maintained at a temperature below 20° C. The reaction mixture was concentrated in vacuo below 40° C. The product was used without further purification.

EXAMPLE 2

Preparation of (2R)-3,4-dihydro-2H-chromene-2-carboxamide

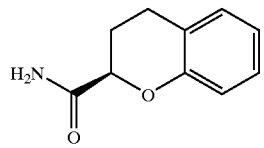

To a solution of (2R)-3,4-dihydro-2H-chromene-2-carboxylic acid (WO 99/32476) (17.8 g, 0.1 mol) in anhydrous dichloromethane (170 mL), cooled in an ice-water bath containing 4 drops of N,N-dimethylformamide, were added oxalyl chloride (13.4 mL, 0.16 mol) via a syringe in 10 minutes under argon. The resulting mixture was then stirred at room temperature for 15 hours. Solvent was removed in vacuo to afford the acid chloride cleanly: $^1$H NMR ($CDCl_3$, δ): 2.31–2.51 (m, 2H), 2.72–2.91 (m, 2H), 5.01 (t, J=4.2 Hz, 1H), 7.04–7.06 (t, J=8.7 Hz, 2H), 7.03–7.06 (d, J=6.9 Hz, 1H); 7.13–7.18 (t, J=8.1 Hz, 1H).

To a 2-L 3-necked round-bottomed flask containing ethyl acetate (633 mL) and ammonium hydroxide (158.2 mL), cooled in an ice-water bath with vigorous stirring, was added a solution of the above acid chloride in ethyl acetate (159 mL) dropwise in 15 minutes. The reaction mixture was stirred for additional 20 minutes. The organic layer was separated and washed with water (200 mL), brine (200 mL), and dried over anhydrous sodium sulfate. Removal of the solvent in vacuo afforded the chroman amide as a white solid (16.9 g, 95% yield): $^1$H NMR ($CDCl_3$, δ): 2.01–2.14 (m, 1H), 2.37–2.46 (m, 1H), 2.75–2.95 (m, 2H), 4.53–4.57 (dd, J=9.3, 2.7 Hz, 1H), 5.75 (s, broad, 1H), 6.60 (s, broad, 1H), 6.86–6.93 (m, 2H); 7.07–7.16 (m, 2H); CI-MS m/z=178 (M+H$^+$)

EXAMPLE 3

Preparation of (2R)-3,4-dihydro-2H-chromen-2-ylmethylamine hydrochloride

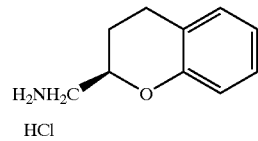

In a dry 1-L 3-necked round-bottomed flask were charged the amide of Example 2 (16.9 g, 95 mmol) and tetrahydrofuran (100 mL). The mixture was heated to reflux under argon with stirring to obtain a clear solution. To this solution was then added borane/dimethyl sulfide complex (95 mL, 2M in THF) in about 30 minutes. After completion of addition, the reaction was further refluxed for 1 hour. Additional borane/dimethyl sulfide (80 mL) was then added to the reaction and the mixture was further refluxed for 1 hour, Heating was removed and replaced with an ice-water bath to cool the reaction mixture to room temperature.

Methanol (43 mL) was then added to the reaction and it was stirred for 30 minutes. The reaction mixture was then concentrated in vacuo to remove 140 mL of liquid. The residue was then treated with ether/HCl (1 M) carefully to obtain a white suspension which was cooled in an ice-water bath for 30 minutes before vacuum filtration to obtain the product as a white powder (16.3 g, 87% yield): $^1$H NMR (DMSO-d$_6$, δ): 1.60–1.77 (m, 1H), 2.00–2.08 (m, 1H), 2.65–2.85 (m, 2H), 2.95–3.20 (m, 2H), 4.20–4.30 (m, 1H), 6.75–6.85 (m, 2H), 7.04–7.09 (m, 2H); 8.30 (s, broad, 3H); CI-MS m/z=164 (M+H$^+$).

EXAMPLE 4

Preparation of N-[(2R)-3,4-dihydro-2H-chromen-2-ylmethyl]-2,2,2-trifluoroacetamide

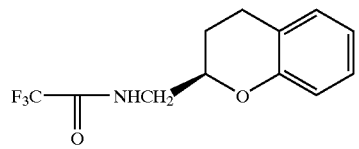

The amine HCl salt of Example 3 (16.3 g, 82.6 mmol) was dissolved in 1N aqueous sodium hydroxide solution (91 mL) followed by extraction with dichloromethane (90 mL×3). The combined organic layer was washed with brine (50 mL) and dried over anhydrous sodium sulfate. Removal of solvent in vacuo afforded the free base chroman amine as colorless oil which was mixed with pyridine (14.2 mL) in dichloromethane (136 mL) under argon.

To this mixture cooled in an ice-water bath was then added trifluoroacetic anhydride (23.3 mL) carefully in about 10 minutes. Cooling bath was removed and the reaction was stirred at room temperature for 4 hours. It was then poured onto crushed ice (130 g). The organic layer was separated, washed with brine (50 mL), and dried over anhydrous sodium sulfate. Removal of solvent in vacuo afforded the product cleanly (19.7 g, 92% yield): $^1$H NMR (CDCl$_3$, δ): 1.75–1.86 (m, 1H), 1.99–2.12 (m, 1H) 2.76–2.97 (m, 2H), 3.46–4.26 (m, 3H), 6.80–6.91 (m, 2H), 7.03–7.14 (m, 2H); CI-MS m/z=260 (M+H$^+$). The crude product was used for next step without further purification.

EXAMPLE 5

Preparation of ethyl (methylsulfanyl)[(2R)-2-(3,3,3-trifluoro-2-oxopropyl)-3,4-dihydro-2H-chromen-6-yl]acetate

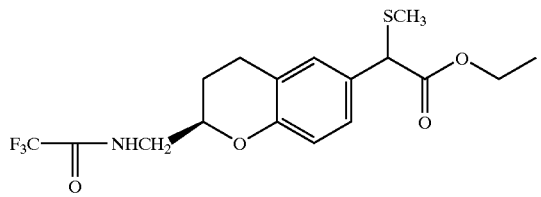

To a solution of N-[(2R)-3,4-dihydro-2H-chromen-2-ylmethyl]-2,2,2-trifluoroacetamide (Example 4, 12.96 g, 50 mmol) and α-chloro-2-(methylthio) acetate (9.28 g, 55 mmol) in dichloromethane (75 mL) at 0° C. was slowly added tin(IV) chloride (55 mL, 1M in CH$_2$Cl$_2$) via a syringe. The mixture became yellow rapidly and precipitation started to form. After completion of addition, the reaction was stirred at room temperature for 30 minutes. It was then quenched by addition of water (100 mL). The organic layer was separated and dried over anhydrous sodium sulfate and concentrated in vacuo to afford the crude product as a brown oil (diastereomeric mixture): $^1$H NMR (CDCl$_3$, δ): 1.30 (m, 3H), 1.76 (m, 2H), 2.18 (m, 4H), 2.90 (m, 2H), 4.20 (m, 5H), 6.65–6.79 (dd, J=8.1, 7.8 Hz, 1H), 7.18 (m, 2H); CI-MS m/z=392 (M+H$^+$). The crude was used without further purification.

EXAMPLE 6

Preparation of (2R)-6-bromo-3,4-dihydro-2H-chromene-2-carboxylic acid

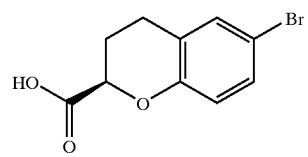

Step 1. Preparation of isobutyl (2R)-6-bromo-3,4-dihydro-2H-chromene-2-carboxylate

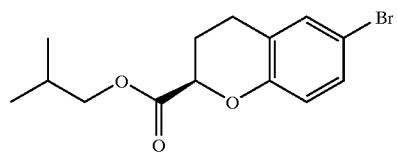

To dichloromethane (2.2 L) in a round-bottom flask equipped with a mechanical stirrer, argon gas inlet, and condenser were charged 255.8 g (1.092 moles, 98% ee) isobutyl (2R)-3,4-dihydro-2H-chromene-2-carboxylate [prepared by esterification of (2R)-3,4-dihydro-2H-chromene-2-carboxylic acid (WO 99/32476)], 156.3 g (0.55 moles) 1,3-dibromo-5,5-dimethylhydantoin, and 10.49 g (0.109 moles) methanesulfonic acid. The mixture was stirred in the dark overnight at room temperature. The reaction mixture was concentrated to 700 ml and the solid hydantoin was filtered and washed once with 50 ml of dichloromethane. The filtrate was concentrated to afford 355.7 g (104% crude yield) of a light brown solid, which by H-NMR, contained residual hydantoin: $^1$H-NMR (DMSO-d6, 300 MHz) δ 0.85 (d, 6H), 1.86 (m, 1H), 2.13 (m, 2H), 2.59 (m, 1H), 2.81 (m, 1H), 3.90 (d, 2H), 4.98 (t, 1H), 6.80 (d, 1H), 7.22–7.27 (m, 2H); EI-MS m/z 312, 314.

Step 2. Preparation of (2R)-6-bromo-3,4-dihydro-2H-chromene-2-carboxylic acid

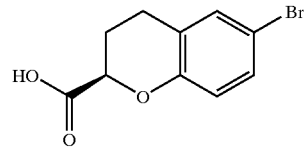

The crude product from step 1 above (1.092 moles) was dissolved in THF (2.1 L) and charged to a round-bottom flask, followed by 700 ml of methanol. A solution of LiOH (32.76 g, 1.365 moles) in 700 ml of water was then added over five minutes, resulting in a 10 degree rise in temperature. The reaction was stirred for five minutes and a sample analyzed by HPLC indicated excellent conversion of the starting material. After stirring for twenty minutes at 50° C., THF and methanol were removed in vacuo. Water (1.1 L) was added to the resulting solution, which was then charged to a round-bottom flask. 1.4 L of 1N HCl was slowly added to the solution to precipitate the product. The mixture was filtered to obtain 342 g of a white solid that was still wet. Water was removed by azeotroping with 700 ml of toluene and the compound was allowed to crystallize upon cooling from refluxing toluene to room temperature overnight. Upon breaking up the solid crystal, the reaction mixture was filtered, and the solid was dried in a vacuum oven overnight to obtain 185 g (66%) of an off-white solid: $^1$H-NMR (DMSO-d6, 300 MHz) δ 2.07 (m, 2H), 2.61 (m, 1H), 2.78 (m, 1H), 4.81 (t, 1H), 6.77 (d, 1H), 7.21–7.25 (m, 2H), 13.08 (s, 1H).

EXAMPLE 7

Method A. Preparation of (2R)-6-iodo-3,4-dihydro-2H-chromene-2-carboxylic acid

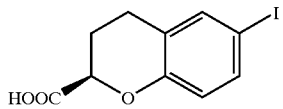

(2R)-3,4-Dihydro-2H-chromene-2-carboxylic acid (WO 99/32476) (26.7 g, 150 mmol), benzyltrimethyl-ammonium dichloroiodate (50.1 g, 144 mmol), and zinc chloride (25.3 g, 186 mmol) were stirred in glacial acetic acid (500 mL) under argon at room temperature for 18 hours. The solid was removed by vacuum filtration and then washed with acetic acid (100 mL). The filtrate was concentrated in vacuo to obtain a solid which was slurried in water (300 mL). The crude product was obtained as a pink solid after vacuum filtration and dried (38.3 g, 84%): $^1$H NMR (DMSO-d$_6$, δ):1.95–2.10 (m, 1H), 2.60 (m, 1H), 2.70–2.80 (m, 1H), 4.79 (dd, J=6.0, 3.9 Hz, 1H), 6.63 (d, J=8.4 Hz, 1H) 7.36 (dd, J=8.1, 1.8 Hz, 1H), 7.38 (d, J=1.8 Hz, 1H). CI-MS m/z=305 (M+H$^+$). The crude was used for next step directly.

Method B. Preparation of (2S)-6-iodo-3,4-dihydro-2H-chromene-2-carboxylic acid

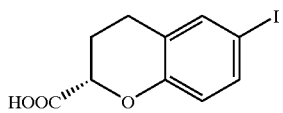

Using the same procedure described in for Method A and (2S)-3,4-dihydro-2H-chromene-2-carboxylic acid as starting material, the title compound was obtained in 89% yield: $^1$H NMR (DMSO-d$_6$) δ 1.95–2.10 (m, 1H), 2.60 (m, 1H), 2.70–2.80 (m, 1H), 4.79 (dd, J=6.0, 3.9 Hz, 1H), 6.63 (d, J=8.4 Hz, 1H), 7.36 (dd, J=8.1, 1.8 Hz, 1H), 7.38 (d, J=1.8 Hz, 1H).

EXAMPLE 8

Preparation of [(2R)-6-iodo-3,4-dihydro-2H-chromen-2-yl]methanol

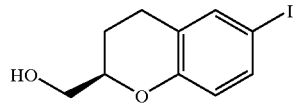

To a solution of (2R)-6-iodo-3,4-dihydro-2H-chromene-2-carboxylic acid (Example 7, 19.5 mmol, 1.0 eq.) in THF (45 mL) at 10° C. was added dropwise a solution of borane-THF complex (1M in THF, 23.4 mmol, 1.2 eq). The resulting reaction mixture was stirred at 45° C. for 1.5 hours and was then cooled to 10° C. Next, water was added followed by saturated NaHCO$_3$ solution. The resulting two-phase mixture was separated and the aqueous phase was extracted with ethyl acetate. The combined organic extracts were washed with brine, dried over anhydrous sodium sulfate, concentrated to afford the product as a white solid in quantitative yield that was used without further purification. GC-MS m/z 290 (M+)

EXAMPLE 9

Preparation of (2R)-6-iodo-3,4-dihydro-2H-chromene-2-carboxamide

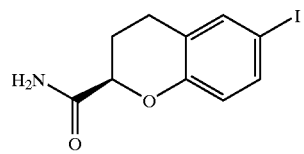

The crude carboxylic acid of Example 7 (30.4 g, 100 mmol) and CDI (19.5 g, 120 mmol) were stirred in N,N-dimethylformamide (300 mL) at room temperature for 2 hours to obtain a yellow solution. To this solution was then added ammonium acetate (23.1 g, 300 mmol). The resulting mixture was stirred for 3 hours. It was then cooled in an ice-water bath and water (400 mL) was then added dropwise to the reaction mixture to obtain a fine white precipitation which was stirred for 12 hours. The solid was collected by vacuum filtration, washed with water, and dried by suction (25.8 g, 85%): $^1$H NMR (DMSO-d$_6$, δ): 1.75–1.90 (m, 1H), 2.00–2.15 (m, 1H), 2.55–2.80 (m, 2H), 4.43–4.47 (dd, J=8.7, 3.3 Hz, 1H), 6.65 (d, J=8.1 Hz, 1H), 7.35 (m, 2H). CI-MS m/z=304 (M+H$^+$)

EXAMPLE 10

Preparation of [(2R)-6-iodo-3,4-dihydro-2H-chromen-2-yl]methylamine hydrochloride

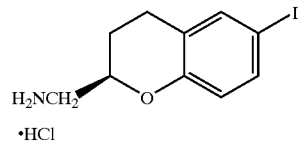

The carboxamide of Example 9 (25.0 g, 82.5 mmol) was suspended in anhydrous tetrahydrofuran (200 mL) at reflux under argon. To this suspension was then added borane/dimethyl sulfide complex (83 mL, 2M in THF) dropwise. The reaction became a clear solution after the addition which was stirred at reflux for 1 hour. Additional borane reagent (70 mL) was added and the reaction was further refluxed for 1 hour. Heating was removed and the reaction was cooled to 0° C. with an ice-water bath. Methanol (38 mL) was added slowly to quench the reaction. The reaction mixture was concentrated in vacuo to about 40% of its initial volume. The residue was then treated with ether/HCl (1 M) to obtain white precipitate which was filtered, washed with ether, and dried by suction (11.7 g, 44%): $^1$H NMR (DMSO-d$_6$, δ): 1.65 (m, 1H), 2.00 (m, 1H), 2.75 (m, 2H), 2.99 (dd, J=13.2, 8.1 Hz, 1H), 3.09–3.1

EXAMPLE 11

Preparation of benzyl [(2R)-6-iodo-3,4-dihydro-2H-chromen-2-yl]methylcarbamate

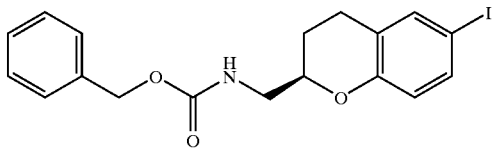

To a mixture of (R)-6-iodo-chroman-2-methylamine hydrochloride of Example 10 (3.3 g, 10 mmol) and benzylchloroformate (1.57 mL, 11 mmol) in tetrahydrofuran (30 mL) cooled in an ice-water bath was added slowly 1N aqueous sodium hydroxide in 20 minutes. The resulting mixture was stirred for 1 hour. The organic layer was separated and concentrated in vacuo. The aqueous layer was extracted with ethyl acetate (50 mL×2). The combined ethyl acetate layer was combined with the above residue and washed with water (50 mL), brine (50 mL), and dried over anhydrous sodium sulfate. Removal of the solvent in vacuo afforded the crude product as a white solid (4.2 g, 99%). $^1$H nmr (DMSO d6) δ 1.5–1.6 (m, 2H), 1.9 2.0 (m, 1H), 2.7 (m, 2H), 3.3 (m, 2H), 4.0 (m, 1H), 5.0 (s, 2H), 6.5 (d, 1H), 7.3 (m, 7H), 7.5 (t, 1H).

EXAMPLE 12

Preparation of tert-butyl [(2R)-6-iodo-3,4-dihydro-2H-chromen-2-yl]methylcarbamate

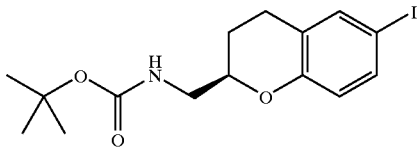

[(2R)-6-iodo-3,4-dihydro-2H-chromen-2-yl]methylamine hydrochloride (Example 10, 3.52 g, 10.83 mmol) was dissolved in THF (20 mL), and treated with 0.91 g (10.83 mmol) of sodium bicarbonate in 2 mL of water, followed by the addition of 2.36 g (10.83 mmol) of di-t-butyldicarbonate. The resulting solution was allowed to stir for 16 hours at room temperature. At this point the solution was concentrated in vacuo and the resulting residue was treated with water and extracted with ethyl acetate. The dried (Na$_2$SO$_4$) ethyl acetate layers were concentrated in vacuo to obtain 4.02 g of product as a yellowish solid; m/z=389.8 [M+].

EXAMPLE 13

Preparation of tert-butyl(dimethyl)silyl [(2R)-6-iodo-3,4-dihydro-2H-chromen-2-yl]methyl ether

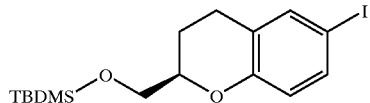

A reaction mixture containing [(2R)-6-iodo-3,4-dihydro-2H-chromen-2-yl]methanol (Example 8, 5 g, 17.2 mmol, 1.0 eq), tert-butyidimethylsilyl chloride (20.6 mmol, 1.2 eq), and imidazole (43 mmol, 2.5 eq) in anhydrous DMF (35 mL) was stirred at 27° C. overnight. The resulting mixture was then cooled to room temperature, poured into water, and extracted with diethyl ether. The organic extract was washed with water, brine, dried over anhydrous sodium sulfate, concentrated, and purified by medium pressure column chromatography (Biotage 40S normal phase silica gel column) providing the product in 79% yield; m/z=405 [MH$^-$].

EXAMPLE 14

Preparation of tert-butyl(dimethyl)silyl [(2R)-6-(4,4,5,5-tetramethyl-1,3,2-dioxaborolan-2-yl)-3,4-dihydro-2H-chromen-2-yl]methyl ether

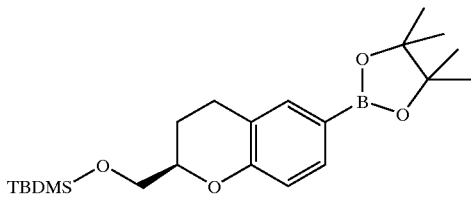

Argon was bubbled through a solution of tert-butyl (dimethyl)silyl [(2R)-6-iodo-3,4-dihydro-2H-chromen-2-yl]methyl ether (Example 13, 11.1 mmol, 1.0 eq.) in dioxane (45 mL) for 10 minutes before Pd(dppf)Cl$_2$ (0.306 mmol, 0.03 eq.), triethylamine (33.4 mmol, 3.0 eq.), and 4,4,5,5-tetramethyl-1,3,2-dioxaborolane (17.8 mmol, 1.6 eq.) were added. The resulting reaction mixture was stirred at 80° C. overnight. The mixture was then filtered through a Celite® pad. The filtrate was concentrated and purified by medium pressure column chromatography (Biotage 40S normal phase silica gel column, hexanes:EtOAc=10:1). The product was obtained as a pale brown waxy solid in 94% yield. MH$^+$=405.3, retention time (LC-MS)=4.79 min.

EXAMPLE 15

Preparation of methyl 4-(4,4,5,5-tetramethyl-1,3,2-dioxaborolan-2-yl)benzoate

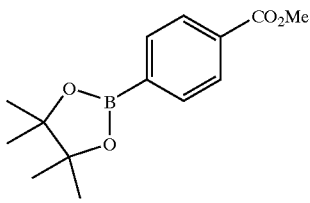

A solution of methyl 4-iodobenzoate (2.00 g, 7.63 mmol) in 30 mL of dioxane was degassed with argon for 10 minutes. Then, 171 mg (3 mol %) Pd(dppf)Cl$_2$, 3.27 mL triethylamine, and 1.47 g (11.45 mmol) pinacolborane were added. The resulting solution was stirred at 85° C. for 16 hours. The mixture was allowed to cool to ambient temperature, filtered through a pad of Celite®, and concentrated in vacuo to obtain 3.97 g of product which was used without further purification. m/z=263 [M+H]$^+$

EXAMPLE 16

Preparation of methyl 4-[(2R)-2-(hydroxymethyl)-3,4-dihydro-2H-chromen-6-yl]benzoate

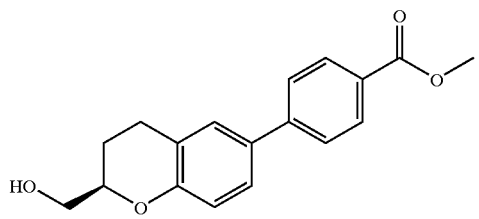

Method (1)

Argon was bubbled through a solution of tert-butyl (dimethyl)silyl [(2R)-6-(4,4,5,5-tetramethyl-1,3,2-dioxaborolan-2-yl)-3,4-dihydro-2H-chromen-2-yl]methyl ether, Example 14, 2.47 mmol, 1.0 eq.) in toluene (60 mL) for 10 minutes. Next, Pd(dppf)Cl$_2$ (0.164 mmol, 0.07 eq.) and methyl 4-iodobenzoate (3.71 mmol, 1.5 eq.) were added in a single portion. The resulting reaction mixture was degassed with argon for an additional 5 minutes before aqueous Na$_2$CO$_3$ (2 M, 26 mmol, 10.5 eq.) was added and the solution was heated at 85° C. overnight. The product mixture was allowed to cool to room temperature, water was added and the two phase mixture was extracted with ethyl acetate. The combined organic extracts were dried over anhydrous sodium sulfate, concentrated, and purified by medium pressure column chromatography (Biotage 40S normal phase silica gel column, hexane:ethyl acetate 10:1). The purified product was dissolved in THF (10 mL) and tetrabutylammonium fluoride (1 M, 5 mL) was added in a single portion. The resulting mixture was stirred at room temperature for 1 hour. The solvents were evaporated and the resulting residue was purified by medium pressure column chromatography (Biotage 40S normal phase silica gel column, hexanes:EtOAc=5:1 to 2:1). The product was obtained as a white solid in yield of 46% (two step yield). MH$^+$=299.2, retention time (LC-MS)=2.79 min.

Method (2)

To a 5-L 3-necked round-bottomed flask were charged 4-methoxycarbonyl phenylboronic acid (72.0 g, 0.4 mol), potassium carbonate (124.4 g, 0.9 mol), and water (900 mL) to obtain a suspension. To this suspension was then added a solution of [(2R)-6-iodo-3,4-dihydro-2H-chromen-2-yl]methanol (Example 8, 105.5 g, 0.36 mol) in acetone (720 mL). The resultant mixture became a near homogeneous solution (internal temperature rose from 20 to 28° C.). Palladium acetate (1.5 g, 0.0067 mol) was then added in one portion. The reaction mixture was then heated at 65° C. under argon for 2 hours. It turned into a suspension. Heating was removed and the reaction was allowed to cool to room temperature. The solid (metallic color) was then collected by filtration and dried by suction. The crude was then dissolved in chloroform (2 L) and filtered through a pad of Celite® (100 g) under vacuum slowly to remove palladium. Removal of solvent in vacuo afforded the desired compound as a white solid (90 g, 84% yield): $^1$H NMR (CDCl$_3$, δ):1.82–2.12 (m, 3H), 2.80–3.02 (m, 2H), 3.75–3.90 (m, 2H) 3.92 (s, 3H), 4.20 (m, 1H), 6.91 (d, J=8.1 Hz, 1H), 7.33 (s, 1H), 7.37 (dd, J=8.1, 2.7 Hz, 1H), 7.60 (d, J=9 Hz, 2H), 8.06 (d, J=8.7 Hz, 2H).

EXAMPLE 17

Preparation of methyl 3-[(2R)-2-(hydroxymethyl)-3,4-dihydro-2H-chromen-6-yl]benzoate

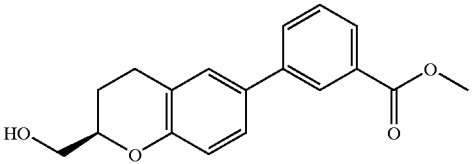

Using essentially the same procedure as Example 16, Method (1), and substituting the appropriate starting materials, methyl 3-[(2R)-2-(hydroxymethyl)-3,4-dihydro-2H-chromen-6-yl]benzoate was prepared in yield of 68% (two steps). MH=313.1, retention time (LC-MS)=3.00 min.

EXAMPLE 18

Preparation of methyl 4-(2R)-2-{[(tert-butoxycarbonyl)amino]methyl}-3,4-dihydro-2H-chromen-6-yl) benzoate

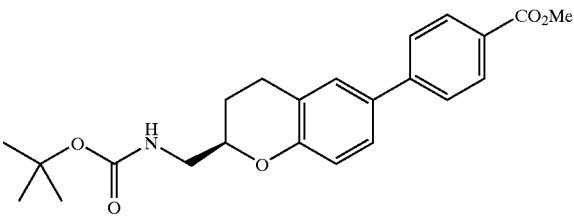

A solution of methyl 4-(4,4,5,5-tetramethyl-1,3,2-dioxaborolan-2-yl)benzoate (Example 15, 1.67 g, 6.36 mmol) in 130 mL toluene and 27 mL 1,4-dioxane was degassed with argon for 10 minutes. tert-Butyl [(2R)-6-iodo-3,4-dihydro-2H-chromen-2-yl]methylcarbamate (Example 12, 1.65 g) and 265 mg (3 mol %) Pd(dppf)Cl$_2$ were then added, and the solution was degassed with argon for an additional 5 minutes. Finally, 26.5 mL of 2M aqueous sodium carbonate was added and the solution was stirred at 85° C. for 16 hours. This mixture was then cooled to ambient temperature, filtered through a pad of Celite®, and concentrated in vacuo. The product was then purified by Biotage (100% methylene chloride to 3% MeOH: methylene chloride) to obtain 1.40 g of product. m/z=397.9 [M+].

EXAMPLE 19

Preparation of methyl 4-[(2R)-2-(aminomethyl)-3,4-dihydro-2H-chromen-6-yl]benzoate

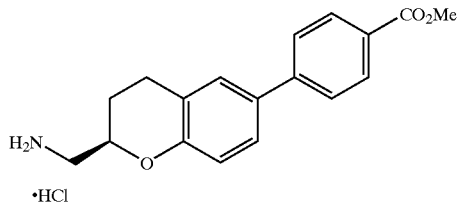

To a solution of methyl 4-(2R)-2-{[(tert-butoxycarbonyl)amino]methyl}-3,4-dihydro-2H-chromen-6-yl) benzoate (Example 18, 0.94 g, 2.37 mmol) in 5 mL 1,4-dioxane was added 1 mL of 4M hydrochloric acid in 1,4-dioxane dropwise. The resulting solution was allowed to stir at room temperature for 16 hours, followed by concentration in vacuo. At this point, diethyl ether was added and the solid was collected to provide 587 mg of product as a white solid. m/z=298.2 [MH+].

EXAMPLE 20

Preparation of methyl 4-[(2R)-2-formyl-3,4-dihydro-2H-chromen-6-yl]benzoate

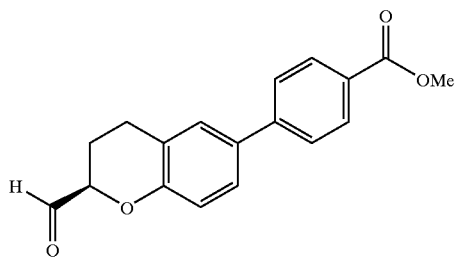

To a solution of 33 mg (0.425 mmol) dimethyl sulfoxide in 2 mL of methylene chloride at −78° C., was added 0.14 mL (0.272 mmol) 2M oxalyl chloride. After the solution had stirred at this temperature for 10 minutes, a solution of 50 mg (0.17 mmol) methyl 4-[(2R)-2-(hydroxymethyl)-3,4-dihydro-2H-chromen-6-yl]benzoate (Example 16) in 2 mL of methylene chloride was added dropwise and the resulting mixture was stirred at −78° C. for an additional 1.6 hours. At this time, 0.14 mL (1.02 mmol) triethylamine was added to the mixture slowly, and then it was allowed to warm to room temperature over 15 minutes. The solution of desired product was used without further purification.

EXAMPLE 21

Preparation of methyl 4-chloro-2-pyridinecarboxylate

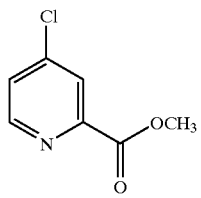

To 50° C. thionyl chloride (14.8 mL, 203.1 mmol, 5.0 eq.) was added dry N,N-dimethylformamide (0.62 mL, 8.12 mmol, 0.20 eq.). The solution was stirred for 15 minutes before picolinic acid (5.0 g, 40.6 mmol) was added as a solid. The reaction was immediately warmed to reflux. After 16 hours at reflux, the mixture was cooled to room temperature and concentrated by rotary evaporation. The residue was diluted with toluene and concentrated again. The resulting oil was poured into a molar excess of methanol and stirred for 1 hour at room temperature. The methanol was removed by rotary evaporation, and the resulting crude was partitioned between ethyl acetate and water. The aqueous layer was adjusted to pH 7 with 1N aqueous sodium hydroxide, and the layers were separated. The organic layer was washed with brine, dried (MgSO$_4$), and concentrated in vacuo to a dark oil. Purification by flash chromatography on silica gel eluted on a gradient from 100:0 to 70:30 hexanes/ethyl acetate provided the title compound as a pale orange solid (3.5 g, 50%): $^1$H NMR (300 MHz, CDCl$_3$) δ 8.61 (d, 1 H), 8.10 (s, 1 H), 7.46 (d, 1 H), 3.98 (s, 3 H); MS m/z 172.1 (MH$^+$).

EXAMPLE 22

Preparation of 4-chloro-2-pyridinecarboxamide

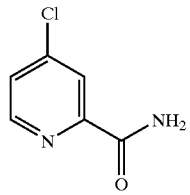

Using the same procedure described in Example 21 and substituting aqueous ammonia (28%) for methanol, the title compound was obtained by filtration (1.91 g, 76% yield): MS m/z 157.8 (MH$^+$), retention time (LC-MS)=1.08 minutes.

EXAMPLE 23

Preparation of ethyl 2-chloro-3-oxo-3-phenylpropanoate

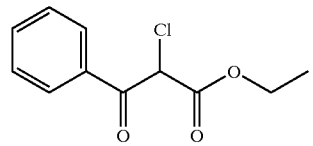

A solution of sulfuryl chloride (12.4 mmol) in toluene (5 mL) was added dropwise via an additional funnel to a solution of ethyl benzoylacetate (12.4 mmol) in toluene (20 mL) over 5 minutes at room temperature. The resulting mixture was stirred at room temperature overnight. Water was added slowly and resulting two-phase mixture was basified with saturated NaHCO$_3$ and extracted with ethyl acetate. The combined organic extracts were washed with brine, dried over anhydrous sodium sulfate, and evaporated to afford 2.2 g (84%) of product as a pale yellow oil; MH$^+$=227.0, retention time (LC-MS)=2.77 min.

EXAMPLE 24

Preparation of ethyl 2-chloro-4-methyl-3-oxopentanoate

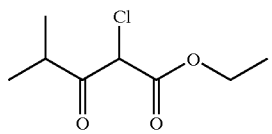

Utilizing the method described for Example 23, the product was obtained in 67% yield (crude). MH$^+$=193.0, retention time (LC-MS)=2.45 min.

EXAMPLE 25

Preparation of methyl 2-amino-5-phenyl-1,3-thiazole-4-carboxylate

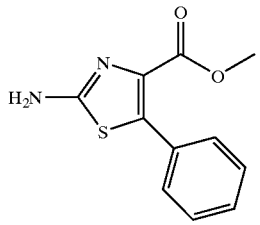

A solution of 25 wt % NaOMe in MeOH (13.4 mmol) was added to a solution of methyl dichloroacetate (13.4 mmol) and benzaldehyde (14.8 mmol, 1.1 eq.) in diethyl ether (8 mL) dropwise at 0° C. The reaction mixture was stirred at 0° C. for 1 hour before diethyl ether and brine were added. The organic layer was separated, dried over anhydrous sodium sulfate, and evaporated to give a crude material which was dissolved in MeOH (16 mL) containing thiourea (11.4 mmol, 0.85 eq.). The resulting reaction mixture was heated to reflux for 18 hours. The crude product mixture was concentrated in vacuo, neutralized with 18M—NH$_4$OH at which time the product precipitated as a white solid. The product was washed with CH$_2$Cl$_2$ (2×), water and was collected by filtration to afford 1.88 g (70%) of product; MH$^+$=235.1, R$_f$=0.18 (Hexanes:EtOAc=1:1), retention time (LC-MS)=1.86 min.

EXAMPLE 26

Preparation of methyl 2-amino-5-isopropyl-1,3-thiazole-4-carboxylate

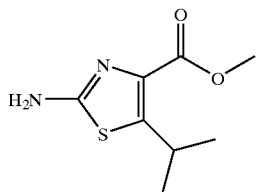

The title compound was prepared according to method of Example 25 in 88% yield. MH$^+$=201.0, retention time (LC-MS)=1.48 min.

EXAMPLE 27

Preparation of ethyl 2-amino-4-phenyl-1,3-thiazole-5-carboxylate

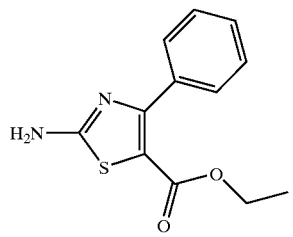

A solution of ethyl 2-chloro-3-oxo-3-phenylpropanoate (Example 23, 9.73 mmol) and thiourea (9.73 mmol) in EtOH (25 mL) was heated at reflux overnight. The resulting mixture was concentrated in vacuo, neutralized with 18M—NH$_4$OH, and extracted with CH$_2$Cl$_2$. The organic phase was washed with brine, dried over anhydrous sodium sulfate, and concentrated to afford a yellow solid that was washed with MeOH (3 mL) and dried to afford the product in 89% yield as a pale yellow solid. MH$^+$=249.1, R$_f$=0.29 (Hexanes:EtOAc=1:1). MH$^+$=249.1, retention time (LC-MS)=2.37 min.

EXAMPLE 28

Preparation of ethyl 2-amino-4-isopropyl-1,3-thiazole-5-carboxylate

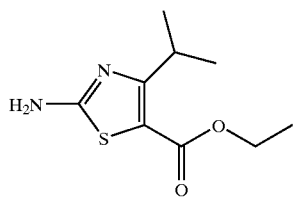

The title compound was prepared according to method of Example 27 in 65% yield. MH$^+$=215.1, R$_f$=0.66 (hexanes:EtOAc=1:1), retention time (LC-MS)=1.98 min.

EXAMPLE 29

Preparation of ethyl 5-phenyl-1,3-oxazole-4-carboxylate

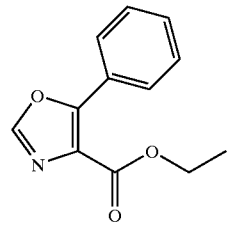

To a mixture of ethyl isocyanoacetate (8.74 mmol) and 1,8-diazabicyclo(5.4.0)undec-7-ene (8.84 mmol) in THF (12 mL) was added a solution of benzoic anhydride (8.84 mmol) in THF (2 mL) at 10° C. with stirring. The resulting mixture was maintained with vigorous stirring for 18 hours at room temperature. The solvent was evaporated to afford a residue that was partitioned between EtOAc and water. The organic extract was dried over anhydrous sodium sulfate and concentrated to afford an amber oil which was purified by medium pressure column chromatography (Biotage 40S normal phase silica gel column, hexanes:EtOAc=6:1 to 4:1 to 2:1). The product was obtained as a clear oil in 42%. MH$^+$=218.1, retention time (LC-MS)=2.52 min.

EXAMPLE 30

Preparation of methyl 2-bromo-5-phenyl-1,3-thiazole-4-carboxylate

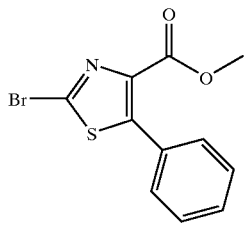

To a dark brown solution of copper(II) bromide (3.85 mmol, 3 eq.) in acetonitrile (5 mL) in a two-neck round-bottomed flask equipped with a condenser was added tert-butyl nitrite (1.92 mmol, 1.5 eq.) slowly at room temperature. The resulting mixture was heated to 60° C. at which time a suspension of methyl 2-amino-5-phenyl-1,3-thiazole-4-carboxylate (Example 25, 1.28 mmol) in acetonitrile (7 mL) was added dropwise. The resulting reaction mixture was heated at 60° C. for 3 hours, allowed to cool to room temperature, poured to 1M NaOH aqueous, and extracted with EtOAc. The organic extracts were dried over anhydrous sodium sulfate, concentrated, and purified by medium pressure column chromatography (Biotage 40S normal phase silica gel column, hexanes:EtOAc=5:1). The product was obtained as a pale yellow oil in 88%. $MH^+$=298.0, $R_f$=0.74 (hexanes:EtOAc=2:1), retention time (LC-MS)=3.01 min.

EXAMPLES 31–33

Preparation of methyl 2-bromo-5-isopropyl-1,3-thiazole-4-carboxylate, ethyl 2-bromo-4-phenyl-1,3-thiazole-5-carboxylate and ethyl 2-bromo-4-isopropyl-1,3-thiazole-5-carboxylate Using essentially the same procedure and substituting the appropriate starting amino compound, the following bromothiazoles were prepared and characterized according to method of Example 30:

TABLE 2

| Ex. No. | Structure | MS [M + H⁺] | Starting Material (Ex. No.) | Rf | RT (min, LC-MS) |
|---|---|---|---|---|---|
| 31 | 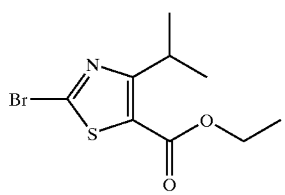 | 264.0 | 28 | 0.51 hexanes:EtOAc 6:1 | 2.83 |
| 32 | 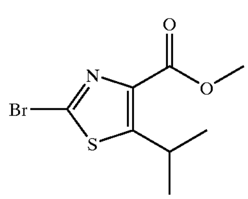 | 312.1 | 26 | 0.65 hexanes:EtOAc 6:1 | 3.46 |
| 33 | 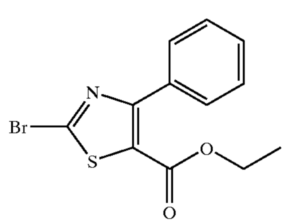 | 278.2 | 27 | 0.74 hexanes:EtOAc 6:1 | 3.54 |

EXAMPLE 34

Preparation of ethyl 2-iodo-5-phenyl-1,3-oxazole-4-carboxylate

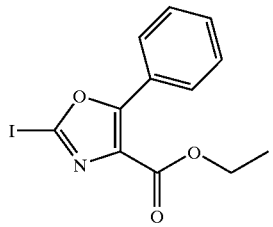

To a solution of ethyl 5-phenyl-1,3-oxazole-4-carboxylate (Example 29, 0.921 mmol, 1 eq.) in THF (7 mL) at −78° C. was added a solution of lithium bis(trimethylsilyl)amide in THF (1M, 1.11 mmol, 1.2 eq.) dropwise by syringe. The resulting solution was stirred at −78° C. for 1 hour at which time a solution of iodine (1.38 mmol, 1.5 eq. in 2 mL THF) was added dropwise by a syringe. The reaction mixture was allowed to warm to room temperature and stirred at this temperature for 1.5 hours. The resulting solution was poured onto 10% aqueous $NaS_2O_3$ (15 mL) and extracted with ethyl acetate. The organic extracts were washed with brine, dried over anhydrous sodium sulfate, concentrated in vacuo and purified by medium pressure column chromatography (Biotage 40S normal phase silica gel column, hexanes:EtOAc=9:1). The product was obtained as a pale yellow solid in 82% yield. $MH^+$=344.0, $R_f$=0.31 (hexanes:EtOAc=6:1), retention time (LC-MS)=3.01 min.

EXAMPLE 35

Method A. Preparation of (2R)-N-[(2R)-2-hydroxy-2-(3-pyridinyl)ethyl]-6-iodo-3,4-dihydro-2H-chromene-2-carboxamide

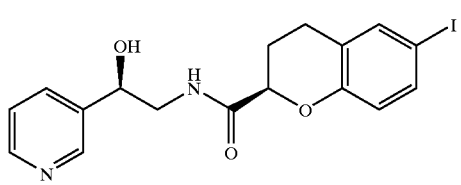

(1R)-2-Amino-1-(3-pyridinyl)ethanol dihydrochloride (U.S. Pat. No. 6,051,586) (5.73 g, 27.1 mmol), 1-hydroxybenzotriazole (6.67 g, 49.3 mmol), 1-(3-dimethylaminopropyl)-3-ethylcabodiimide hydrochloride (9.46 g, 49.3 mmol), and triethylamine (13.8 mL, 9.98 g, 98.7 mmol) were added successively to a stirred solution of (2R)-6-iodo-3,4-dihydro-2H-chromene-2-carboxylic acid (Example 7, Method A, 7.50 g, 24.7 mmol) in dichloromethane (100 mL). The reaction was stirred for 18 hours and then diluted with dichloromethane (300 mL). The solution was washed with saturated aqueous sodium bicarbonate (300 mL) and then the aqueous layer was back-extracted with dichloromethane (2×100 mL). The combined organic extracts were washed with brine, dried over anhydrous magnesium sulfate, filtered, and concentrated in vacuo. Flash chromatography of the residue over silica gel using 5–10% methanol/ethyl acetate gave the product (7.80 g, 74%) as a white solid: $^1$H NMR (acetone-$d_6$, δ): 8.55 (d, J=1.6 Hz, 1 H), 8.44 (dd, J=4.7, 1.6 Hz, 1 H), 7.71 (ddd, J=7.9, 1.8, 1.8 Hz, 1 H), 7.59 (s, 1 H), 7.35–7.42 (m, 2 H), 7.27 (dd, J=7.9, 4.7 Hz, 1 H), 6.63 (d, 9.6 Hz, 1 H), 4.98 (d, J=4.2 Hz, 1 H), 4.85–4.93 (m, 1 H), 4.53 (dd, J=8.8, 3.4 Hz, 1 H), 3.38–3.70 (m, 2 H), 2.61–2.91 (m, 4 H), 2.16–2.28 (m, 2 H), 1.85–1.99 (m, 1 H); mass spectroscopy gave m/z= 425.1 $[M+H]^+$.

Method B. Preparation of (2S)-N-[(2R)-2-hydroxy-2-(3-pyridinyl)ethyl]-6-iodo-3,4-dihydro-2H-chromene-2-carboxamide

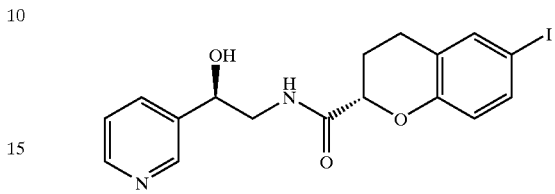

Using the same procedure described in Method A, using (2S)-6-iodo-3,4-dihydro-2H-chromene-2-carboxylic acid (Example 7, Method B) and (1R)-2-amino-1-(3-pyridinyl)ethanol dihydrochloride (U.S. Pat. No. 6,051,586), the title compound was obtained as a white solid in 87% yield. $^1$H NMR (DMSO-$d_6$) δ 8.47 (d, J=2.2 Hz, 1 H), 8.43 (dd, J=6.6, 1.8 Hz, 1 H), 7.90 (t, J=7.1 Hz, 1 H), 7.69–7.60 (m, 1 H), 7.40–7.37 (m, 2 H), 7.30–7.26 (m, 1 H), 6.66 (d, J=9.1 Hz, 1 H), 5.66 (d, J=4.6 Hz, 1 H), 4.72 (q, J=5.0 Hz, 1 H), 4.52 (dd, J=8.3, 3.3 Hz, 1 H), 4.12 (dd, J=6.1, 1.8 Hz, 1 H), 3.36–3.32 (m, 1 H), 2.77–2.65 (m, 1 H), 2.58–2.52 (m, 1 H), 2.08–2.00 (m, 1 H), 1.85–1.73 (m, 1 H). LC-MS m/z 425.1 ($MH^+$), RT=2.07 minutes.

EXAMPLE 36

Method A. Preparation of (1R)-2-({[(2R)-6-iodo-3,4-dihydro-2H-chromen-2-yl]methyl}amino)-1-(3-pyridinyl)ethanol

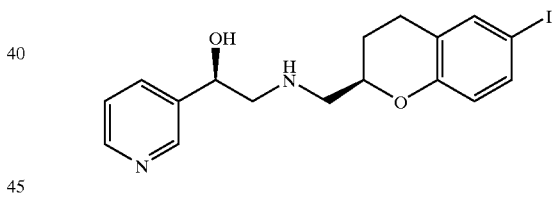

Borane-dimethylsulfide complex (2.0 M in tetrahydrofuran, 46 mL, 92 mmol) was added dropwise (20 minutes) to a cooled (0° C.) and stirred solution of (2R)-N-[(2R)-2-hydroxy-2-(3-pyridinyl)ethyl]-6-iodo-3,4-dihydro-2H-chromene-2-carboxamide (Example 35, Method A, 7.75 g, 18.3 mmol) in tetrahydrofuran (300 mL). The solution was warmed to reflux for 1 hour and then cooled to room temperature. The reaction was quenched with addition of methanol (12 mL) and 2 M hydrochloric acid (95 mL), and then the resulting solution was heated at reflux for 1 hour. The reaction was cooled to room temperature and then the solution was adjusted to pH 9 using 1 M aqueous sodium hydroxide. The mixture was diluted with brine (500 mL) and the layers were separated. The aqueous layer was extracted with ethyl acetate (2×200 mL) and then the combined organic extracts were washed with brine, dried over anhydrous magnesium sulfate, and concentrated in vacuo. Flash chromatography of the residue over silica gel using 30–50% ethyl acetate/hexane afforded product (6.32 g, 84%) as a waxy yellow solid: $^1$H NMR (acetone-$d_6$, δ): 8.59 (d, J=1.9 Hz, 1 H), 8.44 (dd, J=5.0, 1.5 Hz, 1 H), 7.77 (ddd, J=8.0, 1.8, 1.8 Hz, 1 H), 7.25–7.39 (m, 3 H), 6.56 (d, J=8.4 Hz, 1 H), 4.80 (dd, J=8.4, 4.0 Hz, 1 H), 4.08–4.18 (m, 1 H), 2.67–3.00 (m, 10 H), 1.67–1.82 (m, 1 H); mass spectroscopy gave m/z=410.9 [M+H]⁺.

Method B. Preparation of (1R)-2-({[(2S)-6-iodo-3,4-dihydro-2H-chromen-2-yl]methyl}amino)-1-(3-pyridinyl)ethanol

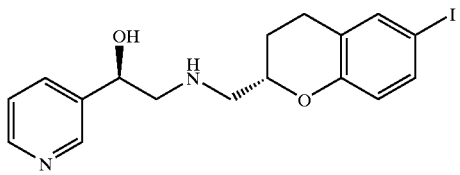

Using the same procedure described in Method A using (2S)-N-[(2R)-2-hydroxy-2-(3-pyridinyl)ethyl]-6-iodo-3,4-dihydro-2H-chromene-2-carboxamide (Example 35, Method B), the title compound was obtained as a crude oil after quench and extractive workup. The crude material was not purified before carrying on to the next step. LC-MS m/z 411.3 (MH⁺), RT=2.23 minutes.

EXAMPLE 37

Method A. Preparation of tert-butyl (2R)-2-hydroxy-2-(3-pyridinyl)ethyl{[(2R)-6-iodo-3,4-dihydro-2H-chromen-2-yl]methyl}carbamate

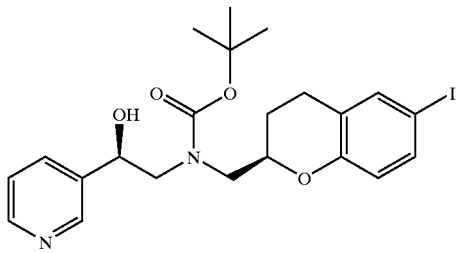

A solution of di-tert-butyl dicarbonate (3.46 g, 15.9 mmol) in tetrahydrofuran (20+5 mL rinse) was added to a cooled (0° C.) and stirred solution of (1R)-2-({[(2R)-6-iodo-3,4-dihydro-2H-chromen-2-yl]methyl}amino)-1-(3-pyridinyl)ethanol (Example 36, Method A, 6.20 g, 15.1 mmol) in tetrahydrofuran (75 mL). The mixture was stirred at 0° C. for 1 hour, warmed to room temperature, and stirred for 18 hours. The solution was concentrated in vacuo and then flash chromatography of the residue over silica gel using ethyl acetate gave product (7.23 g, 93%) as a glassy white solid: ¹H NMR (acetone-d₆, δ): 8.57 (s, 1 H), 8.46 (s, 1 H), 7.70 (d, J=7.5 Hz, 1 H), 7.27–7.40 (m, 3 H), 6.57 (d, J=8.5 Hz, 1 H), 4.76–5.11 (m, 2 H), 4.17–4.28 (m, 1 H), 3.42–3.75 (m, 4 H), 2.69–2.90 (m, 1 H), 1.94–2.06 (m, 1 H), 1.58–1.75 (m, 1 H), 1.41 (d, J=7.6 Hz, 9 H); mass spectroscopy gave m/z=510.9 [M+H]⁺.

Method B. Preparation of tert-butyl (2R)-2-hydroxy-2-(3-pyridinyl)ethyl{[(2S)-6-iodo-3,4-dihydro-2H-chromen-2-yl]methyl}carbamate

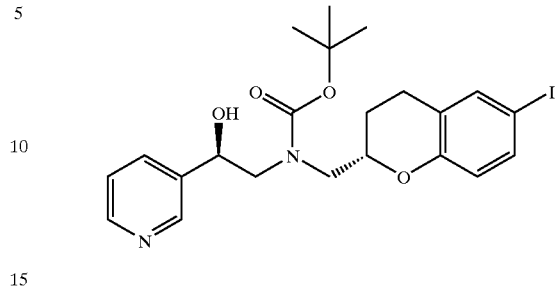

Using the same procedure described in Method A, with (1R)-2-({[(2S)-6-iodo-3,4-dihydro-2H-chromen-2-yl]methyl}amino)-1-(3-pyridinyl)ethanol (Example 36, Method B), the title compound was obtained (55% overall yield for the reduction to the amine and protection as the carbamate). LC-MS m/z 511.1 (MH⁺), RT=2.59 minutes.

EXAMPLE 38

Method A. Preparation of tert-butyl (2R)-2-{[tert-butyl(dimethyl)silyl]oxy}-2-(3-pyridinyl)ethyl{[(2R)-6-iodo-3,4-dihydro-2H-chromen-2-yl]methyl}carbamate

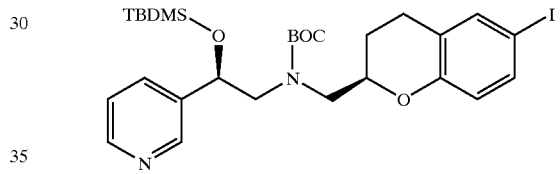

A mixture of tert-butyl (2R)-2-hydroxy-2-(3-pyridinyl)ethyl([(2R)-6-iodo-3,4-dihydro-2H-chromen-2-yl]methyl}carbamate (Example 37, Method A, 6.35 g, 12.4 mmol), TBDMSCl (2.25 g, 14.9 mmol) and imidazole (2.10 g, 30.9 mmol) in DMF (10 mL) was stirred at room temperature under argon for 24 hours. The reaction mixture was then poured into a saturated NaHCO₃ solution (50 mL). The mixture was extracted with ether (100 mL×2). The ether layer was washed with water (50 mL) and dried over anhydrous sodium sulfate. Removal of the solvent in vacuo afforded a near white syrup which was purified by column chromatography (silica gel, hexanes/ethyl acetate (5/1, v/v)) giving the desired compound as a colorless oil. LC-MS m/z 625.0 (MH+), RT=4.09 minutes.

Method B. Preparation of tert-butyl (2R)-2-{[tert-butyl(dimethyl)silyl]oxy}-2-(3-pyridinyl)ethyl{[(2S)-6-iodo-3,4-dihydro-2H-chromen-2-yl]methyl}carbamate

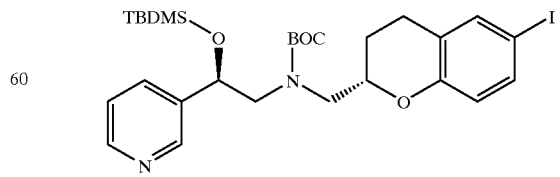

Using the same procedure described in Method A, using tert-butyl (2R)-2-hydroxy-2-(3-pyridinyl)ethyl{[((2S)-6- iodo-3,4-dihydro-2H-chromen-2-yl]methyl}carbamate (Example 37, Method B) as starting material, the title compound was obtained in 65% yield. LC-MS m/z 625.3 (MH⁺), RT=3.54 minutes.

EXAMPLE 39

Preparation of (1R)-2-({[(2R)-6-(3,4-dichlorophenyl)-3,4-dihydro-2H-chromen-2-yl]methyl}amino)-1-(3-pyridinyl)ethanol

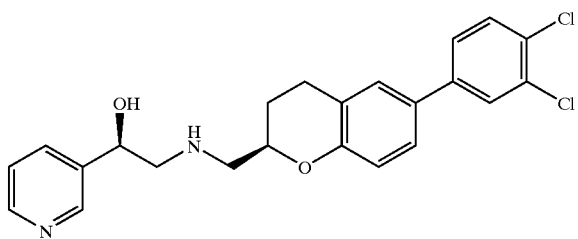

3,4-Dichlorophenylboronic acid (34 mg, 0.18 mmol), a solution of palladium acetate (3 mg, 0.01 mmol) and triphenylphosphine (12 mg, 0.05 mmol) in toluene (1 mL), and 2 M aqueous sodium carbonate (1 mL) were added successively to a solution of tert-butyl (2R)-2-hydroxy-2-(3-pyridinyl)ethyl{[(2R)-6-iodo-3,4-dihydro-2H-chromen-2-yl]methyl}carbamate (Example 37, 60 mg, 0.12 mmol) in toluene (2 mL). The mixture was heated (80° C.) and stirred for 16 hours. After cooling the reaction was diluted with dichloromethane (5 mL) and the layers were separated. The organic layer was concentrated in vacuo and the residue was dissolved in a solution of 4 M hydrogen chloride in dioxane (4 mL). The solution was stirred for 16 hours and then concentrated in vacuo. Preparative reverse phase HPLC of the residue using acetonitrile/water afforded 10.3 mg (20%) of the desired product (retention time=2.19 min.): $^1$H NMR (CD$_3$OD, δ): 8.71 (d, J=2.2 Hz, 1 H), 8.59 (dd, J=5.1, 1.5 Hz, 1 H), 8.11 (ddd, J=7.9, 1.7, 1.7 Hz, 1 H), 7.71 (d, J=2.3 Hz, 1 H), 7.61 (dd, J=7.9, 5.1 Hz, 1 H), 7.37–7.56 (m, 4 H), 6.99 (d, 9.2 Hz, 1 H), 5.22 (dd, J=10.5, 2.9 Hz, 1 H), 4.43–4.54 (m, 1 H), 3.26–3.55 (m, 4 H), 2.87–3.10 (m, 2 H), 2.11–2.22 (m, 1 H), 1.76–1.92 (m, 1 H); mass spectroscopy gave m/z=429.2 [M+H]⁺.

Using essentially the same method as described for Example 39 and using Example 37 and appropriate substituted phenylboronic acid as starting materials, the following compounds were prepared and characterized in Table 3.

TABLE 3

| Example No. | Y | MS [M+ H⁺] | HPLC RT (min) |
|---|---|---|---|
| 40 | 2-CF₃-phenyl | 429.2 | 2.00 |
| 41 | 3-Cl-phenyl | 395.2 | 2.03 |
| 42 | 3-NO₂-phenyl | 406.2 | 1.86 |
| 43 | 3-OMe-phenyl | 391.2 | 1.75 |

TABLE 3-continued

| Example No. | MS Y | RT [M+ H+] | HPLC (min) |
|---|---|---|---|
| 44 | 4-CF₃-phenyl | 429.2 | 2.07 |
| 45 | 4-methyl-phenyl | 375.2 | 1.94 |
| 46 | 4-Cl-phenyl | 395.2 | 1.99 |
| 47 | 4-phenyl-phenyl (biphenyl) | 437.3 | 2.27 |
| 48 | 4-F-phenyl | 379.2 | 1.86 |
| 49 | 4-SMe-phenyl | 407.2 | 1.98 |
| 50 | benzo[1,3]dioxol-5-yl | 405.2 | 1.80 |
| 51 | 2,4-dichloro-phenyl | 429.2 | 2.14 |
| 52 | 4-F-3-Cl-phenyl | 413.2 | 2.04 |

TABLE 3-continued
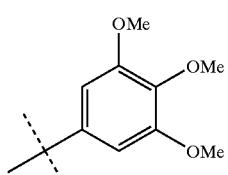
| Example No. | MS Y | RT [M+ H+] | HPLC (min) |
|---|---|---|---|
| 53 | 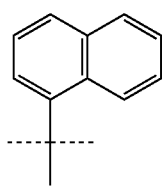 3,4,5-tri-OMe phenyl | 451.2 | 1.72 |
| 54 | 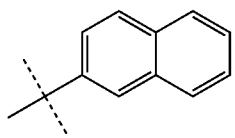 1-naphthyl | 411.2 | 2.09 |
| 55 | 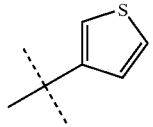 2-naphthyl | 411.2 | 2.15 |
| 56 | 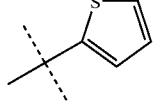 3-thienyl | 367.2 | 1.77 |
| 57 | 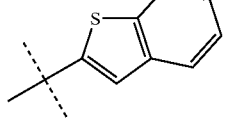 2-thienyl | 367.2 | 1.74 |
| 58 | 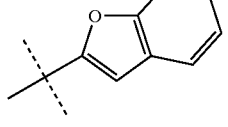 benzothiophene | 417.2 | 2.09 |
| 59 | 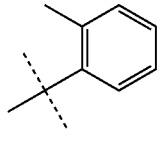 benzofuran | 401.2 | 2.04 |
| 60 | 2-methylphenyl | 375.2 | 1.92 |

TABLE 3-continued
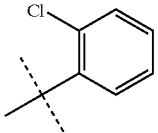
| Example No. | MS Y | RT [M+ H⁺] | HPLC (min) |
|---|---|---|---|
| 61 | 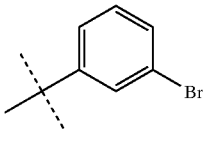 | 395.2 | 1.95 |
| 62 | 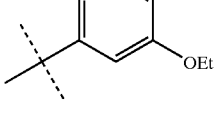 | 439.2 | 2.06 |
| 63 | 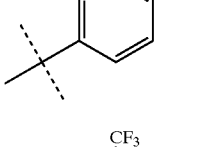 | 405.2 | 1.95 |
| 64 | 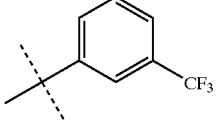 | 439.2 | 2.06 |
| 65 | 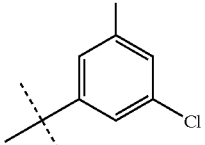 | 497.2 | 2.30 |
| 66 | 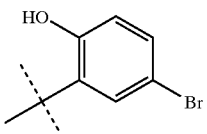 | 429.1 | 2.20 |
| 67 | 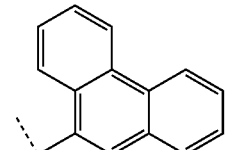 | 455.2 | 1.93 |
| 68 |  | 461.3 | 2.32 |

TABLE 3-continued

| Example No. | MS Y | RT [M+ H⁺] | HPLC (min) |
|---|---|---|---|
| 69 | (4-methyl-3-nitrophenyl) | 420.2 | 1.99 |

EXAMPLE 70

Preparation of 4-{(2R)-2-[([(2R)-2-{[(1,1-dimethylethyl)(dimethyl)silyl]oxy}-2-(3-pyridinyl)ethyl]{[(1,1-dimethylethyl)oxy]carbonyl}amino)methyl]-3,4-dihydro-2H-chromen-6-yl}-2-pyridinecarboxylic acid

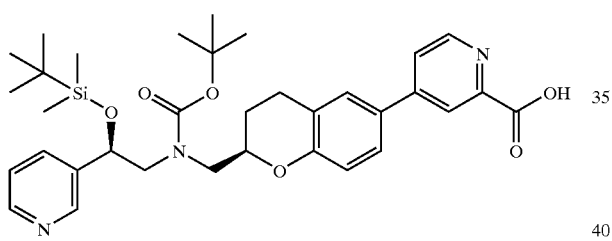

Argon was bubbled through a mixture of (1R)-1-(3-pyridinyl)-2-({[(2R)-6-(4,4,5,5-tetramethyl-1,3,2-dioxaborolan-2-yl)-3,4-dihydro-2H-chromen-2-yl]methyl}amino)ethanol (Example 81, 1, 0.50 g, 0.80 mmol) and methyl 4-chloro-2-pyridinecarboxylate (Example 21, 0.15 g, 0.88 mmol, 1.1 eq.) in toluene (2 mL), ethanol (2 mL), and 2M aqueous sodium carbonate (2 mL) for 15 minutes. Triphenylphosphine (0.04 g, 0.16 mmol, 0.2 eq.) and palladium (II) acetate (0.01 g, 0.04 mmol, 0.05 eq.) were added, and the mixture was stirred vigorously under argon at 85° C. overnight. The reaction was cooled and filtered through a pad of Celite® with the aid of ethyl acetate. The filtrate was transferred to a separatory funnel where the layers were separated. The organic layer was concentrated in vacuo to remove excess solvents, and the resulting oil was dissolved in ethyl acetate. The ethyl acetate solution was extracted with a 1:1 solution of saturated aqueous sodium bicarbonate and water. The aqueous layer was adjusted to pH 4 with 1N aqueous HCl, then extracted with chloroform (2×). The combined organic layers were dried (Na₂SO₄) and concentrated in vacuo to provide the title compound as an orange oil (0.24 g, 48%): $^1$H NMR (300 MHz, CDCl₃) δ 8.62 (d, 1 H), 8.55 (broad s, 1H), 8.39 (s, 1 H), 7.78–7.66 (m, 2 H), 7.51–7.48 (m, 1 H), 7.42 (broad s, 2 H), 7.34–7.31 (m, 1 H), 6.82 (dd, 1 H), 5.15–4.97 (m, 1 H), 4.24–4.12 (m, 3 H), 3.76–3.61 (m, 1 H), 3.46–3.30 (m, 1 H), 2.88–2.83 (m, 1 H), 2.05–1.95 (m, 1 H), 1.72–1.62 (m, 2 H), 1.21 (s, 9 H), 0.86 (s, 9 H), 0.03 (s, 3 H), −0.15 (s, 3 H); MS m/z 620.3 (MH⁺).

EXAMPLE 71

Preparation of 4-[(2R)-2-({[(2R)-2-hydroxy-2-(3-pyridinyl)ethyl]amino}methyl)-3,4-dihydro-2H-chromen-6-yl]-2-pyridinecarboxylic acid

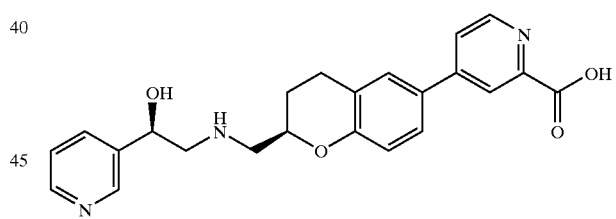

4-{(2R)-2-[([(2R)-2-{[(1,1-Dimethylethyl)(dimethyl)silyl]oxy}-2-(3-pyridinyl)ethyl]{[(1,1-dimethylethyl)oxy]carbonyl}amino)methyl]-3,4-dihydro-2H-chromen-6-yl}-2-pyridinecarboxylic acid (Example 70, 29 mg, 0.05 mmol) was stirred in an excess of 4M HCl in dioxane at room temperature for 18 hours. The volatile components were removed by rotary evaporation, and the residue was washed with dichloromethane. After drying under vacuum, the title compound was collected as the tri-hydrochloride salt (23 mg, 93%): $^1$H NMR (300 MHz, CD₃OD) δ 9.07 (broad s, 1 H), 8.90 (d, 1 H), 8.83–8.78 (m, 3 H), 8.49 (d, 1 H), 8.18 (t, 1 H), 7.94–7.89 (m, 2 H), 7.20 (d, 1 H), 5.52–5.46 (m, 1 H), 4.67–4.61 (m, 1 H), 3.76–3.57 (m, 2 H), 3.51–3.39 (m, 2 H), 3.10–3.05 (m, 2 H), 2.29–2.20 (m, 1 H), 1.95–1.83 (m, 1 H); MS m/z 406.2 (MH⁺ of the free base).

EXAMPLE 72

Preparation of methyl 4-[(2R)-2-({[(2R)-2-hydroxy-2-(3-pyridinyl) ethyl]amino}methyl)-3,4-dihydro-2H-chromen-6-yl]-2-pyridinecarboxylate

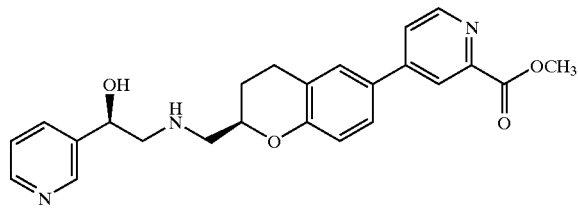

Argon was bubbled through a mixture of (1R)-1-(3-pyridinyl)-2-({[(2R)-6-(4,4,5,5-tetramethyl-1,3,2-dioxaborolan-2-yl)-3,4-dihydro-2H-chromen-2-yl]methyl}amino)ethanol (Example 81, 0.50 g, 0.80 mmol) and methyl 4-chloro-2-pyridinecarboxylate (Example 21, 0.15 g, 0.88 mmol, 1.1 eq.) in toluene (2 mL), ethanol (2 mL), and 2M aqueous sodium carbonate (2 mL) for 15 minutes. Triphenylphosphine (0.04 g, 0.16 mmol, 0.2 eq.) and palladium (II) acetate (0.01 g, 0.04 mmol, 0.05 equivalent) were added, and the mixture was stirred vigorously under argon at 85° C. overnight. The reaction was cooled and filtered through a pad of Celite® with the aid of ethyl acetate. The filtrate was transferred to a separatory funnel where the layers were separated. The organic layer was dried ($Na_2SO_4$) and concentrated in vacuo. The residue was purified by flash chromatography on silica gel flushed with ethyl acetate followed by elution with 95:5 chloroform/methanol. The coupling product was obtained as a yellow oil (63 mg, 12%); MS m/z 634.3 ($MH^+$). The intermediate oil was stirred in 4N HCl in dioxane overnight at room temperature. The reaction was concentrated in vacuo and the residue was washed with dichloromethane to provide the title compound as the tri-hydrochloride salt (32 mg, 77%): $^1$H NMR (300 MHz, DMSO-$d_6$) δ 9.51 (broad s, 1 H), 9.36 (broad s, 1 H) 8.95 (s, 1 H), 8.89 (d, 1 H), 8.71 (d, 1 H), 8.62 (d, 1 H), 8.27 (s, 1 H), 8.10–8.06 (m, 1 H), 7.96–7.94 (m, 1 H), 7.70–7.65 (m, 2 H), 6.98 (d, 1 H), 5.42–5.39 (m, 2 H), 4.60–4.55 (m, 1 H), 3.91 (s, 3 H), 3.46–3.30 (m, 4 H), 2.94–2.88 (m, 1 H), 2.16–2.12 (m, 1 H), 1.83–1.68 (m, 1 H); MS m/z 420.1 ($MH^+$ of the free base).

EXAMPLE 73

Preparation of trifluoro-N-({4-[(2R)-2-({[(2R)-2-hydroxy-2-(3-Pyridinyl)ethyl]amino}methyl)-3,4-dihydro-2H-chromen-6-yl]-2-pyridinyl}carbonyl)methanesulfonamide

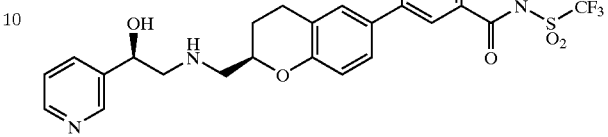

Into a solution of 4-{(2R)-2-[([(2R)-2-{[(1,1-dimethylethyl)(dimethyl)silyl]oxy}-2-(3-pyridinyl)ethyl]{[(1,1-dimethylethyl)oxy]carbonyl}amino)methyl]-3,4-dihydro-2H-chromen-6-yl}-2-pyridinecarboxylic acid (Example 70, 113 mg, 0.18 mmol) in dichloromethane (2 mL) was added trifluoromethylsulfonamide (30 mg, 0.20 mmol, 1.1 eq.), 1-[3-(dimethylamino)propyl]-3-ethylcarbodiimide hydrochloride (42 mg, 0.22 mmol, 1.2 eq.), and N,N-dimethylaminopyridine (22 mg, 0.18 mmol, 1.0 eq.). The solution was stirred overnight at room temperature before being concentrated in vacuo to remove volatile components. The crude residue was purified by flash chromatography on silica gel flushed with ethyl acetate followed by elution with 3:1 ethyl acetate/methanol. The coupling product was obtained as a yellow oil (36 mg, 27%); MS m/z 751.2 ($MH^+$). The protected intermediate was stirred in an excess of 4N HCl in dioxane overnight at room temperature. The reaction was concentrated in vacuo, and the residue was washed with dichloromethane to provide the title compound as the tri-hydrochloride salt (19 mg, 61%): $^1$H NMR (300 MHz, $CD_3OD$) δ 9.11 (s, 1 H), 8.89 (d, 1 H), 8.75–8.60 (m, 2 H), 8.34 (d, 1 H), 8.18 (t, 1 H), 7.92–7.74 (m, 2 H), 7.68–7.54 (m, 1 H), 7.20–7.08 (m, 1 H), 4.70–4.60 (m, 1 H), 3.74–3.59 (m, 5 H), 3.02–2.90 (m, 2 H), 2.24–2.16 (m, 1 H), 1.89–1.77 (m, 1 H); MS m/z 537.1 ($MH^+$ of the free base).

By employing the methods described in Example 73 and by using the compound of Example 70 with the appropriate amide or sulfonamide as starting materials, the following were similarly prepared and characterized:

TABLE 4

| Example No. | R' | Y | Calculated MW | MS [M + H⁺] | RT (minutes) LC-MS |
|---|---|---|---|---|---|
| 74 | —CH₃ | | 418.2 | 419.2 | 0.93 |

TABLE 4-continued

| Example No. | R' | Y | Calculated MW | MS [M + H+] | RT (minutes) LC-MS |
|---|---|---|---|---|---|
| 75 | phenyl | pyridine-2-carboxamide (4-position) | 480.22 | 481.2 | 2.01 |
| 76 | 3,4-difluorophenyl | pyridine-2-carboxamide (4-position) | 516.2 | 517.2 | 2.18 |
| 77 | —SO₂CH₃ | pyridine-2-carboxamide (4-position) | 482.16 | 483.1 | 0.75 |
| 78 | —SO₂CH₂CH₂CH₃ | pyridine-2-carboxamide (4-position) | 510.19 | 511.2 | 1.03 |
| 79 | 4-fluorophenylsulfonyl | pyridine-2-carboxamide (4-position) | 562.17 | 563.2 | 2.02 |
| 80 | 4-methoxyphenylsulfonyl | pyridine-2-carboxamide (4-position) | 574.19 | 575.2 | 1.73 |

EXAMPLE 81

Method A. Preparation of (1R)-1-(3-pyridinyl)-2-({[(2R)-6-(4,4,5,5-tetramethyl-1,3,2-dioxaborolan-2-yl)-3,4-dihydro-2H-chromen-2-yl]methyl}amino)ethanol

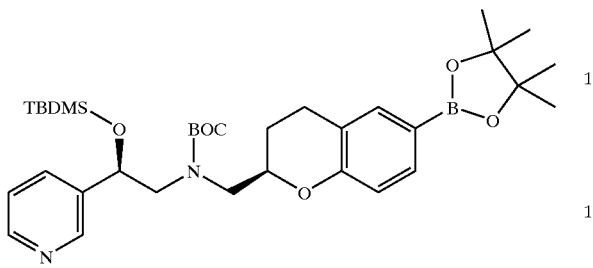

According to the procedure of Murata et al., (J. Org. Chem. 62:6458, 1997), Ar was bubbled into a dioxane solution (40 mL) of (tert-butyl (2R)-2-{[tert-butyl(dimethyl)silyl]oxy}-2-(3-pyridinyl)ethyl{[(2R)-6-iodo-3,4-dihydro-2H-chromen-2-yl]methyl}carbamate (Example 38, Method A, 3.90 g, 6.126 mmol) for 10 minutes. To this solution was then added Pd(dppf)Cl$_2$ (100 mg) and Et$_3$N (4.0 mL), and then pinacolborane (2.0 mL, 13.78 mmol, Aldrich Chemical Co.) was added slowly via syringe. The reaction mixture was stirred at 80° C. for 12 hours and allowed to cool to room temperature. It was filtered through a pad of Celite® and concentrated in vacuo to an oily residue. The residue was purified on silica gel with EtOAc-Hexane (1:4) as the eluant to provide (II) (3.73 g, 97%); $^1$H NMR (CDCl$_3$, δ): −0.1 (s, 3H), 0.10 (s, 3 H), 0.90 (s, 9 H), 1.32 (s, 12 H), 1.50 (s, 9 H), 1.60–1.80 (m, 1 H), 1.95–2.10 (m, 1 H), 2.80 (dd, 2 H), 3.30–3.50 (m, 2 H), 3.60–3.64 (dd, 1 H), 3.76–3.80 (dd, 1 H), 4.20–4.26 (m, 1 H), 5.02 (bs, 1 H), 6.78 (d, 1 H), 7.40 (s, 1 H), 7.50 (m, 2 H), 7.75 (m, 1 H), 8.54 (m, 2 H); m/z=625.4 [M+H]$^+$.

Method B. Preparation of (1R)-1-(3-pyridinyl)-2-({[(2S)-6-(4,4,5,5-tetramethyl-1,3,2-dioxaborolan-2-yl)-3,4-dihydro-2H-chromen-2-yl]methyl}amino)ethanol

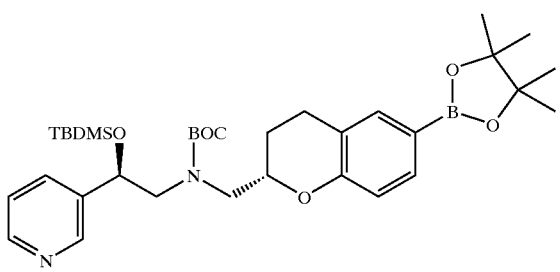

Using the same procedure described in Method A, with tert-butyl (2R)-2-{[tert-butyl(dimethyl)silyl]oxy}-2-(3-pyridinyl)ethyl{[(2S)-6-iodo-3,4-dihydro-2H-chromen-2-yl]methyl}carbamate (Example 38, Method B), the title compound was obtained in 63% yield. $^1$H NMR (DMSO-d$_6$) δ 8.52–8.48 (m, 2 H), 7.72–7.67 (m, 1 H), 7.40–7.32 (m, 3 H), 6.67 (d, J=8.2 Hz, 1 H), 5.09–5.00 (m, 1 H), 4.26–4.16 (m, 1 H), 3.56–3.38 (m, 4 H), 2.76–2.69 (m, 2 H), 1.95–1.89 (m, 1 H), 1.63–1.52 (m, 1 H), 1.25 (s, 9 H), 0.82 (s, 9 H), 0.00 s, 3 H), −0.15 (s, 3 H). LC-MS m/z 625.4 (MH$^+$), RT=3.66 minutes.

EXAMPLE 82

Preparation of methyl 2-[(2R)-2-({(tert-butoxycarbonyl)[(2R)-2-{[tert-butyl(dimethyl)silyl]oxy}-2-(3-pyridinyl)ethyl]amino}methyl)-3,4-dihydro-2H-chromen-6-yl]benzoate

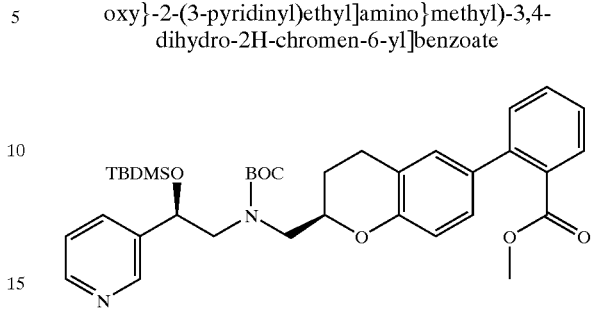

Argon gas was bubbled through a solution of (1R)-1-(3-pyridinyl)-2-({[(2R)-6-(4,4,5,5-tetramethyl-1,3,2-dioxaborolan-2-yl)-3,4-dihydro-2H-chromen-2-yl]methyl}amino)ethanol (Example 81, 115 mg, 0.184 mmol) in toluene (5 mL) and dioxane (1 mL) for 10 minutes and then Pd(dppf)Cl$_2$ (10 mg) and methyl 2-iodobenzoate (72 mg, 0.276 mmol, Aldrich Chemical Co.) were added and the mixture was bubbled with argon for an additional 5 minutes. The mixture was treated with Na$_2$CO$_3$ (1.0 mL of a 2.0 M aq.) and the bi-phase mixture stirred vigorously under Ar at 85° C. for 12 hours. The cooled reaction mixture was filtered through a pad of Celite® and the filtrate was extracted with EtOAc (2×20 mL). Concentration of the organic extracts in vacuo and purification on silica gel using a gradient of 20–30% EtOAc/Hexanes provided the product as colorless oil (61 mg, 52%); $^1$H NMR (CDCl$_3$, δ): 0.01 (s, 3H), 0.20 (s, 3 H), 0.99 (s, 9 H), 1.59 (s, 9 H), 1.64–1.82 (m, 1 H), 1.98–2.10 (m, 1 H), 2.80–3.00 (dd, 2 H), 3.40–3.58 (m, 2 H), 3.80 (s, 3 H), 3.80–3.90 (dd, 1 H), 4.20–4.40 (m, 2 H), 5.02 (bs, 1 H), 6.78 (d, 1 H), 7.10 (bs, 2 H), 7.40–7.60 (m, 3 H), 7.90–8.00 (m, 3 H), 8.60–8.80 (m, 2 H); MS: [M+H]$^+$633.3

EXAMPLE 83

Preparation of methyl 2-[(2R)-2-({[(2R)-2-hydroxy-2-(3-pyridinyl)ethyl]amino}methyl)-3,4-dihydro-2H-chromen-6-yl]benzoate

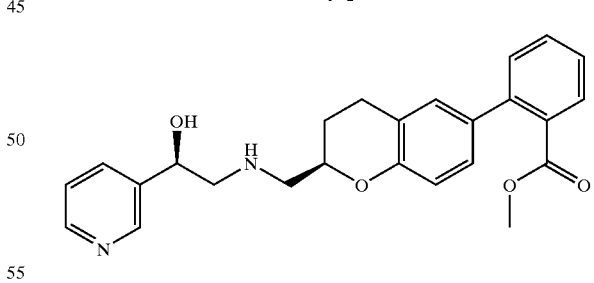

A stirred solution of methyl 2-[(2R)-2-({(tert-butoxycarbonyl)[(2R)-2-{[tert-butyl(dimethyl)silyl]oxy}-2-(3-pyridinyl)ethyl]amino}methyl)-3,4-dihydro-2H-chromen-6-yl]benzoate (Example 82, 61 mg, 0.096 mmol) in MeOH (0.50 mL) was treated with HCl in dioxane (1 mL of a 4N solution in dioxane, Aldrich Chemical Co.) at room temperature and stirring continued for 60 minutes. The mixture was concentrated in vacuo and purified on silica gel using a gradient of 5–10% MeOH/EtOAc to provide 31 mg of product as colorless oil (77%); $^1$H NMR (DMSO-d$_6$, δ): 1.65–2.04 (m, 2 H), 2.50–3.10 (m, 6 H), 3.65 (s, 3 H), 4.10

(dd, 1 H), 4.80 (d, 1 H), 6.80 (d, 1 H), 7.00 (bs, 2 H), 7.25–7.40 (m, 3 H), 7.42–7.52 (m, 1 H), 7.78–7.80 (m, 2 H), 8.52 (s, 1 H), 8.60 (s, 1 H); MS: m/z=419.3 [M+H]⁺.

EXAMPLE 84

Preparation of 2-[(2R)-2-({[(2R)-2-hydroxy-2-(3-pyridinyl)ethyl]amino}methyl)-3,4-dihydro-2H-chromen-6-yl]benzoic acid

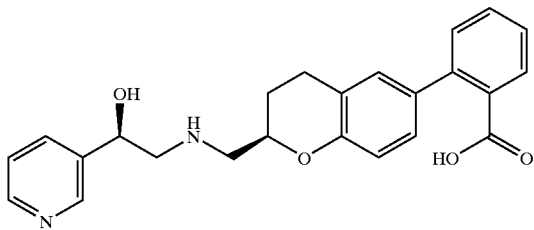

To a solution of methyl 2-[(2R)-2-({[(2R)-2-hydroxy-2-(3-pyridinyl)ethyl]amino}-methyl)-3,4-dihydro-2H-chromen-6-yl]benzoate (Example 83, 60 mg, 0.143 mmol) in THF (0.50 mL) and MeOH (0.50 mL) was added LiOH (1.0 mL of a 2.0 M aq solution), and the mixture was stirred at room temperature for 2 hours. The mixture was diluted with 1.0 mL H₂O and purified via preparative HPLC (gradient of 100:0 0.1% TFA/H₂O:acetonitrile to 30:70 0.1% TFA/H₂O:acetonitrile). The peak of interest was collected and concentrated in vacuo to provide 41 mg of desired final product as a bis-trifluoroacetic acid (TFA) salt; ¹H NMR (DMSO-d₆, δ): 1.68–1.80 (m, 1 H), 2.04–2.18 (m, 1 H), 2.72–2.90 (m, 2 H), 3.22–3.50 (m, 4 H), 4.58 (dd, 1 H), 5.41 (d, 1 H), 6.82 (d, 1 H), 7.02 (d, 1 H), 7.04 (s, 1 H), 7.30–7.40 (m, 2 H), 7.50 (t, 1 H), 7.62 (d, 1 H), 8.01 (t, 1 H), 8.58 (d, 1 H), 8.82 (d, 1 H), 8.90 (s, 1 H), 9.44 (bs, 1 H), 9.64 (bs, 1 H) MS: m/z=415.2 [M+H]⁺.

EXAMPLE 85

Preparation of Methyl 3-[(2R)-2-({(tert-butoxycarbonyl)[(2R)-2-{[tert-butyl(dimethyl) silyl]oxy}-2-(3-pyridinyl)ethyl]amino}methyl)-3,4-dihydro-2H-chromen-6-yl]benzoate

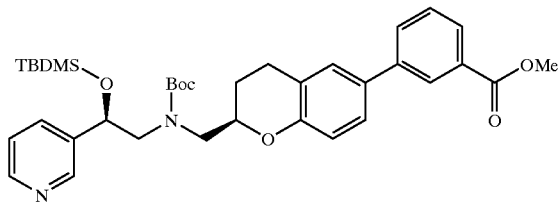

Argon was bubbled through a solution of the compound of Example 81 (5 g, 8 mmol) in toluene (100 mL) for 10 minutes. Then, [1,1′-bis(diphenylphosphino)ferrocene] dichloropalladium (II) (460 mg, 0.56 mmol) and methyl 3-bromobenzoate (2.6 g, 12 mmol) were added in a single portion. The resulting reaction mixture was degassed with argon for an additional 5 minutes before aqueous Na₂CO₃ (2M, 40 mL, 80 mmol) was added and the solution was heated at 85° C. overnight. The product mixture was allowed to cool to room temperature, water was added and the biphasic mixture was extracted with ethyl acetate. The combined organic extracts were dried over anhydrous sodium sulfate, concentrated and purified with a Biotage column, gradient 10–30% ethyl acetate/hexanes to obtain 3.83 g (77%) of the title compound. MH⁺=633.5

EXAMPLE 86

Preparation of 3-[(2R)-2-({(tert-Butoxycarbonyl)[(2R)-2-{[tert-butyl(dimethyl)silyl]oxy}-2-(3-pyridinyl)ethyl]amino}methyl)-3,4-dihydro-2H-chromen-6-yl]benzoic acid

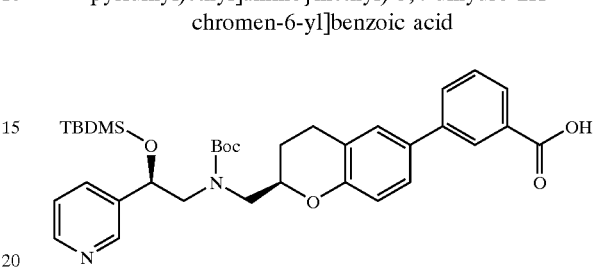

The product from Example 85 (3.0 g, 4.8 mmol) was diluted with 10 mL each of tetrahydrofuran, water, and methanol; 15 mL of 1 N sodium hydroxide (14.4 mmol) was added; and allowed solution to stir overnight at room temperature. The solution was concentrated, water added, and neutralized with 1 N phosphoric acid. The aqueous layer was extracted with methylene chloride, dried over anhydrous sodium sulfate, and concentrated in vacuo. Purified by Biotage in gradient 10–30% ethyl acetate/hexanes, then flushed column with ethyl acetate to 5% methanol/ethyl acetate. Yielded 2.3 g (78%) of product. MH+=619.6

EXAMPLE 87

Preparation of N-{3-[(2R)-2-({[(2R)-2-Hydroxy-2-(3-pyridinyl)ethyl]amino}methyl)-3,4-dihydro-2H-chromen-6-yl]benzoyl}methanesulfonamide

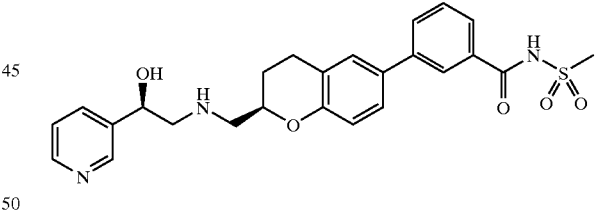

The product of Example 86 (100 mg, 0.16 mmol), 1-[(3-dimethylamino)propyl]-3-ethylcarbodiimide (36 mg, 0.19 mmol), dimethylaminopyridine (20 mg, 0.16 mmol), and methylsulfonamide (17 mg, 0.18 mmol) were dissolved in 2 mL methylene chloride and stirred overnight at room temperature. The mixture was treated with 0.5 mL 4 M HCl in 1,4-dioxane was added, the solution stirred for 0.5 hours, concentrated to dryness and the residue was purified by preparative HPLC to obtain the title compound (47 mg, 62%). ¹H NMR (CD₃CN-d₃) δ: 8.91 (s, 1 H), 8.76 (d, 1 H), 8.51 (d, 1 H), 8.07 (s, 1 H), 7.97 (t, 1 H), 7.88–7.83 (m, 2 H), 7.62–7.56 (m, 1 H), 7.50–7.47 (m, 2 H), 6.98 (d, 1 H), 5.46 (d, 1 H), 4.54–4.47 (m, 1 H), 3.52 (dd, 2 H), 3.37 (s, 3 H), 3.39–3.25 (m, 2 H), 2.99–2.90 (m, 2 H), 2.14–2.09 (m, 1 H), 1.86–1.79 (m, 1 H). MH+=482.2

EXAMPLE 88

Method A. Preparation of 4-[(2R)-2-({[(2R)-2-hydroxy-2-(3-pyridinyl)ethyl]amino}methyl)-3,4-dihydro-2H-chromen-6-yl]-3-methylbenzoic acid

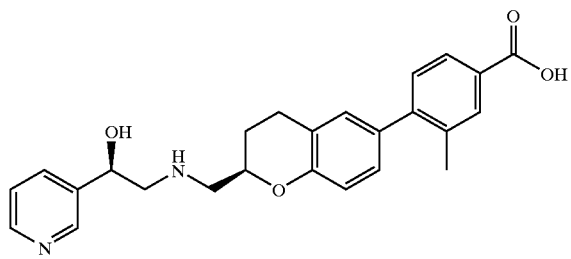

Argon was bubbled through a solution of Example 81 (100 mg, 0.16 mmol) in toluene (2 mL) for 10 minutes. Then, palladium acetate (2 mg, 0.008 mmol), 2-(di-tert-butylphosphino)biphenyl (5 mg, 0.016 mmol), and methyl 4-bromo-3-methylbenzoate (55 mg, 0.24 mmol) were added in a single portion. The resulting reaction mixture was degassed with argon for an additional 5 minutes before aqueous Na$_2$CO$_3$ (2M, 1 mL, 1.68 mmol) was added and the solution was heated at 85° C. overnight. The product mixture was allowed to cool to room temperature, water was added, and the biphasic mixture was extracted with ethyl acetate. 1 mL of 4 M HCl/dioxane was added to the combined organic extracts, stirred for 0.5 hour, and concentrated in vacuo. Then, 1 mL of 1 N sodium hydroxide was added, stirred for 0.5 hour, filtered, and purified by preparative HPLC to obtain 8 (7 mg, 11%). MH$^+$=419.3

Method B. Preparation of 4-[(2S)-2-({[(2R)-2-hydroxy-2-(3-pyridinyl)ethyl]amino}methyl)-3,4-dihydro-2H-chromen-6-yl]-3-methylbenzoic acid

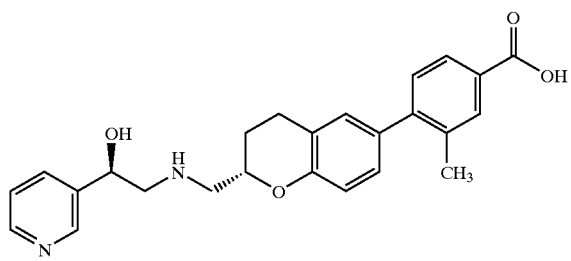

Using the same procedure described in Method A with (1R)-1-(3-pyridinyl)-2-({[(2S)-6-(4,4,5,5-tetramethyl-1,3,2-dioxaborolan-2-yl)-3,4-dihydro-2H-chromen-2-yl]methyl}amino)ethanol (Example 81, Method B), the title compound was obtained in 38% yield: $^1$H NMR (CD$_3$OD) δ 7.08 (d, J=2.3 Hz, 1 H), 6.95 (dd, J=5.1, 1.8 Hz, 1 H), 6.41–6.37 (m, 1 H), 6.30–6.28 (m, 1 H), 6.24–6.21 (m, 1 H), 5.94–5.89 (m, 1 H), 5.60 (d, J=8.0 Hz, 1 H), 5.50–5.47 (m, 2 H), 5.33 (d, J=8.8 Hz, 1 H), 3.52 (dd, J=9.6, 3.6 Hz, 1 H), 3.38–3.33 (m, 1 H), 2.84–2.78 (m, 1 H), 1.78 (s, 3 H), 1.75–1.72 (m, 1 H), 1.68–1.60 (m, 1 H), 1.43–1.33 (m, 1 H), 1.31–1.25 (m, 1 H), 0.58–0.52 (m, 1 H), 0.32–0.23 (m, 1 H). LC-MS m/z 419.2 (MH$^+$).

Method C. Preparation of 4-[(2S)-2-({[2-hydroxy-2-(3-pyridinyl)ethyl]amino}methyl)-3,4-dihydro-2H-chromen-6-yl]-3-methylbenzoic acid

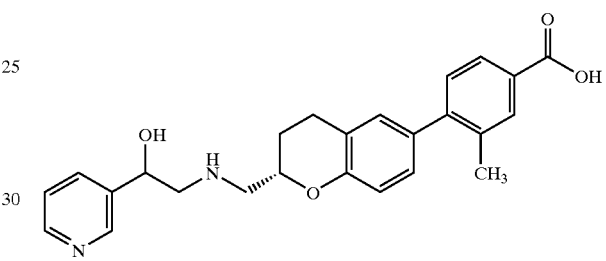

Starting with the (2S)-6-iodo-3,4-dihydro-2H-chromene-2-carboxylic acid (Example 7, Method B) and racemic 2-amino-1-(3-pyridinyl)ethanol dihydrochloride, and using the procedures described in Examples 35–38 and Method A above, the title compound was prepared. LC-MS m/z 419.2 (MH$^+$), RT=1.45 minutes.

Using the procedures outlined in Examples 69–88 and using the appropriate aryl halides, trifluoromethanesulfonates, sulfonamides and/or benzoates, the following compounds were prepared and characterized.

TABLE 5

| Example | R' | Y | Calculated MW | MS [M + H$^+$] | RT (minutes) LC-MS |
|---------|-----|---|---------------|----------------|---------------------|
| 89 | phenyl-SO$_2$ | benzamide-NHR' | 481 | 482.2 | 1.33 |

TABLE 5-continued

| Example | R' | Y | Calculated MW | MS [M + H+] | RT (minutes) LC-MS |
|---|---|---|---|---|---|
| 90 | 4-methylphenyl-SO2- | 3-C(O)NHR'-phenyl- | 557 | 558.2 | 2.05 |
| 91 | 2-methylphenyl-SO2- | 3-C(O)NHR'-phenyl- | 557 | 558.31 | 2.01 |
| 92 | 4-methoxyphenyl-SO2- | 3-C(O)NHR'-phenyl- | 573 | 574.2 | 1.98 |
| 93 | 4-fluorophenyl-SO2- | 3-C(O)NHR'-phenyl- | 561 | 562.2 | 2 |
| 94 | 4-chlorophenyl-SO2- | 3-C(O)NHR'-phenyl- | 577 | 578.2 | 2.15 |
| 95 | 3-chloro-4-methylphenyl-SO2- | 3-C(O)NHR'-phenyl- | 591 | 592.2 | 2.25 |
| 96 | benzothiazol-2-yl-SO2- (6-O-CH2- linker) | 3-C(O)NHR'-phenyl- | 644 | 645.2 | 2.24 |
| 97 | propyl-SO2- | 3-C(O)NHR'-phenyl- | 509 | 510.2 | 1.76 |

TABLE 5-continued
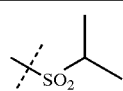
| Example | R' | Y | Calculated MW | MS [M + H+] | RT (minutes) LC-MS |
|---|---|---|---|---|---|
| 98 | 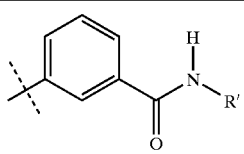 | 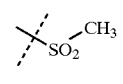 | 509 | 510 | 1.75 |
| 99 | 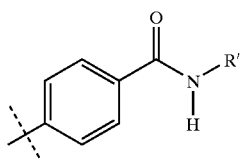 | 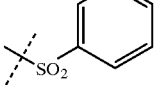 | 481 | 482.2 | 1.14 |
| 100 | 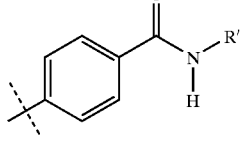 | 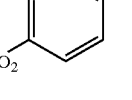 | 543 | 544.2 | 1.88 |
| 101 | 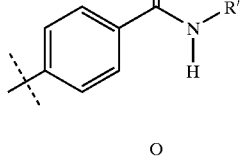 | 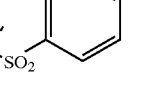 | 573 | 574.2 | 1.86 |
| 102 | 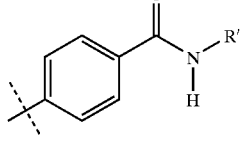 | 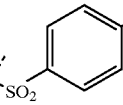 | 561 | 562.2 | 1.89 |
| 103 | 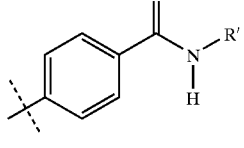 | 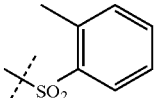 | 557 | 558.3 | 1.96 |
| 104 | 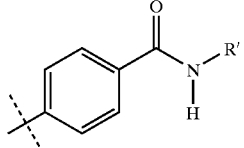 | 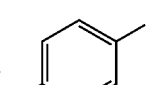 | 557 | 558.2 | 1.9 |
| 105 | 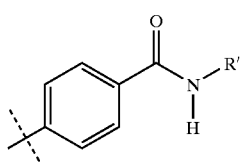 | | 577 | 578.2 | 2.02 |

TABLE 5-continued
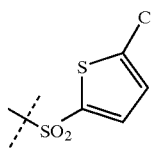
| Example | R' | Y | Calculated MW | MS [M + H⁺] | RT (minutes) LC-MS |
|---|---|---|---|---|---|
| 106 | 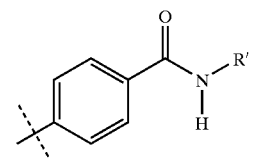 | 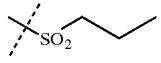 | 584 | 583, 585 | 2.01 |
| 107 | 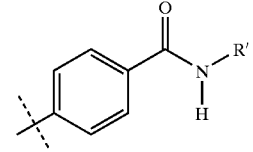 | 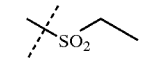 | 509 | 510 | 0.39 |
| 108 | 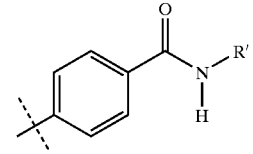 | 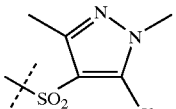 | 495 | 496 | 0.17 |
| 109 | 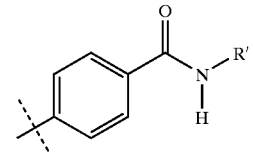 | 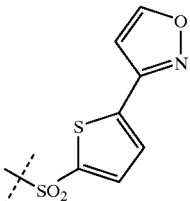 | 596 | 595, 597 | 1.68 |
| 110 | 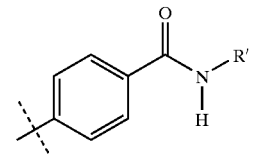 | 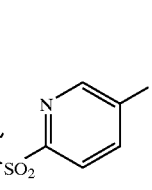 | 616 | 617 | 1.89 |
| 111 | 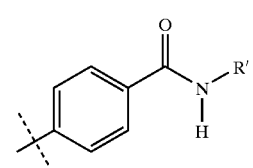 | 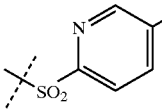 | 636 | 637 | 1.16 |
| 112 | 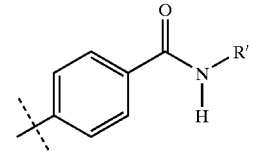 | | 558 | 559 | 0.47 |

TABLE 5-continued

| Example | R' | Y | Calculated MW | MS [M + H⁺] | RT (minutes) LC-MS |
|---|---|---|---|---|---|
| 113 | -SO₂CH₂CF₃ | -C₆H₄-C(O)NH-R' | 549 | 550 | 1.79 |
| 114 | -SO₂CH(CH₃)₂ | -C₆H₄-C(O)NH-R' | 509 | 510 | 2.04 |
| 115 | -SO₂(CH₂)₃CH₃ | -C₆H₄-C(O)NH-R' | 523 | 524 | 2.12 |
| 116 | -SO₂CF₃ | -C₆H₄-C(O)NH-R' | 535 | 536 | 0.8 |
| 117 | -SO₂-cyclopropyl | -C₆H₄-C(O)NH-R' | 507 | 508 | 1.9 |
| 118 | -SO₂-(3,5-dimethylisoxazol-4-yl) | -C₆H₄-C(O)NH-R' | 562 | 563 | 3.4 |

TABLE 6

Structure: (R)-1-(pyridin-3-yl)-2-[[(chroman-2-yl)methyl]amino]ethanol with Y substituent at 6-position of chroman

| Example No | Y | MS [M + H]+ | HPLC RT (min) |
|---|---|---|---|
| 119 | 4-methyl-benzoic acid (3-CO₂H, 4-Me-Ph) | 419.3 | 1.61 |
| 120 | 3,5-dimethoxy-benzoic acid | 465.1 | 1.37 |
| 121 | 2,6-dimethyl-benzoic acid | 433 | 1.42 |
| 122 | 5-fluoro-2-chloro-benzoic acid | 457 | 1.68 |
| 123 | 2-(NHC(=O)Me)-benzoic acid | 462 | 1.56 |
| 124 | 3-chloro-benzoic acid | 439 | 1.1 |
| 125 | 3-methoxy-benzoic acid (OMe) | 435 | 0.92 |
| 126 | 5-(O-i-Bu)-2-COOH-phenyl | 477.2 | |

TABLE 6-continued

| Example No | Y | MS [M + H]+ | HPLC RT (min) |
|---|---|---|---|
| 127 | 4-t-Bu-Ph (3-CO₂H) | 537.3 | 2.30 |
| 128 | n-Bu—CH=CH, 3-CO₂H-Ph | 487.4 | 2.21 |
| 129 | MeO—(CH₂)₂O, 3-CO₂H-Ph | 479.2 | 1.74 |
| 130 | n-PrO, 3-CO₂H-Ph | 463.2 | 1.86 |
| 131 | i-PrO, 3-CO₂H-Ph | 463.1 | 1.88 |
| 132 | cyc-PrCH₂O, 3-CO₂H-Ph | 475.2 | 1.95 |
| 133 | i-BuO, 3-CO₂H-Ph | 477.2 | 2.08 |
| 134 | n-PentO, 3-CO₂H-Ph | 491.2 | 2.17 |

TABLE 6-continued

Structure: (R)-1-(pyridin-3-yl)-2-{[(chroman-2-yl)methyl]amino}ethanol with 6-Y substituent on chroman

| Example No | Y | MS [M + H]+ | HPLC RT (min) |
|---|---|---|---|
| 135 | 2-OMe, 5-COOH phenyl (attached para to tBu position) — OMe, COOH | 435.2 | 1.66 |
| 136 | OMe, COOMe phenyl | 449.2 | 1.87 |
| 137 | NO2, COOMe phenyl | 464.2 | 1.91 |
| 138 | NO2, COOH phenyl | 450.2 | 1.59 |
| 139 | CH2COOH phenyl | 419.5 | 1.68 |
| 140 | 3-COOH phenyl | 405.2 | 1.68 |
| 141 | 3-COOMe phenyl | 419.2 | 1.91 |
| 142 | 5-COOH pyridin-3-yl | 406.2 | 0.79 |
| 143 | 1-Me-indole-2-COOH | 458.2 | 1.95 |
| 144 | 4,5-di-OMe, CH2COOH phenyl | 479.3 | 1.55 |
| 145 | OMe, OH, CH2COOH phenyl | 465.3 | 1.13 |
| 146 | NH2, COOH phenyl | 420.2 | 1.15 |
| 147 | tri-OMe, COOH phenyl | 495.3 | 1.63 |
| 148 | 4-COOH phenyl | 405.2 | 1.53 |
| 149 | 2-Me, COOH phenyl | 419.2 | 1.55 |

TABLE 6-continued
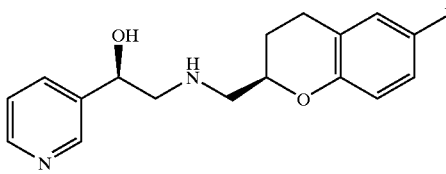
| Example No | Y | MS [M + H]+ | HPLC RT (min) |
|---|---|---|---|
| 150 | 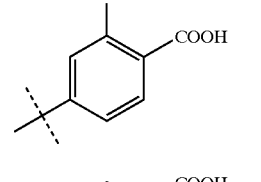 | 423.2 | 1.26 |
| 151 | 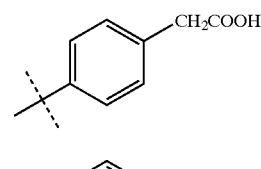 | 406.2 | 0.62 |
| 152 | 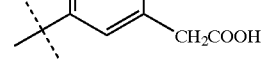 | 419.3 | 1.58 |
| 153 | 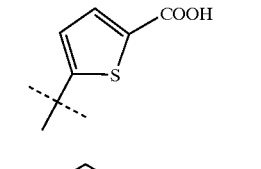 | 419.2 | 1.69 |
| 154 | 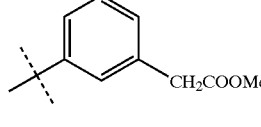 | 411.1 | 1.18 |
| 155 | 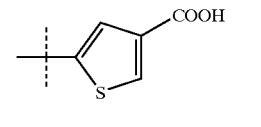 | 433.3 | 1.94 |
| 156 | 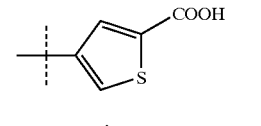 | 411.3 | 1.52 |
| 157 | 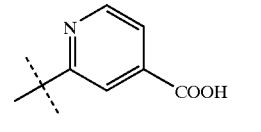 | 411.3 | 1.33 |
| 158 | 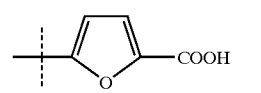 | 406.3 | 0.62 |
| 159 | 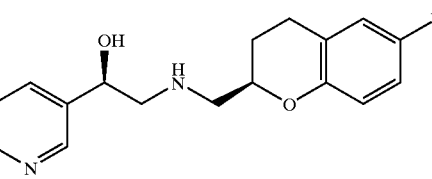 | 395.2 | 1.07 |
| 160 | 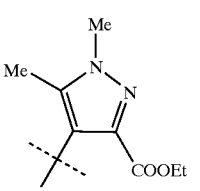 | 455.3 | 1.99 |
| 161 | 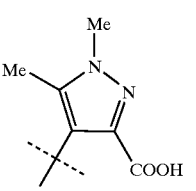 | 451.3 | 1.17 |
| 162 | 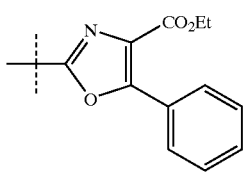 | 423.3 | 0.63 |
| 163 | 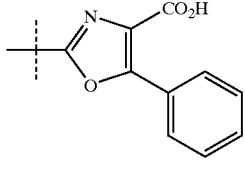 | 500.6 | 2.27 |
| 164 | 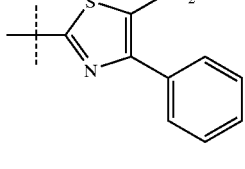 | 472.4 | 1.99 |
| 165 | 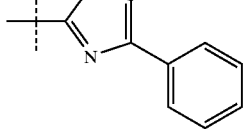 | 516.5 | 2.38 |
| 166 | | 488.3 | 1.96 |

EXAMPLE 167

Preparation of methyl 4-[((2R)-2-{[(tert-butoxycarbonyl)((2R)-2-(3-pyridinyl)-2-{[(1,1,2,2-tetramethylpropyl)silyl]oxy}ethyl)amino]methyl}-3,4-dihydro-2H-chromen-6-yl)methyl]benzoate

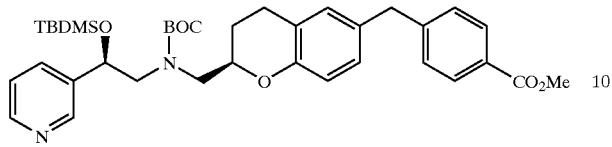

A solution of 100 mg (0.16 mmol) of (1R)-1-(3-pyridinyl)-2-({[(2R)-6-(4,4,5,5-tetramethyl-1,3,2-dioxaborolan-2-yl)-3,4-dihydro-2H-chromen-2-yl]methyl}amino)ethanol (Example 81) dissolved in 5 mL of toluene and 1 mL 1,4-dioxane, was bubbled under argon for 10 minutes. Then, 10 mg (0.0122 mmol) of Pd(dppf)Cl$_2$ complex with methylene chloride (1:1) and 54.98 mg (0.24 mmol) of methyl 4-(bromomethyl)benzoate (Aldrich Chemical Co.) were added, and the mixture was bubbled under argon for another 5 minutes. Finally, 1.0 mL (2.0 mmol) of 2M aqueous sodium carbonate was added, and the mixture was stirred under argon at 85° C. for 16 hours. After this time, the mixture was allowed to cool to ambient temperature, filtered through Celite®, rinsed with ethyl ether, and concentrated in vacuo. The product was purified by flash chromatography using 30% ethyl acetate/hexanes as the eluant to provide 77.2 mg of product; MH+ 647.4.

EXAMPLE 168

Preparation of 4-{[(2R)-2-({[(2R)-2-hydroxy-2-(3-pyridinyl)ethyl]amino}methyl)-3,4-dihydro-2H-chromen-6-yl]methyl}benzoic acid

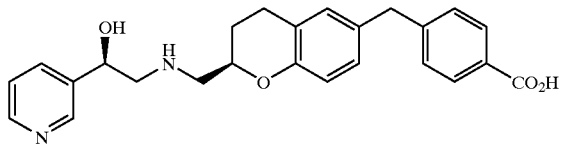

To a solution of 77.2 mg (0.11 mmol) methyl 4-[((2R)-2-{[(tert-butoxycarbonyl)((2R)-2-(3-pyridinyl)-2-{[([(1,1,2,2-tetramethylpropyl)silyl]oxy}ethyl)amino]-methyl}-3,4-dihydro-2H-chromen-6-yl)methyl]benzoate (Example 167) in 1 mL of tetrahydrofuran was added 0.54 mL of 1 M LiOH and 0.27 mL methanol. The mixture was stirred at room temperature for 3 hours after which point 0.5 mL of 1N phosphoric acid was added to the solution. The mixture was partitioned between ethyl acetate (3×5 mL) and water (5 mL). The organic layer was washed with saturated sodium chloride, dried over sodium sulfate, filtered, and concentrated. To the residue was added 0.4 mL of hydrochloric acid in dioxane. This solution was stirred at room temperature for 0.5 hour. The solution was then washed with water and concentrated in vacuo, followed by purification by preparative HPLC (gradient of 100:0 0.1% TFA/H$_2$O:acetonitrile to 30:70 0.1% TFA/H$_2$O:acetonitrile) to obtain 16.4 mg of product as the TFA salt. MH+ 419.3.

$^1$H NMR (DMSO d$_6$, δ): 8.89 (br. s, 1 H), 8.63 (s, 1 H), 8.57 (d, 1 H), 7.88 (dt, 1 H), 7.85 (s, 1 H), 7.82 (s, 1 H), 7.50 (dd, 1 H), 7.32 (s, 1 H), 7.29 (s, 1 H), 6.96 (m, 2 H), 6.73 (d, 1 H), 6.38 (br. s, 1 H), 5.08 (m, 1 H), 4.38 (m, 1 H), 2.76 (m, 1 H), 2.71 (m, 1 H), 1.99 (m, 1 H), 1.67 (m, 1 H).

EXAMPLE 169

Preparation of (2R)-N-[(2R)-2-hydroxy-2-(3-pyridinyl)ethyl]-6-nitro-3,4-dihydro-2H-chromene-2-carboxamide

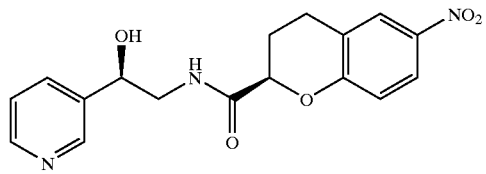

(2R)-6-Nitro-3,4-dihydro-2H-chromene-2-carboxylic acid (4.1 g, 18 mmol) and (1R)-2-amino-1-(3-pyridinyl)ethanol (5.0 g, 24 mmol) (both described in U.S. Pat. No. 6,051,586) were suspended in CH$_2$Cl$_2$ and stirred vigorously. Triethylamine (9.2 mL, 66 mmol) was added followed by hydroxybenzotriazole (4.9 g, 36 mmol) and EDCl (6.9 g, 36 mmol), and the reaction was stirred overnight. After 18 hours, TLC showed no remaining acid starting material, so the reaction was partitioned between water and CH$_2$Cl$_2$ and the organic layer was washed 3×100 mL of water. The organic layer was washed with 1N HCl, which removed the product into the aqueous layer. This aqueous layer was washed with CH$_2$Cl$_2$ and the organic was discarded. The aqueous solution was then basified and became cloudy with a white precipitate. The basified mixture was extracted with 3×100 mL of CH$_2$Cl$_2$.

The combined organic layer was concentrated, affording the product (4.5 g) as a light yellow foam. $^1$H NMR (DMSO-d$_6$, δ): 8.4 (d, 2H), 8.1 (t, 1H), 8.0 (m, 2H), 7.6 (d, 1H), 7.3 (m, 1H), 7.0 (d, 1H), 5.6 (s, 1H), 4.7 (m, 2H), 3.3 (m, 2H) 2.8 (m, 1H), 2.6 (m, 1H), 2.2 (m, 1H), 1.9 (m, 1H); LC/MS: m/z 343, MH$^+$ 344.

EXAMPLE 170

Preparation of (1R)-2-({[(2R)-6-nitro-3,4-dihydro-2H-chromen-2-yl]methyl}amino)-1-(3-pyridinyl)ethanol

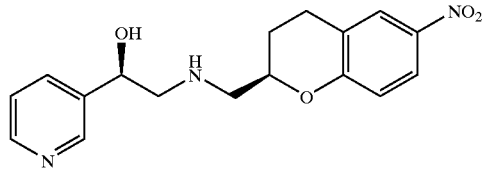

(2R)-N-[(2R)-2-Hydroxy-2-(3-pyridinyl)ethyl]-6-nitro-3,4-dihydro-2H-chromene-2-carboxamide (Example 169, 1.0 g, 3 mmol) was dissolved in 15 mL of THF and borane-dimethylsulfide complex (1.4 mL, 12.6 mmol) was added dropwise. The reaction was refluxed for one hour after which TLC showed no remaining starting material. Methanol (0.5 mL) was then added dropwise followed by 6N HCl (0.5 mL) and the reaction was refluxed an additional 1.5 hours. The solution was then cooled and diluted with water and ethyl acetate, and adjusted to about pH 9 with 1N NaOH. The organic layer was dried and evaporated to afford the product (650 mg) as a yellow solid. $^1$H NMR (DMSO-d$_6$, δ): 8.6 (s, 1H), δ 8.5 (d, 1H), δ 8.1 (s, 1H), δ 8.0 (d, 1H), δ 7.8 (d, 1H), δ 7.4 (m, 1H), δ 7.0 (d, 1H), δ 5.6 (s, 1H), δ 4.8 (m, 1H), δ 4.3 (m, 1H), δ 3.2 (s, 1H), δ 2.9 (m, 2H), δ 2.8 (m, 2H), δ 2.1 (m, 1H), δ 1.8 (m, 1H); LC/MS: m/z 329, MH$^+$ 330

EXAMPLE 171

Preparation of tert-butyl (2R)-2-hydroxy-2-(3-pyridinyl)ethyl{[(2R)-6-nitro-3,4-dihydro-2H-chromen-2-yl]methyl}carbamate

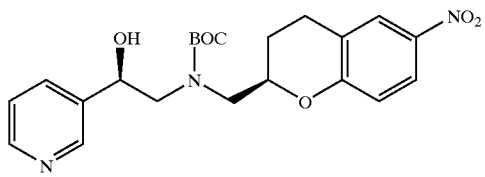

(1R)-2-({[(2R)-6-nitro-3,4-dihydro-2H-chromen-2-yl]methyl}amino)-1-(3-pyridinyl)ethanol (Example 170, 650 mg, 2 mmol) was dissolved in 12 mL THF, di-tert-butyl-dicarbonate (440 mg, 2 mmol) was added, and the reaction was stirred and monitored by TLC. Upon completion, when the disappearance of starting material was observed, the reaction was partitioned between water and ethyl acetate. The crude product obtained by concentration of the organic layer was purified by filtration through a silica plug to give 777 mg of material as a white foam. $^1$H NMR (DMSO-$d_6$, δ): 8.4 (m, 2H), 8.1 (s, 1H), 7.9 (d, 1H), 7.7 (m, 1H), 7.4 (m, 1H), 6.9 (d, 1H), 5.6 (d, 1H), 4.8 (m, 1H), 4.4 (m, 1H), 3.5 (m, 4H), 2.8 (m, 2H), 2.0 (m, 1H), 1.6 (m, 1H), 1.2 (s, 9H); LC/MS: m/z 429, MH$^+$ 430.

EXAMPLE 172

Preparation of tert-butyl [(2R)-6-amino-3,4-dihydro-2H-chromen-2-yl]methyl[(2R)-2-hydroxy-2-(3-pyridinyl)ethyl]carbamate

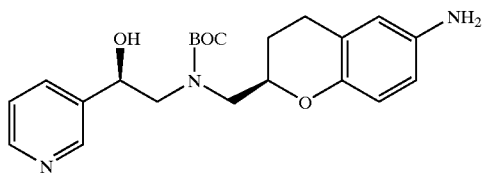

tert-Butyl (2R)-2-hydroxy-2-(3-pyridinyl)ethyl{[(2R)-6-nitro-3,4-dihydro-2H-chromen-2-yl]methyl}carbamate (Example 171, 500 mg, 1.2 mmol) was dissolved in degassed THF, and to the solution was added Pd/C (50 mg, 10%) under argon and cooled to 0° C. NaBH$_4$ was dissolved in ethanol and added to the reaction slowly to avoid excessive bubbling. After gas evolution had stopped, the reaction was warmed to room temperature and monitored by TLC. When complete, the reaction was cooled to 0° C. and quenched by the addition of ice. The black precipitate was then filtered through Celite® and the filtrate was concentrated in vacuo until cloudy. The filtrate was then extracted with ethyl acetate and the crude material was purified via flash chromatography to yield the product (30%). $^1$H NMR (DMSO-$d_6$, δ): 8.4 (m, 2H), 7.7 (m, 1H), 7.4 (m, 1H), 6.4 (d, 1H), 6.3 (s, 1H), 6.2 (d, 1H), 5.6 (d, 1H), 4.8 (m, 1H), 4.5 (m, 1H), 3.5 (m, 2H), 3.4 (m, 2H), 2.8 (m, 2H), 1.8 (m, 1H), 1.5 (m, 1H), 1.2 (d, 9H); LC/MS: m/z 399, MH$^+$ 400

EXAMPLE 173

Preparation of 3-{[(2R)-2-({(tert-butoxycarbonyl)[(2R)-2-hydroxy-2-(3-pyridinyl)ethyl]amino}methyl)-3,4-dihydro-2H-chromen-6-yl]sulfanyl}benzoic acid

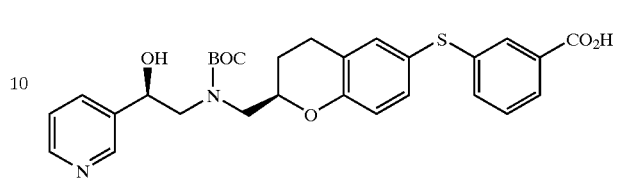

Utilizing a procedure reported by Schutze (EP 0067352 B2), a solution of 510 mg (1.25 mmol) of Example 172 in 15 mL of acetone was cooled to 0° C., and 1.3 mL (2.5 mmol) of 2N hydrochloric acid was added. Sodium nitrite (95 mg, 1.38 mmol) dissolved in 1.3 mL of water at 0° C. was added slowly to the reaction flask.

The resulting mixture was then allowed to stir at 0° C. for 1 hour while 270 mg (1.75 mmol) 3-mercaptobenzoic acid, 279 mg (1.75 mmol) copper sulfate, and 1.24 mL water were mixed together at room temperature for 0.5 hour. After this time, the cold (0° C.) solution was added slowly to the room temperature solution. The resulting mixture was stirred at room temperature for 16 hours. The reaction mixture was then added to 100 mL water and extracted 3 times with 25 mL ethyl acetate. The combined organic phases were washed with water and brine, and dried over anhydrous sodium sulfate, filtered, and concentrated in vacuo. The crude product was used without further purification.

EXAMPLE 174

Preparation of 3-{[(2R)-2-({[(2R)-2-hydroxy-2-(3-pyridinyl)ethyl]amino}methyl)-3,4-dihydro-2H-chromen-6-yl]sulfanyl}benzoic acid

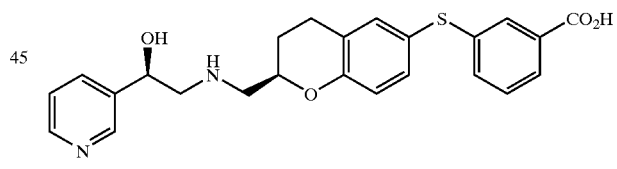

To 670 mg (1.25 mmol) of crude 3-{[(2R)-2-({(tert-butoxycarbonyl)[(2R)-2-hydroxy-2-(3-pyridinyl)ethyl]amino}methyl)-3,4-dihydro-2H-chromen-6-yl]sulfanyl}benzoic acid (Example 173) diluted in 5 mL 1,4-dioxane, was added 0.5 mL of 6N hydrochloric acid slowly. The resulting mixture was stirred at 45° C. for 2 hours. After this time the mixture was concentrated in vacuo, dissolved in 2 mL of 1:1 methanol to water, and purified by HPLC (0–70% acetonitrile/0.1% TFA) to afford 28.5 mg (5% yield) of the desired product as the bis TFA salt. MH+ 437.3. $^1$H NMR (CDCl$_3$, δ): 8.91(br. S, 1 H), 8.63 (d, 1 H), 8.56 (dd, 1 H), 7.89 (m, 1 H), 7.72 (dt, 1 H), 7.62 (m, 1 H), 7.49 (m, 1 H), 7.39 (m, 1 H), 7.31 (m, 1 H), 7.27 (m, 1 H), 7.24 (dd, 1 H), 6.90 (d, 1 H), 6.35 (br. S, 1 H), 5.07 (m, 1 H), 4.48 (m, 1 H), 3.32 (m, 4 H), 3.16 (m, 1 H), 2.78 (m, 2 H), 2.04 (m, 1 H), 1.71 (m, 1 H).

EXAMPLE 175

Preparation of methyl 3-{[(2R)-2-({(tert-butoxycarbonyl)[(2R)-2-hydroxy-2-(3-pyridinyl)ethyl]amino}methyl)-3,4-dihydro-2H-chromen-6-yl]sulfanyl}benzoate

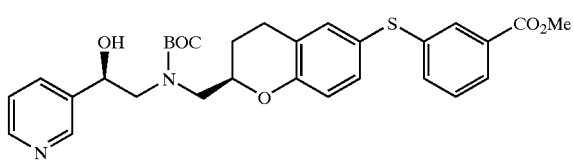

To 650 mg (1.25 mmol) of 3-{[(2R)-2-({(tert-butoxycarbonyl)[(2R)-2-hydroxy-2-(3-pyridinyl)ethyl]amino}methyl)-3,4-dihydro-2H-chromen-6-yl]sulfanyl}benzoic acid (Example 173) dissolved in 10 mL 1:1 methanol/ethyl acetate, was added 3 mL of 2M trimethylsilyl diazomethane dropwise. The resulting solution was then allowed to stir at room temperature for 16 hours. The solution was then diluted with ethyl acetate, washed with water and brine, and concentrated in vacuo. The crude mixture was purified by Biotage with 75% ethyl acetate/hexanes to obtain 223 mg (33% yield) of product; MH+ 551.2.

EXAMPLE 176

Preparation of methyl 3-{[(2R)-2-({(tert-butoxycarbonyl)[(2R)-2-hydroxy-2-(3-pyridinyl)ethyl]amino}methyl)-3,4-dihydro-2H-chromen-6-yl]sulfonyl}benzoate

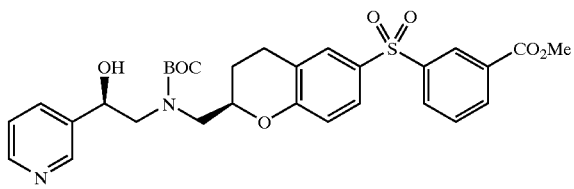

A solution of 0.5 mL (3.6 mmol) of trifluoroacetic anhydride in 2 mL methylene chloride was cooled to 0° C., and then 0.11 mL (1.1 mmol) of 30% hydrogen peroxide was added to the solution slowly, allowing the solution to stir at this temperature for 5 minutes. Then a solution of 200 mg (0.36 mmol) methyl 3-{[(2R)-2-({(tert-butoxycarbonyl)[(2R)-2-hydroxy-2-(3-pyridinyl)ethyl]amino}methyl)-3,4-dihydro-2H-chromen-6-yl]sulfanyl}benzoate (Example 175) in 1 mL of methylene chloride was added to the cold solution dropwise and the reaction mixture was stirred at 0° C. for 1 hour, followed by stirring at room temperature for 0.5 hour. The mixture was diluted with 10 mL ethyl ether and washed with 20 mL of 1N aqueous sodium hydroxide. The aqueous layer was extracted with ethyl ether, and the organic phase was washed sequentially with 20% aqueous sodium sulfite, water and brine, dried over sodium sulfate, filtered, and concentrated in vacuo to obtain 66.3 mg (21% yield) of crude product; MH+ 583.2.

EXAMPLE 177

Preparation of 3-{[(2R)-2-({[(2R)-2-hydroxy-2-(3-pyridinyl)ethyl]amino}methyl)-3,4-dihydro-2H-chromen-6-yl]sulfonyl}benzoic acid

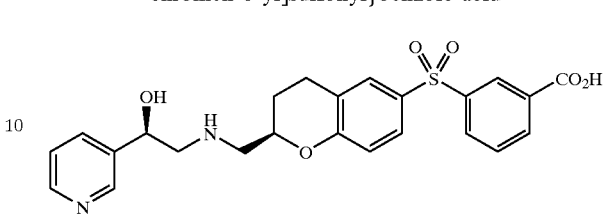

To a solution of 66.3 mg (0.11 mmol) methyl 3-{[(2R)-2-({(tert-butoxycarbonyl)[(2R)-2-hydroxy-2-(3-pyridinyl)ethyl]amino}methyl)-3,4-dihydro-2H-chromen-6-yl]sulfonyl}benzoate (Example 176) diluted in 5 mL 1,4-dioxane, was slowly added 0.05 mL of 6N hydrochloric acid. The resulting mixture was then stirred at 45° C. for 2 hours. The crude mixture was concentrated in vacuo, then purified by preparative HPLC. The purified intermediate product was then treated with 0.8 mL of 2N sodium hydroxide and allowed to stir for 36 hours and then concentrated in vacuo. The crude product was then purified by preparative HPLC (0–70% Acetonitrile/0.1% aq TFA) to obtain 6.5 mg of product as the bis-TFA salt. MH+ 469.3 (free base)

EXAMPLE 178

Preparation of 2,2-dimethyl-4-oxo-4H-1,3-benzodioxin-7-yl trifluoromethanesulfonate

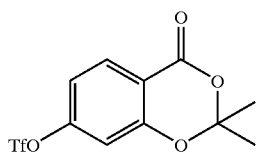

To 2,4-dihydroxybenzoic acid (Aldrich) (10.0 g, 64.9 mmol, 1.0 eq.) was added trifluoroacetic acid (80 mL), trifluoroacetic anhydride (50 mL), and acetone (10 mL) at 0° C. The reaction mixture was allowed to warm up slowly to room temperature and stirred for 48 hours. The mixture was then concentrated under reduced pressure. The resulting residue was washed with saturated sodium bicarbonate (100 mL), extracted with ethyl acetate (3×100 mL). The combined extracts were dried over magnesium sulfate, filtered, and concentrated under reduced pressure to give crude product 9.2 g as yellow solid.

The crude product was treated with trifluoromethanesulfonic anhydride (8.8 mL, 52.11 mmol, 1.1 eq.) in the presence of pyridine (50 mL) at 0° C. for 8 hours. The resulting mixture was then diluted with distilled water (100 mL), extracted with ethyl acetate (3×50 mL), and washed with saturated sodium bicarbonate (60 mL) and brine (100 mL). The combined extracts were dried over magnesium sulfate, filtered, and concentrated under reduced pressure to give brown oil. Purification by flash chromatography on a silica gel column (20%–40% ethyl acetate/hexanes) yielded the desired product as a white solid (8.3 g, 40%). $^1$H NMR (CDCl$_3$) δ 8.08 (d, 1H), 7.03 (d, 1H), 6.94 (s, 1H), 1.77 (s, 6H), GC-MS: 326 (M$^+$), retention time: 7.557 min.

EXAMPLE 179

Preparation of tert-butyl (2R)-2-{[tert-butyl(dimethyl)silyl]oxy}-2-(3-pyridinyl)ethyl{[(2S)-6-(2,2-dimethyl-4-oxo-4H-1,3-benzodioxin-7-yl)-3,4-dihydro-2H-chromen-2-yl]methyl}carbamate

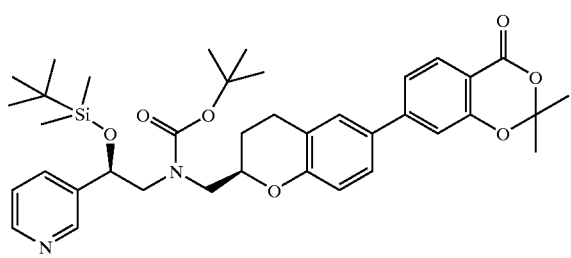

By using procedure described in Example 85, the compounds of Example 178 and Example 81 were coupled to provide the desired compound. LC-MS: 421.4 (MH$^+$-Boc), retention time: 1.54 min.

EXAMPLE 180

Preparation of 2-hydroxy-4-[(2S)-2-({[(2R)-2-hydroxy-2-(3-pyridinyl)ethyl]amino}methyl)-3,4-dihydro-2H-chromen-6-yl]benzoic acid

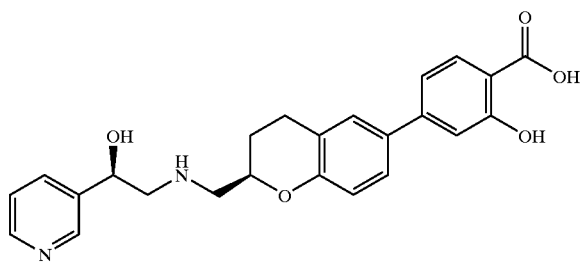

To a solution of tert-butyl (2R)-2-{[tert-butyl(dimethyl)silyl]oxy}-2-(3-pyridinyl) ethyl{[(2S)-6-(2,2-dimethyl-4-oxo-4H-1,3-benzodioxin-7-yl)-3,4-dihydro-2H-chromen-2-yl]methyl}carbamate (Example 179, 0.07 g, 0.104 mmol, 1.0 eq.) in tetrahydrofuran (3 mL) was added 4N hydrochloric acid in 1,4-dioxane (2 mL) at room temperature. The reaction mixture was allowed to stir at room temperature for 16 hours. The mixture was then concentrated under reduced pressure. Purification by HPLC afforded the desired HCl salt as a white solid (0.005 g, 10%). LC-MS: 421.4 (MH$^+$), retention time: 1.54 min.

EXAMPLE 181

Preparation of methyl 4-[(2S)-2-({(tert-butoxycarbonyl)[(2R)-2-{[tert-butyl(dimethyl)silyl]oxy}-2-(3-pyridinyl)ethyl]amino}methyl)-3,4-dihydro-2H-chromen-6-yl]-2-hydroxybenzoate

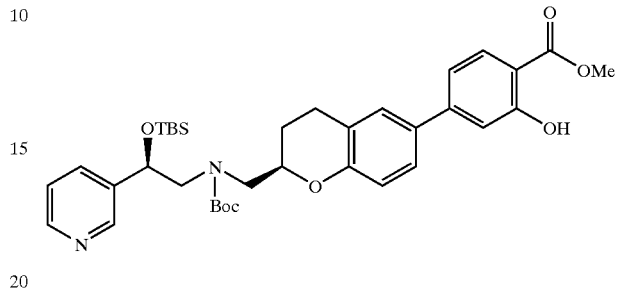

To a solution of the compound of Example 179 in methanol (10 mL) was added potassium carbonate (0.12 g) at room temperature. The reaction mixture was allowed to stir at room temperature for 18 hours and then concentrated under reduced pressure. The resulting residue was washed with distilled water (10 mL) and extracted with ethyl acetate (3×10 mL). The combined extracts were dried over magnesium sulfate, filtered and concentrated under reduced pressure to afford the desired product as pale yellow oil (0.68 g, 94%). LC-MS: 649.8 (MH$^+$), retention time: 3.80 min.

EXAMPLE 182

Preparation of methyl 4-[(2S)-2-({(tert-butoxycarbonyl)[(2R)-2-{[tert-butyl(dimethyl)silyl]oxy}-2-(3-pyridinyl)ethyl]amino}methyl)-3,4-dihydro-2H-chromen-6-yl]-2-isobutoxybenzoate

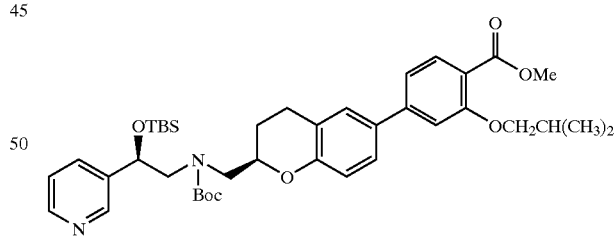

To a solution of the compound of Example 181 (0.097 g, 0.0015 mmol, 1.0 eq.) in N,N-dimethylformamide (0.5 mL) were added 1-iodo-2-methylpropane (0.10 ml) and potassium carbonate (0.10 g). The reaction mixture was stirred at 60° C. for 16 hours. The mixture was diluted with distilled water (2 mL) and extracted with ethyl acetate (3×2 mL). The combined extracts were dried over magnesium sulfate, filtered and concentrated under reduced pressure to give the crude as clear oil (0.076 g, 74%). LC-MS: 705.3 (MH$^+$), retention time: 4.01 min.

EXAMPLE 183

Preparation of 4-[(2S)-2-({[(2R)-2-hydroxy-2-(3-pyridinyl)ethyl]amino}methyl)-3,4-dihydro-2H-chromen-6-yl]-2-isobutoxybenzoic acid

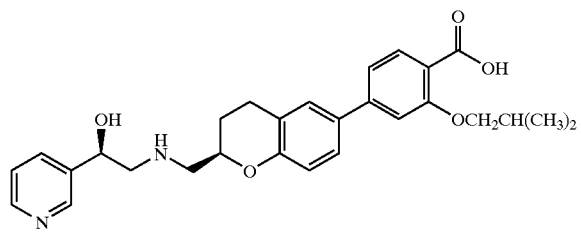

To a solution of the compound of Example 182 (0.076 g, 0.11 mmol, 1.0 eq.) in methanol (1.0 mL) was added 1M lithium hydroxide (1.0 mL). The reaction mixture was stirred at room temperature for 16 hours. The mixture was neutralized by 1N hydrochloric acid and then extracted with ethyl acetate (3×2 mL). The extracts were concentrated under reduced pressure to give white solid. To this crude was added 4N hydrochloric acid in 1,4-dioxane (1.5 mL) and the mixture was stirred for 3 hours at room temperature. The resulting mixture was concentrated under reduced pressure to give white solid. Purification by HPLC yielded the desired HCl salt as a white solid (15.7 mg, 26%). LC-MS: 477.2 (MH$^+$), retention time: 1.97 min.

By using procedure described in Examples 182 and 183, the following analogs were prepared.

TABLE 7

| Example | R' | Calculated MW | MS [M + H$^+$] | RT (minutes) LC-MS |
|---|---|---|---|---|
| 184 | ⟍O⟋ | 434 | 435.1 | 1.45 |
| 185 | ⟍O⟋⟍ | 448 | 449.1 | 1.73 |
| 186 | ⟍O⟋⟍⟍ | 462 | 463.2 | 1.87 |
| 187 | ⟍O⟋⟍O⟋ | 478 | 479.2 | 1.63 |
| 188 | ⟍O⟋⟍(iPr) | 462 | 463.2 | 1.83 |

EXAMPLE 189

Preparation of phenylmethyl 4-bromo-2-fluorobenzoate

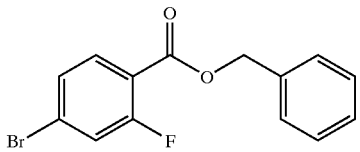

Benzyl bromide (0.86 g, 5.0 mmol, 1.1 eq.) was added neat to a solution of 4-bromo-2-fluorobenzoic acid (1.0 g, 4.6 mmol) and 1,8-diazabicyclo[5.4.0]undec-7-ene (1.36 mL, 9.2 mmol, 2.0 eq.) in anhydrous acetonitrile (20 mL). The reaction was stirred at room temperature for 18 hours before removing the solvent in vacuo. The residue was diluted with ether and washed with water, saturated aqueous sodium bicarbonate, saturated aqueous ammonium chloride, and brine. The organic layer was dried (MgSO$_4$) and concentrated in vacuo to provide the title compound as a pale yellow oil that crystallized into long needles upon standing (1.4 g, 99%): $^1$H NMR (300 MHz, CDCl$_3$) δ 7.82 (t, 1 H), 7.42–7.31 (m, 7 H), 5.35 (s, 2 H); GC/MS m/z 308/310 (M$^+$ and M$^{+2}$).

EXAMPLE 190

Preparation of phenylmethyl 4-bromo-2-(phenyloxy)benzoate

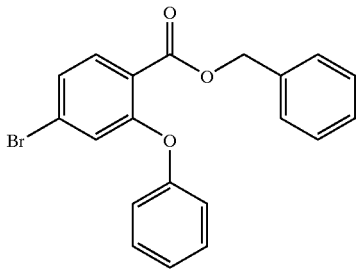

Phenylmethyl 4-bromo-2-fluorobenzoate (Example 189, 260 mg, 0.84 mmol) was combined with phenol (160 mg, 1.68 mmol, 2.0 eq.) and solid potassium carbonate (580 mg, 4.21 mmol, 5.0 eq.) in anhydrous N,N-dimethylformamide and was heated at 85° C. for 5 hours. The mixture was cooled and partitioned between diethyl ether and water. The aqueous layer was separated and extracted with fresh ether. The organic layers were combined, washed with brine (4×), dried (MgSO$_4$), and concentrated in vacuo to a crude oil. The crude was purified by flash chromatography on silica gel eluted with 95:5 hexanes/ether to provide the title compound as a colorless oil that crystallized upon standing (110 mg, 34%): $^1$H NMR (300 MHz, CDCl$_3$) δ 7.84 (d, 1 H), 7.39–7.27 (m, 7 H), 7.17–7.10 (m, 1 H), 6.98–6.91 (m, 2 H), 6.85 (d, 2 H), 5.30 (s, 2 H); R$_f$ 0.51 (4:1 hexanes/diethyl ether).

EXAMPLE 191

Preparation of Phenylmethyl 4-((2R)-2-[([(2R)-2-{ [(1,1-dimethylethyl)(dimethyl)silyl]oxy}-2-(3-pyridinyl)ethyl]{[(1,1-dimethylethyl)oxy]carbonyl}amino) methyl]-3,4-dihydro-2H-chromen-6-yl}-2-(Phenyloxy)benzoate

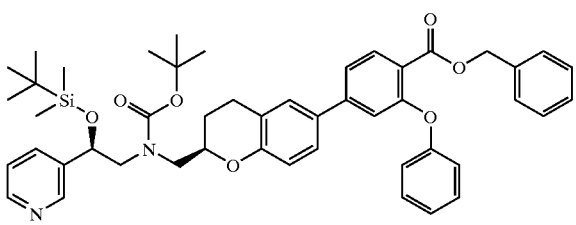

Argon gas was bubbled through a solution of the compound of Example 81 (160 mg, 0.25 mmol) in toluene (5 mL), dioxane (1 mL), and aqueous Na₂CO₃ (0.5 mL of a 2.0 M solution) for 10 minutes. Pd(dppf)Cl₂(20 mg, 0.025 mmol, 0.1 eq.) and phenylmethyl 4-bromo-2-(phenyloxy)benzoate (Example 190, 110 mg, 0.27 mmol, 1.1 eq.) were added, and argon was bubbled through the mixture for an additional 5 minutes before being stirred vigorously at 85° C. for 3 hours. The reaction mixture was cooled and filtered through a pad of Celite® with the aid of ethyl acetate. The filtrate was transferred to a separatory funnel where the water layer was removed. The organic layer was dried (MgSO₄) and concentrated in vacuo to a crude oil. The crude was purified by flash chromatography on silica gel eluted on a gradient from 100:0 to 70:30 hexanes/ethyl acetate to provide the title compound as a colorless oil (69 mg, 34%): $^1$H NMR (300 MHz, CDCl₃) δ 8.58–8.47 (m, 2 H), 7.96 (d, 1 H), 7.64 (dd, 1 H), 7.32 (d, 1 H), 7.27–7.20 (m, 10 H), 7.17–7.12 (m, 1 H), 7.00 (t, 1 H), 6.89 (d, 2 H), 6.72 (d, 1 H), 5.20 (s, 2 H), 5.11–4.90 (m, 1 H), 4.21–4.03 (m, 1 H), 3.73 (d, 1 H), 3.63–3.54 (m, 1 H), 3.42–3.14 (m, 2 H), 2.81–2.70 (m, 2 H), 1.98–1.89 (m, 1 H), 1.68–1.60 (m, 1 H), 1.42 (s, 9 H), 0.83 (s, 9 H), –0.01 (s, 3 H), –0.018 (s, 3 H); MS m/z 801.2 (MH⁺).

EXAMPLE 192

Preparation of 4-[(2R)-2-({[(2R)-2-hydroxy-2-(3-pyridinyl)ethyl]amino}methyl)-3,4-dihydro-2H-chromen-6-yl]-2-(Phenyloxy)benzoic acid

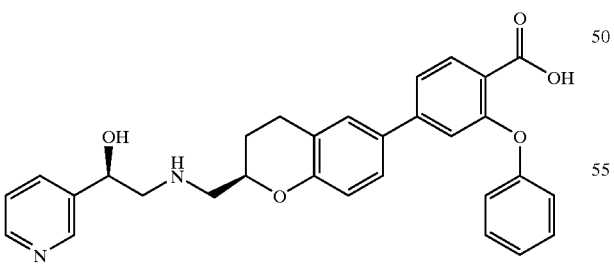

Phenylmethyl 4-{(2R)-2-[([(2R)-2-{[(1,1-dimethylethyl)(dimethyl)silyl]oxy}-2-(3-pyridinyl)ethyl]{[(1,1-dimethylethyl)oxy]carbonyl}amino)methyl]-3,4-dihydro-2H-chromen-6-yl}-2-(phenyloxy)benzoate (Example 191, 69 mg, 0.086 mmol) was stirred over a suspension of 10% Pd/C (7 mg) in ethanol (5 mL) under a hydrogen atmosphere for 15 hours. Solids were removed by filtration through Celite®, and the filtrate was concentrated in vacuo. The carboxylic acid intermediate was collected as a colorless oil (25 mg, 41%): $^1$H NMR (300 MHz, CD₃OD) δ 8.66–8.58 (m, 2 H), 7.99 (d, 1 H), 7.92 (d, 1 H), 7.58–7.54 (m, 2 H), 7.51–7.41 (m, 2 H), 7.37–7.34 (m, 2 H), 7.21–7.16 (m, 2 H), 7.10 (d, 2 H), 6.86 (d, 1 H), 5.27–5.15 (m, 1 H), 4.38–4.31 (m, 1 H), 3.86–3.54 (m, 4 H), 2.96–2.90 (m, 2 H), 2.13–2.00 (m, 1 H), 1.87–1.75 (m, 1 H), 1.56 (d, 9 H), 1.00 (s, 9 H), 0.18 (d, 3 H), 0.00 (s, 3 H). The carboxylic acid intermediate (25 mg, 0.04 mmol) was stirred in an excess of 4M HCl in dioxane at room temperature for 18 hours. The volatile components were removed by rotary evaporation, and the residue was washed with dichloromethane. After drying under vacuum, the title compound was collected as the di-hydrochloride salt (16 mg, 80%): $^1$H NMR (300 MHz, CD₃OD) δ 9.04 (broad s, 1 H), 8.89 (broad s, 1 H), 8.77 (d, 1 H), 8.15 (t, 1 H), 8.00 (d, 1 H), 7.46 (d, 1 H), 7.38–7.33 (m, 4 H), 7.14–7.08 (m, 2 H), 6.98 (d, 3 H), 5.45 (d, 1 H), 4.50 (t, 1 H), 3.76–3.55 (m, 5 H), 3.52–3.35 (m, 2 H), 2.99–2.85 (m, 2 H), 2.18–2.11 (m, 1 H), 1.85–1.75 (m, 1 H); MS m/z 497.2 (MH⁺ of the free base).

By employing the methods described above for Examples 190–192, the following were similarly prepared and characterized:

TABLE 8

| Example No. | R" | Calculated MW | MS [M + H⁺] | LC-MS RT (min) |
|---|---|---|---|---|
| 193 | —F | 514.19 | 515.1 | 1.88 |
| 194 | —Cl | 530.16 | 531.2 | 2.01 |
| 195 | —CH₃ | 510.22 | 511.2 | 1.96 |
| 196 | —OCH₃ | 526.21 | 527.2 | 1.94 |
| 197 | —CO₂Et | 568.22 | 569.2 | 1.99 |
| 198 | —SO₂CH₃ | 574.18 | 575.1 | 1.77 |

EXAMPLE 199

Preparation of tert-butyl benzyl{[(2S)-6-bromo-3,4-dihydro-2H-chromen-2-yl]methyl}carbamate

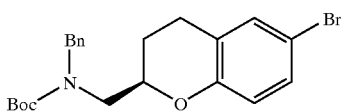

To a solution of N-benzyl[(2R)-6-bromo-3,4-dihydro-2H-chromen-2-yl]methanamine (Example 217, 20.0 g, 60.2 mmol, 1.0 mmol) in tetrahydrofuran (200 mL) was added di-tert-butyl dicarbonate (14.45 g, 66.22 mmol, 1.1 eq.) at room temperature. The reaction mixture was stirred at room temperature for 18 hours and then quenched with distilled water (100 mL). The resulting mixture was extracted with ethyl acetate (3×50 mL) and washed with saturated sodium bicarbonate (50 mL) and brine (80 mL). The combined extracts were dried over magnesium sulfate, filtered through silica gel, and concentrated under reduced pressure to yield the desired product as colorless oil which was used without further purification (25 g, 100%).

EXAMPLE 200

Preparation of tert-butyl benzyl{[(2R)-6-(4,4,5,5-tetramethyl-1,3,2-dioxaborolan-2-yl)-3,4-dihydro-2H-chromen-2-yl]methyl}carbamate

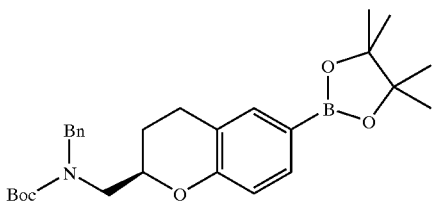

To a degassed solution of the compound of Example 199 (15.0 g, 57.24 mmol, 1.0 mmol) in dimethyl sulfoxide (120 mL) was added bis(pinacolato)diboron (15.0 g, 57.24 mmol, 1.0 eq.), dichloro[1,1'-bis(diphenylphospphino)ferrocene]palladium(II) dichloromethane adduct (1.46 g, 1.72 mmol, 0.03 eq.) and potassium acetate (17.0 g, 171.72 mmol, 3.0 eq.) under argon atmosphere at room temperature. The reaction mixture was allowed to heat up at 85° C. under argon atmosphere for 24 hours. The mixture was then allowed to cool down to room temperature and filter through silica gel. The filtrates were extracted with diethyl ether (3×100 mL). The combined extracts were washed with saturated sodium bicarbonate (50 mL) and brine (80 mL), dried over magnesium sulfate, filtered through silica gel, and concentrated under reduced pressure to yield yellow oil. Purification by flash chromatography on a silica gel column (5%–10% ethyl acetate/hexanes) yielded the desired product as yellow oil (13.5 g, 81%). LC-MS: 479.9 (MH$^+$), retention time: 4.41 min.

EXAMPLE 201

Preparation of tert-butyl benzyl{[(2R)-6-(2,2-dimethyl-4-oxo-4H-1,3-benzodioxin-7-yl)-3,4-dihydro-2H-chromen-2-yl]methyl}carbamate

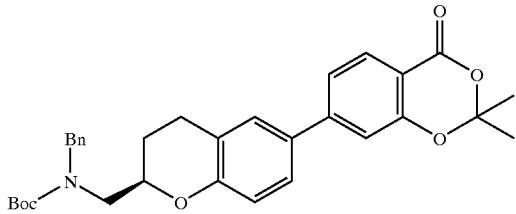

By using the procedure described in Example 85, the compounds of Example 200 and Example 178 were coupled to provide the desired compound. LC-MS: 529.9 (MH$^+$), retention time: 4.36 min.

EXAMPLE 202

Preparation of methyl 4-((2R)-2-{[benzyl(tert-butoxycarbonyl)amino]methyl}-3,4-dihydro-2H-chromen-6-yl)-2-hydroxybenzoate

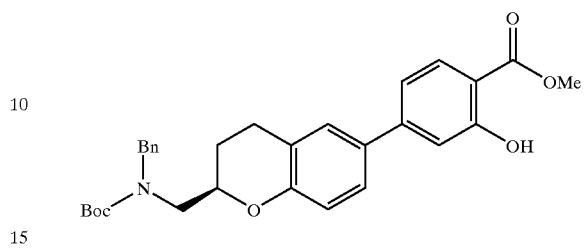

By using the procedure described in Example 181, the title compound was prepared. LC-MS: 503.7 (MH$^+$), retention time: 4.51 min.

EXAMPLE 203

Preparation of methyl 4-((2R)-2-{[benzyl(tert-butoxycarbonyl)amino]methyl}-3,4-dihydro-2H-chromen-6-yl)-2-{[(trifluoromethyl)sulfonyl]oxy}benzoate

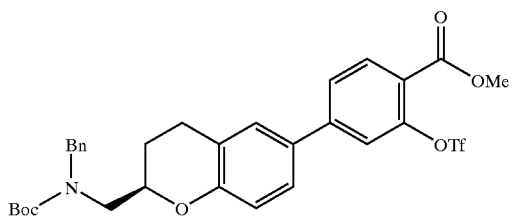

By using the procedure described in Example 12, the compound of Example 202 was converted into the title compound. LC-MS: 635.6 (MH$^+$), retention time: 4.48 min.

EXAMPLE 204

Preparation of methyl 5-{(2R)-2-[(benzylamino)methyl]-3,4-dihydro-2H-chromen-6-yl}-4'-methyl-1,1'-biphenyl-2-carboxylate

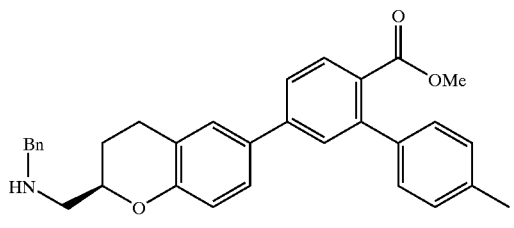

To a degassed solution of the compound of Example 203 (0.31 g, 0.49 mmol, 1.0 eq.) in toluene (1.0 mL) was added 4-methylphenylboronic acid (0.10 g, 0.73 mmol, 1.5 eq.), dichloro[1,1'-bis(diphenylphosphino)ferrocene]palladium(II) dichloromethane adduct (0.028 g, 0.034 mmol, 0.07 eq.) and 2M sodium carbonate (2.4 mL, 4.88 mmol, 10.0 eq.) under argon atmosphere at room temperature. The reaction mixture was allowed to heat up at 80° C. under argon atmosphere for 18 hours. The mixture was diluted with distilled water (3 mL) and extracted with diethyl ether (3×2 mL). The combined extracts were dried over magnesium sulfate, filtered, and concentrated under reduced pressure. The resulting residue was then treated with 4N hydrochloric acid (1.0 mL) in tetrahydrofuran (3 ml) and stirred at room temperature for 48 hours. The mixture was concentrated under reduced pressure to give white solid. Purification by HPLC followed yielded the desired product as clear oil (0.18 g, 77%). LC-MS: 578.0 (MH+), retention time: 4.63 min.

EXAMPLE 205

Preparation of 5-[(2R)-2-({[(2R)-2-hydroxy-2-(3-pyridinyl)ethyl]amino}methyl)-3,4-dihydro-2H-chromen-6-yl]-4'-methyl-1,1'-biphenyl-2-carboxylic acid

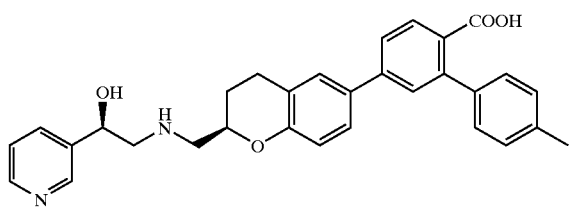

To a solution of the compound of Example 204 (0.18 g, 0.38 mmol, 1.0 eq.) in isopropanol (4.0 mL) were added the compound of Example 1 (0.09 g, 0.57 mmol, 1.5 eq.) and potassium carbonate (0.16 g, 1.13 mmol, 3.0 eq.) at room temperature. The reaction mixture was allowed to heat up at 95° C. for 16 hours. The mixture was diluted with distilled water (6 mL) and extracted with ethyl acetate (3×6 mL). The combined extracts were dried over magnesium sulfate, filtered and concentrated under reduced pressure. Purification by HPLC yielded the intermediate as a colorless oil. The pure intermediate was then treated with 1M lithium hydroxide (1.0 mL) in the presence of methanol (2.0 mL) and stirred at 80° C. for 15 hours. The mixture was neutralized by 1N hydrochloric acid and then extracted with ethyl acetate (3×2 mL). The extracts were concentrated under reduced pressure to give white solid. To this crude in methanol (1 mL) was added palladium hydroxide (0.04 g) and ammonium formate (0.045 g) under argon atmosphere and the mixture was stirred at 65° C. for 14 hours. The resulting mixture was filtered through celite and concentrated under reduced pressure to give white solid. Purification by HPLC yielded the desired TFA salt as a white solid (10 mg, 10%). LC-MS: 585.3 (MH+), retention time: 2.35 min.

EXAMPLE 206

Preparation of methyl 4-(benzyloxy)-2-{[(trifluoromethyl)sulfonyl]oxy}benzoate

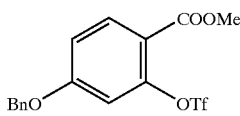

To a solution of methyl-4-benzyloxy-2-hydroxybenzoate (5.34 g, 21 mmol) and pyridine (2.5 g, 31.5 mmol) in dichloromethane (100 mL) was added trifluoromethanesulfonic anhydride (8.17 g, 29 mmol) slowly. The resulting mixture was stirred overnight, washed with 1N HCl, brine, dried, evaporated to afford 4.3 g yellow solid. (53% yield). ¹HNMR Chloroform-d δ 4.01 (d, 3H), 5.17 (d, 2H), 6.89 (d, 1H), 7.2 (d, 1H), 7.30–7.41 (m, 5H), 8.10 (t, 1H). Rf=0.37 ethyl acetate/hexane (1/9).

EXAMPLE 207

Preparation of methyl 4-(benzyloxy)-2-isobutylbenzoate

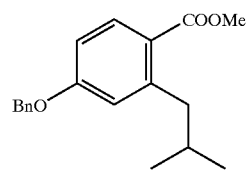

To a condensed liquid 2-methyl-1-propene in THF (10 mL) at −78° C. was added 0.5 M 9-BBN (3 mL, 1.5 mmol), the mixture was allowed to warm up to room temperature with stirring. The mixture was transferred via a syringe to a degassed solution containing the compound of Example 206 (0.5 g, 1.3 mmol), Pd(dppf)Cl₂ (82 mg, 0.1 mmol), K₂CO₃ (0.23 g, 1.7 mmol), water (2 mL) in DMF (21 mL). The resulting mixture was heated at 60° C. overnight. After removal of solvent, the residue was purified by chromatography to afford the title compound (0.11 g, 31% yield). ¹HNMR Chloroform-d δ 0.85 (d, 6H), 1.75–1.80 (m, 1H), 2.88 (d, 2H), 3.78 (s, 3H), 5.13 (s, 2H), 6.71–6.80 (m, 2H), 7.30–7.41 (m, 5H), 7.90 (d, 1H). Rf=0.65 ethyl acetate/hexane (1/9).

EXAMPLE 208

Preparation of methyl 4-(hydroxy)-2-isobutylbenzoate

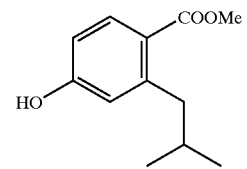

A solution of the compound of Example 207 (0.8 g, 2.6 mmol), 10% Pd—C in MeOH (30 mL) was hydrogenated overnight. The mixture passed through Celite® and concentrated to yellow residue (0.5 g, 89% yield). ¹HNMR Chloroform-d δ 0.90 (d, 6H), 1.82–1.90 (m, 1H), 2.89 (d, 2H), 3.90 (s, 3H), 6.73–6.80 (m, 2H), 7.88 (d, 1H). Rf=0.41 ethyl acetate/hexane (4/6).

EXAMPLE 209

Preparation of methyl 2-isobutyl-4-{[(trifluoromethyl)sulfonyl]oxy}benzoate

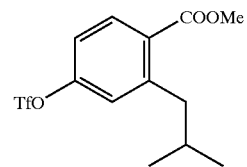

To a solution of the compound of Example 198 (0.5 g, 2.4 mmol) and pyridine (0.21 g, 2.6 mmol) in dichloromethane (50 mL) was added trifluoromethanesulfonic anhydride (0.75 g, 2.6 mmol) slowly. The resulting mixture was stirred overnight, washed with 1N HCl, brine, dried, evaporated to afford 0.51 g yellow solid. (64% yield). R=0.63 ethyl acetate/hexane (1/9).

EXAMPLE 210

Preparation of methyl 4-[(2S)-2-[(4S)-4-{[tert-butyl (dimethyl)silyl]oxy}-4-(3-pyridinyl)butyl]-3,4-dihydro-2H-chromen-6-yl]-2-isobutylbenzoate

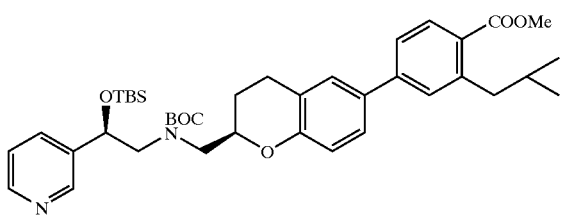

The reaction mixture of the compound of Example 81 (1.3 g, 2.1 mmol), the compound of Example 209 (0.7 g, 2.1 mmol) and potassium carbonate (0.9 g, 6.3 mmol) in toluene (20 mL) was flushed with Ar for 5 minutes, and Pd(PPh$_3$)$_4$ was added quickly to the reaction. The reaction mixture was refluxed overnight at 45° C. After removal of solvent in vacuo, the crude product was purified by silica gel chromatography to afford 0.32 g of white solid in 23% yield. Rf=0.63 ethyl acetate/hexane (3/7), MS: m/z (M+1) 690.43.

EXAMPLE 211

Preparation 4-[(2R)-2-({[(2R)-2-hydroxy-2-(3-pyridinyl)ethyl]amino}methyl)-3,4-dihydro-2H-chromen-6-yl]-2-isobutylbenzoic acid

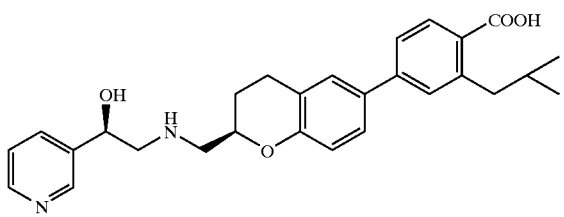

The compound of Example 210 (0.3 g, 0.4 mmol) was dissolved in 4.0 M HCl in dioxane (30 mL) and stirred overnight. After removal of the solvent, the residue was dissolved in MeOH—THF (1:1) (26 mL). NaOH (0.6 g), water (3 mL) was added to the solution and refluxed for 3 hours. After the reaction cooled to room temperature, 2N HCl was added to pH=3. White solid was formed and filtered to collect the white solid. The solid was purified by HPLC to afford 0.15 g yellow solid (50% yield). $^1$HNMR Methanol-d$_4$ δ 0.93 (d, 2H), 1.81–1.91 (m, 2H), 2.20–2.25 (m, 1H), 2.91–3.08 (m, 4H), 3.35–3.41 (m, 4H), 4.53 (t, 1H), 5.43 (d, 1H), 7.03 (d, 1H), 7.43–7.50 (m, 4H), 7.95 (d, 1H), 8.09 (t, 1H), 8.70 (d, 1H), 8.87 (s, 1H), 9.0 (s, 1H). R$_f$=0.21 methanol/dichloromethane (2/8), MS: m/z (M+1) 461.30.

EXAMPLE 212

Preparation of methyl 4-(benzyloxy)-2-(2-phenylethyl)benzoate

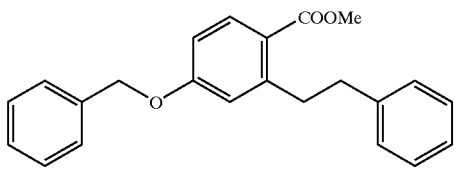

To a solution of styrene in THF (50 mL), 9-BBN was added slowly, stirring at room temperature for overnight. The solution was degassed for 5 minutes and the compound of Example 206, Pd(dppf)Cl$_2$, and Et$_3$N were added at once. The reaction mixture was heated to reflux for 3–4 hours. The solvent was stripped. Residue was partitioned between EtOAc and H$_2$O (100 mL/50 mL), aqueous layer was extracted with EtOAc (2×100 mL). Organic solvent was dried over anhydrous Na$_2$SO$_4$ and removed under the reduced pressure. The crude product was purified by column chromatography to give 0.40 g of the desired compound (25%). $^1$H NMR (MeOH-d$_4$, δ ppm): 8.10–8.18 (m, 2H), 10.28–10.32 (m, 2H), 3.90 (s, 3H), 7.11–7.18 (m, 2H), 7.10–7.31 (m, 10H), 8.20–8.91 (m, 2H), 8.01 (d, 1H). Rf=0.51 (CH$_2$Cl$_2$:MeOH=95:5)

EXAMPLE 213

4-[(2R)-2-({[(2R)-2-hydroxy-2-(3-pyridinyl)ethyl]amino}methyl)-3,4-dihydro-2H-chromen-6-yl]-2-(2-phenylethyl)benzoic acid

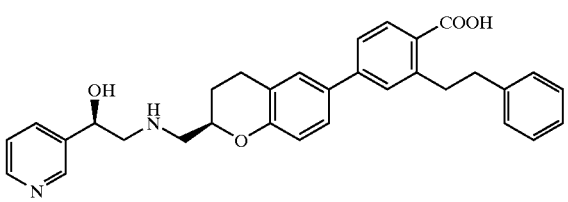

Using the procedures outlined in Examples 208–211, Example 212 was converted to the title compound. MS [M+H]+ 508.2, Rf=0.24 (CH$_2$Cl$_2$:MeOH=95:5). H$^1$ NMR (MeOD-d4, δ ppm): 1.64 (2H, d), 1.73–1.85 (1H, m), 2.07–2.10 (1H, m), 2.90–2.96 (2H, m), 3.31 (2H, d), 3.36–3.56 (4H, m), 4.47 (1H, m), 5.38 (1H, dd), 6.95 (1H, dd), 7.13–7.46 (9H, m), 7.87 (1H, d), 8.03–8.05 (1H, m), 8.60 (1H, d), 8.82 (1H, br.s.), 8.95 (1H, br.s.)

EXAMPLE 214

Preparation of methyl 4-{2-[(2S)-2-({(tert-butoxycarbonyl)[(2R)-2-{[tert-butyl(dimethyl)silyl]oxy}-2-(3-pyridinyl)ethyl]amino}methyl)-3,4-dihydro-2H-chromen-6-yl]ethyl}benzoate

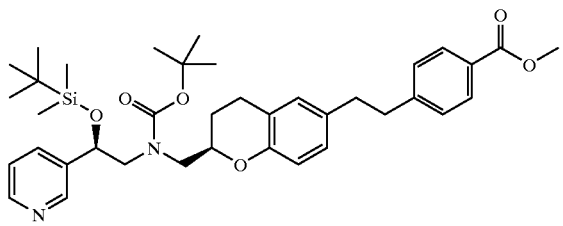

Using the procedure outlined in Example 212, methyl 4-vinylbenzoate was hydroborated with 9-BBN and coupled with the compound of Example 38 to provide the title compound. MS [M+H]+ 661.4, Rf=0.43 (Hex:EtOAc=2:1). H¹ NMR (CDCl₃, δ ppm): 0.12 (s, 6H), 0.67–0.72 (s, 9H), 1.43 (s, 9H), 1.55–1.59 (m, 1H), 1.81–1.95 (m, 2H), 2.68–2.93 (m, 5H), 3.15–3.72 (m, 4H), 3.80 (s, 3H), 4.01–4.21 (m, 1H), 4.91–5.02 (m, 1H), 6.55–6.60 (m, 1H), 6.70–6.78 (m, 2H), 7.25–7.38 (m, 3H), 7.60–7.73 (m, 1H), 7.83–7.92 (m, 2H), 8.41–8.58 (m, 2H).

EXAMPLE 215

Preparation of 4-[2-[(2S)-2-({[(2R)-2-hydroxy-2-(3-pyridinyl)ethyl]amino}methyl)-3,4-dihydro-2H-chromen-6-yl]ethyl]benzoic acid

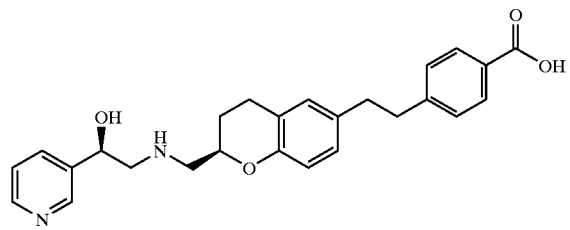

Using the procedures outlined in Examples 208–211, the compound of Example 214 was converted to the title compound. MS [M+H]+ 432.2, Rf=0.5 (CH₂Cl₂:MeOH=7:3) H¹ NMR (MeOH-d4, δ ppm): 1.66–1.80 (1H, m), 2.01–2.12 (1H, m), 2.82–2.92 (6H, m), 3.18–3.30 (6H, m), 4.32 (1H, t), 5.10 (1H, dd), 6.72 (1H, d), 6.85–6.88 (2H, m), 7.16 (2H, d), 7.48 (1H, dd), 7.84 (2H, d), 7.94 (1H, d), 8.51 (1H, d), 8.63 (1H, s)

EXAMPLE 216

Preparation of 3-[2-[(2S)-2-({[(2R)-2-hydroxy-2-(3-pyridinyl)ethyl]amino}methyl)-3,4-dihydro-2H-chromen-6-yl]ethyl]benzoic acid

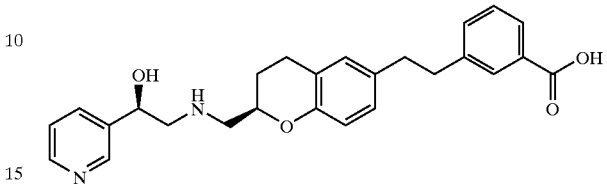

Using the procedures outlined in Examples 208–211, the compound of Example 215 was converted to the title compound. MS [M+H]+ 432.2, Rf=0.5 (CH₂Cl₂:MeOH=7:3) H¹ NMR (MeOH-d4, δ ppm): 1.66–1.80 (1H, m), 1.99–2.12 (1H, m), 2.80–2.92 (6H, m), 3.18–3.30 (6H, m), 4.32 (1H, t), 5.10 (1H, dd), 6.72 (1H, d), 6.85–6.88 (2H, m), 7.15–7.17 (2H, m), 7.46 (1H, dd), 7.81–7.85 (2H, m), 7.94 (1H, d), 8.51 (1H, d), 8.63 (1H, s)

EXAMPLE 217

Preparation of N-benzyl-N-{[(2R)-6-bromo-3,4-dihydro-2H-chromen-2-yl]methyl}amine

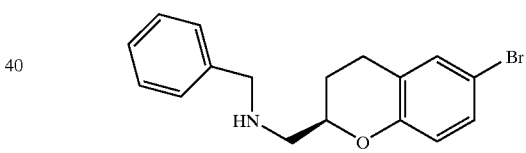

In a 30 L reaction vessel, N-benzyl[(2R)-3,4-dihydro-2H-chromen-2-yl]methanamine hydrobromide (2173 g, 6.5 moles, 1.0 eq.) was suspended in 11.4 L formic acid. The suspension was cooled to 16° C., then bromine (1071 g, 6.7 moles, 1.03 eq.) was added over a 60 minutes, maintaining the reaction temperature between 15 and 16° C. After 70 minutes, a HPLC probe indicated the reaction to be complete. To the reaction mixture was then added 15.6 L water (temperature increased to 21° C.). The light reaction mixture was then stirred for 30 minutes at room temperature, then the product was filtered and washed with 3.9 L water. The 3.14 kg of light gray moist product was then suspended in 9.75 L dichloromethane. To this suspension was added 13 L 1M NaHCO₃. Foaming ensued and the suspension became a bi-phasic solution. The aqueous phase was separated (14.5 L; pH=8) and the organic phase was washed with 6.5 L water. The phases were separated and the organic phase evaporated at 45° C. to yield 1820 g of N-benzyl-N-{[(2R)-6-bromo-3,4-dihydro-2H-chromen-2-yl]methyl}amine.

EXAMPLE 218

Preparation of 4-bromo-N-(2-pyrimidinyl)benzenesulfonamide

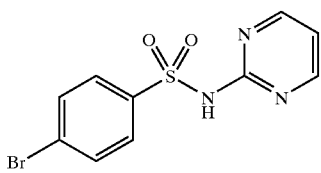

A mixture of 4-bromobenzene sulfonyl chloride (3.0 g, 11.74 mmol) and 2-aminopyrimidine (1.17 g, 12.3 mmol, 1.05 eq) in anhydrous pyridine (23 mL) was stirred at 50° C. for 17 hours. The reaction was quenched with 2N aqueous hydrochloric acid (100 mL) and the resultant reaction mixture was extracted with ethyl acetate (2×150 mL). The combined organic layers were washed with water (1×100 mL) and brine (1×100 mL), dried ($Na_2SO_4$), filtered, and evaporated under reduced pressure. Recrystallization from ethyl acetate-dichloromethane gave the desired product as a white solid (2.95 g, 80%). LC-MS (ES $MH^+$=314/316); TLC ($R_f$=0.42, 75% ethyl acetate-hexane).

Using the procedure outline in Example 208 and the appropriate amine and sulfonyl chloride, the following sulfonamides were prepared.

TABLE 9-continued

| Example No. | Structure |
|---|---|
| 230 | 3-bromo-N-(pyrimidin-2-yl)benzenesulfonamide |
| 231 | 3-bromo-N-(pyridin-3-yl)benzenesulfonamide |
| 232 | 3-bromo-N-(2-cyano-4-nitrophenyl)benzenesulfonamide |
| 233 | 4-bromo-N-(thiazol-2-yl)benzenesulfonamide |
| 234 | 5-bromo-2-methoxy-N-(thiazol-2-yl)benzenesulfonamide |
| 235 | 4-bromo-N-(4-methylpyrimidin-2-yl)benzenesulfonamide |
| 236 | 5-bromo-2-methoxy-N-(4-methylpyrimidin-2-yl)benzenesulfonamide |
| 237 | 5-bromo-2-methoxy-N-(4,6-dimethoxypyrimidin-2-yl)benzenesulfonamide |
| 238 | 5-bromo-2-methoxy-N-(4-methoxy-6-methylpyrimidin-2-yl)benzenesulfonamide |
| 239 | 5-bromo-2-methoxy-N-(pyrimidin-2-yl)benzenesulfonamide |
| 240 | 5-bromo-2-methoxy-N-(4-acetylphenyl)benzenesulfonamide |
| 241 | 4-bromo-N-(pyridin-2-yl)benzenesulfonamide |
| 242 | 5-bromo-2-methoxy-N-(4-cyanophenyl)benzenesulfonamide |
| 243 | 4-bromo-N-(benzothiazol-2-yl)benzenesulfonamide |

TABLE 9-continued

| Example No. | Structure |
|---|---|
| 244 | 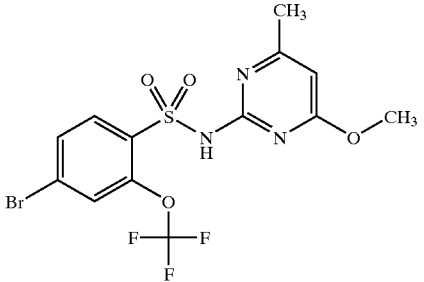 |
| 245 | 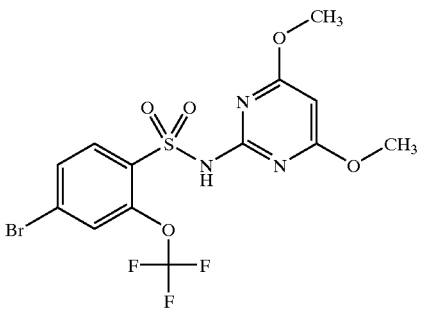 |
| 246 | 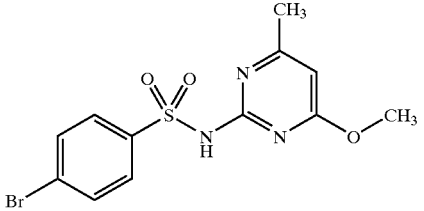 |

EXAMPLE 247

Preparation of tert-butyl (2R)-2-{[tert-butyl (dimethyl)silyl]oxy}-2-(3-pyridinyl)ethyl[((2R)-6-{4-[(2-pyrimidinylamino)sulfonyl]phenyl}-3,4-dihydro-2H-chromen-2-yl)methyl]carbamate

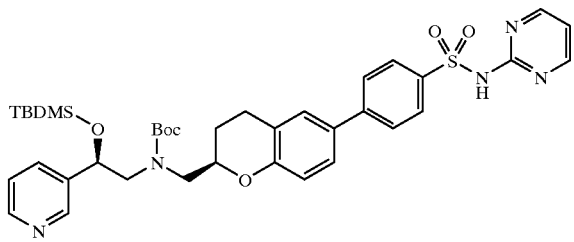

A solution of the compound of Example 81, (1.08 g, 1.73 mmol) in toluene (10 mL) and ethanol (10 mL) was degassed with argon for 10 minutes. At this time, the compound of Example 218 (815 mg, 2.59 mmol) was added followed by [1,1'-bis(diphenylphosphino)-ferrocene] dichloropalladium(II) complex with dichloromethane (1:1) (98 mg, 0.12 mmol) and 2M aqueous $Na_2CO_3$ (8.5 mL). The reaction was bubbled with argon for another 10 minutes and then heated to 80° C. overnight. The reaction was diluted with ethyl acetate, washed with water, brine, and dried over magnesium sulfate. The solvent was removed at reduced pressure and the residue was coated on silica. The silica coated product was purified on the MPLC (Biotage) with 30–100% ethyl acetate in hexanes then 2% methanol in methylene chloride to afford 796 mg (1.09 mmol, 63%) of product. LC-MS (ES $MH^+$=732, Rt=3.27 min); TLC ($R_f$= 0.31, 100% ethyl acetate).

EXAMPLE 248

Preparation of tert-butyl (2R)-2-hydroxy-2-(3-pyridinyl)ethyl[((2R)-6-{3-[(2-pyrimidinylamino)sulfonyl]phenyl}-3,4-dihydro-2H-chromen-2-yl)methyl]carbamate

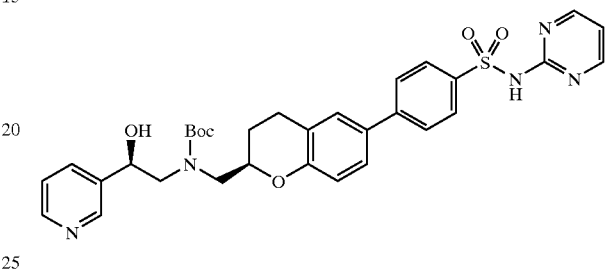

A solution of the compound of Example 247 (796 mg, 1.09 mmol) in tetrahydrofuran (20 mL) was treated with a 1.0 M solution of tetrabutylammonium fluoride in tetrahydrofuran (4.4 mL, 4.40 mmol). The reaction was stirred at room temperature for 2 hours. At this time, the product was coated on silica, concentrated at reduced pressure, and purified on the MPLC (Biotage) with 2–4% methanol in methylene chloride to afford 650 mg (1.05 mmol, 96%) of the desired product. TLC ($R_f$=0.13, 100% ethyl acetate).

EXAMPLE 249
Method A. Preparation of 4-[(2R)-2-([{(2R)-2-hydroxy-2-(3-pyridinyl)ethyl]amino}methyl)-3,4-dihydro-2H-chromen-6-yl]-N-(2-pyrimidinyl)benzenesulfonamide

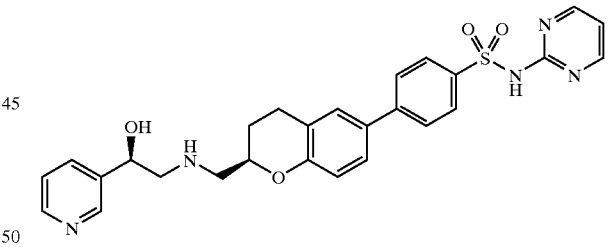

A solution of the compound of Example 248 (1.32 g, 2.13 mmol) in ethyl acetate (20 mL) and methylene chloride (2 mL) was treated with 4 N HCl in 1,4-dioxane (5.5 mL, 22.0 mmol). A suspension was formed and was allowed to stir at room temperature under argon overnight. The reaction was then diluted with diethyl ether and decanted. The solid was rinsed several times with diethyl ether and dried on high vacuum to afford 1.13 g (1.80 mmol, 85%) of product as the hydrochloride salt. $^1$H-NMR (CD$_3$OD-d$_6$) δ 9.04 (s, 1H), 8.88 (d, J=5.7 Hz, 1H), 8.79 (d, J=8.1 Hz, 1H), 8.44 (d, J=4.8 Hz, 2H), 8.17 (dd, J=5.8 Hz, 8.0 Hz, 1H), 8.09 (d, J=8.7 Hz, 2H), 7.73 (d, J=8.9 Hz, 2H), 7.46–7.42 (m, 2H), 7.02–6.96 (m, 2H), 5.44 (dd, J=3.0 Hz, 10.5 Hz, 1H), 4.50 (t, J=9.8 Hz, 1H), 3.62–3.35 (m, 4H), 3.02–2.94 (m, 2H), 2.21–2.14 (m, 1H), 1.87–1.80 (m, 1H); LC-MS (ES $MH^+$=518), Rt=1.05 min.

Method B. Preparation of 4-[(2S)-2-({[-2-hydroxy-2-(3-pyridinyl)ethyl]amino}methyl)-3,4-dihydro-2H-chromen-6-yl]-N-(2-pyrimidinyl)benzenesulfonamide

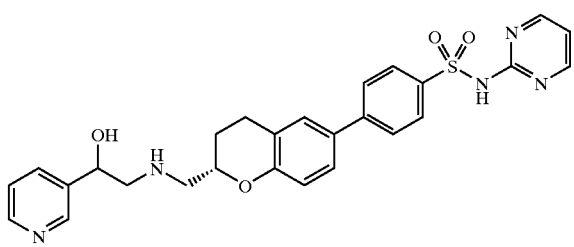

Starting with the (2S)-6-iodo-3,4-dihydro-2H-chromene-2-carboxylic acid (Example 7, Method B) and 2-amino-1-(3-pyridinyl)ethanol dihydrochloride and following the procedures described in Examples 247–248 and Method A above, the title compound was prepared. $^1$H NMR (CD$_3$OD) δ 9.10 (s, 1 H), 8.93–8.85 (m, 1 H), 8.61 (d, J=5.2 Hz, 2 H), 8.55 (d, J=4.6 Hz, 1 H), 8.23–8.17 (m, 1 H), 8.11 (d, J=8.0 Hz, 1 H), 7.74 (d, J=8.3, 1 H), 7.44 (s, 1 H), 7.12–7.08 (m, 1 H), 7.06–7.01 (m, 1 H), 5.58–5.53 (m, 1 H), 4.60–4.52 (m, 1 H), 3.75–3.50 (m, 3 H), 3.52–3.41 (m, 1 H), 3.08–2.88 (m, 2 H), 2.22–2.18 (m, 1 H), 1.90–1.75 (m, 1 H). LC-MS m/z 518.2 (MH$^+$), Rt=0.71 minutes.

Using the procedures described in Examples 247–248, and the starting materials described in Examples 218–246, the following compounds were prepared:

TABLE 10

| Example No. | Structure | MS [M + H$^{+}$] | RT (min, LC-MS) |
|---|---|---|---|
| 250 | 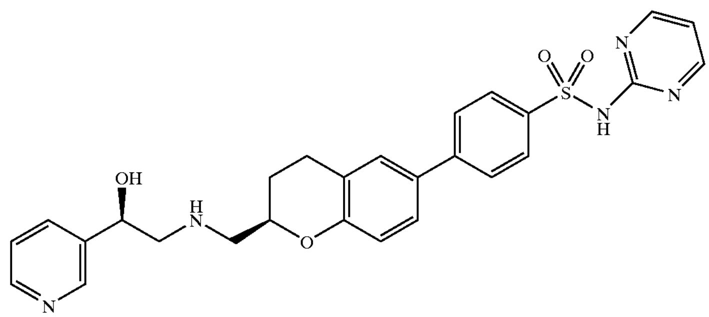 | 518 | 1.01 |
| 251 | 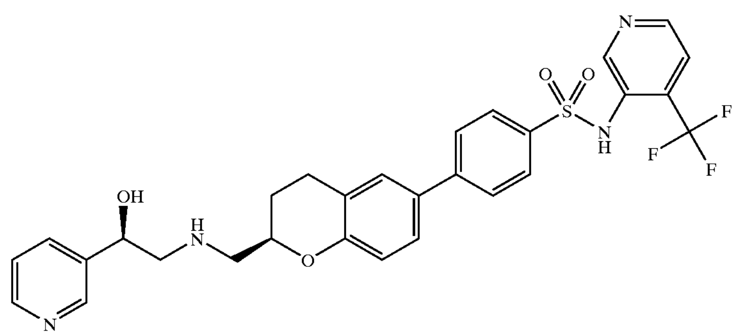 | 585 | 1.91 |
| 252 | 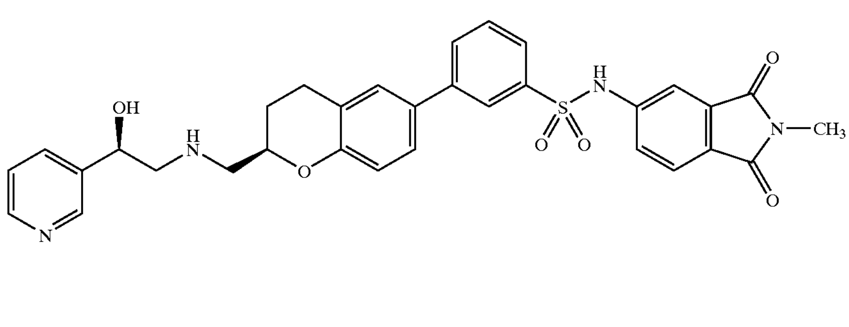 | 599 | 1.94 |

TABLE 10-continued

| Example No. | Structure | MS [M + H⁺] | RT (min, LC-MS) |
|---|---|---|---|
| 253 | 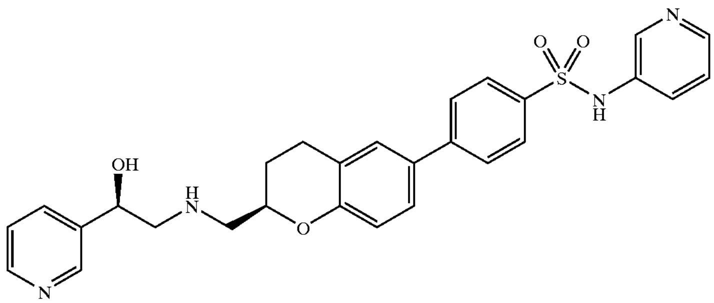 | 517 | 1.53 |
| 254 | 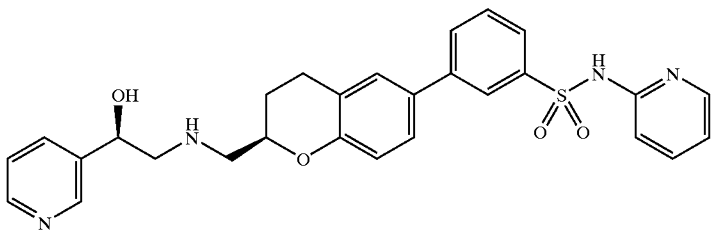 | 517 | 1.44 |
| 255 | 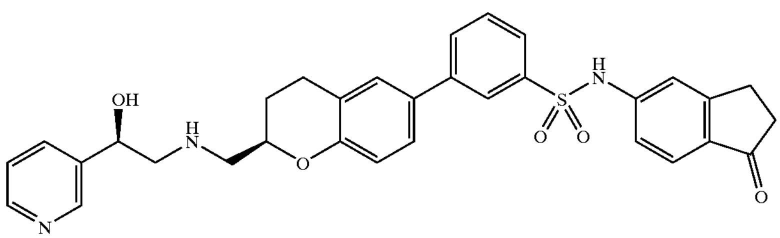 | 570 | 1.96 |
| 256 | 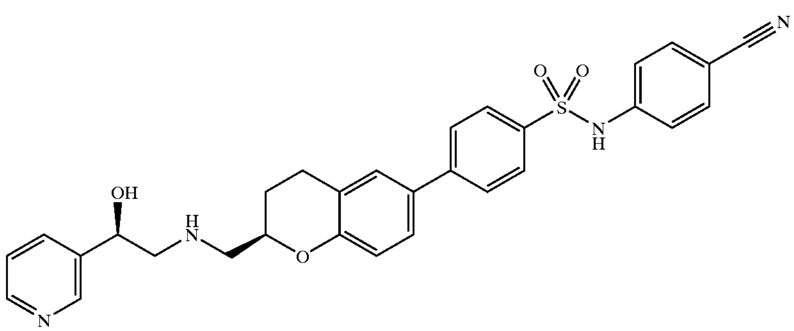 | 541 | 2.02 |
| 257 | 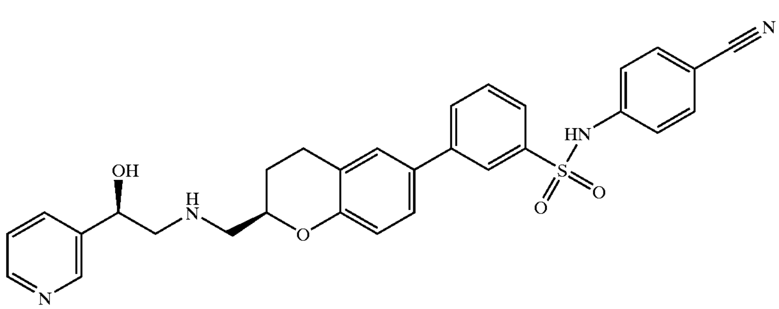 | 541 | 2.02 |

TABLE 10-continued

| Example No. | Structure | MS [M + H+] | RT (min, LC-MS) |
|---|---|---|---|
| 258 | 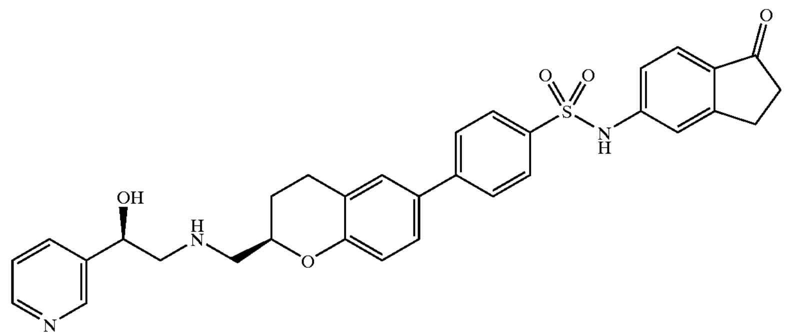 | 570 | 1.94 |
| 259 | 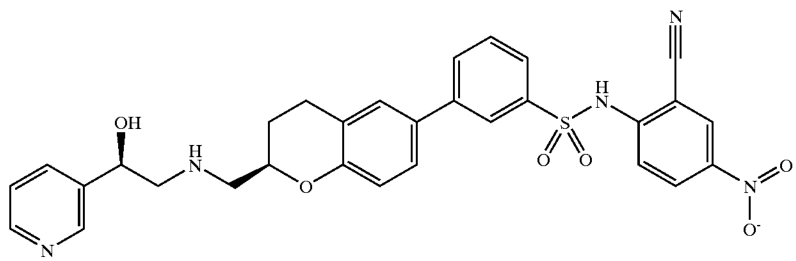 | 586 | 2.04 |
| 260 | 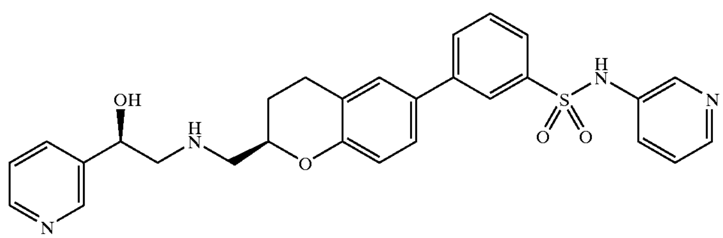 | 517 | 1.55 |
| 261 | 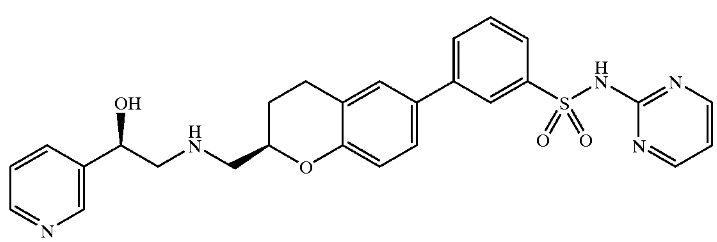 | 518 | 1.37 |
| 262 | 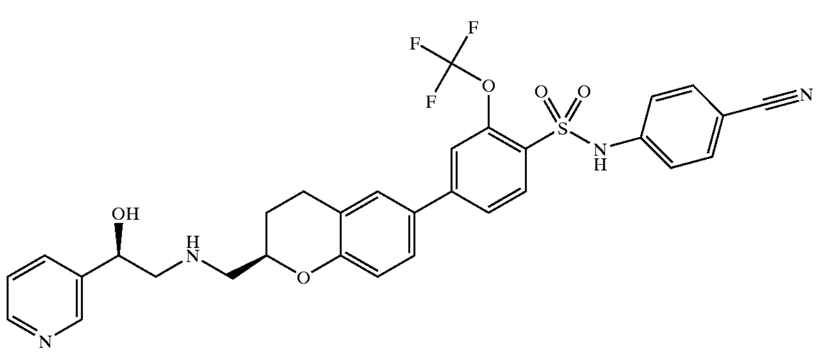 | 625 | 2.14 |

TABLE 10-continued

| Example No. | Structure | MS [M + H+] | RT (min, LC-MS) |
|---|---|---|---|
| 263 | 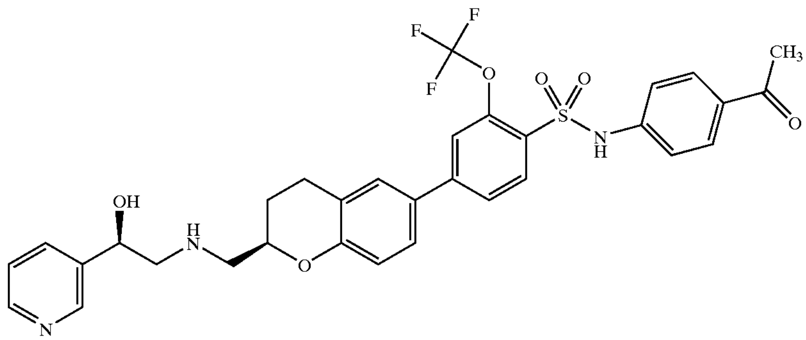 | 642 | 2.17 |
| 264 | 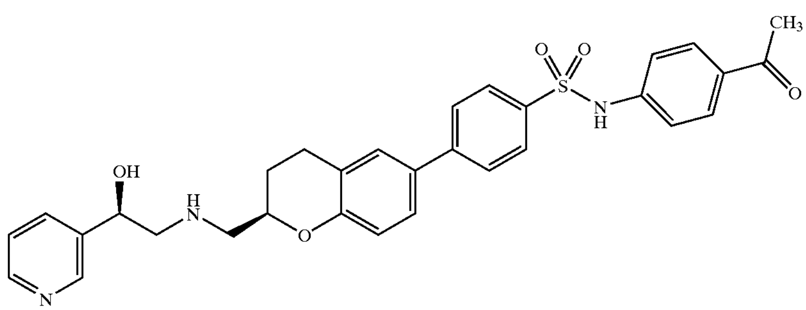 | 558 | 2.01 |
| 265 | 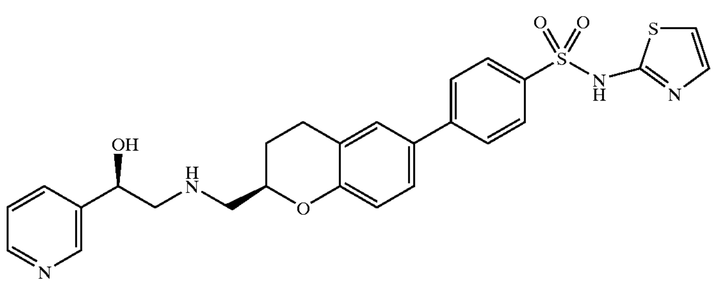 | 523 | 1.55 |
| 266 | 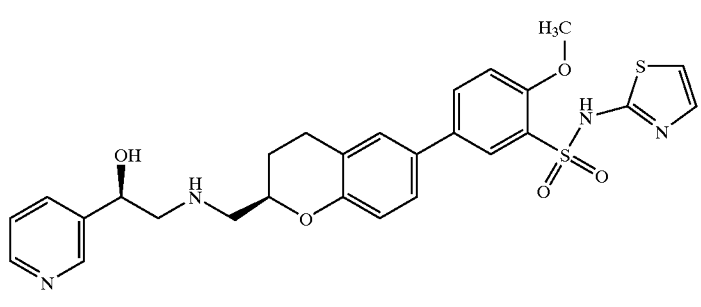 | 653 | 2.32 |

TABLE 10-continued
| Example No. | Structure | MS [M + H+] | RT (min, LC-MS) |
|---|---|---|---|
| 267 | 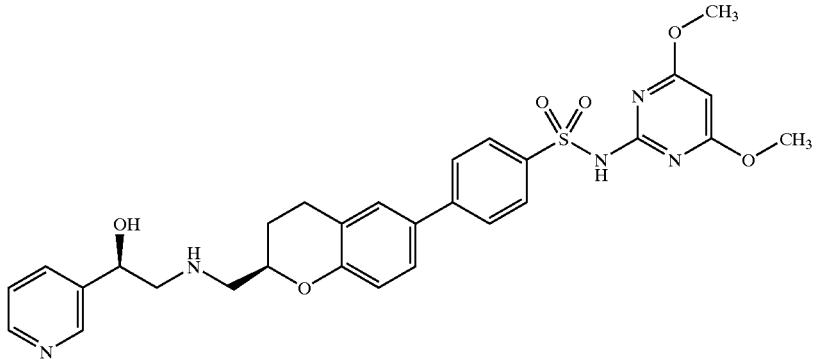 | 578 | 1.95 |
| 268 | 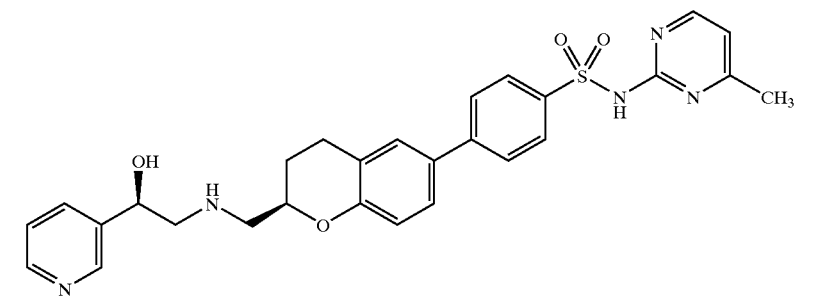 | 532 | 1.35 |
| 269 | 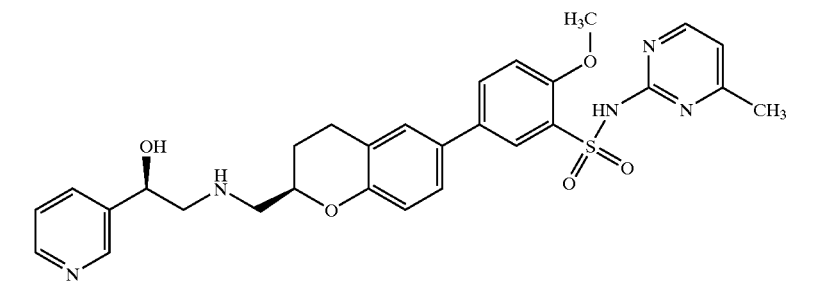 | 562 | 1.53 |
| 270 | 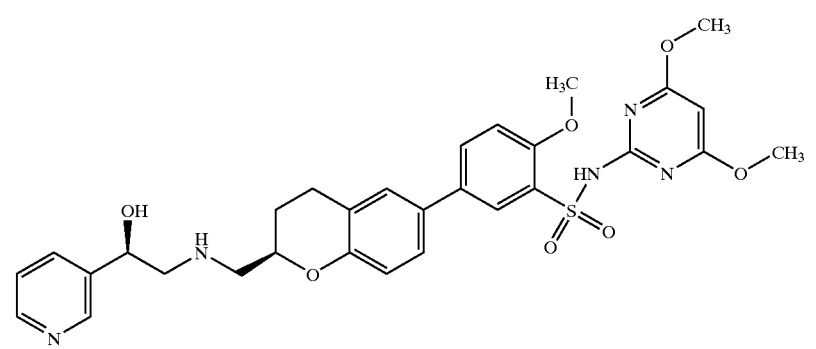 | 608 | 1.92 |

TABLE 10-continued

| Example No. | Structure | MS [M + H+] | RT (min, LC-MS) |
|---|---|---|---|
| 271 | 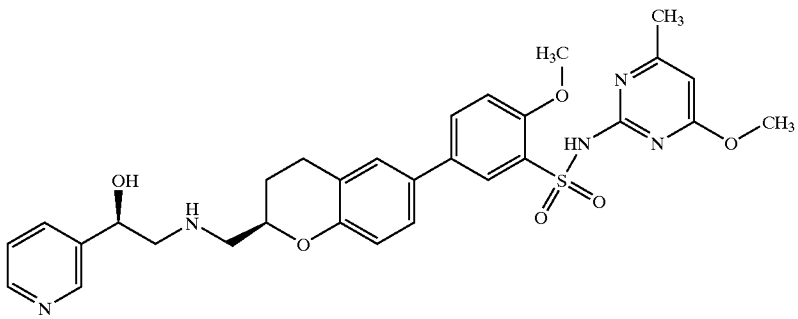 | 592 | 1.66 |
| 272 | 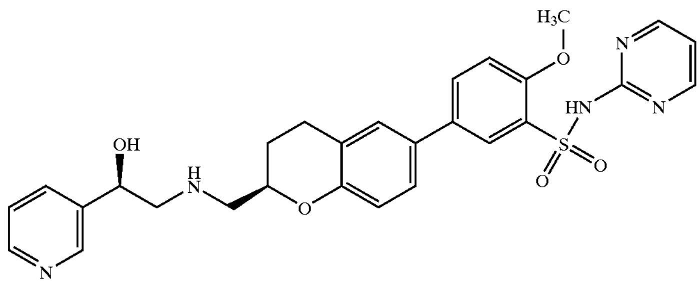 | 548 | 1.3 |
| 273 | 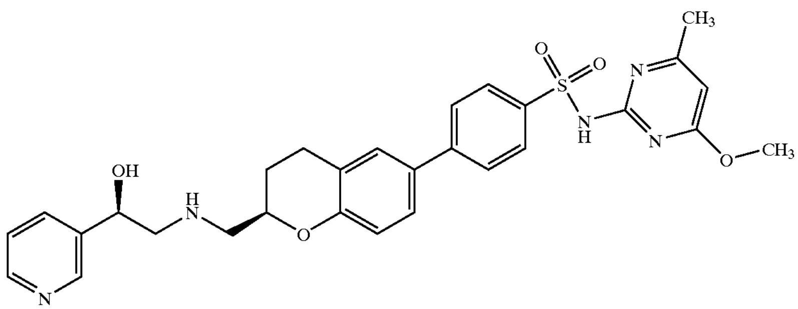 | 562 | 1.52 |
| 274 | 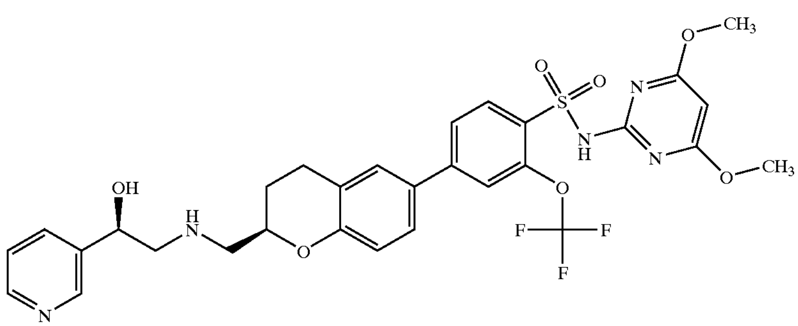 | 662 | 2.14 |
| 275 | 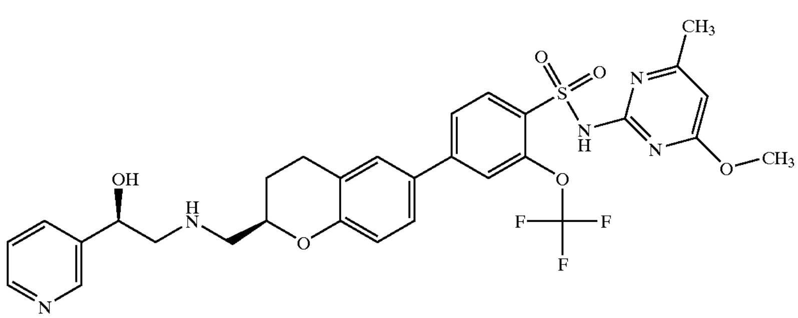 | 616 | 1.74 |

TABLE 10-continued

| Example No. | Structure | MS [M + H+] | RT (min, LC-MS) |
|---|---|---|---|
| 276 | 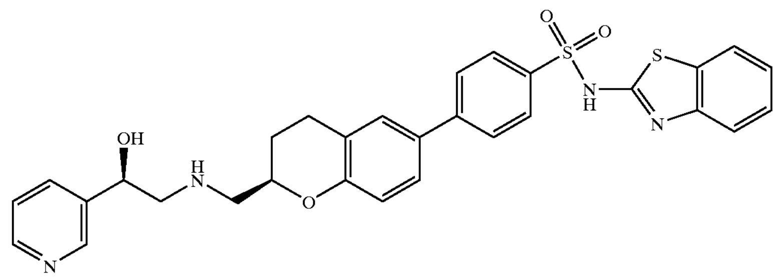 | 573 | 2.07 |
| 277 | 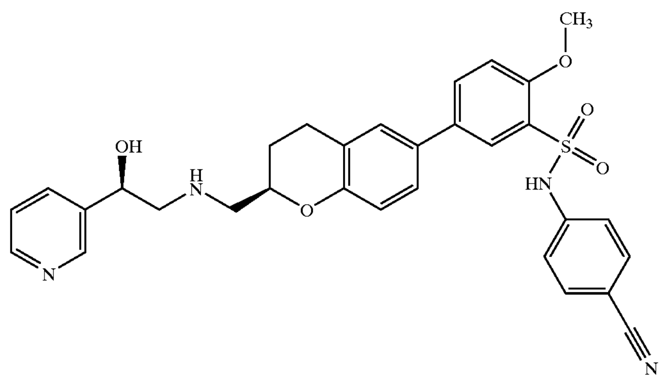 | 571 | 1.94 |
| 278 | 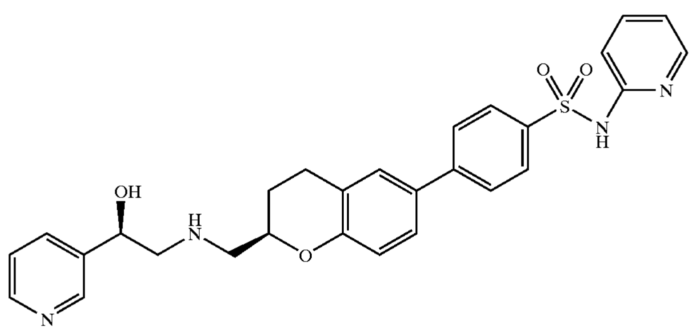 | 603 | 2.03 |
| 279 | 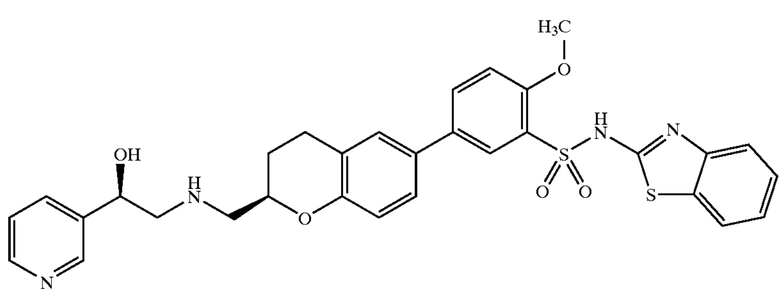 | 517 | 1.23 |

TABLE 10-continued

| Example No. | Structure | MS [M + H+] | RT (min, LC-MS) |
|---|---|---|---|
| 280 | 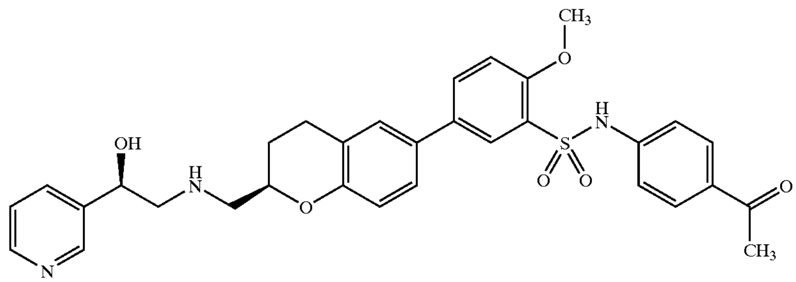 | 588 | 1.87 |

EXAMPLE 281 tert-Butyl {(2S)-6-[3-(aminosulfonyl)phenyl]-3,4-dihydro-2H-chromen-2-yl}methyl[(2R)-2-{[tert-butyl(dimethyl)silyl]oxy}-2-(3-pyridinyl)ethyl]carbamate

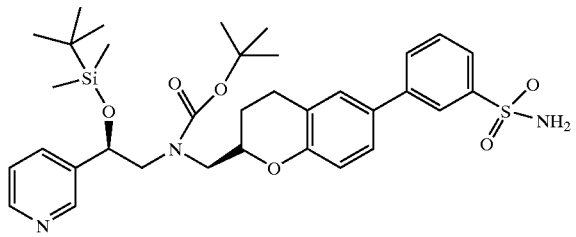

The solution of Na₂CO₃ (2 N, 6 mL), toluene (6 mL), and ethanol (6 mL) was degassed for 10 minutes. Then the compound of Example 81 (1001 mg, 1.62 mmol), 3-bromobenzenesulphonamide (458 mg, 1.94 mmol) and PdCl₂(dppf) (132 mg, 0.16 mmol) were added to the above solution and it was degassed for another 5 minutes. Then, the reaction mixture was heated to reflux overnight. After it was allowed to cool down, the reaction mixture was poured into water and was extracted with EtOAc. The combined organic layer was washed by water, brine, dried over Na₂SO₄, and concentrated. Chromatography with 20%–30% ethyl acetate in hexane provided the title compound (670 mg) as a pale yellow oil. ESLC-MS: m/z=654 (MH+); 1H NMR (MeOH-d₄): 8.576~8.451 (m, 2H), 8.077 (s, 1H), 7.906~7.752 (m, 3H), 7.565 (t, 1H), 7.459 (m, 1H), 7.383 (m, 2H), 6.813 (d, 1H), 5.185~5.050 (m, 1H), 4.251 (t, 1H), 3.772~3.348 (m, 4H), 2.879 (m, 2H), 2.045 (m, 1H), 1.741 (m, 1H), 1.447 (d, 9H), 0.897 (s, 9H), 0.083 (s, 3H), −0.102 (s, 3H).

EXAMPLE 282 tert-Butyl (2R)-2-{[tert-butyl(dimethyl)silyl]oxy}-2-(3-pyridinyl)ethyl{[(2S)-6-(3-{[(methoxyacetyl)amino]sulfonyl}phenyl)-3,4-dihydro-2H-chromen-2-yl]methyl}carbamate

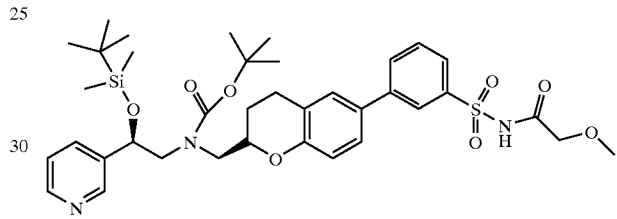

A solution of the compound of Example 281 (60 mg, 0.091 mmol), methoxyacetic acid (13 mg, 0.13 mmol), EDCl (26 mg, 0.14 mmol), and DMAP (11 mg, 0.091 mmol) in CH₂Cl₂ (1.5 mL) was stirred at room temperature overnight. The reaction mixture was concentrated down and the crude product was purified by preparative TLC plate with CH₂Cl₂:MeOH:NH₄OH (90:15:2) to obtain (60 mg). ESLC-MS: m/z=725 (MH+); 1H NMR (MeOH-d₄): 8.566~8.439 (m, 2H), 8.077 (s, 1H), 7.889~7.780 (m, 1H), 7.675 (m, 1H), 7.453 (m, 2H), 7.313(m, 2H), 6.767 (d, 1H), 5.180~5.035 (m, 1H), 4.220 (s, b, 1H), 3.907 (s, 2H), 3.760~3.333 (m, 4H), 2.835 (m, 2H), 2.041 (m, 1H), 1.711 (m, 1H), 1.445 (d, 9H), 0.892 (s, 9H), 0.076 (s, 3H), −0.109 (s, 3H).

EXAMPLE 283

3-[(2S)-2-({[(2R)-2-hydroxy-2-(3-pyridinyl)ethyl]amino}methyl)-3,4-dihydro-2H-chromen-6-yl]-N-(methoxyacetyl)benzenesulfonamide

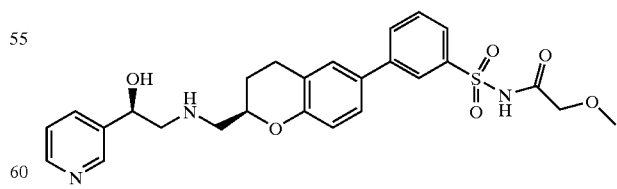

Using the procedure described in Example 249, the title compound was prepared. ESLC-MS m/z=512 (MH+), HPLC retention time=1.53 min.

Using the procedures described in Examples 281–283, the compounds described below were similarly prepared.

TABLE 11

| Example No. | Structure | MS [M + H+] | RT (min, LC-MS) |
|---|---|---|---|
| 284 | 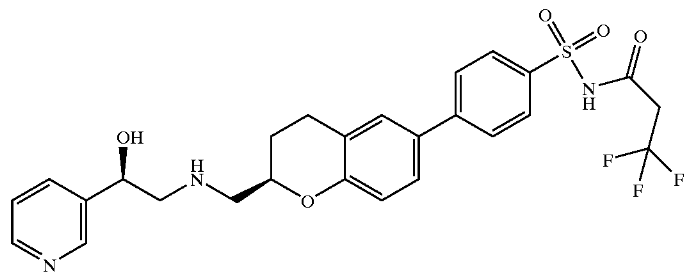 | 550.1 | 1.97 |
| 285 | 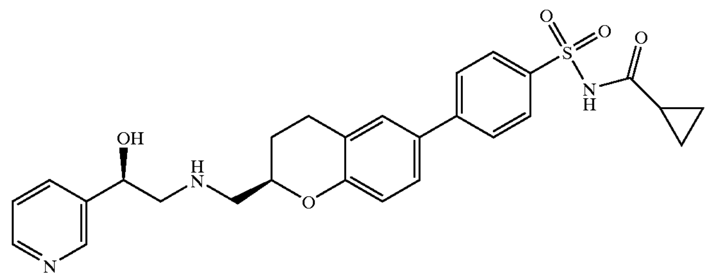 | 508.2 | 1.75 |
| 286 | 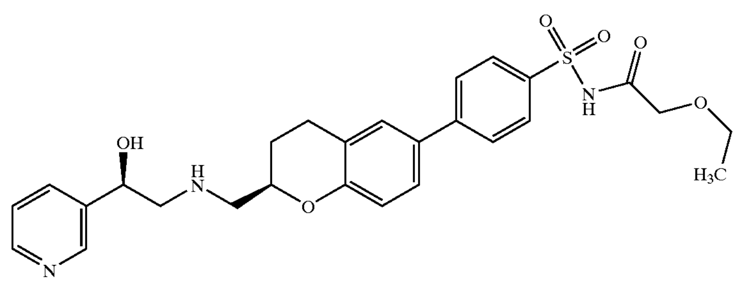 | 526.2 | 1.89 |
| 287 | 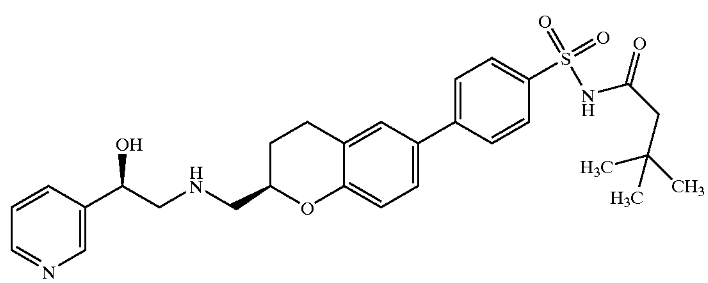 | 528.2 | 0.54 |
| 288 | 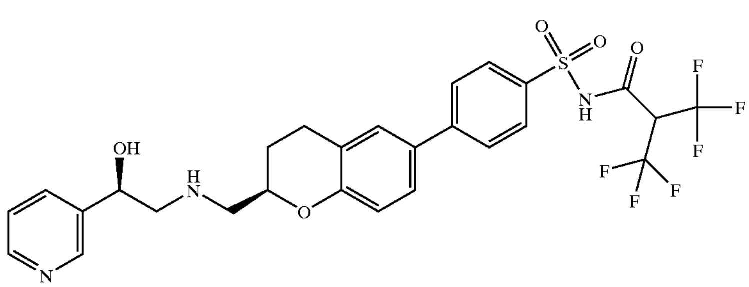 | 618.1 | 2.04 |

TABLE 11-continued

| Example No. | Structure | MS [M + H⁺] | RT (min, LC-MS) |
|---|---|---|---|
| 289 | 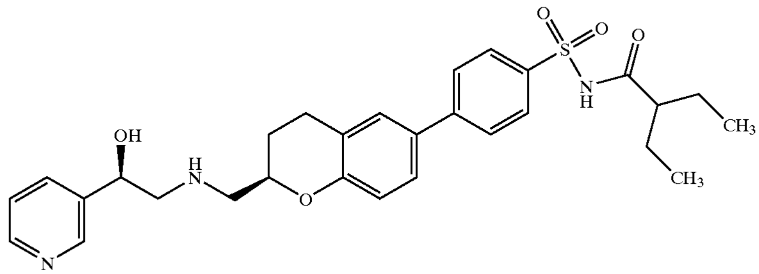 | 538.3 | 0.36 |
| 290 | 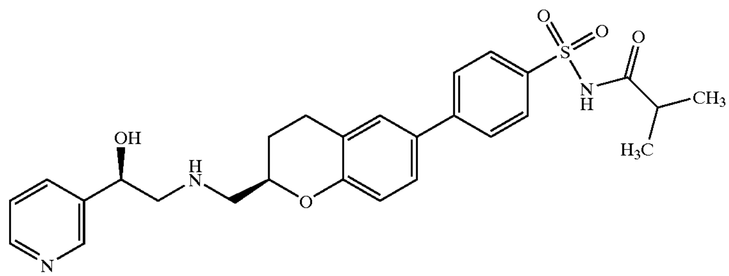 | 510.2 | 0.25 |
| 291 | 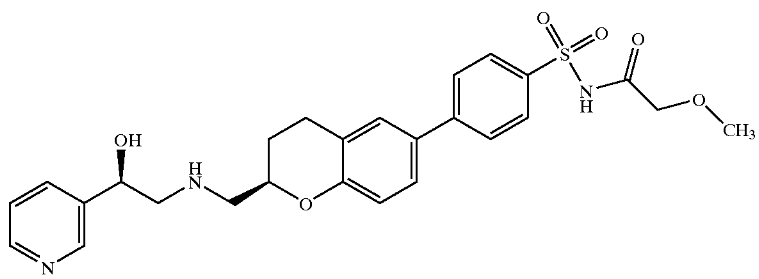 | 512.2 | 0.21 |
| 292 | 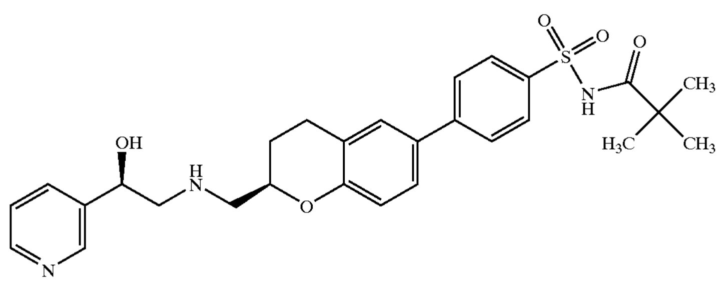 | 524 | 2.01 |
| 293 | 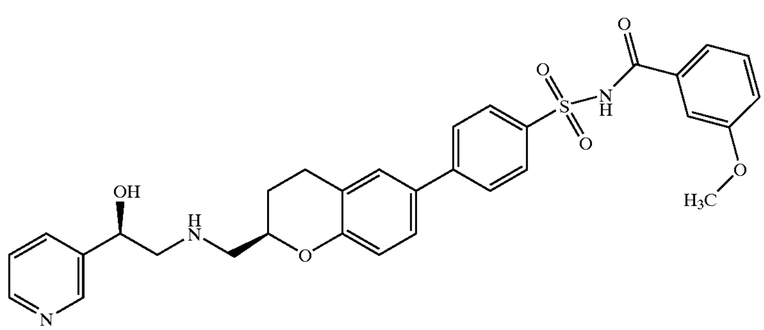 | 574 | 1.86 |

TABLE 11-continued

| Example No. | Structure | MS [M + H⁺] | RT (min, LC-MS) |
|---|---|---|---|
| 294 | 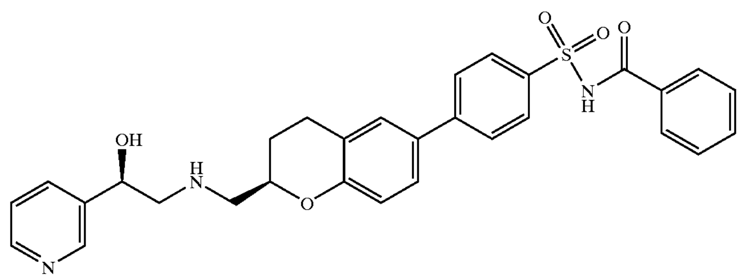 | 544 | 1.55 |
| 295 | 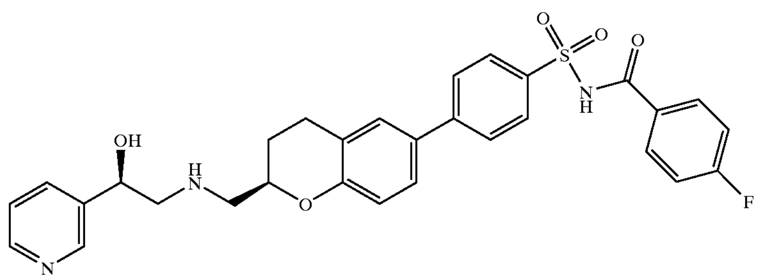 | 562 | 1.93 |
| 296 | 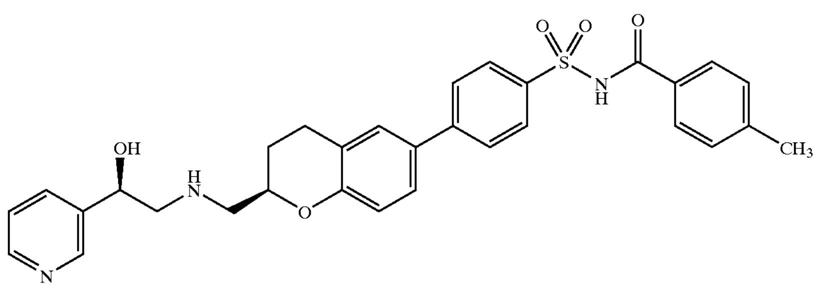 | 558 | 2.01 |
| 297 | 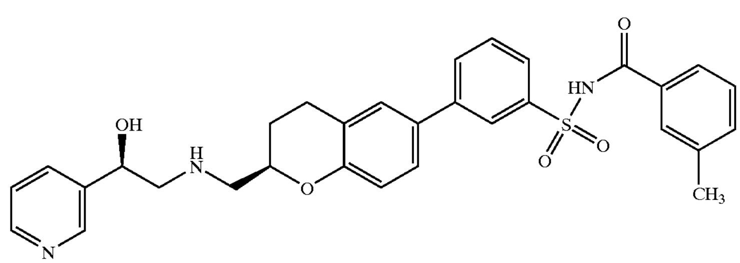 | 558 | 2.01 |
| 298 | 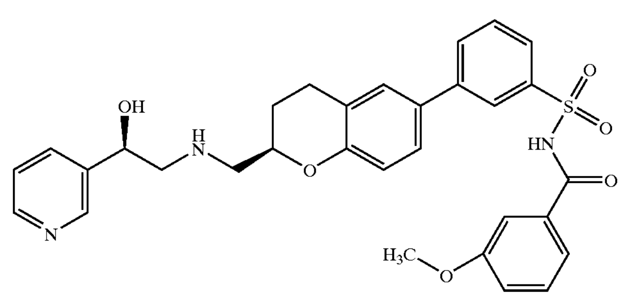 | 574 | 2.18 |

TABLE 11-continued
| Example No. | Structure | MS [M + H+] | RT (min, LC-MS) |
|---|---|---|---|
| 299 | 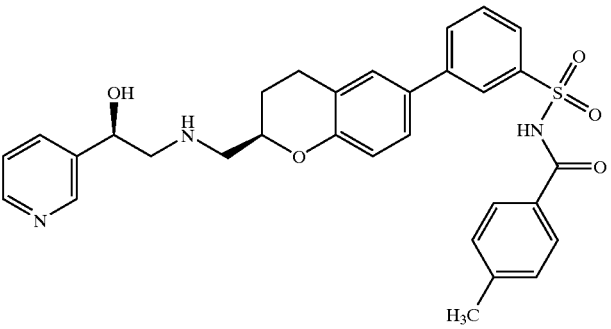 | 558 | 2.13 |
| 300 | 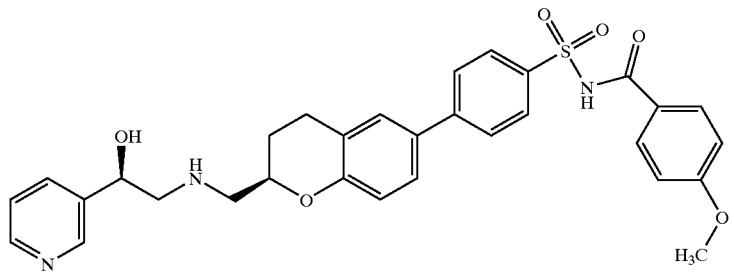 | 573 | 2.15 |
| 301 | 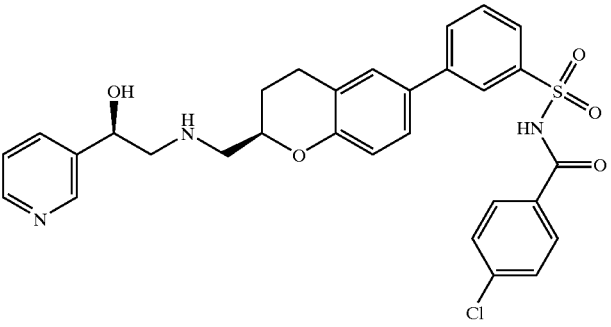 | 577 | 2.27 |
| 302 | 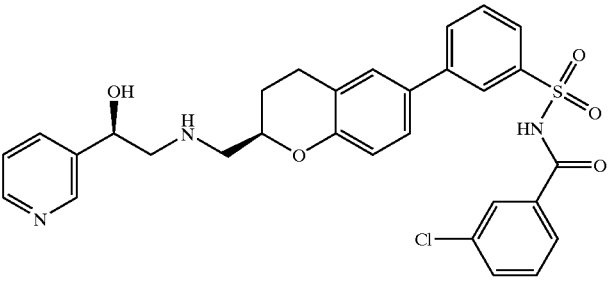 | 577 | 2.26 |

TABLE 11-continued

| Example No. | Structure | MS [M + H⁺] | RT (min, LC-MS) |
|---|---|---|---|
| 303 | 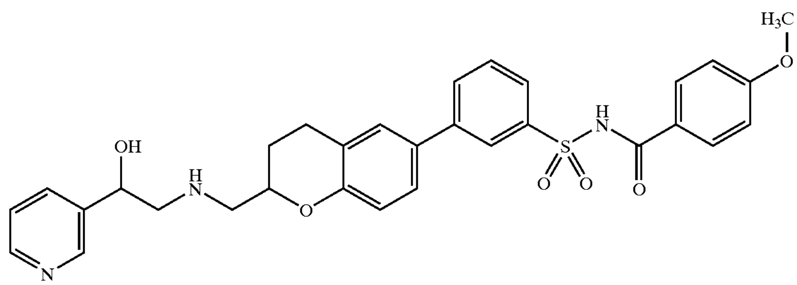 | 574 | 1.94 |
| 304 | 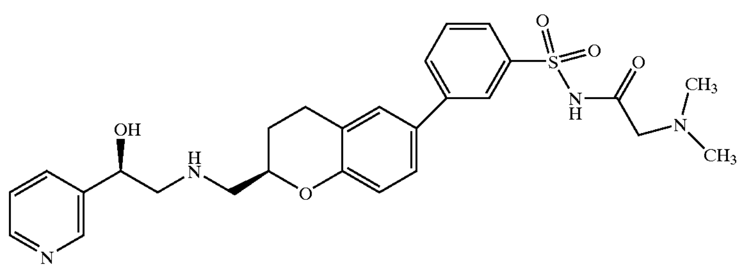 | 525 | 0.76 |
| 305 | 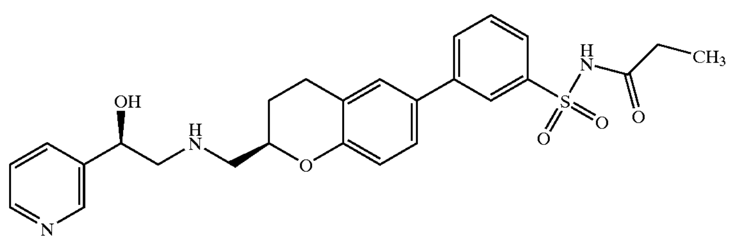 | 496 | 1.57 |

EXAMPLE 306

Preparation of 1-(4-bromophenyl)-2-[(phenyl)sulfonyl]ethan-1-one

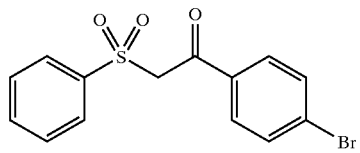

To benzenesulfonyl chloride (0.5 mL, 3.92 mmol) in 4:1 v/v tetrahydrofuran—water (20 mL) was added powdered zinc (282 mg, 4.31 mmol, 1.1 eq.) followed by 4-bromophenacyl bromide (1.31 g, 4.70 mmol, 1.2 eq.). The reaction mixture was stirred at room temperature for 17 hours. The volatile solvent was evaporated under reduced pressure and poured into water. The reaction was extracted with ethyl acetate (2×150 mL), and the combined organic layers were washed with brine (1×100 mL), dried (MgSO₄), filtered, and evaporated under reduce pressure. The crude product was purified using MPLC (Biotage) eluted with 5:1 v/v hexane-ethyl acetate. Crystallization from dichloromethane-hexane gave the desired product as a white fluffy solid (486 mg, 36.6% yield). MS LC-MS (ES MH⁺= 340); TLC (R$_f$=0.30, 25% ethyl acetate-hexane)

EXAMPLE 307

Preparation of tert-butyl (2R)-2-{[tert-butyl(dimethyl)silyl]oxy}-2-(3-pyridinyl)ethyl[((2R)-6-{4-[(phenylsulfonyl)acetyl]phenyl}-3,4-dihydro-2H-chromen-2-yl)methyl]carbamate

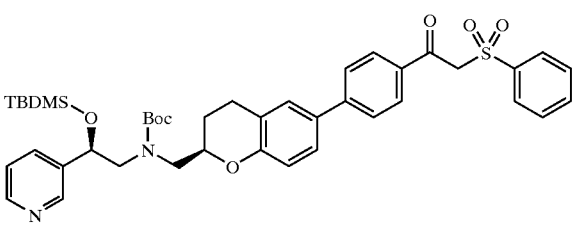

The procedure was analogous to that described in Example 247 except 1-(4-bromophenyl)-2-[(phenyl)sulfonyl]ethan-1-one was used instead of 4-bromo-N-(2-pyrimidinyl)benzene-sulfonamide. TLC (R$_f$=0.16, 40% ethyl acetate-hexane); LC-MS (ES MH⁺=757), Rt=3.70 min.

EXAMPLE 308

Preparation of 1-{4-[(2R)-2-({[(2R)-2-hydroxy-2-(3-pyridinyl)ethyl]amino}methyl)-3,4-dihydro-2H-chromen-6-yl]phenyl}-2-(phenylsulfonyl)ethanone Dihydrochloride

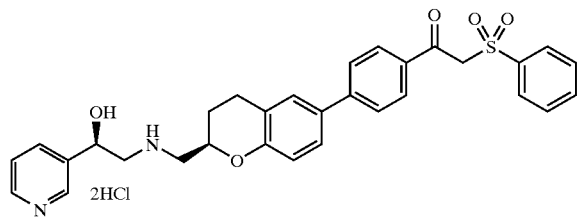

Using the procedure described in Examples 248 and 249, the title compound was prepared. $^1$H-NMR (CD$_3$OD-d$_6$) δ 9.02 (s, 1H), 8.86 (d, J=5.6 Hz, 1H), 8.73 (d, J=8.0 Hz, 1H), 8.15–8.08 (m, 2H), 7.92–7.41 (m, 10H), 7.02 (d, J=9.0 Hz, 1H), 5.44 (dd, J=2.9 Hz, 10.7 Hz, 1H), 4.52 (t, J=10.2 Hz, 1H), 3.65–3.33 (m, 6H), 3.15–2.89 (m, 2H), 2.22–2.15 (m, 1H), 1.93–1.80 (m, 1H); LC-MS (ES MH$^+$=543), Rt=2.06 min.

Using the procedures described in Examples 306–308 and using the appropriate sulfonyl chlorides, the following compounds were similarly prepared.

TABLE 12

| Example No. | Structure | MS [M + H]$^+$ | RT (min, LC-MS) |
|---|---|---|---|
| 309 | 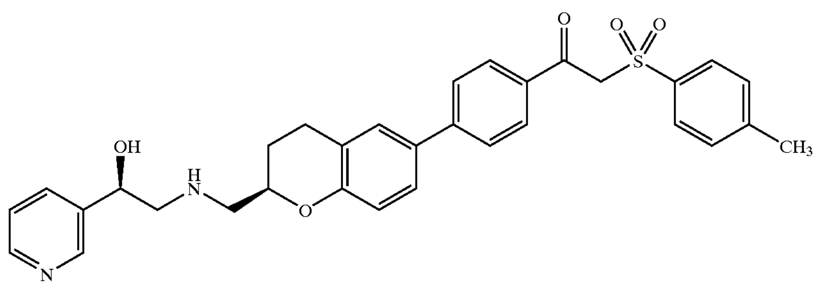 | 557 | 2.06 |
| 310 | 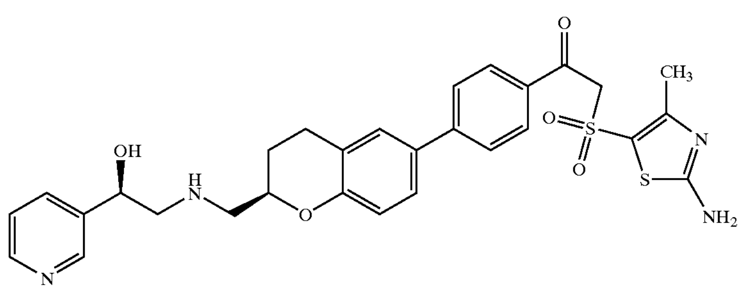 | 578 | 1.83 |
| 311 | 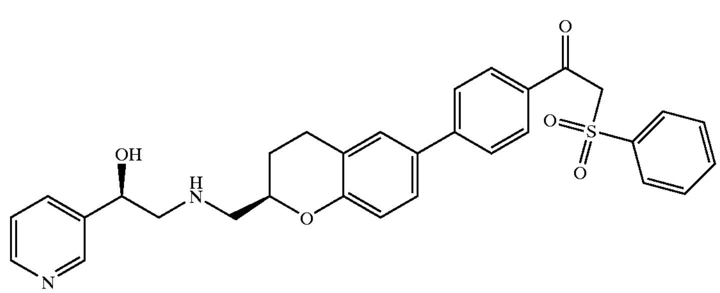 | 543 | 2.06 |

EXAMPLE 312

Preparation of 1-(3-bromophenyl)-5-hydroxy-4-methyl-1,2-dihydro-3H-pyrazol-3-one

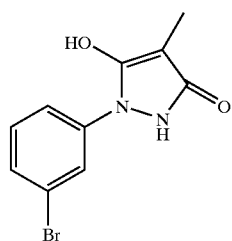

To a suspension of 1-(3-bromophenyl)hydrazine hydrochloride (1.0 g, 4.47 mmol) in ethanol (8.9 mL) was added dropwise 2.0 M sodium ethoxide in ethanol (0.77 mL, 9.84 mmol, 2.2 eq.). Diethyl 2-methylmalonate (0.85 mL, 4.92 mmol, 1.1 eq.) was then added. The reaction mixture was stirred at 90° C. for 16 hours and then quenched with 2 N aqueous hydrochloric acid (50 mL). The reaction was extracted with ethyl acetate (3×50 mL), and the combined organic layers were dried (MgSO$_4$), filtered, and evaporated under reduced pressure. Purification using MPLC (Biotage) eluted with 3:1 v/v ethyl acetate-hexane gave the desired product as a white solid (125 mg, 0.46 mmol, 10.4% yield). MS LC-MS (ES MH$^+$=269/271); TLC (R$_f$=0.10, 50% ethyl acetate-hexane).

EXAMPLE 313

Preparation of tert-butyl (2R)-2-{[tert-butyl (dimethyl)silyl]oxy}-2-(3-pyridinyl)ethyl ({(2S)-6-[3-(4-hydroxy-4-methyl-3,5-dioxo-1-pyrazolidinyl)phenyl]-3,4-dihydro-2H-chromen-2-yl}methyl)carbamate

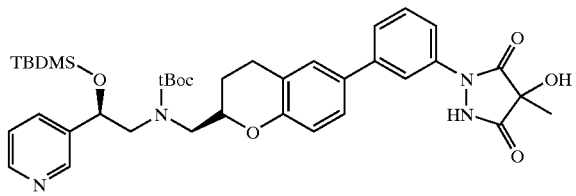

Using the procedures described in Example 247, Example 312 was converted to the title compound. LC-MS (ES MH$^+$=783); TLC (R$_f$=0.19, 20% methanol-dichloromethane).

EXAMPLE 314

Preparation of 4-hydroxy-1-{3-[(2S)-2-({[(2R)-2-hydroxy-2-(3-pyridinyl)ethyl]amino}methyl)-3,4-dihydro-2H-chromen-6-yl]phenyl}-4-methyl-3,5-pyrazolidinedione dihydrochloride

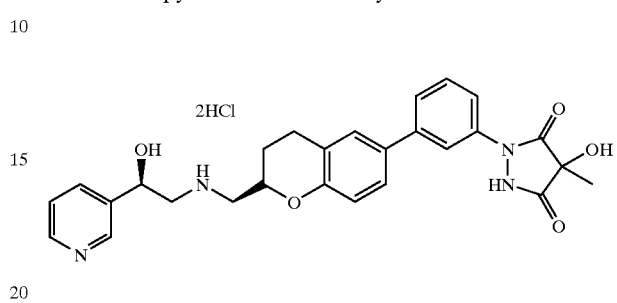

Using the procedure described in Examples 248 and 249, the title compound was prepared. $^1$H-NMR (CD$_3$OD-d$_6$) δ 8.96 (s, 1H), 8.84 (d, J=5.4 Hz, 1H), 8.64 (d, J=8.1 Hz, 1H), 8.07 (dd, J=8.07 Hz, 6.0 Hz, 1H), 7.91 (s, 1H), 7.58 (dt, J=7.2 Hz, 2.1 Hz, 1H), 7.49 to 7.41 (m, 4H), 7.00 (d, J=9.6 Hz, 1H), 5.38 (dd, J=10.8 Hz, 2.7 Hz, 1H), 4.48 (t, J=7.2 Hz, 1H), 3.65 to 3.35 (m, 4H), 3.13 to 2.95 (m, 3H), 2.19 to 2.14 (m, 1H), 1.87 to 1.75 (m, 1H), 1.70 to 1.64 (m, 1H), 1.51 (s, 3H), 1.44 to 1.28 (m, 2H); LC-MS (ES MH$^+$=489), Rt=1.10 min.

EXAMPLE 315

Preparation of tert-butyl (2R)-2-{[tert-butyl (dimethyl)silyl]oxy}-2-(3-pyridinyl)ethyl {[(2R)-6-(5-nitro-2-pyridinyl)-3,4-dihydro-2H-chromen-2-yl]methyl}carbamate

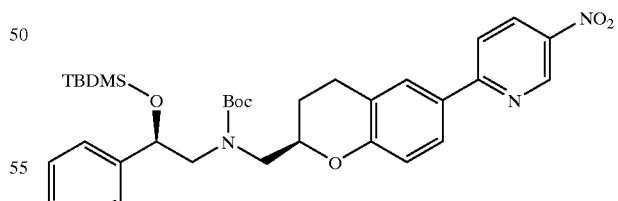

The procedure was analogous to that of Example 247 except methyl 2-chloro-5-nitropyridine was used instead of 3-bromo-N-(2-pyrimidinyl)benzene-sulfonamide. LC-MS (ES MH$^+$=621), Rt=3.68 min; TLC (R$_f$=0.05, 25% ethyl acetate-hexane).

EXAMPLE 316

Preparation of tert-butyl [(2R)-6-(5-amino-2-pyridinyl)-3,4-dihydro-2H-chromen-2-yl]methyl[(2R)-2-{[tert-butyl(dimethyl)silyl]oxy}-2-(3-pyridinyl)ethyl]carbamate

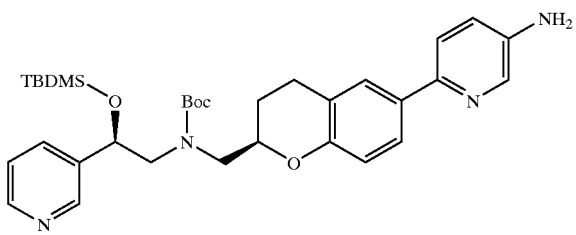

A dry flask under argon was charged with 10% Pd on C (50 mg) and ethanol (10 mL) followed by the addition of Example 315 (700 mg, 1.13 mmol). The reaction was stirred under hydrogen (1 atm) overnight. TLC analysis showed complete reaction. The reaction was then filtered through celite and the filtrate was concentrated at reduced pressure. The crude product was then purified on the MPLC (biotage) with 100% ethyl acetate to afford the desired product (610 mg, 91%). LC-MS (ES MH$^+$=591), Rt=2.57 min; TLC (R$_f$=0.27, 100% ethyl acetate).

EXAMPLE 317

Preparation of (1R)-2-({[(2R)-6-(5-amino-2-pyridinyl)-3,4-dihydro-2H-chromen-2-yl]methyl}amino)-1-(3-pyridinyl)ethanol Tetrahydrochloride

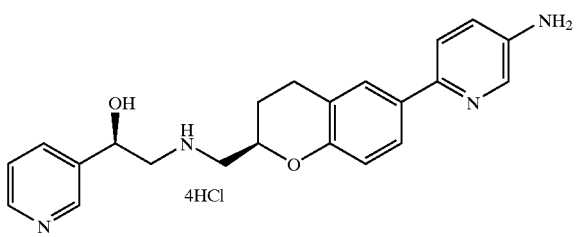

Using the procedure described in Examples 248 and 249, the title compound was prepared. $^1$H-NMR (CD$_3$OD-d$_6$) δ 9.06 (s, 1H), 8.89 (d, J=5.6 Hz, 1H), 8.82 (d, J=7.9 Hz, 1H), 8.18 (dd, J=6.1 and 8.2 Hz, 1H), 7.96–7.91 (m, 2H), 7.75 (dd, J=2.6 Hz and 9.2 Hz, 1H), 7.60–7.56 (m, 2H), 7.14 (d, J=8.1 Hz, 1H), 5.49 (d, J=10.2 Hz, 1H), 4.59 (t, J=8.5 Hz, 1H), 3.75–3.36 (m, 4H), 3.13–2.92 (m, 2H), 2.26–2.20 (m, 1H), 1.91–1.84 (m, 1H); LC-MS (ES MH$^+$=377), Rt=0.70 min.

EXAMPLE 318

Preparation of tert-butyl (2R)-2-{[tert-butyl(dimethyl)silyl]oxy}-2-(3-pyridinyl)ethyl[((2R)-6-[5-[(phenylsulfonyl)amino]-2-pyridinyl}-3,4-dihydro-2H-chromen-2-yl)methyl]carbamate

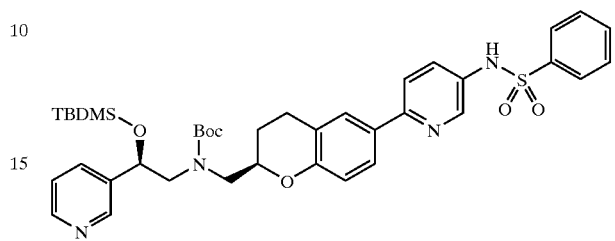

A solution of Example 316 (80 mg, 0.135 mmol) and benzene sulfonyl chloride (41 mg, 0.233 mmol) in pyridine (1.5 mL) was stirred at 50° C. overnight. The reaction was diluted with ethyl acetate, washed with water, brine, and dried over magnesium sulfate. The crude product was coated on silica and purified on the MPLC (Biotage) with 40–70% ethyl acetate in hexanes to afford the desired product (91 mg, 92%). LC-MS (ES MH$^+$=731), Rt=3.32 min, TLC R$_f$=0.25 60% ethyl acetate in hexanes).

EXAMPLE 319

Preparation of N-{6-[(2R)-2-({[(2R)-2-hydroxy-2-(3-pyridinyl)ethyl]amino}methyl)-3,4-dihydro-2H-chromen-6-yl]-3-pyridinyl}benzenesulfonamide trihydrochloride

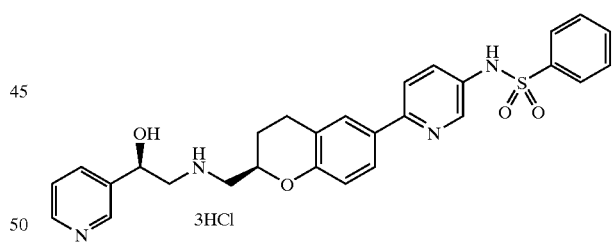

Using the procedure described in Examples 248 and 249, Example 318 was converted to the title compound. $^1$H-NMR (CD$_3$OD-d$_6$) δ 9.05 (s, 1H), 8.88 (d, J=5.2 Hz, 1H), 8.79 (d, J=7.8 Hz, 1H), 8.43 (d, J=1.7, 1H), 8.18–7.90 (m, 5H), 7.70–7.55 (m, 5H), 7.15 (d, J=8.3 Hz, 1H), 5.47 (d, J=9.2 Hz, 1H), 4.60 (t, J=10.0 Hz, 1H), 3.67–3.32 (m, 4H), 3.11–2.92 (m, 2H), 2.26–2.19 (m, 1H), 1.91–1.84 (m, 1H); LC-MS (ES MH$^+$=517), Rt=1.70 min.

Using the procedures described in Examples 318 and 319, and using the appropriate acyl or sulfonyl chloride, the following compounds were prepared.

TABLE 13

| Example No. | Structure | MS [M + H]+ | RT (min, LC-MS) |
|---|---|---|---|
| 320 | 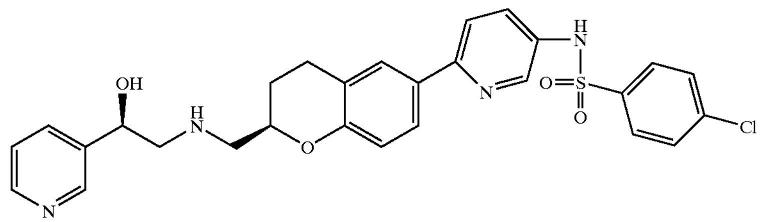 | 551 | 1.98 |
| 321 | 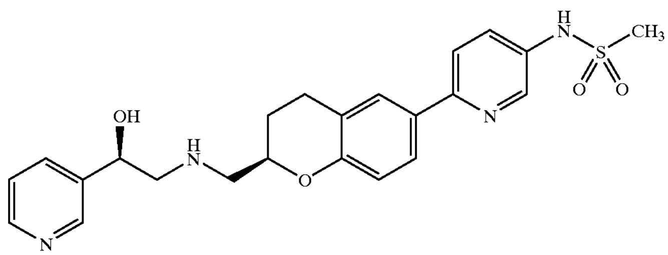 | 455 | 0.8 |
| 322 | 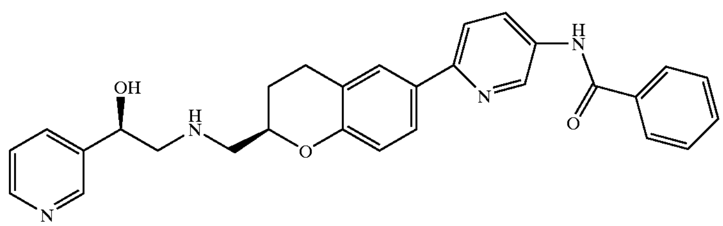 | 481 | 1.41 |
| 323 | 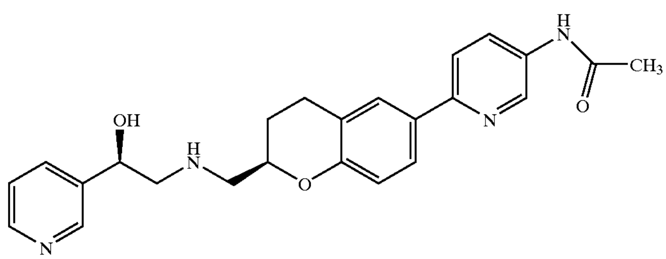 | 419 | 0.74 |

EXAMPLE 324

Preparation of 3-((1R)-1-hydroxy-2-{[((2R)-6-{3-[({[(4-methylphenyl) amino]carbonyl}amino) sulfonyl]phenyl}-3,4-dihydro-2H-chromen-2-yl) methyl]amino}ethyl)pyridine hydrochloride

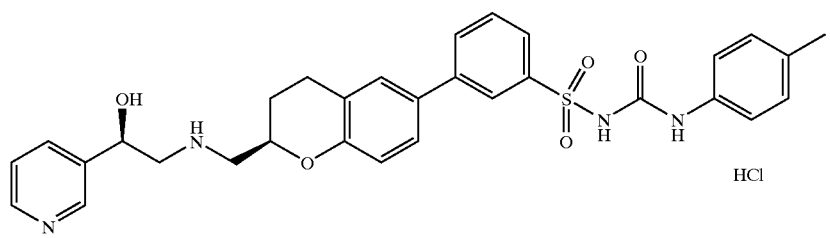

To a stirred solution of Example 281 (45 mg) in dichloroethane (10 mL), were added Et₃N (0.014 mL) and 4-methylphenyl isocyanate (0.013 mL). Stirring was continued at room temperature over a 2–3 hour period. The solvent was removed under reduced pressure. Crude product was purified by combiflash column chromatography to give the free base of the desired product (27 mg, 50% yield). This material was treated with HCl (4 M) in dioxane and stirred at room temperature overnight. The solvent was removed under reduced pressure to provide the crude product, which was purified by preparative HPLC to provide the title compound. MS [M+H]+573.21, Rf=0.68 (CH2Cl2:MeOH=

50:50); H¹ NMR (MeOH-d4, δ ppm): 2.25 (s, 3H), 2.85–3.08 (m, 2H) 3.38–3.67 (m, 6H), 4.50 4.54(m, 1H), 5.45–5.47 (m, 1H), 7.04–7.07 (m, 4H), 7.24 (d, 2H, J=6.3 Hz), 7.40 (dd, 1H, J=6.3 Hz), 7.42–7.45 (m, 2H), 7.63 (t, 1H, J=6.0 Hz) 7.87 (d, 1H, J=6.0 Hz), 7.93 (d, 1H, J=6.0 Hz), 8.10–8.20 (m, 1H), 8.22 (s, 1H), 8.78–8.79 (m, 1H).

Using the procedures outline in Examples 281 and 324, the following compounds were similarly prepared.

TABLE 14

| Example No. | Structure | MS [M + H]⁺ | HPLC (RT) | TLC Rf (solvent) |
|---|---|---|---|---|
| 325 | 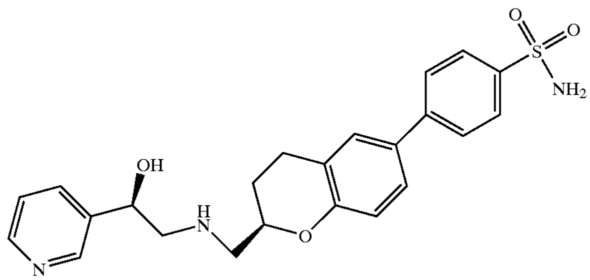 | 654.3 | | 0.22(7:3 ethyl acetate/ hexanes) |
| 326 | 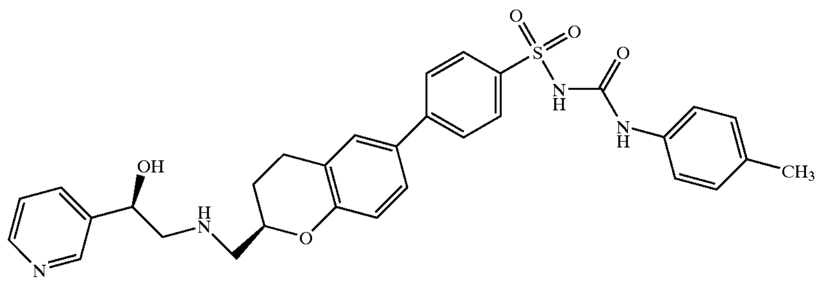 | 573.2 | | 0.25(1:9 MeOH CH2Cl2) |
| 327 | 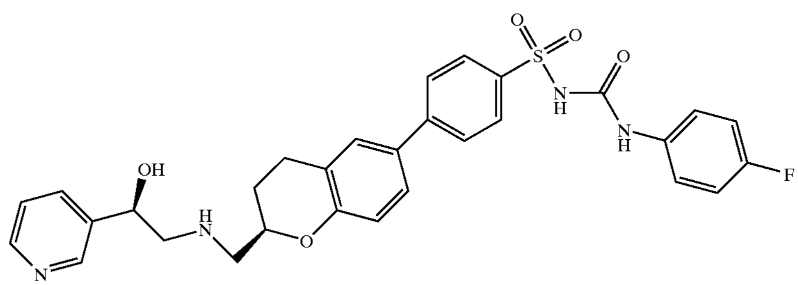 | 577.3 | | 0.21(1:9 MeOH CH2Cl2) |
| 328 | 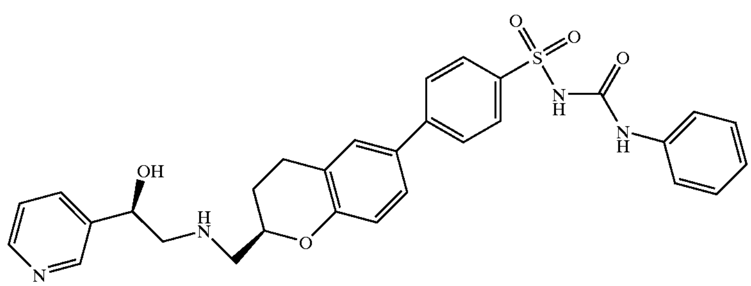 | 559.3 | | 0.23(1:9 MeOH CH2Cl2) |
| 329 | 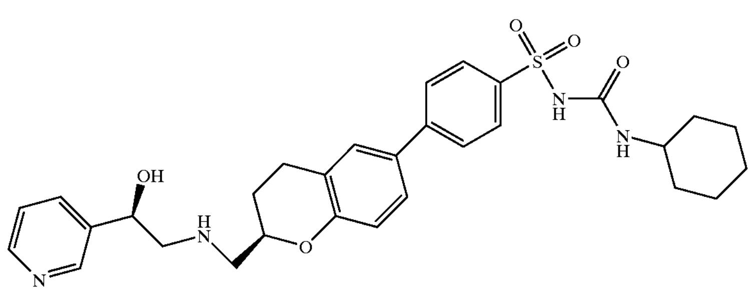 | 565.37 | | 0.31(1:9 MeOH CH2Cl2) |

TABLE 14-continued
| Example No. | Structure | MS [M + H]+ | HPLC (RT) | TLC Rf (solvent) |
|---|---|---|---|---|
| 330 | 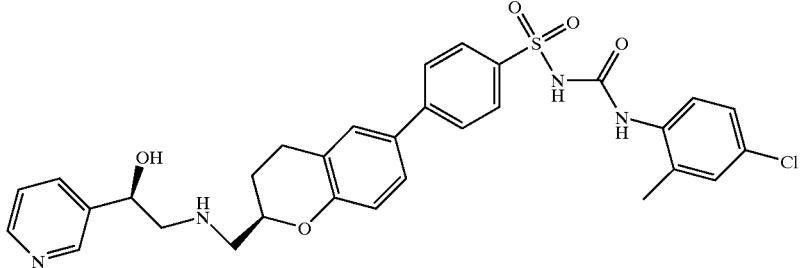 | 623.34 | | 0.21(1:9 MeOH CH2Cl2) |
| 331 | 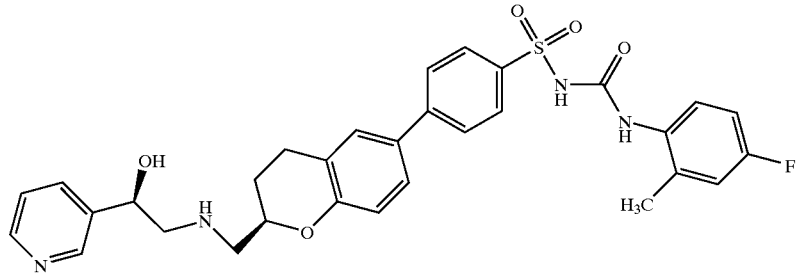 | 595.42 | | 0.22(1:9 MeOH CH2Cl2) |
| 332 | 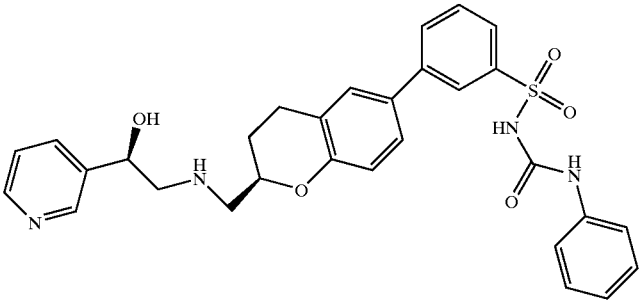 | 559.2 | 8.2 min | |
| 333 | 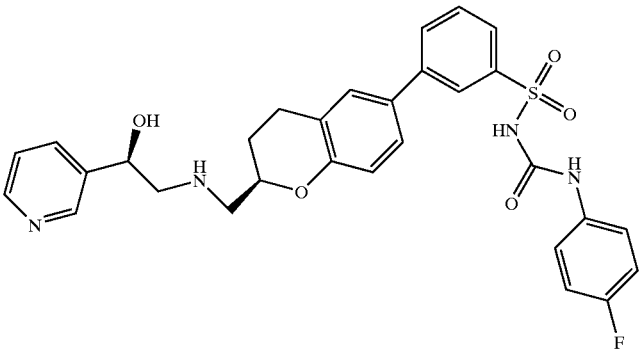 | 577.2 | 9.3 | |

TABLE 14-continued

| Example No. | Structure | MS [M + H]+ | HPLC (RT) | TLC Rf (solvent) |
|---|---|---|---|---|
| 334 | 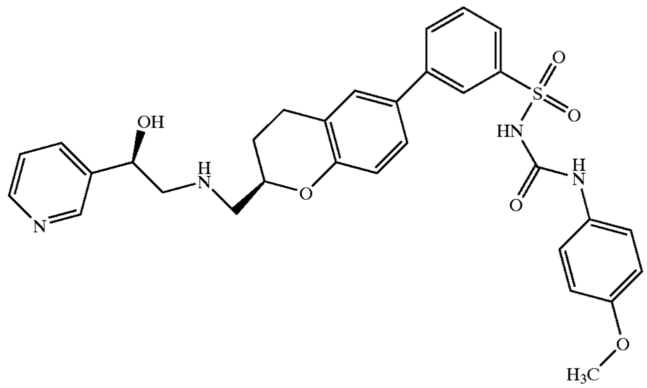 | 589.2 | 6.6 | |
| 335 | 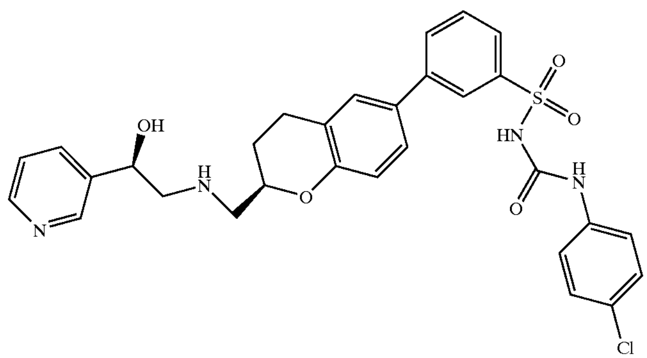 | 592.2 | 10.1 | |
| 336 | 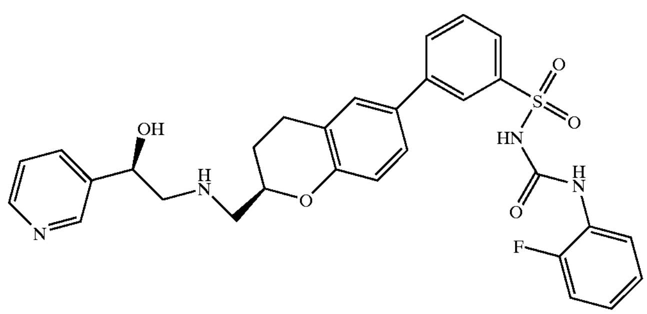 | 577.2 | 6.4 | |
| 337 | 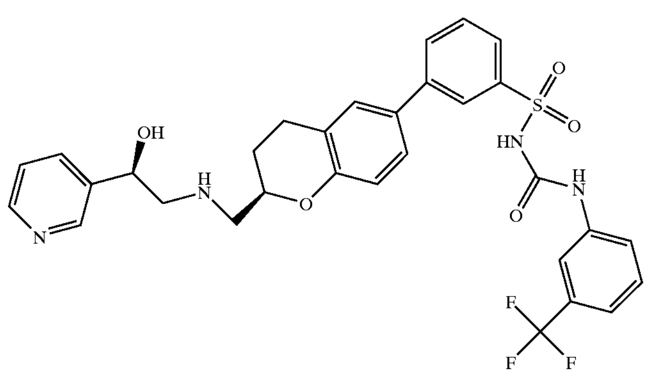 | 627.2 | 5.7 | |

TABLE 14-continued

| Example No. | Structure | MS [M + H]+ | HPLC (RT) | TLC Rf (solvent) |
|---|---|---|---|---|
| 338 | 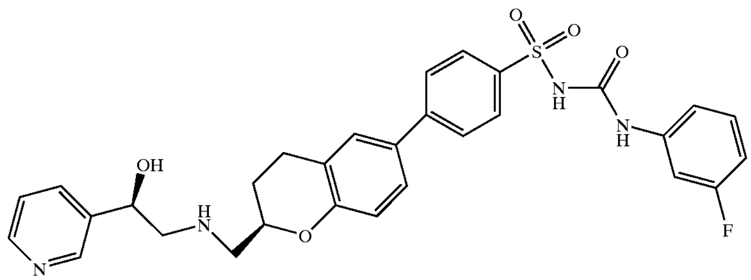 | 577.31 | | 0.23(1:9 MeOH CH2Cl2) |
| 339 | 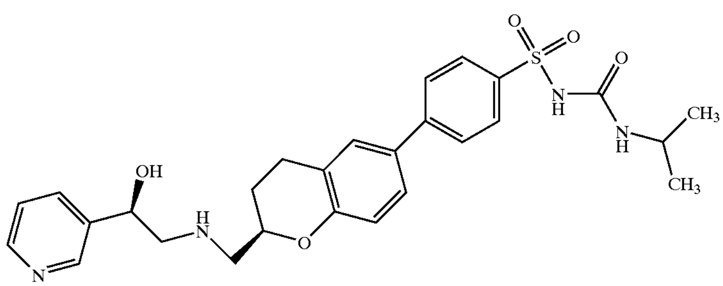 | 525.32 | | 0.27(1:9 MeOH CH2Cl2) |
| 340 | 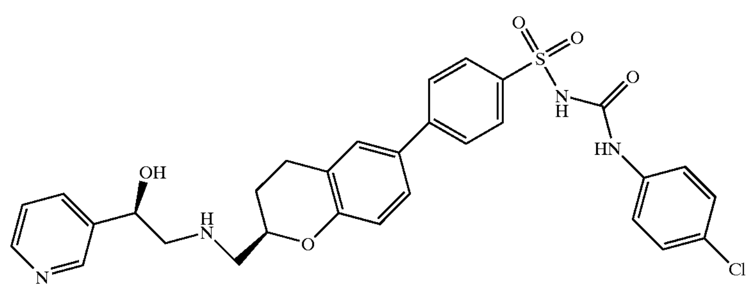 | 593.31 | | 0.31(1:9 MeOH CH2Cl2) |

EXAMPLE 341

Preparation of 3,4-Dimethylphenyloxirane

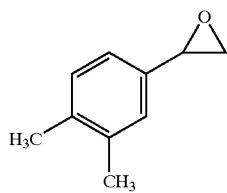

The procedure was based on methods described by Brandes and Jacobsen, (Tetrahedron Asym. 8:3927, 1997); and Kaufman (Syn. Commun. 23:473, 1993). A solution of trimethylsulfonium methylsulfate (3.95 g, 0.021 mol) in 8 mL water was added slowly to a biphasic mixture of 50% NaOH (20 mL), 3,4-dimethyl-benzaldehyde (1.34 g, 0.01 mmol), tetrabutylammonium bromide (0.025 g, 0.0782 mmol), and CH$_2$Cl$_2$ (26 mL). The reaction was heated at 50° C. for 13 hours and then cooled to room temperature. The reaction was diluted carefully with brine (50 mL) and diethyl ether (3×70 mL), then filtered to remove the solids. The aqueous layer was extracted with diethyl ether (3×70 mL), and the combined organic layers were washed with brine (50 mL) and dried over Na$_2$SO$_4$, filtered, and concentrated in vacuo to afford the product 3,4-dimethylphenyl oxirane as a light yellow oil (1.15 g, yield 78%). TLC Rf=0.9 (1:2 EtOAc/Hexane); $^1$H NMR (300 MHz, CDCl$_3$) δ 7.39 (s, 1 H), 7.21 (d, 1 H), 7.19 (s, 1 H), 3.80 (m, 1 H), 3.17 (m, 1 H), 2.80 (m, 1 H), 2.23 (s, 6 H).

EXAMPLE 342–354

General Procedure for Coupling Epoxides (4-[(2R)-2-({[2-(3,4-dimethylphenyl)-2-hydroxyethyl]amino}methyl)-3,4-dihydro-2H-chromen-6-yl]benzoic acid)

Step 1: Condensation of the Chroman Amine with Epoxides

Into an 8-mL screw-cap vial were dispensed 200 μL of a 0.5 M solution of 6-(4-methoxycarbonylphenyl)-(R)-chroman-2-methylamine (Example 19 free base, 0.01 mmol) and 200 μL of the appropriate epoxide solution (commercial or prepared as in Example 341, 0.01 mmol). Dioxane (500 μL) and water (100 μL) were then added to each vial, and the mixture was heated at 80° C. with mixing by orbital shaking for 2 days. After the mixture was allowed to cool to room temperature, the solvent was removed under reduced pressure by using a multiple sample evaporator (GeneVac).

Step 2: Hydrolysis of the Methyl Ester

The residue obtained from the previous procedure was heated in 1 mL 2 M lithium hydroxide solution in 3:1 methanol/water at 60° C. overnight. After allowing the reaction mixture to cool to room temperature, 1.1 mL hydrochloric acid (2 N) was slowly added to each vial. Precipitate was formed in the vial. The solvent was removed under reduced pressure by using a multiple sample evaporator (GeneVac). The residue was dissolved in 1 mL MeOH, and then purified by preparative reversed phase HPLC, using aqueous MeCN containing 0.1% trifluoroacetic acid as eluant.

In a typical example, 6-(4-methoxycarbonylphenyl)-(R)-chroman-2-methylamine and 3,4-dimethylphenyl oxirane were reacted by following the procedure described above to provide 4-[(2R)-2-({[2-(3,4-dimethylphenyl)-2-hydroxyethyl]amino}methyl)-3,4-dihydro-2H-chromen-6-yl]benzoic acid as the trifluoroacetate salt (17% yield). $^1$H NMR (300 MHz, DMSO) δ 7.95 (d, 2 H), 7.72 (d, 2 H), 7.50 (d, 2 H), 7.15–7.00 (m, 3 H), 6.95 (m, 1 H), 4.45 (m, 2 H), 3.80 (m, 1 H), 3.30 (s, 4 H), 2.95–2.80 (m, 2 H), 2.10 (d, 6 H), 1.70 (m, 1 H); LC-MS m/z432 (MH$^+$), ret. time 2.19 min.

Using the procedure outlined above, Examples 342–354 were prepared.

TABLE 15

| Example No. | Structure | | LC/MS RT (min) | MS + [M + H]$^+$ |
|---|---|---|---|---|
| 342 | 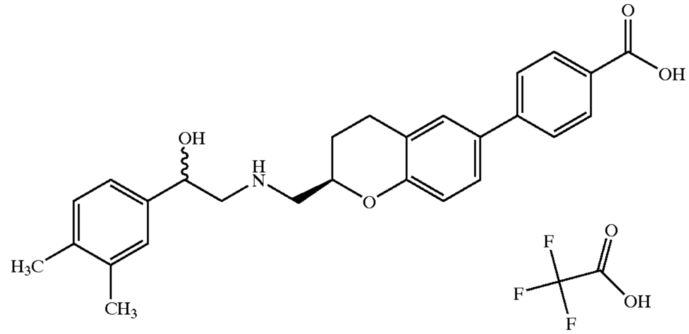 | Chiral | 2.19 | 432 |
| 343 | 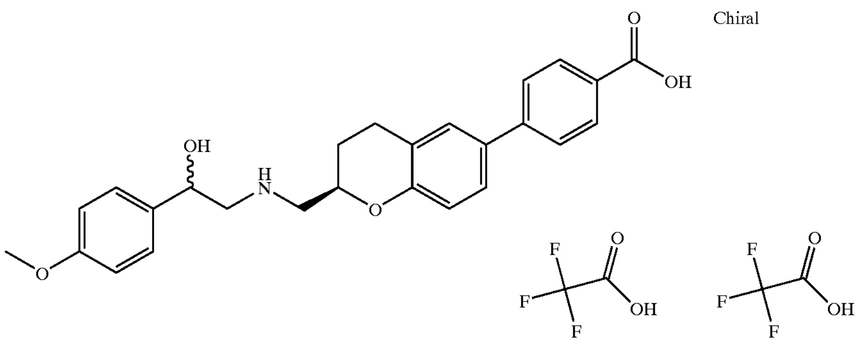 | Chiral | 1.82 | 435 |
| 344 | 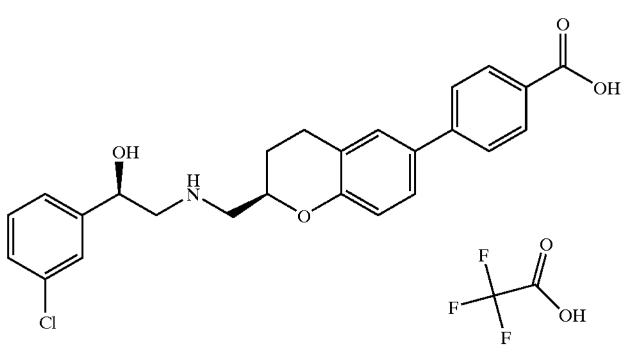 | Chiral | 2.12 | 438 |

TABLE 15-continued

| Example No. | Structure | | LC/MS RT (min) | MS + [M + H]⁺ |
|---|---|---|---|---|
| 345 | (structure) | Chiral | 2.04 | 404 |
| 346 | (structure) | Chiral | 2.04 | 404 |
| 347 | (structure) | Chiral | 2.09 | 449 |
| 348 | (structure) | Chiral | 2.19 | 474 |

TABLE 15-continued

| Example No. | Structure | LC/MS RT (min) | MS + [M + H]+ |
|---|---|---|---|
| 349 | Chiral | 2.12 | 456 |
| 350 | Chiral | 2.19 | 436 |
| 351 | Chiral | 2.13 | 448 |
| 352 | Chiral | 2.25 | 456 |

TABLE 15-continued

| Example No. | Structure | LC/MS RT (min) | MS + [M + H]+ |
|---|---|---|---|
| 353 | Chiral | 2.27 | 472 |
| 354 | Chiral | 2.32 | 472 |

EXAMPLE 355

Preparation of (2R)-N-{(2R)-2-[6-(2,5-dimethyl-1H-pyrrol-1-yl)-3-pyridinyl]-2-hydroxyethyl}-6-iodo-3,4-dihydro-2H-chromene-2-carboxamide

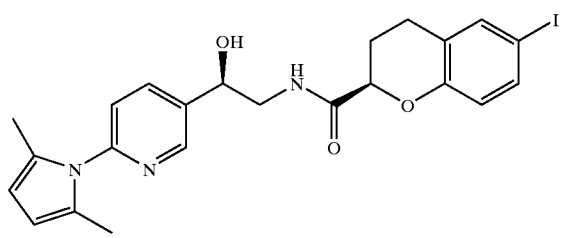

A reaction mixture containing (2R)-6-iodo-3,4-dihydro-2H-chromene-2-carboxylic acid (Example 7, 5.39 mmol, 1.0 eq.), (1R)-2-amino-1-[6-(2,5-dimethyl-1H-pyrrol-1-yl)-3-pyridinyl]ethanol dihydrochloride (U.S. Pat. No. 6,051,586) (6.47 mmol, 1.2 eq.), 1-(3-dimethylaminopropyl)-3-ethylcarbodiimide hydrochloride (EDCl, 10.8 mmol, 2.0 eq.), 1-hydroxybenzotriazole hydrate (HOBT, 10.8 mmol, 2.0 eq.), and triethylamine (16.2 mmol, 3.0 eq.) in $CH_2Cl_2$ (30 mL) was stirred at room temperature for 18 hours. Water was added to the reaction mixture and the resulting two-phase mixture was extracted with $CH_2Cl_2$. The combined organic extracts were washed with water and brine, dried over anhydrous sodium sulfate, concentrated and purified by medium pressure column chromatography (Biotage 40S normal phase silica gel column, $CH_2Cl_2$:MeOH=100:4). The product was obtained as a pale yellow foam in 56% yield. $MH^+$=518.2, RT=3.74 min.

EXAMPLE 356

Preparation of (1R)-1-[6-(2,5-dimethyl-1H-pyrrol-1-yl)-3-pyridinyl]-2-({[(2R)-6-iodo-3,4-dihydro-2H-chromen-2-yl]methyl}amino)ethanol

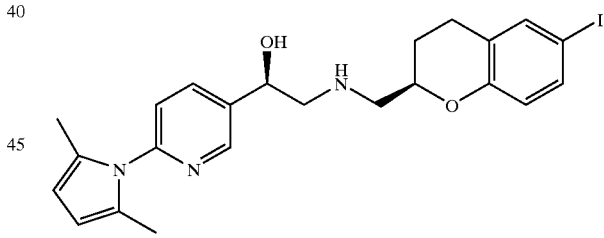

To a solution of (2R)-N-{(2R)-2-[6-(2,5-dimethyl-1H-pyrrol-1-yl)-3-pyridinyl]-2-hydroxyethyl}-6-iodo-3,4-dihydro-2H-chromene-2-carboxamide (Example 355, 7.67 mmol, 1 eq.) in THF (150 mL) at room temperature was added slowly borane-methyl sulfide complex (2M in THF, 38.4 mmol, 5.0 eq.). After completion of the addition, the reaction mixture was heated to reflux for 2 hours and was then cooled to room temperature. The excess borane was quenched by the dropwise addition of EtOH (9 mL) followed by the slow addition of 2 M HCl (40 mL). The resulting mixture was heated to reflux for 1 hour and was then allow to cool to room temperature. The mixture was basified with 1N NaOH and extracted with ethyl acetate. The organic extract was washed with brine, dried over anhydrous sodium sulfate, concentrated, and purified by medium pressure column chromatography (Biotage 40S normal phase silica gel column, using a gradient of 1:4 hexanes:EtOAc to

EXAMPLE 357

Preparation of tert-butyl (2R)-2-[6-(2,5-dimethyl-1H-pyrrol-1-yl)-3-pyridinyl]-2-hydroxyethyl{[(2R)-6-iodo-3,4-dihydro-2H-chromen-2-yl]methyl}carbamate

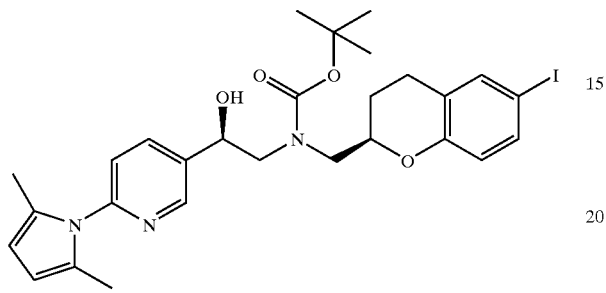

A reaction mixture containing (1R)-1-[6-(2,5-dimethyl-1H-pyrrol-1-yl)-3-pyridinyl]-2-({[(2R)-6-iodo-3,4-dihydro-2H-chromen-2-yl]methyl}amino)ethanol (Example 356, 3.28 mmol, 1.0 eq.) and di-tert-butyl dicarbonate (3.44 mmol, 1.05 eq.) in THF (15 mL) was stirred at room temperature for 18 hours.

The solvent was evaporated and the residue was purified by medium pressure column chromatography (Biotage 40S normal phase silica gel column, 2:1 hexanes:EtOAc). The product was obtained as a beige foam in 68% yield. MH$^+$=603.9, RT=4.43 min.

EXAMPLE 358

Preparation of tert-butyl (2R)-2-{[tert-butyl(dimethyl)silyl]oxy}-2-[6-(2,5-dimethyl-1H-pyrrol-1-yl)-3-pyridinyl]ethyl{[(2R)-6-iodo-3,4-dihydro-2H-chromen-2-yl]methyl}carbamate

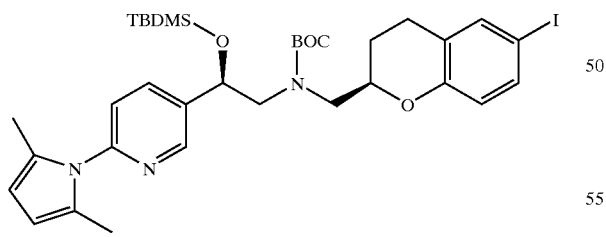

A mixture of tert-butyl (2R)-2-[6-(2,5-dimethyl-1H-pyrrol-1-yl)-3-pyridinyl]-2-hydroxyethyl{[(2R)-6-iodo-3,4-dihydro-2H-chromen-2-yl]methyl}carbamate (Example 357, 7.5 g, 12.4 mmol), TBDMSCl (2.25 g, 14.9 mmol), and imidazole (2.10 g, 30.9 mmol) in DMF (10 mL) was stirred at room temperature under argon for 24 hours. The reaction mixture was then poured into a saturated NaHCO$_3$ solution (50 mL). The mixture was extracted with ether (100 mL×2). The ether layer was washed with water (50 mL) and dried over anhydrous sodium sulfate. Removal of the solvent in vacuo afforded a near white syrup which was purified by column chromatography (silica gel, hexanes/ethyl acetate (5/1, v/v)) and gave the desired compound as a colorless oil (6.5 g, 72%).

EXAMPLE 359

Preparation of ethyl (2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromene-6-carboxylate

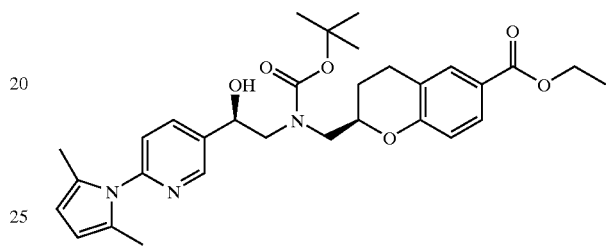

A solution of tert-butyl (2R)-2-[6-(2,5-dimethyl-1H-pyrrol-1-yl)-3-pyridinyl]-2-hydroxyethyl{[(2R)-6-iodo-3,4-dihydro-2H-chromen-2-yl]methyl}carbamate (Example 357, 1.72 mmol, 1.0 eq.) in EtOH (6.5 mL) was treated with Pd(OAc)$_2$ (0.09 mmol, 0.05 eq.) and triethylamine (4.31 mmol, 2.5 eq.). The reaction mixture was vigorously stirred and degassed with argon. This suspension was heated to reflux for 18 hours under 1 atmosphere of carbon monoxide. The resulting solution was cooled to room temperature and filtered through a Celite® pad, washing with more EtOH. The filtrate was concentrated and purified by medium pressure column chromatography (Biotage 40S normal phase silica gel column, using a gradient of 8:1 to 2:1 hexanes:EtOAc). The product was obtained as a colorless oil in 62%. MH$^+$=550.3, 3.79 min.

EXAMPLE 360

Preparation of (2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromene-6-carboxylic acid

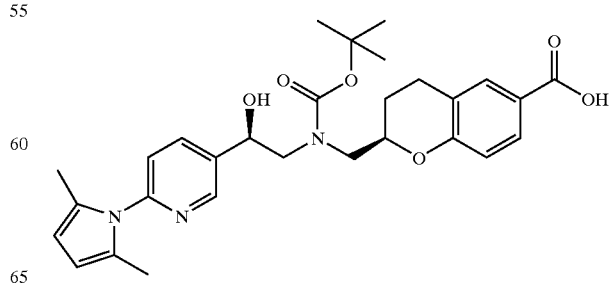

A solution of ethyl (2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromene-6-carboxylate (Example 359, 0.21 mmol, 1.0 eq.) and 1N NaOH (0.63 mmol, 3.0 eq.) in EtOH (2 mL) was heated to reflux for 1.5 hours. The reaction mixture was allowed to cool to room temperature and was concentrated in vacuo to afford a residue that was purified by medium pressure column chromatography (Biotage 40S normal phase silica gel column, 100:5 $CH_2Cl_2$:MeOH). The product was obtained as a white foam in 72% yield. $MH^+$=522.3, RT=3.11 min.

EXAMPLE 361

Preparation of ethyl N-([{(2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromen-6-yl}carbonyl)glycinate

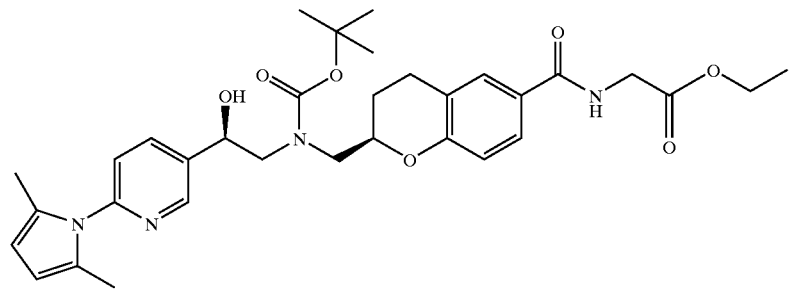

The product was obtained in 44% yield via a coupling reaction between (2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromene-6-carboxylic acid (Example 360) and glycine ethyl ester hydrochloride utilizing the method described for Example 355; $MH^+$=607.3, RT=3.18 min.

EXAMPLE 362

Preparation of N-{[(2R)-2-({[(2R)-2-(6-amino-3-pyridinyl)-2-hydroxyethyl]amino}methyl)-3,4-dihydro-2H-chromen-6-yl]carbonyl}glycine

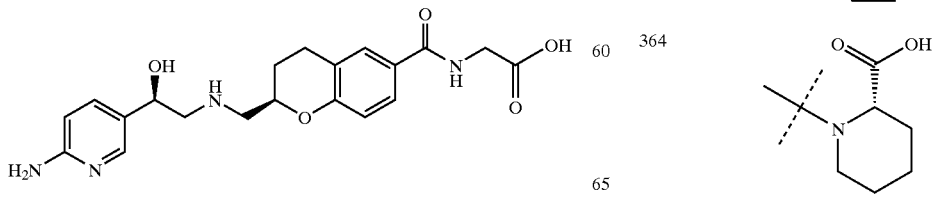

A mixture of ethyl N-({(2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromen-6-yl}carbonyl)glycinate (Example 361, 0.08 mmol, 1.0 eq.) in EtOH/$H_2O$ (0.8 mL/0.2 mL) was treated with 2 N HCl (0.42 mmol, 5.0 eq), followed by hydroxylamine hydrochloride (0.084 mmol, 10.0 eq.). The resulting reaction mixture was heated at reflux for 18 hours. Solvents were evaporated in vacuo and the brown residue was purified by reverse phase HPLC. The product was obtained as the TFA salt in 15%. $MH^+$=401.1, RT=0.79 min.

Following the procedures described above for Examples 361–362, and using Example 360 and the appropriate amino acid esters as starting materials, the following compounds were similarly prepared:

TABLE 16

| Example No. | R" | RT (LC-MS min.) | MS [M + H]⁺ |
|---|---|---|---|
| 363 | ![pyrrolidine-2-carboxylic acid] | 0.79 | 441.2 |
| 364 | ![piperidine-2-carboxylic acid] | 0.78 | 455.2 |

| 365 | 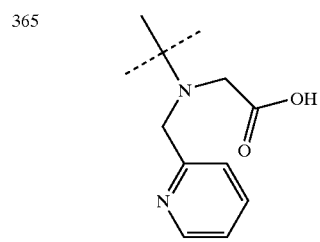 | 0.76 | 492.2 |
| 366 | 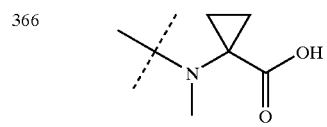 | 0.77 | |
| 367 | 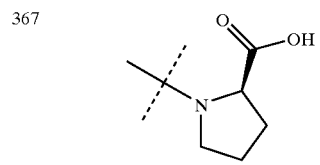 | 0.62 | 441.3 |
| 368 | 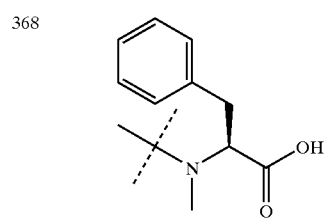 | 1.26 | 505.2 |
| 369 | 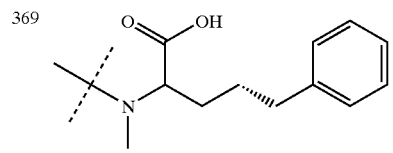 | 1.52 | 491.2 |

EXAMPLE 370

Preparation of tert-butyl (2R)-2-{[tert-butyl(dimethyl)silyl]oxy}-2-[6-(2,5-dimethyl-1H-pyrrol-1-yl)-3-pyridinyl]ethyl{[(2R)-6-(4,4,5,5-tetramethyl-1,3,2-dioxaborolan-2-yl)-3,4-dihydro-2H-chromen-2-yl]methyl}carbamate

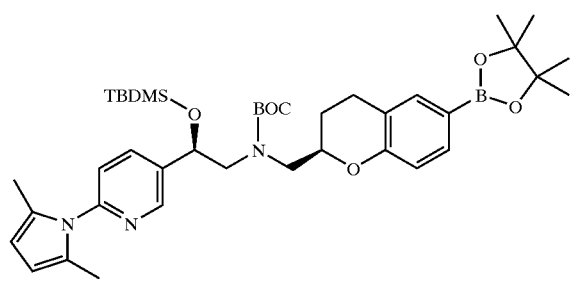

The product was prepared from tert-butyl (2R)-2-{[tert-butyl(dimethyl)silyl]oxy}-2-[6-(2,5-dimethyl-1H-pyrrol-1-yl)-3-pyridinyl]ethyl([(2R)-6-iodo-3,4-dihydro-2H-chromen-2-yl]methyl}carbamate (Example 358) according to the method described for Example 81.

EXAMPLE 371

Preparation of methyl 4-[(2R)-2-[((tert-butoxycarbonyl)[(2R)-2-{[tert-butyl(dimethyl)silyl]oxy}-2-[6-(2,5-dimethyl-1H-pyrrol-1-yl)-3-pyridinyl]ethyl}amino)methyl]-3,4-dihydro-2H-chromen-6-yl}benzoate

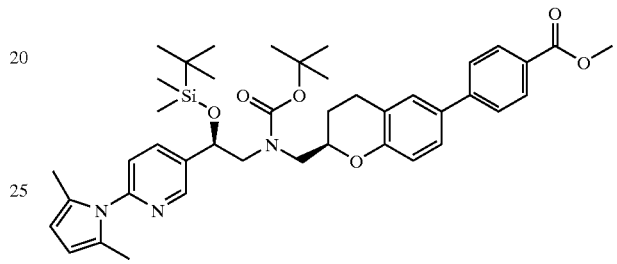

Argon was bubbled through a solution of tert-butyl (2R)-2-{[tert-butyl(dimethyl)silyl]oxy}-2-[6-(2,5-dimethyl-1H-pyrrol-1-yl)-3-pyridinyl]ethyl{[(2R)-6-(4,4,5,5-tetramethyl-1,3,2-dioxaborolan-2-yl)-3,4-dihydro-2H-chromen-2-yl] methyl}carbamate (Example 370, 395 mg, 0.55 mmol) in toluene (15 mL) and 1,4-dioxane (3 mL) for 10 minutes. Bis(diphenylphosphino)ferrocene-palladium (40 mg) and methyl 4-iodobenzoate (216 mg, 0.83 mmol) were added, and bubbling with argon was continued for another 5 minutes. 2 N aq. sodium carbonate solution (3 mL, 6 mmol) was added and the reaction mixture was heated (85° C.) for 16 hours. After cooling, the mixture was filtered through a pad of silica gel and Celite® using ethyl acetate to rinse. The filtrate was concentrated in vacuo and then flash chromatography of the residue over silica gel using 20% ethyl acetate/hexanes afforded 276 mg (69%) of the desired product. The product had: $^1$H NMR (CDCl$_3$, δ): 8.65 (d, J=20.0 Hz, 1 H), 8.13 (d, J=7.9 Hz, 2 H), 7.91 (dd, J=16.8, 8.1 Hz, 1 H), 7.67 (d, J=7.6 Hz, 2 H), 7.24–7.47 (m, 3 H), 6.93 (dd, J=8.1, 1.8 Hz, 1 H), 5.98 (d, J=3.9 Hz, 1 H), 5.23 (dd, J=43.5, 5.5 Hz, 1 H), 4.21–4.43 (m, 1 H), 4.00 (s, 3 H), 3.37–3.95 (m, 4 H), 2.84–3.09 (m, 2 H), 2.22 (s, 3 H), 2.20 (s, 3 H), 2.03–2.18 (m, 1 H), 1.74–1.91 (m, 1 H), 1.59 (d, J=10.4 Hz, 9 H), 0.99 (s, 9 H), 0.17 (s, 3 H), 0.00 (s, 3 H); mass spectroscopy gave m/z=726.4 [M+H]$^+$ (calc'd exact mass for $C_{42}H_{55}N_3O_6Si$=725.4).

Using the method described above for Example 371, the following compounds were similarly prepared using Example 81 and the appropriate halobenzene starting material:

TABLE 17

| Example No. | Structure | MS [M + H⁺] | HPLC RT (min) |
|---|---|---|---|
| 372 | 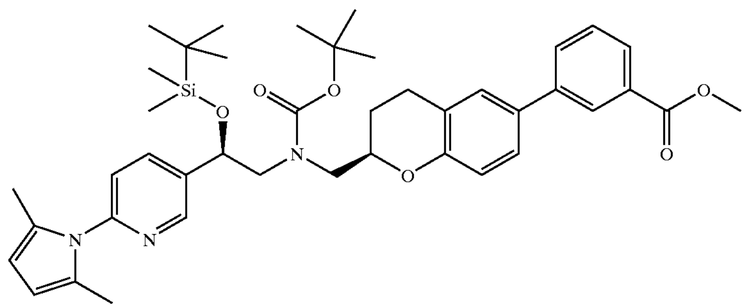 | 726.4 | 5.18 |
| 373 | 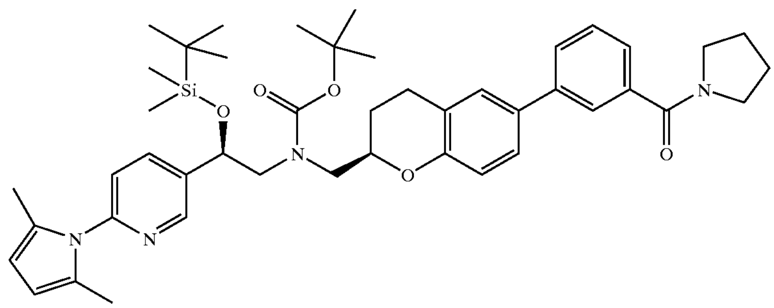 | 765.4 | 4.85 |
| 374 | 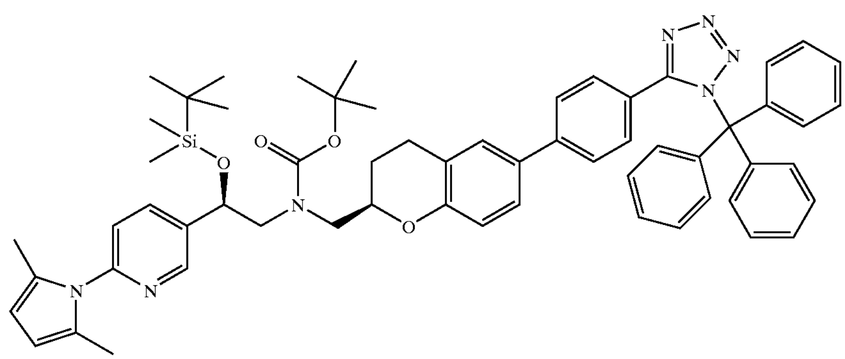 | 978 | 5.29 |

EXAMPLE 375

Preparation of methyl 4-{(2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromen-6-yl}benzoate

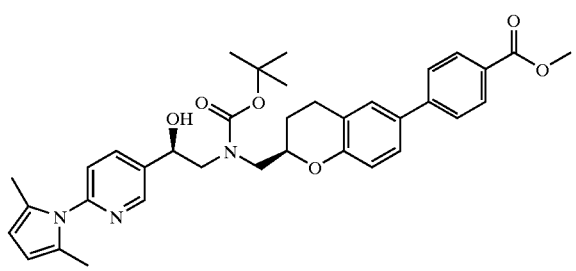

To a solution of methyl 4-{(2R)-2-[((tert-butoxycarbonyl){(2R)-2-{[tert-butyl(dimethyl)silyl]-oxy}-2-[6-(2,5-dimethyl-1H-pyrrol-1-yl)-3-pyridinyl]ethyl}-amino)methyl]-3,4-dihydro-2H-chromen-6-yl}benzoate (Example 371, 213 mg, 0.29 mmol) in THF (5 mL) was added a solution of 1 M tetrabutylammonium fluoride (0.59 mL, 0.59 mmol). The mixture was stirred at room temperature for 16 hours and then concentrated in vacuo. Flash chromatography of the residue over silica gel using 40% ethyl acetate/hexanes afforded 213 mg (92%) of the desired product. The product had: $^1$H NMR (CDCl$_3$δ): 8.62 (s, 1 H), 8.06 (d, J=8.9 Hz, 2 H), 7.92 (d, J=7.2 Hz, 1 H), 7.58 (d, J=8.8 Hz, 2 H), 7.31–7.40 (m, 2 H), 7.22 (d, J=7.8 Hz, 1 H), 6.89 (d, J=7.9 Hz, 1 H), 5.89 (s, 2 H), 5.10–5.26 (m, 2 H), 4.21–4.50 (m, 1 H), 3.93 (s, 3 H), 3.56–3.88 (m, 4 H), 3.15–3.42 (m, 1 H), 2.78–3.04 (m, 2 H), 2.12 (s, 6 H), 1.65–1.83 (m, 2 H), 1.50 (s, 9 H).

EXAMPLE 376

Preparation of methyl 3-[(2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromen-6-yl]benzoate

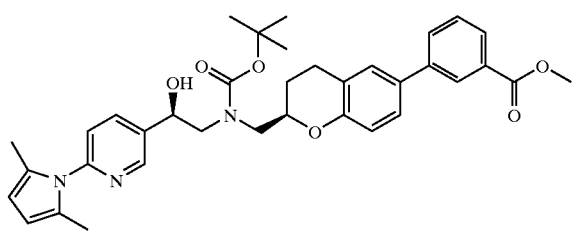

In similar fashion to that described above for Example 375, the title compound was prepared from Example 372 and used without further purification.

EXAMPLE 377

Preparation of methyl 4-((2R)-2-{[[(2R)-2-(6-amino-3-pyridinyl)-2-hydroxyethyl](tert-butoxycarbonyl)amino]methyl}-3,4-dihydro-2H-chromen-6-yl)benzoate

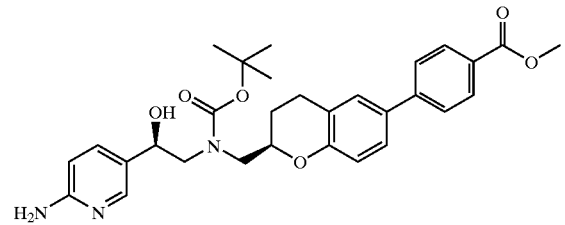

To a solution of methyl 4-{(2R)-2-[((tert-butoxycarbonyl){(2R)-2-[6-(2,5-dimethyl-1H-pyrrol-1-yl)-3-pyridinyl]-2-hydroxyethyl}amino)methyl]-3,4-dihydro-2H-chromen-6-yl}benzoate (Example 375, 162 mg, 0.26 mmol) in ethanol (4 mL) was added hydroxylamine monohydrate (182 mg, 2.65 mmol) and 2 N aq. potassium hydroxide (0.66 mL, 1.32 mmol). The mixture was stirred at room temperature for 70 hours and then concentrated in vacuo. Flash chromatography of the residue using 10% methanol/ethyl acetate afforded 80 mg (43%) of the desired product containing trace impurities. This material was taken on without further purification. Mass spectroscopy gave m/z=534.3 [M+H]$^+$ (calc'd exact mass for $C_{30}H_{35}N_3O_6$=533.3).

Using the method described above for Example 377 and substituting the appropriate starting materials, the following compounds were made and characterized:

TABLE 18

| Example No. | Structure | MS [M + H$^+$] | Starting Material | HPLC RT (min) |
|---|---|---|---|---|
| 378 | 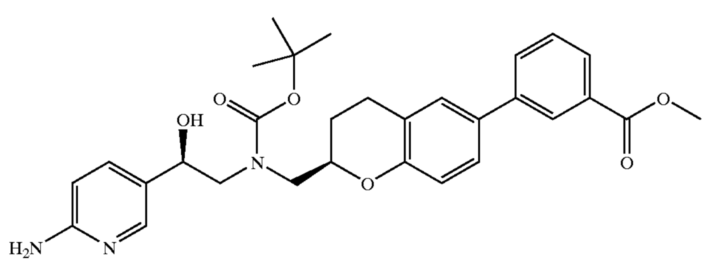 | used crude | 370 | — |
| 379 | 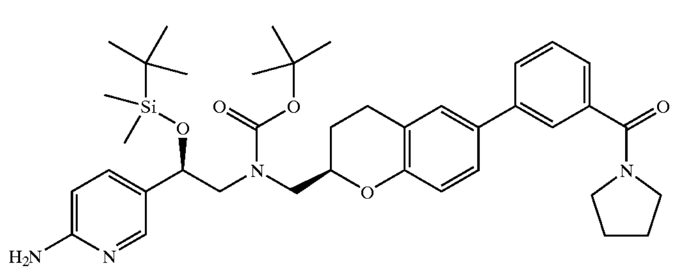 | 687.4 | 367 | 3.08 |

TABLE 18-continued

| Example No. | Structure | MS [M + H+] | Starting Material | HPLC RT (min) |
|---|---|---|---|---|
| 380 | 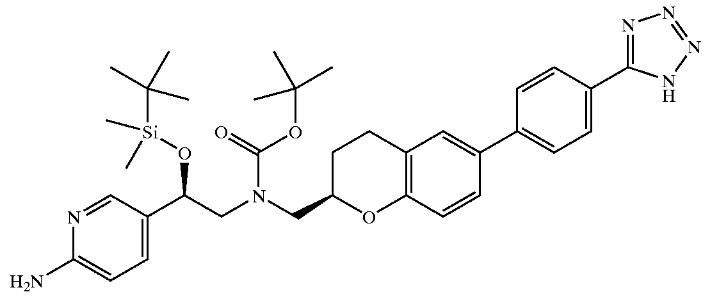 | 658.3 | 368 | 2.95 |

EXAMPLE 381

Preparation of methyl 4-[(2R)-2-({[(2R)-2-(6-amino-3-pyridinyl)-2-hydroxyethyl]amino}-methyl)-3,4-dihydro-2H-chromen-6-yl]benzoate

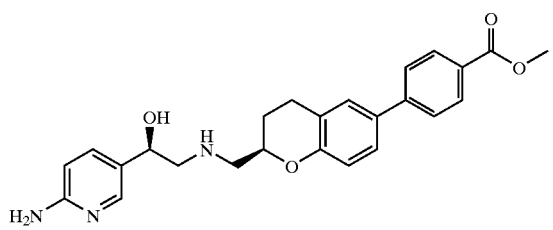

Methyl 4-((2R)-2-{[[(2R)-2-(6-amino-3-pyridinyl)-2-hydroxyethyl](tert-butoxycarbonyl)-amino]methyl}-3,4-dihydro-2H-chromen-6-yl)benzoate (Example 377, 80 mg, 0.15 mmol) was added to 4 M hydrochloric acid in dioxane (3 mL, 12 mmol). The solution was stirred at room temperature for 18 hours and then concentrated in vacuo. The residue was purified by prep. HPLC, afforded 40 mg (62%) of the desired product. The product had: $^1$H NMR (CD$_3$OD$\delta$): 8.04 (d, J=8.1 Hz, 2 H), 7.89–8.03 (m, 2 H), 7.68 (d, J=7.8 Hz, 2 H), 7.42–7.49 (m, 2 H), 6.95–7.07 (m, 2 H), 5.02–5.10 (m, 1 H), 4.24–4.52 (m, 1 H), 3.91 (s, 3 H), 3.20–3.52 (m, 4 H), 2.81–3.04 (m, 2 H), 2.11–2.24 (m, 1 H), 1.74–1.92 (m, 1 H); mass spectroscopy gave m/z=434.2 [M+H]$^+$ (calc'd exact mass for C$_{25}$H$_{27}$N$_3$O$_4$=433.2).

Using the method described above for Example 381 and substituting the appropriate starting materials, the following compounds were made and characterized:

TABLE 19

| Example No. | Structure | MS [M + H+] | Starting Material | HPLC RT (min) |
|---|---|---|---|---|
| 382 | 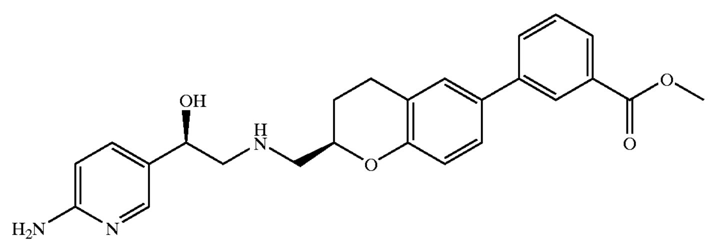 | 434.2 | 372 | 1.95 |
| 383 | 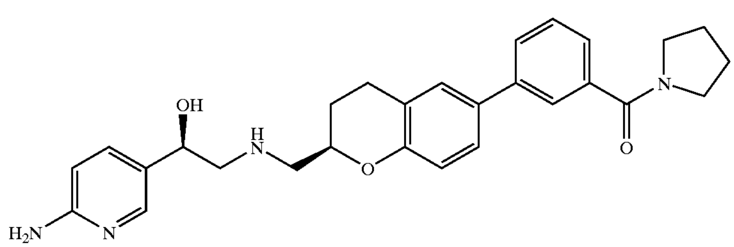 | 473.3 | 373 | 1.56 |

TABLE 19-continued

| Example No. | Structure | MS [M + H⁺] | Starting Material | HPLC RT (min) |
|---|---|---|---|---|
| 384 | 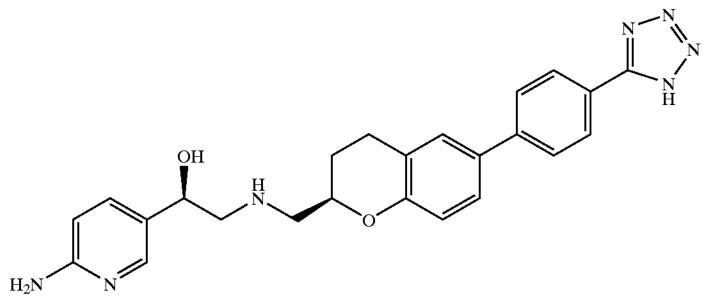 | 444.2 | 374 | 1.46 |

EXAMPLE 385

Preparation of 4-[(2R)-2-({[(2R)-2-(6-amino-3-pyridinyl)-2-hydroxyethyl]amino}methyl)-3,4-dihydro-2H-chromen-6-yl]benzoic acid

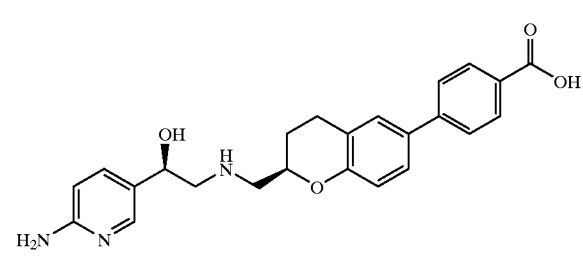

To a solution of methyl 4-[(2R)-2-({[(2R)-2-(6-amino-3-pyridinyl)-2-hydroxyethyl]amino}-methyl)-3,4-dihydro-2H-chromen-6-yl]benzoate (Example 381, 40 mg, 0.1 mmol) in THF (2 mL) and methanol (2 mL) was added 2 M aq. lithium hydroxide (0.5 mL, 1 mmol). The mixture was stirred at room temperature for 18 hours and then concentrated in vacuo. Prep. HPLC of the residue afforded 10.8 mg (28%) of the desired product. The product had: $^1$H NMR (CDCl$_3$, δ): 7.96 (d, J=8.2 Hz, 2 H), 7.90 (d, J=2.2 Hz, 1 H), 7.49–7.56 (m, 3 H), 7.32–7.39 (m, 2 H), 6.82 (d, J=9.0 Hz, 1 H), 6.59 (d, J=8.6 Hz, 1 H), 4.70 (dd, J=8.3, 4.4 Hz, 1 H), 4.14–4.23 (m, 1 H), 2.75–3.02 (m, 6 H), 1.99–2.10 (m, 1 H), 1.70–1.85 (m, 1 H); mass spectroscopy gave m/z=420.2 [M+H]⁺ (calc'd exact mass for C$_{24}$H$_{25}$N$_3$O$_4$=419.2).

EXAMPLE 386

Preparation of 3-[(2R)-2-({[(2R)-2-(6-amino-3-pyridinyl)-2-hydroxyethyl]amino}methyl)-3,4-dihydro-2H-chromen-6-yl]benzoic acid

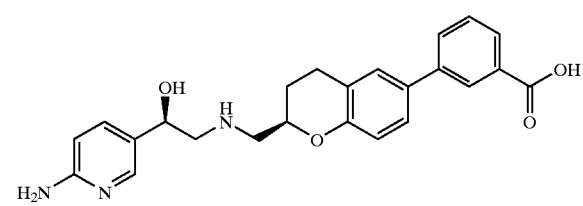

The title compound was made from Example 382 and characterized using the method described above for Example 385; m/z=420.2 [M+H]⁺; RT 1.9 min.

EXAMPLES 387–388

Reaction of Chroman-2-Methylamines with Epoxides: Method for Combinatorial/Parallel Synthesis

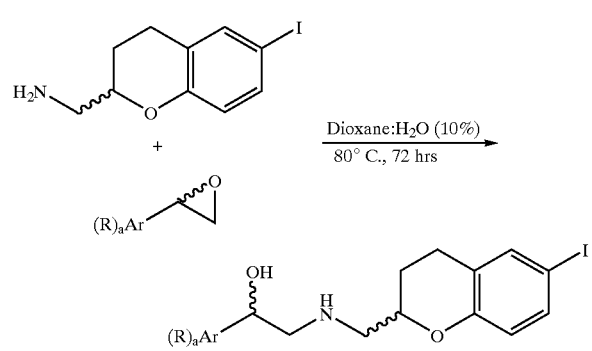

The apparatus used was as described in the general experimentals methods above. In a typical procedure, a solution of (2R)-6-iodo-3,4-dihydro-2H-chromen-2-yl]methylamine (Example 10) and an epoxide (commercially-available or prepared as described in WO99/32475) were freshly prepared as a 0.5 M solution in dioxane. To each reaction well in a polypropylene reaction block was added a solution of the desired amine (200 µL, 0.1 mmol), a solution of the desired epoxide (200 µL, 0.1 mmol), and 500 µL of dioxane as well as 100 µL of water. The reaction block was sealed with rubber gaskets and clamped, then heated at 80° C. for 72 hours, with mixing by rotation. After allowing the reaction block to cool to room temperature, the block was disassembled, and the reaction well contents were filtered into a collection 96-well deep-well microtiter plate, washing with 2 portion of 200 µL of dioxane. The filtrate solutions were evaporated to dryness using a multiple sample centrifugal vacuum evaporator. Products were analyzed for purity and correct identity by LC/MS.

Utilizing the above procedures and starting from (2R)-6-iodo-3,4-dihydro-2H-chromen-2-yl]methylamine (Example 10) and the appropriate epoxide starting material, the following compounds were prepared and characterized:

TABLE 20

| Example No. | Structure | RT (min) LC/MS | MS m/z [M + H]+ |
|---|---|---|---|
| 387 | (structure) | 2.52 | 410 |
| 388 | (structure) | 2.63 | 444 |

An embodiment of the present invention is the administration of the compounds of this invention to a human or animal for the treatment of beta-3 adrenergic receptor mediated conditions such as diabetes, obesity, gastrointestinal disorders including irritable bowel syndrome and intestinal hypermotility disorders, peptic ulcerations, esophagitis, gastritis, and duodenitis, intestinal ulcerations including inflammatory bowel disease, ulcerative colitis, Crohn's disease and proctitis, and gastrointestinal ulcerations, as well as neurogenetic inflammation such as cough and asthma, and depression. It is also believed that the compounds of this invention are effective in the treatment of hypertriglyceridemia, hypercholesterolemia and conditions of low or high density lipoprotein levels, artherosclerotic disease and cardiovascular disease and related conditions. Additionally, it is also believed that the compounds of this invention are effective in the treatment of ocular hypertension and glaucoma, and in the treatment of urinary disorders including pollakiuria and incontinence, as well as in the treatment of prostate disease and as topical anti-inflammatory agents.

Therefore, the compounds of this invention are expected to be valuable as therapeutic agents. An embodiment of this invention includes a method of treating beta-3 adrenergic receptor mediated conditions in a mammal which comprises administering to said mammal a composition containing an amount of the compound of Formula I that is effective in treating the target condition.

The specificity of the compounds of this invention as beta-3 adrenergic receptor agonists can readily be determined by evaluating the affinity of the compound for the different beta adrenergic receptor subtypes and comparing the activity with various receptor subtypes affinities to discover specificity as well as activity using standard and well-known procedures. Such a procedure is described in more detail in the specific example below.

EXAMPLE 389

Biological Evaluation of Compounds

The utility of the compounds of this invention can be demonstrated by the following procedure.

Chinese hamster ovary (CHO) cells that stably express full-length human beta-3-adrenergic receptor (Granneman et al., Mol. Pharmacol. 44:264–270, 1993) can be used in the following procedure. The cell line is grown in 90% F12 nutrient mixture (HAM), 10% fetal bovine serum, 100 units/ml penicillin G sodium, 100 mg/ml streptomycin sulfate, and 2 mM L-glutamine at 37° C. in 95% air and 5% $CO_2$. The transfected cell line is maintained with G-418 (800 μg/ml).

To test the agonist activity, cells are exposed to test compound and then assayed for cAMP production. CHO cells (100 μl) are plated at $5\times10^4$ cells/well of a 96-well plate (Costar, Cambridge, Mass.) to achieve 70% confluency the next day. After overnight incubation at 37° C., media is removed and the cells are treated for 30 minutes at 37° C. with KRP buffer (120 mM NaCl, 5.1 mM KCl, 0.6 mM $MgSO_4.7H_2O$, 0.8 mM $CaCl_2.H_2O$, 12.5 μM phosphate buffer, 20 μM Hepes pH 7.4)+0.2 μM IBMX (100 μM/well), +1% DMSO, +/−test compounds (10 μM DMSO stocks). Test compounds are assayed from 10 μM to 3 nM with 3-fold serial dilutions. The control agonist, isoproterenol (10 mM stock in 1.1 mM ascorbate), is assayed by 3-fold dilution beginning at 1 μM. After a 30-minute incubation with the test compounds, the buffer/compound mixture is removed. The cells are lysed and cAMP levels are measured using the cAMP SPA screening assay system (Amersham, Arlington Heights, Ill.). The cAMP values are then plotted to determine the $EC_{50}$ of each compound tested.

In tests utilizing the above described procedure, the compounds of the present invention were found to have beta-3 adrenergic agonist activity with levels of activity summarized in Table 21.

TABLE 21

| Beta-3 Agonistic Activity | |
|---|---|
| Compounds with $EC_{50}$ values ≤1 μM (Example No.) | Compounds with $EC_{50}$ values >1 μM (Example No.) |
| 36 | 39 |
| 40 | 41 |
| 47 | 42 |
| 48 | 43 |
| 54 | 45 |
| 184–188 | 363 |

TABLE 21-continued

Beta-3 Agonistic Activity

| Compounds with $EC_{50}$ values ≤1 μM (Example No.) | Compounds with $EC_{50}$ values >1 μM (Example No.) |
|---|---|
| 192 | 364 |
| 193–198 | 365 |
| 205 | 367 |
| 211 | |
| 215 | |
| 216 | |
| 249A | |
| 249B | |
| 250–280 | |
| 283–305 | |
| 308–311 | |
| 314 | |
| 317 | |
| 319–340 | |
| 343 | |
| 344 | |
| 348 | |
| 352 | |
| 362 | |
| 366 | |
| 369 | |
| 381–386 | |

Beta-3 adrenergic receptor agonists may be useful for correcting the insulin resistance that underlies two prediabetic states, impaired glucose tolerance (Harris, Diabetes Care 12:464–474, 1989) and impaired fasting glucose (Weyer et al., Diabetes 48:2197–2203, 1999). The ability of a beta-3 adrenergic receptor agonist to restore insulin sensitivity has been demonstrated in a diabetic animal model with marked insulin resistance. Treatment of KK-Ay/Ta diabetic obese mice with a beta-3 adrenergic receptor agonist resulted in marked improvement in the animals' responses to insulin (Kato et al., Diabetes 50:113–122, 2001). Insulin resistance in human subjects with impaired glucose tolerance has been treated by troglitazone, another class of insulin sensitizers (Saltiel et al., Diabetes 45:1661–1669, 1996; Saleh et al., Diabetes Rev. 7:55–76, 1999). In such studies, improvement in the insulin responses of these subjects were demonstrated. These overall findings support treating the insulin resistance in prediabetic conditions with insulin sensitizers, including beta-3 adrenergic receptor agonists, to delay or prevent the onset of type 2 diabetes.

Based upon the above and other standard laboratory techniques known to evaluate compound receptor site inhibition, by standard toxicity tests and by standard pharmacological assays for the determination of treatment of the beta-3 adrenergic receptor mediated conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.01 mg/kg to about 100 mg/kg, and preferably from about 0.1 mg/kg to about 20 mg/kg body weight per day. A unit dosage may contain from about 5 mg to about 1500 mg of active ingredient, and may be administered one or more times per day. Of course, the specific initial and continuing dosage regimen for each patient will vary according to the nature and severity of the condition as determined by the attending diagnostician.

The compounds of this invention may be utilized to achieve the desired pharmacological effect by administration to a patient in need thereof in an appropriately formulated pharmaceutical composition. A patient, for the purpose of this invention, is a mammal, including a human, in need of treatment for a particular beta-3 adrenergic receptor mediated condition or disease. Therefore, the present invention includes pharmaceutical compositions which are comprised of a pharmaceutically acceptable carrier and a pharmaceutically effective amount of a compound of Formula I, or a pharmaceutically acceptable salt or ester thereof. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compounds of Formula I may be administered with a pharmaceutically-acceptable carrier using any effective conventional dosage unit forms, including immediate and timed release preparations, orally, parenterally, topically, or the like.

For oral administration, the compounds may be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms may be a capsule which can be of the ordinary hard- or soft-shelled gelatin type containing, for example, surfactants, lubricants, and inert fillers such as lactose, sucrose, calcium phosphate, and corn starch.

In another embodiment, the compounds of this invention may be tableted with conventional tablet bases such as lactose, sucrose, and cornstarch in combination with binders such as acacia, cornstarch, or gelatin; disintegrating agents intended to assist the break-up and dissolution of the tablet following administration such as potato starch, alginic acid, corn starch, and guar gum; lubricants intended to improve the flow of tablet granulation and to prevent the adhesion of tablet material to the surfaces of the tablet dies and punches, for example, talc, stearic acid, or magnesium, calcium, or zinc stearate; dyes; coloring agents; and flavoring agents intended to enhance the aesthetic qualities of the tablets and make them more acceptable to the patient. Suitable excipients for use in oral liquid dosage forms include diluents such as water and alcohols, for example, ethanol, benzyl alcohol, and polyethylene alcohols, either with or without the addition of a pharmaceutically acceptable surfactant, suspending agent, or emulsifying agent.

Dispersible powders and granules are suitable for the preparation of an aqueous suspension. They provide the active ingredient in admixture with a dispersing or wetting agent, a suspending agent, and one or more preservatives. Suitable dispersing or wetting agents and suspending agents are exemplified by those already mentioned above. Additional excipients, for example those sweetening, flavoring, and coloring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Oily suspensions may be formulated by suspending the active ingredient in a vegetable oil such as, for example, arachis oil, olive oil, sesame oil, or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more coloring agents; one or more flavoring agents; and one or more sweetening agents such as sucrose or saccharin.

Syrups and elixirs may be formulated with sweetening agents such as, for example, glycerol, propylene glycol, sorbitol, or sucrose. Such formulations may also contain a demulcent, and preservative, flavoring, and coloring agents.

The compounds of this invention may also be administered parenterally, that is, subcutaneously, intravenously, intramuscularly, or interperitoneally, as injectable dosages of the compound in a physiologically acceptable diluent with a pharmaceutical carrier which can be a sterile liquid or mixture of liquids such as water; saline; aqueous dextrose and related sugar solutions; an alcohol such as ethanol, isopropanol, or hexadecyl alcohol; glycols such as propylene glycol or polyethylene glycol; glycerol ketals such as 2,2-dimethyl-1,1-dioxolane-4-methanol; ethers such as poly (ethyleneglycol) 400; an oil; a fatty acid; a fatty acid ester or glyceride; or an acetylated fatty acid glyceride with or without the addition of a pharmaceutically acceptable surfactant such as a soap or a detergent; suspending agent such as pectin, carbomers, methycellulose, hydroxypropylmethylcellulose, or carboxymethylcellulose; or emulsifying agent and other pharmaceutical adjuvants.

Illustrative of oils which may be used in the parenteral formulations of this invention are those of petroleum, animal, vegetable, or synthetic origin, for example, peanut oil, soybean oil, sesame oil, cottonseed oil, corn oil, olive oil, petrolatum, and mineral oil. Suitable fatty acids include oleic acid, stearic acid, and isostearic acid. Suitable fatty acid esters are, for example, ethyl oleate and isopropyl myristate. Suitable soaps include fatty alkali metal, ammonium, and triethanolamine salts and suitable detergents include cationic detergents, for example, dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; nonionic detergents, for example, fatty amine oxides, fatty acid alkanolamides, and polyoxyethylenepolypropylene copolymers; and amphoteric detergents, for example, alkyl-beta-aminopropionates, and 2-alkylimidazoline quarternary ammonium salts, as well as mixtures.

The parenteral compositions of this invention will typically contain from about 0.5% to about 25% by weight of the active ingredient in solution. Preservatives and buffers may also be used advantageously. In order to minimize or eliminate irritation at the site of injection, such compositions may contain a non-ionic surfactant having a hydrophile-lipophile balance (HLB) of from about 12 to about 17. The quantity of surfactant in such formulation may range from about 5% to about 15% by weight. The surfactant may be a single component having the above HLB or may be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethylcellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadecaethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example, polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, and isotonic sodium chloride solution. In addition, sterile fixed oils are conventionally employed as solvents or suspending media. For this purpose, any bland, fixed oil may be employed including synthetic mono or diglycerides. In addition, fatty acids such as oleic acid may be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Another formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art (see, e.g., U.S. Pat. No. 5,023,252, incorporated herein by reference). Such patches may be constructed for continuous, pulsatile, or on demand delivery of pharmaceutical agents.

It may be desirable or necessary to introduce the pharmaceutical composition to the patient via a mechanical delivery device. The construction and use of mechanical delivery devices for the delivery of pharmaceutical agents is well known in the art. Direct techniques for, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472.

The compositions of the invention may also contain other conventional pharmaceutically acceptable compounding ingredients, generally referred to as carriers or diluents, as necessary or desired. Any of the compositions of this invention may be preserved by the addition of an antioxidant such as ascorbic acid or by other suitable preservatives. Conventional procedures for preparing such compositions in appropriate dosage forms can be utilized.

EXAMPLE 390

A capsule formula is prepared from

| A compound of Formula I | 40 mg |
|---|---|
| Starch | 109 mg |
| Magnesium stearate | 1 mg |

The components are blended, passed through an appropriate mesh sieve, and filled into hard gelatin capsules.

EXAMPLE 391

A tablet is prepared from

| A compound of Formula I | 25 mg |
|---|---|
| Cellulose, microcrystalline | 200 mg |
| Colloidal silicon dioxide | 10 mg |
| Stearic acid | 5.0 mg |

The ingredients are mixed and compressed to form tablets.

The compound of this invention may be administered as the sole pharmaceutical agent or in combination with one or more other pharmaceutical agents where the combination causes no unacceptable adverse effects. For example, the compounds of this invention may be combined with known antiobesity or other indication agents, and the like, as well as with admixtures and combinations thereof.

The compounds of Formula I may also be utilized, in free base form or in compositions, in research and diagnostics, or as analytical references standards, and the like. Therefore, the present invention includes compositions which are comprised of an inert carrier and an effective amount of a compound of Formula I, or a salt or ester thereof. An inert carrier is any material which does not interact with the compound to be carried and which lends support, means of conveyance, bulk, traceable material, and the like, to the compound to be carried. An effective amount of compound is that amount which produces a result or exerts an influence on the particular procedure being performed.

It should be apparent to one of ordinary skill in the art that changes and modifications can be made to this invention without departing from the spirit or scope of the invention as it is set froth herein.

We claim:

1. A compound of Formula I

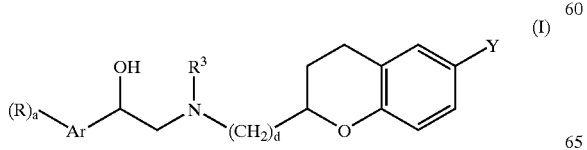

(I)

wherein,
R is independently
hydroxy,
oxo,
halo,
cyano,
nitro,
$C_1$–$C_{10}$ alkyl,
$C_1$–$C_{10}$ haloalkyl,
$CF_3$,
$NR^1R^1$,
$SR^1$,
$OR^1$,
$SO_2R^2$,
$OCOR^2$,
$NR^1COR^2$,
$COR^2$,
$NR^1SO_2R^2$,
phenyl, or
a 5- or 6-membered heterocycle with from 1 to 4 heteroatoms selected from O, S, and N;
each cyclic moiety being optionally substituted with
hydroxy,
$R^1$,
halo,
cyano,
$NR^1R^1$,
$SR^1$,
$CF_3$,
$OR^1$,
$C_3$–$C_8$ cycloalkyl,
$NR^1COR^2$,
$COR^2$,
$SO_2R^2$,
$OCOR^2$,
$NR^1SO_2R^2$,
$C_1$–$C_{10}$ alkyl, or
$C_1$–$C_{10}$ alkoxy;
$R^1$ is
hydrogen,
$(CH_2)_d$—O—$(CH_2)_dR^5$ where each d is selected independently, or
$C_1$–$C_{10}$ alkyl optionally substituted with 1 to 4 substituents each independently selected from
hydroxy,
halo,
$CO_2C_1$–$C_4$-alkyl,
$CO_2H$,
$C_1$–$C_{10}$ alkoxy,
$S(O)_bC_1$–$C_{10}$ alkyl,
$S(O)_b$-phenyl optionally substituted with halo, $C_1$–$C_4$ alkyl, $C_1$–$C_4$ alkoxy, $SO_2$—$C_1$–$C_4$alkyl, or $CO_2$ $C_1$–$C_4$alkyl; or
phenyl optionally substituted with $CO_2C_1$–$C_4$-alkyl, $CO_2H$, halo, or $C_1$–$C_{10}$ alkyl; or
$C_3$–$C_8$ cycloalkyl, phenyl, or naphthyl, each optionally substituted with 1 to 4 substituents each independently selected from halo, nitro, oxo, $C_1$–$C_{10}$ alkyl, $C_1$–$C_{10}$ alkoxy, $C_1$–$C_{10}$ alkylthio, $CO_2C_1$–$C_4$-alkyl, and $CO_2H$, and
when two $R^1$ groups are attached to N as $NR^1R^1$, these $R^1$ groups may form together with the nitrogen to which they are attached, a heterocyclic ring containing 4 to 7 C atoms, 1 to 2 N atoms, and 0 to 10 or S atoms;
$R^2$ is
$R^1$,
$OR^1$, $NR^1R^1$,
NHS(O)$_b$phenyl optionally substituted with $C_1$–$C_4$ alkyl, $C_1$–$C_4$ alkoxy, halo or nitro;
NHS(O)$_b$naphthyl,
NHS(O)$_b$$C_1$–$C_{10}$ alkyl optionally substituted with fluoro up to the perfluoro level, or
a 5- or 6-membered heterocycle with one or more heteroatoms selected from O, S, and N, said heterocyclic moiety being optionally substituted with $R^1$;

$R^3$ is hydrogen, $C_1$–$C_{10}$ alkyl, or $COR^2$;

$R^4$ is hydrogen, $C_1$–$C_{10}$ alkyl, $C_1$–$C_{10}$ alkyl-phenyl, or $C_1$–$C_{10}$ alkyl-pyridyl;

$R^5$ is hydrogen or COOH;

$R^6$ is
hydrogen,
$C_1$–$C_{10}$ alkyl optionally substituted with 1 to 4 substituents each independently selected from halo, phenyl, or phenyl-$COR^2$, or
$C_1$–$C_{10}$ alkyl-S(O)$_b$$C_1$–$C_{10}$ alkyl optionally substituted with $COR^2$ or $C_3$–$C_8$ cycloalkyl;

Ar is
phenyl;

Y is
halo,
$NO_2$,
$R^6$,
$SR^1$,
S(O)$_b$-phenyl-$CO_2R^1$,

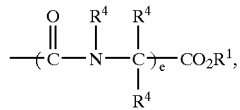

where, when the two $R^4$ groups attached to the same C are both alkyl, they optionally may be joined so that, when taken together with the C to which they are attached, they form a spiro ring of 3, 5, or 6 C atoms, or where the $R^4$ attached to N and one $R^4$ attached to the adjacent C are both alkyl, they optionally may be joined so that, taken together with the atoms to which they are attached, they form a 5- or 6-membered heterocyclic ring;
with the proviso that when e is 1, at least one $R^4$ group must be $C_1$–$C_{10}$alkyl-phenyl or $C_1$–$C_{10}$alkyl-pyridyl, or two $R^4$ groups must form one of said spiro or heterocyclic ring moieties;

phenyl optionally fused to one or two phenyl rings, or to a 5- or 6-membered heterocycle containing one or more heteroatoms each independently selected from N, S, and O, or a 5- or 6-membered heterocycle containing one or more heteroatoms each independently selected from N, S and O, optionally fused to a phenyl ring, each cyclic moiety being optionally substituted with one or more substituents independently selected from
$COR^2$,
$CONR^1S(O)_2R^9$,
$COCH_2SO_2$-thiazolyl optionally substituted with alkyl or amino,
halo,
$NO_2$,
$OR^1$,
$R^1$,
$SR^1$, O—$C_1$–$C_6$-alkyl substituted by $C_3$–$C_6$-cycloalkyl,
O-phenyl optionally substituted by $SO_2CH_3$,
$SO_2NH_2$,
$SO_2NR^1R^7$,
$NR^1R^1$,
$NR^1COC_1$–$C_6$alkyl,

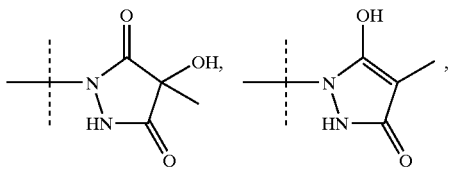

$C_1$–$C_{10}COR^2$,
phenyl optionally substituted with halo, $C_1$–$C_4$ alkyl, or $C_1$–$C_4$alkoxy,
tetrazolo;

$R^7$ is
phenyl or heteroaryl containing 3–6 C and 1–3 O, N, or S atoms, each optionally substituted by $C_1$–$C_4$alkyl, CN, $NO_2$, CO—$C_1$–$C_4$alkyl, C1–$C_4$alkoxy, or $C_1$–$C_4$ haloalkyl,
CO—$R^8$,

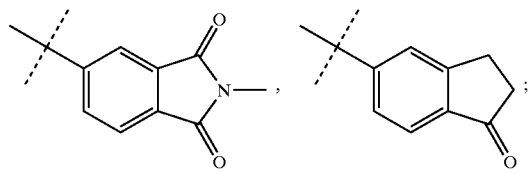

$R^8$ is
$C_1$–$C_6$ alkyl optionally substituted with $C_1$–$C_4$ alkoxy, $N(CH_3)_2$, or one or two $CF_3$,
$C_3$–$C_6$-cycloalkyl,
phenyl optionally substituted with $C_1$–$C_4$ alkoxy, halo, or $C_1$–$C_4$ alkyl,
NH-phenyl optionally substituted with $C_1$–$C_4$ alkyl, halo, $C_1$–$C_4$ alkoxy, or $C_1$–$C_4$ haloalkoxy,
NH-cyclohexyl;

$R^9$ is
$C_3$–$C_6$ cycloalkyl,
thienyl optionally substituted with $C_1$–$C_4$ alkyl or isoxazolyl,
pyridyl optionally substituted with —$SO_2$—$C_1$–$C_4$alkyl,
pyrazolyl optionally substituted with halo or $C_1$–$C_4$ alkyl,
isoxazolyl optionally substituted with $C_1$–$C_4$ alkyl, or

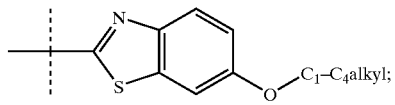

a is 0, 1, 2, 3, 4, or 5;
b is 0, 1, or 2;
d is 1, 2, or 3;
e is 1 or 2;
and pharmaceutically acceptable salts and esters thereof.

2. The compound of claim 1 wherein Y is
halo,
$R^6$,
$SR^1$,
$S(O)_b$-phenyl-$CO_2R^1$,
phenyl optionally fused to one or two phenyl rings, or to a 5- or 6-membered heterocycle containing one or more heteroatoms each independently selected from N, S, and O, or
a 5- or 6-membered heterocycle containing one or more heteroatoms each independently selected from N, S and O, optionally fused to a phenyl ring,
each cyclic moiety being optionally substituted with one or more substituents independently selected from
$COR^2$,
halo,
$NO_2$,
$OR^1$,
$R^1$,
$SR^1$,
$SO_2NR^1R^7$,
$NR^1NR^1$,
$NR^1COC_1$–$C_6$alkyl,
$C_1$–$C_{10}COR^2$,
phenyl,
tetrazolo;
and pharmaceutically acceptable salts and esters thereof.

3. The compound of claim 1 wherein Y is
phenyl optionally fused to one or two phenyl rings, or to a 5- or 6-membered heterocycle containing one or more heteroatoms each independently selected from N, S, and O, or
a 5- or 6-membered heterocycle containing one or more heteroatoms each independently selected from N, S and O, optionally fused to a phenyl ring,
each cyclic moiety being optionally substituted with one or more substituents independently selected from
$COR^2$,
halo,
$NO_2$,
$OR^1$,
$R^1$,
$SR^1$,
$SO_2NR^1R^7$,
$NR^1R^1$,
$NR^1COC_1$–$C_6$alkyl,
$C_1$–$C_{10}COR^2$,
phenyl,
tetrazolo;
and d is 1 or 2;
and pharmaceutically acceptable salts and esters thereof.

4. The compound of claim 1 wherein
Y is
phenyl optionally fused to one or two phenyl rings, or to a 5- or 6-membered heterocycle containing one or more heteroatoms each independently selected from N, S, and O, or
a 5- or 6-membered heterocycle containing one or more heteroatoms each independently selected from N, S and O, optionally fused to a phenyl ring,
each cyclic moiety being optionally substituted with one or more substituents independently selected from
$COR^2$,
halo,
$NO_2$,
$OR^1$,
$R^1$,
$SR^1$,
$SO_2NR^1R^7$,
$NR^1R^1$,
$C_1$–$C_{10}COR^2$,
phenyl,
tetrazolo;
Ar is
phenyl;
and d is 1 or 2;
and pharmaceutically acceptable salts and esters thereof.

5. The compound of claim 1 wherein
Y is
phenyl optionally fused to one or two phenyl rings, or to a 5- or 6-membered heterocycle containing one or more heteroatoms each independently selected from N, S, and O, or
a 5- or 6-membered heterocycle containing one or more heteroatoms each independently selected from N, S and O, optionally fused to a phenyl ring,
each cyclic moiety being optionally substituted with one or more substituents independently selected from
$COR^2$,
halo,
$OR^1$,
$R^1$,
$NR^1R^1$,
Ar is
phenyl;
a is 0, 1, 2, or 3; and
d is 1;
and pharmaceutically acceptable salts and esters thereof.

6. A compound selected from the group consisting of:
4-[(2R)-2-({[(2R)-2-(3-chlorophenyl)-2-hydroxyethyl]amino}methyl)-3,4-dihydro-2H-chromen-6-yl]benzoic acid.

7. A method of treating obesity comprising the step of administering to a patient in need thereof a pharmaceutically effective amount of a compound of claim 1.

8. A method of treating diabetes comprising the step of administering to a patient in need thereof a pharmaceutically effective amount of a compound of claim 1.

9. A method of treating a patient with impaired fasting glucose or impaired glucose tolerance comprising the step of administering to said patient in need thereof a pharmaceutically effective amount of a compound of claim 1.

10. A method of treating gastrointestinal disorders comprising the step of administering to a patient in need thereof a pharmaceutically effective amount of a compound of claim 1.

11. A method of treating hypertriglyceridemia, hypercholesteolemia, atherosclerotic disorders, or cardiovascular disorders comprising the step of administering to a patient in need thereof a pharmaceutically effective amount of a compound of claim 1.

12. A method for lowering high-density lipoprotein levels comprising the step of administering to a patient in need thereof a pharmaceutically effective amount of a compound of claim 1.

13. A method for treating urinary disorders comprising the step of administering to a patient in need thereof a pharmaceutically effective amount of a compound of claim 1.

14. The method of claim 13, wherein said urinary disorders is selected from the group consisting of pollakiuria and incontinence.

15. A method of treating obesity comprising the step of administering to a patient in need thereof a pharmaceutically effective amount of a compound of claim 6.

16. A method of treating diabetes comprising the step of administering to a patient in need thereof a pharmaceutically effective amount of a compound of claim 6.

17. A method of treating a patient with impaired fasting glucose or impaired glucose tolerance comprising the step of administering to said patient in need thereof a pharmaceutically effective amount of a compound of claim 6.

18. A method of treating gastrointestinal disorders comprising the step of administering to a patient in need thereof a pharmaceutically effective amount of a compound of claim 6.

19. A method of treating hypertriglyceridemia, hypercholesteolemia, atherosclerotic disorders, or cardiovascular disorders comprising the step of administering to a patient in need thereof a pharmaceutically effective amount of a compound of claim 6.

20. A method for lowering high-density lipoprotein levels comprising the step of administering to a patient in need thereof a pharmaceutically effective amount of a compound of claim 6.

21. A method for treating urinary disorders comprising the step of administering to a patient in need thereof a pharmaceutically effective amount of a compound of claim 6.

22. The method of claim 21, wherein said urinary disorders is selected from the group consisting of pollakiuria and incontinence.

23. A pharmaceutical composition comprising an effective amount of a compound of claim 1 or a pharmaceutically acceptable salt and esters thereof in combination with a pharmaceutically acceptable carrier.

24. A pharmaceutical composition comprising an effective amount of a compound of claim 6 or a pharmaceutically acceptable salt and esters thereof in combination with a pharmaceutically acceptable carrier.

* * * * *